(12) United States Patent
Cuillerot et al.

(10) Patent No.: US 12,377,144 B2
(45) Date of Patent: *Aug. 5, 2025

(54) METHODS OF TREATING CANCER USING MULTI-SPECIFIC BINDING PROTEINS THAT BIND NKG2D, CD16 AND A TUMOR-ASSOCIATED ANTIGEN

(71) Applicant: Dragonfly Therapeutics, Inc., Waltham, MA (US)

(72) Inventors: Jean-Marie Cuillerot, Somerville, MA (US); Mark DeRose, Wilmington, MA (US); Christopher Ryan Morgan, Southborough, MA (US); Michael C. Naill, Stow, MA (US); Avni Shah, Framingham, MA (US)

(73) Assignee: Dragonfly Therapeutics, Inc., Waltham, MA (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/686,238

(22) Filed: Mar. 3, 2022

(65) Prior Publication Data

US 2023/0034186 A1 Feb. 2, 2023

Related U.S. Application Data

(60) Provisional application No. 63/156,214, filed on Mar. 3, 2021.

(51) Int. Cl.
| | | |
|---|---|---|
| *A61K 39/395* | (2006.01) | |
| *A61K 31/138* | (2006.01) | |
| *A61K 31/167* | (2006.01) | |
| *A61K 31/573* | (2006.01) | |
| *A61K 39/00* | (2006.01) | |
| *A61K 47/22* | (2006.01) | |
| *A61K 47/26* | (2006.01) | |
| *A61P 1/00* | (2006.01) | |
| *A61P 35/00* | (2006.01) | |
| *A61P 35/04* | (2006.01) | |
| *C07K 16/28* | (2006.01) | |
| *C07K 16/32* | (2006.01) | |

(52) U.S. Cl.
CPC ...... *A61K 39/39591* (2013.01); *A61K 31/138* (2013.01); *A61K 31/167* (2013.01); *A61K 31/573* (2013.01); *A61K 39/3955* (2013.01); *A61K 39/39558* (2013.01); *A61K 47/22* (2013.01); *A61K 47/26* (2013.01); *A61P 1/00* (2018.01); *A61P 35/00* (2018.01); *A61P 35/04* (2018.01); *C07K 16/283* (2013.01); *C07K 16/2851* (2013.01); *C07K 16/32* (2013.01); A61K 2039/505 (2013.01); A61K 2039/54 (2013.01); A61K 2039/545 (2013.01); C07K 2317/31 (2013.01)

(58) Field of Classification Search
CPC ............ A61K 39/39591; A61K 31/138; A61K 31/167; A61K 31/573; A61K 39/3955; A61K 39/39558; A61K 47/22; A61K 47/26; A61K 2039/505; A61K 2039/54; A61K 2039/545; A61P 1/00; A61P 35/04; A61P 35/00; C07K 16/283; C07K 16/2851; C07K 16/32; C07K 2317/31
See application file for complete search history.

(56) References Cited

U.S. PATENT DOCUMENTS

| | | |
|---|---|---|
| 5,776,427 A | 7/1998 | Thorpe et al. |
| 5,807,706 A | 9/1998 | Carter et al. |
| 5,863,538 A | 1/1999 | Thorpe et al. |
| 5,959,084 A | 9/1999 | Ring et al. |
| 6,036,955 A | 3/2000 | Thorpe et al. |
| 6,054,297 A | 4/2000 | Carter et al. |
| 6,129,914 A | 10/2000 | Weiner et al. |
| 6,165,464 A | 12/2000 | Hudziak et al. |
| 6,210,670 B1 | 4/2001 | Berg |
| 6,294,167 B1 | 9/2001 | Lindhofer et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,572,856 B1 | 6/2003 | Taylor et al. |
| 6,737,056 B1 | 5/2004 | Presta |

(Continued)

FOREIGN PATENT DOCUMENTS

| | | |
|---|---|---|
| CA | 2990511 A1 | 12/2016 |
| CN | 102378768 A | 3/2012 |

(Continued)

OTHER PUBLICATIONS

Nersesian et al (NK cell infiltration is associated with improved overall survival in solid cancers: A systematic review and meta-analysis, Translational Oncology 14, 2020 (Year: 2020).*

(Continued)

*Primary Examiner* — Nelson B Moseley, II
*Assistant Examiner* — Dennis J Sullivan

(57) ABSTRACT

This disclosure relates to methods of treating cancer using multi-specific binding proteins that bind NKG2D, CD16 and a tumor-associated antigen such as HER2. Provided are uses of the multi-specific binding protein in combination with a corticosteroid to reduce the risk of infusion-related reactions. Also provided are uses of the multi-specific binding protein in treating cancer that has low or moderate HER2 expression level. The present disclosure also relates to pharmaceutical formulations comprising the multi-specific binding proteins.

20 Claims, 32 Drawing Sheets

Specification includes a Sequence Listing.

(56) References Cited

U.S. PATENT DOCUMENTS

| | | |
|---|---|---|
| 7,112,324 B1 | 9/2006 | Dorken et al. |
| 7,235,641 B2 | 6/2007 | Kufer et al. |
| 7,575,923 B2 | 8/2009 | Dorken et al. |
| 7,635,472 B2 | 12/2009 | Kufer et al. |
| 7,642,228 B2 | 1/2010 | Carter et al. |
| 7,695,936 B2 | 4/2010 | Carter et al. |
| 7,820,166 B2 | 10/2010 | Lanzavecchia |
| 7,879,985 B2 | 2/2011 | Urso et al. |
| 7,951,917 B1 | 5/2011 | Arathoon et al. |
| 8,007,796 B2 | 8/2011 | Baeuerle et al. |
| 8,076,459 B2 | 12/2011 | Hofmeister et al. |
| 8,101,722 B2 | 1/2012 | Kufer et al. |
| 8,236,308 B2 | 8/2012 | Kischel et al. |
| 8,409,577 B2 | 4/2013 | Thompson et al. |
| 8,518,403 B2 | 8/2013 | Hoffmann et al. |
| 8,591,897 B2 | 11/2013 | Bryant |
| 8,592,562 B2 | 11/2013 | Kannan et al. |
| 8,658,765 B2 | 2/2014 | Martin, Jr. et al. |
| 8,679,785 B2 | 3/2014 | Carter et al. |
| 8,709,421 B2 | 4/2014 | Heiss et al. |
| 8,759,494 B2 | 6/2014 | Bachmann et al. |
| 8,784,821 B1 | 7/2014 | Kufer et al. |
| 8,796,420 B2 | 8/2014 | Martin, Jr. et al. |
| 8,840,888 B2 | 9/2014 | Nagorsen et al. |
| 8,931,406 B2 | 1/2015 | Detloff et al. |
| 9,079,969 B2 | 7/2015 | Martin, Jr. et al. |
| 9,102,736 B2 | 8/2015 | Hofmeister et al. |
| 9,127,064 B2 | 9/2015 | Urso et al. |
| 9,150,656 B2 | 10/2015 | Johnson et al. |
| 9,150,663 B2 | 10/2015 | Labrijn et al. |
| 9,200,078 B2 | 12/2015 | Bachmann |
| 9,248,181 B2 | 2/2016 | De Kruif et al. |
| 9,248,182 B2 | 2/2016 | De Kruif et al. |
| 9,273,136 B2 | 3/2016 | Rader et al. |
| 9,334,331 B2 | 5/2016 | Igawa et al. |
| 9,447,185 B2 | 9/2016 | Romagne et al. |
| 9,493,578 B2 | 11/2016 | Lazar et al. |
| 9,562,109 B2 | 2/2017 | Von Kreudenstein et al. |
| 9,587,036 B2 | 3/2017 | Kufer et al. |
| 9,637,557 B2 | 5/2017 | Scheer et al. |
| 9,683,053 B2 | 6/2017 | Blein et al. |
| 9,690,969 B2 | 6/2017 | Okamoto |
| 9,718,893 B2 | 8/2017 | Jung et al. |
| 9,951,145 B2 | 4/2018 | Kim et al. |
| 9,963,513 B2 | 5/2018 | Vu et al. |
| 10,040,853 B2 | 8/2018 | Spies et al. |
| 10,047,167 B2 | 8/2018 | Demarest et al. |
| 10,059,765 B2 | 8/2018 | Velardi et al. |
| 10,377,827 B2 | 8/2019 | Swanson et al. |
| 10,421,807 B2 | 9/2019 | Gonzales et al. |
| 10,526,409 B2 | 1/2020 | Urso et al. |
| 10,767,760 B2 | 9/2020 | Ando |
| 11,084,880 B2 | 8/2021 | Brogdon et al. |
| 11,124,582 B2 | 9/2021 | Ambrogelly et al. |
| 11,787,864 B2 | 10/2023 | Cheung et al. |
| 11,834,506 B2 | 12/2023 | Chang et al. |
| 11,884,732 B2 | 1/2024 | Chang et al. |
| 11,884,733 B2 | 1/2024 | Chang et al. |
| 11,939,384 B1 | 3/2024 | Chang et al. |
| 2002/0103345 A1 | 8/2002 | Zhu |
| 2002/0193569 A1 | 12/2002 | Hanna |
| 2003/0095965 A1 | 5/2003 | Van Beneden et al. |
| 2004/0038339 A1 | 2/2004 | Kufer et al. |
| 2004/0052783 A1 | 3/2004 | Weiner et al. |
| 2004/0115198 A1 | 6/2004 | Spies et al. |
| 2005/0037002 A1 | 2/2005 | Velardi et al. |
| 2005/0054019 A1 | 3/2005 | Michaud et al. |
| 2005/0058639 A1 | 3/2005 | Gudas et al. |
| 2005/0158307 A1 | 7/2005 | Spies et al. |
| 2005/0244416 A1 | 11/2005 | Jung |
| 2006/0018899 A1 | 1/2006 | Kao et al. |
| 2006/0235201 A1 | 10/2006 | Kischel |
| 2006/0246004 A1 | 11/2006 | Adams et al. |
| 2007/0004909 A1 | 1/2007 | Johnson et al. |
| 2007/0071759 A1 | 3/2007 | Shin et al. |
| 2007/0179086 A1 | 8/2007 | Gliniak et al. |
| 2007/0190063 A1 | 8/2007 | Bahjat et al. |
| 2008/0025975 A1 | 1/2008 | Weiner et al. |
| 2008/0299137 A1 | 12/2008 | Svendsen et al. |
| 2008/0305105 A1 | 12/2008 | Kufer et al. |
| 2009/0142352 A1 | 6/2009 | Jackson et al. |
| 2009/0175867 A1 | 7/2009 | Thompson et al. |
| 2009/0226442 A1 | 9/2009 | Huet et al. |
| 2009/0226466 A1 | 9/2009 | Fong et al. |
| 2009/0252729 A1 | 10/2009 | Farrington et al. |
| 2009/0304693 A1 | 12/2009 | Ghayur et al. |
| 2009/0304696 A1 | 12/2009 | Lawson et al. |
| 2010/0009866 A1 | 1/2010 | Prinz et al. |
| 2010/0055034 A1 | 3/2010 | Martin et al. |
| 2010/0056764 A1 | 3/2010 | Urso et al. |
| 2010/0124764 A1 | 5/2010 | Hufton et al. |
| 2010/0174053 A1 | 7/2010 | Johnson et al. |
| 2010/0178298 A1 | 7/2010 | Lindhofer |
| 2010/0260765 A1 | 10/2010 | Barry et al. |
| 2010/0272718 A1 | 10/2010 | Urso et al. |
| 2010/0286374 A1 | 11/2010 | Kannan et al. |
| 2010/0291112 A1 | 11/2010 | Kellner et al. |
| 2010/0310463 A1 | 12/2010 | Cicortas Gunnarsson et al. |
| 2011/0008335 A1 | 1/2011 | Velardi et al. |
| 2011/0020273 A1 | 1/2011 | Chang et al. |
| 2011/0044980 A1 | 2/2011 | Ghayur et al. |
| 2011/0054151 A1 | 3/2011 | Lazar et al. |
| 2011/0150870 A1 | 6/2011 | Rader et al. |
| 2011/0311535 A1 | 12/2011 | Dranoff et al. |
| 2012/0014957 A1 | 1/2012 | Ghayur et al. |
| 2012/0058082 A1 | 3/2012 | Kaplan et al. |
| 2012/0058906 A1 | 3/2012 | Smider et al. |
| 2012/0093823 A1 | 4/2012 | Van Den Brink et al. |
| 2012/0149876 A1 | 6/2012 | Von Kreudenstein et al. |
| 2012/0171173 A1 | 7/2012 | Ideno et al. |
| 2012/0195900 A1 | 8/2012 | Ghayur et al. |
| 2012/0263722 A1 | 10/2012 | Ghayur et al. |
| 2012/0269723 A1 | 10/2012 | Brinkmann et al. |
| 2012/0294796 A1 | 11/2012 | Johnson et al. |
| 2012/0294857 A1 | 11/2012 | Sentman et al. |
| 2012/0321626 A1 | 12/2012 | Zhou |
| 2012/0328619 A1 | 12/2012 | Fey et al. |
| 2013/0115208 A1 | 5/2013 | Ho et al. |
| 2013/0177555 A1 | 7/2013 | Wilkinson et al. |
| 2013/0209514 A1 | 8/2013 | Gilboa et al. |
| 2013/0216528 A1 | 8/2013 | Cheung et al. |
| 2013/0216544 A1 | 8/2013 | Bachmann |
| 2013/0230525 A1 | 9/2013 | Li et al. |
| 2013/0336977 A1 | 12/2013 | Thompson et al. |
| 2014/0044739 A1 | 2/2014 | Teng et al. |
| 2014/0072579 A1 | 3/2014 | De Kruif et al. |
| 2014/0072581 A1 | 3/2014 | Dixit et al. |
| 2014/0105889 A1 | 4/2014 | Igawa et al. |
| 2014/0112926 A1 | 4/2014 | Liu et al. |
| 2014/0120096 A1 | 5/2014 | Bakker et al. |
| 2014/0127203 A1 | 5/2014 | Thompson et al. |
| 2014/0140999 A1 | 5/2014 | De Kruif et al. |
| 2014/0141022 A1 | 5/2014 | Thompson et al. |
| 2014/0154250 A1 | 6/2014 | Thompson et al. |
| 2014/0154252 A1 | 6/2014 | Thompson et al. |
| 2014/0199294 A1 | 7/2014 | Mimoto et al. |
| 2014/0234342 A1 | 8/2014 | Narni-Mancinelli et al. |
| 2014/0242077 A1 | 8/2014 | Choi et al. |
| 2014/0271617 A1 | 9/2014 | Igawa et al. |
| 2014/0288275 A1 | 9/2014 | Moore et al. |
| 2014/0294827 A1 | 10/2014 | Gastwirt et al. |
| 2014/0302064 A1 | 10/2014 | Moore |
| 2014/0363426 A1 | 12/2014 | Moore et al. |
| 2014/0364340 A1 | 12/2014 | Vasquez et al. |
| 2014/0377269 A1 | 12/2014 | Mabry et al. |
| 2015/0050269 A1 | 2/2015 | Igawa et al. |
| 2015/0056206 A1 | 2/2015 | Zhou |
| 2015/0079088 A1 | 3/2015 | Lowman et al. |
| 2015/0119555 A1 | 4/2015 | Jung et al. |
| 2015/0166636 A1 | 6/2015 | Igawa et al. |
| 2015/0166654 A1 | 6/2015 | Igawa et al. |
| 2015/0175697 A1 | 6/2015 | Bonvini et al. |
| 2015/0175700 A1 | 6/2015 | Lum et al. |
| 2015/0203591 A1 | 7/2015 | Yancopoulos et al. |

(56) References Cited

U.S. PATENT DOCUMENTS

| | | |
|---|---|---|
| 2015/0210765 A1 | 7/2015 | Roschke et al. |
| 2015/0259431 A1 | 9/2015 | Stemmer et al. |
| 2015/0259434 A1 | 9/2015 | Johnson et al. |
| 2015/0274838 A1 | 10/2015 | Johnson et al. |
| 2015/0299319 A1 | 10/2015 | Velardi et al. |
| 2015/0307617 A1 | 10/2015 | Du et al. |
| 2015/0307628 A1 | 10/2015 | Kim et al. |
| 2015/0329637 A1 | 11/2015 | Urech et al. |
| 2015/0353636 A1 | 12/2015 | Parren et al. |
| 2016/0017038 A1 | 1/2016 | Koenig |
| 2016/0024214 A1 | 1/2016 | Urso et al. |
| 2016/0032009 A1 | 2/2016 | Cheung et al. |
| 2016/0039942 A1 | 2/2016 | Cobbold et al. |
| 2016/0046727 A1 | 2/2016 | Labrijn et al. |
| 2016/0046730 A1 | 2/2016 | Ghayur et al. |
| 2016/0077105 A1 | 3/2016 | Bobrowicz et al. |
| 2016/0090426 A1 | 3/2016 | Zhou et al. |
| 2016/0096892 A1 | 4/2016 | Brogdon et al. |
| 2016/0122432 A1 | 5/2016 | Baty et al. |
| 2016/0159882 A1 | 6/2016 | Landgraf et al. |
| 2016/0159924 A1 | 6/2016 | Padkjaer et al. |
| 2016/0176968 A1 | 6/2016 | Chang et al. |
| 2016/0289341 A1 | 10/2016 | Wu |
| 2016/0326249 A1 | 11/2016 | Ng et al. |
| 2016/0347849 A1 | 12/2016 | Cai et al. |
| 2016/0369002 A1 | 12/2016 | Gauthier et al. |
| 2017/0022291 A1 | 1/2017 | Baruah et al. |
| 2017/0029529 A1 | 2/2017 | Croasdale et al. |
| 2017/0066827 A1 | 3/2017 | Pule et al. |
| 2017/0114141 A1 | 4/2017 | Amann et al. |
| 2017/0233472 A1 | 8/2017 | Barat et al. |
| 2017/0291955 A1 | 10/2017 | Li et al. |
| 2017/0362321 A1 | 12/2017 | Campbell et al. |
| 2017/0368169 A1 | 12/2017 | Loew et al. |
| 2017/0369595 A1 | 12/2017 | Brinkmann et al. |
| 2018/0044415 A1 | 2/2018 | Escarpe et al. |
| 2018/0057608 A1 | 3/2018 | Jung et al. |
| 2018/0105594 A1 | 4/2018 | Urso et al. |
| 2018/0105599 A1 | 4/2018 | Cobbold et al. |
| 2018/0118851 A1 | 5/2018 | Comeau et al. |
| 2018/0237519 A1 | 8/2018 | Caligiuri et al. |
| 2018/0237541 A1 | 8/2018 | Kim et al. |
| 2018/0273633 A1 | 9/2018 | Jiang et al. |
| 2018/0312592 A1 | 11/2018 | Junutula et al. |
| 2018/0346600 A1 | 12/2018 | Kim et al. |
| 2019/0048079 A1 | 2/2019 | Spies et al. |
| 2019/0225702 A1 | 7/2019 | Baeuerle et al. |
| 2019/0359716 A1 | 11/2019 | Chang et al. |
| 2019/0375838 A1 | 12/2019 | Chang et al. |
| 2020/0002436 A1 | 1/2020 | Chang et al. |
| 2020/0024353 A1 | 1/2020 | Chang et al. |
| 2020/0048347 A1 | 2/2020 | Miao et al. |
| 2020/0055939 A1 | 2/2020 | Lombana et al. |
| 2020/0095327 A1 | 3/2020 | Chang et al. |
| 2020/0157174 A1 | 5/2020 | Chang et al. |
| 2020/0157226 A1 | 5/2020 | Chang et al. |
| 2020/0157227 A1 | 5/2020 | Chang et al. |
| 2020/0165344 A1 | 5/2020 | Chang et al. |
| 2020/0216544 A1 | 7/2020 | Chang et al. |
| 2020/0231678 A1 | 7/2020 | Chang et al. |
| 2020/0231679 A1 | 7/2020 | Chang et al. |
| 2020/0231700 A1 | 7/2020 | Cheung et al. |
| 2020/0277383 A1 | 9/2020 | Chang et al. |
| 2020/0277384 A1 | 9/2020 | Chang et al. |
| 2020/0306304 A1* | 10/2020 | Posey .............. C07K 14/70507 |
| 2020/0376034 A1 | 12/2020 | Chang et al. |
| 2021/0009718 A1 | 1/2021 | Ambrogelly et al. |
| 2021/0032349 A1 | 2/2021 | Dengl et al. |
| 2021/0054082 A1 | 2/2021 | Chang et al. |
| 2021/0070887 A1 | 3/2021 | Ambrogelly et al. |
| 2021/0079102 A1 | 3/2021 | Chang et al. |
| 2021/0101976 A1 | 4/2021 | Chang et al. |
| 2021/0130471 A1 | 5/2021 | Chang et al. |
| 2021/0130474 A1 | 5/2021 | Chang et al. |
| 2021/0130496 A1 | 5/2021 | Chang et al. |
| 2021/0198369 A1 | 7/2021 | Chang et al. |
| 2021/0206859 A1 | 7/2021 | Chang et al. |
| 2021/0214436 A1 | 7/2021 | Chang et al. |
| 2021/0221894 A1 | 7/2021 | Bigelow et al. |
| 2021/0238290 A1 | 8/2021 | Chang et al. |
| 2021/0261668 A1 | 8/2021 | Chang et al. |
| 2021/0292420 A1 | 9/2021 | Chang et al. |
| 2021/0363261 A1 | 11/2021 | Chang et al. |
| 2022/0025037 A1 | 1/2022 | Baruah et al. |
| 2022/0089760 A1 | 3/2022 | Bigelow et al. |
| 2022/0119533 A1 | 4/2022 | Cheung et al. |
| 2022/0119534 A1 | 4/2022 | Baruah et al. |
| 2022/0153848 A1 | 5/2022 | Chang et al. |
| 2022/0195065 A1 | 6/2022 | Chang et al. |
| 2022/0380459 A1 | 12/2022 | Chang et al. |
| 2023/0034186 A1 | 2/2023 | Cuillerot et al. |
| 2023/0203202 A1 | 6/2023 | Bigelow et al. |
| 2023/0227562 A1 | 7/2023 | Chang et al. |
| 2023/0250176 A1 | 8/2023 | Cheung et al. |
| 2023/0257467 A1 | 8/2023 | Cheung et al. |
| 2023/0272041 A1 | 8/2023 | Bigelow et al. |
| 2023/0303702 A1 | 9/2023 | Chang et al. |
| 2023/0357409 A1 | 11/2023 | Chang et al. |
| 2023/0391877 A1 | 12/2023 | Chang et al. |
| 2023/0416402 A1 | 12/2023 | Cuillerot et al. |

FOREIGN PATENT DOCUMENTS

| | | |
|---|---|---|
| CN | 105814084 A | 7/2016 |
| CN | 105906722 A | 8/2016 |
| DE | 102013019352 A1 | 9/2015 |
| EP | 627940 A1 | 12/1994 |
| EP | 845998 A1 | 6/1998 |
| EP | 871673 A1 | 10/1998 |
| EP | 1124568 A1 | 8/2001 |
| EP | 1769000 B1 | 4/2007 |
| EP | 2185595 A1 | 5/2010 |
| EP | 2222706 B2 | 9/2010 |
| EP | 2927321 A1 | 10/2015 |
| EP | 2930188 A1 | 10/2015 |
| EP | 2942629 A1 | 11/2015 |
| EP | 2982380 A1 | 2/2016 |
| EP | 2990416 A1 | 3/2016 |
| KR | 10-2013-0103325 A | 9/2013 |
| KR | 10-2014-0067944 A | 6/2014 |
| RU | 2588668 C2 | 7/2016 |
| RU | 2593720 C2 | 8/2016 |
| WO | WO-1988008854 A1 | 11/1988 |
| WO | WO-1989006544 A1 | 7/1989 |
| WO | WO-1996/027011 A1 | 9/1996 |
| WO | WO-2001071005 A2 | 9/2001 |
| WO | WO-2004056873 A1 | 7/2004 |
| WO | WO-2005/003172 A2 | 1/2005 |
| WO | WO-2005/009465 A1 | 2/2005 |
| WO | WO-2005/105849 A1 | 11/2005 |
| WO | WO-2006037960 A2 | 4/2006 |
| WO | WO-2007002905 A1 | 1/2007 |
| WO | WO-2007042573 A2 | 4/2007 |
| WO | WO-2007044756 A2 | 4/2007 |
| WO | WO-2007055926 A1 | 5/2007 |
| WO | WO-2007097812 A2 | 8/2007 |
| WO | WO-2008/127735 A1 | 10/2008 |
| WO | WO-2009007124 A1 | 1/2009 |
| WO | WO-2009077483 A1 | 6/2009 |
| WO | WO-2009/089004 A1 | 7/2009 |
| WO | WO-2010017103 A2 | 2/2010 |
| WO | WO-2010080124 A2 | 7/2010 |
| WO | WO-2011014659 A2 | 2/2011 |
| WO | WO-2011/076922 A1 | 6/2011 |
| WO | WO-2011075636 A1 | 6/2011 |
| WO | WO-2011109400 A2 | 9/2011 |
| WO | WO-2011/131746 A2 | 10/2011 |
| WO | WO-2011/143545 A1 | 11/2011 |
| WO | WO-2012006490 A2 | 1/2012 |
| WO | WO-2012/025530 A1 | 3/2012 |
| WO | WO-2012/032080 A1 | 3/2012 |
| WO | WO-2012034039 A2 | 3/2012 |
| WO | WO-2012/045752 A1 | 4/2012 |
| WO | WO-2012/058768 A1 | 5/2012 |

(56) References Cited

FOREIGN PATENT DOCUMENTS

| | | |
|---|---|---|
| WO | WO-2012/115241 A1 | 8/2012 |
| WO | WO-2012125850 A1 | 9/2012 |
| WO | WO-2012/131555 A2 | 10/2012 |
| WO | WO-2012158818 A2 | 11/2012 |
| WO | WO-2012162482 A1 | 11/2012 |
| WO | WO-2012/163805 A1 | 12/2012 |
| WO | WO-2013013700 A1 | 1/2013 |
| WO | WO-2013036799 A2 | 3/2013 |
| WO | WO-2013092001 A1 | 6/2013 |
| WO | WO-2013192594 A2 | 12/2013 |
| WO | WO-2014001324 A1 | 1/2014 |
| WO | WO-2014012085 A2 | 1/2014 |
| WO | WO-2014079000 A1 | 5/2014 |
| WO | WO-2014/084607 A1 | 6/2014 |
| WO | WO-2014/116051 A1 | 7/2014 |
| WO | WO-2014110601 A1 | 7/2014 |
| WO | WO-2014124326 A1 | 8/2014 |
| WO | WO-2014/145806 A2 | 9/2014 |
| WO | WO-2014131712 A1 | 9/2014 |
| WO | WO-2014144763 A2 | 9/2014 |
| WO | WO-2014159940 A1 | 10/2014 |
| WO | WO-2014165818 A2 | 10/2014 |
| WO | WO-2014198748 A1 | 12/2014 |
| WO | WO-2015009856 A2 | 1/2015 |
| WO | WO-2015036582 A2 | 3/2015 |
| WO | WO-2015036606 A1 | 3/2015 |
| WO | WO-2015063187 A1 | 5/2015 |
| WO | WO-2015070061 A1 | 5/2015 |
| WO | WO-2015077891 A1 | 6/2015 |
| WO | WO-2015089344 A1 | 6/2015 |
| WO | WO-2015095412 A1 | 6/2015 |
| WO | WO-2015095539 A1 | 6/2015 |
| WO | WO-2015095972 A1 | 7/2015 |
| WO | WO-2015/150447 A1 | 10/2015 |
| WO | WO-2015153765 A1 | 10/2015 |
| WO | WO-2015153912 A1 | 10/2015 |
| WO | WO-2015158636 A1 | 10/2015 |
| WO | WO-2015169781 A1 | 11/2015 |
| WO | WO-2015/184203 A1 | 12/2015 |
| WO | WO-2015181282 A1 | 12/2015 |
| WO | WO-2015184207 A1 | 12/2015 |
| WO | WO-2015197582 A1 | 12/2015 |
| WO | WO-2015197593 A1 | 12/2015 |
| WO | WO-2015197598 A2 | 12/2015 |
| WO | WO-2016001810 A1 | 1/2016 |
| WO | WO-2016011571 A1 | 1/2016 |
| WO | WO-2016023909 A1 | 2/2016 |
| WO | WO-2016025880 A1 | 2/2016 |
| WO | WO-2016028672 A1 | 2/2016 |
| WO | WO-2016032334 A1 | 3/2016 |
| WO | WO-2016070959 A1 | 5/2016 |
| WO | WO-2016090278 A2 | 6/2016 |
| WO | WO-2016097408 A1 | 6/2016 |
| WO | WO-2016100533 A2 | 6/2016 |
| WO | WO-2016109774 A1 | 7/2016 |
| WO | WO-2016115274 A1 | 7/2016 |
| WO | WO-2016122701 A1 | 8/2016 |
| WO | WO-2016134371 A2 | 8/2016 |
| WO | WO-2016135041 A1 | 9/2016 |
| WO | WO-2016135066 A1 | 9/2016 |
| WO | WO-2016142768 A1 | 9/2016 |
| WO | WO-2016146702 A1 | 9/2016 |
| WO | WO-2016161390 A1 | 10/2016 |
| WO | WO-2016164369 A2 | 10/2016 |
| WO | WO-2016164637 A1 | 10/2016 |
| WO | WO-2016166139 A1 | 10/2016 |
| WO | WO-2016184592 A1 | 11/2016 |
| WO | WO-2016187220 A2 | 11/2016 |
| WO | WO-2016191305 A1 | 12/2016 |
| WO | WO-2016196237 A1 | 12/2016 |
| WO | WO-2016201300 A1 | 12/2016 |
| WO | WO-2016201389 A2 | 12/2016 |
| WO | WO-2016207273 A2 | 12/2016 |
| WO | WO-2016207278 A1 | 12/2016 |
| WO | WO-2017005732 A1 | 1/2017 |
| WO | WO-2017008169 A1 | 1/2017 |
| WO | WO-2017011342 A1 | 1/2017 |
| WO | WO-2017021349 A1 | 2/2017 |
| WO | WO-2017048824 A1 | 3/2017 |
| WO | WO-2017075432 A2 | 5/2017 |
| WO | WO-2017079694 A2 | 5/2017 |
| WO | WO-2017081190 A1 | 5/2017 |
| WO | WO-2017083545 A1 | 5/2017 |
| WO | WO-2017114694 A1 | 7/2017 |
| WO | WO-2017124002 A1 | 7/2017 |
| WO | WO-2017125897 A1 | 7/2017 |
| WO | WO-2017143406 A1 | 8/2017 |
| WO | WO-2017/165683 A1 | 9/2017 |
| WO | WO-2017165464 A1 | 9/2017 |
| WO | WO-2017177337 A1 | 10/2017 |
| WO | WO-2017180813 A1 | 10/2017 |
| WO | WO-2017211873 A1 | 12/2017 |
| WO | WO-2017218707 A2 | 12/2017 |
| WO | WO-2018045090 A1 | 3/2018 |
| WO | WO-2018098365 A2 | 5/2018 |
| WO | WO-2018119171 A1 | 6/2018 |
| WO | WO-2018/152518 A1 | 8/2018 |
| WO | WO-2018148445 A1 | 8/2018 |
| WO | WO-2018148447 A1 | 8/2018 |
| WO | WO-2018148566 A1 | 8/2018 |
| WO | WO-2018148610 A1 | 8/2018 |
| WO | WO-2018152516 A1 | 8/2018 |
| WO | WO-2018152530 A1 | 8/2018 |
| WO | WO-2018152547 A1 | 8/2018 |
| WO | WO-2018157147 A1 | 8/2018 |
| WO | WO-2018201051 A1 | 11/2018 |
| WO | WO-2018217799 A1 | 11/2018 |
| WO | WO-2018217945 A1 | 11/2018 |
| WO | WO-2018217947 A1 | 11/2018 |
| WO | WO-2019/035939 A1 | 2/2019 |
| WO | WO-2019028027 A1 | 2/2019 |
| WO | WO-2019040727 A1 | 2/2019 |
| WO | WO-2019/051308 A1 | 3/2019 |
| WO | WO-2019055677 A1 | 3/2019 |
| WO | WO-2019157332 A1 | 8/2019 |
| WO | WO-2019157366 A1 | 8/2019 |
| WO | WO-2019164929 A1 | 8/2019 |
| WO | WO-2019164930 A1 | 8/2019 |
| WO | WO-2019195408 A1 | 10/2019 |
| WO | WO-2019195409 A1 | 10/2019 |
| WO | WO-2019/217332 A1 | 11/2019 |
| WO | WO-2019222449 A1 | 11/2019 |
| WO | WO-2019/231920 A1 | 12/2019 |
| WO | WO-2020/033630 A1 | 2/2020 |
| WO | WO-2020033587 A1 | 2/2020 |
| WO | WO-2020033664 A1 | 2/2020 |
| WO | WO-2020033702 A1 | 2/2020 |
| WO | WO-2020/086758 A1 | 4/2020 |
| WO | WO-2020172189 A1 | 8/2020 |
| WO | WO-2021041878 A1 | 3/2021 |
| WO | WO-2021/076554 A1 | 4/2021 |
| WO | WO-2021076564 A1 | 4/2021 |
| WO | WO-2021/216916 A1 | 10/2021 |
| WO | WO-2021/226163 A2 | 11/2021 |
| WO | WO-2021226193 A1 | 11/2021 |
| WO | WO-2022/031935 A1 | 2/2022 |
| WO | WO-2022031965 A1 | 2/2022 |
| WO | WO-2022/187539 A1 | 9/2022 |
| WO | WO-2023/056243 A1 | 4/2023 |
| WO | WO-2023/056252 A1 | 4/2023 |
| WO | WO-2023/107954 A1 | 6/2023 |
| WO | WO-2023/107956 A1 | 6/2023 |
| WO | WO-2023/154796 A2 | 8/2023 |
| WO | WO-2023/168384 A2 | 9/2023 |

OTHER PUBLICATIONS

Affimed, Affimed Enters Into Collaboration With Merck to Evaluate AFM13 in Combination With . . . Retreived < URL:https ://www.affimed.com/affi med-enters-into-collaboration-with-merck-to-evaluate-afm 13-i n-combination-with-keytruda-pembrolizumab-for-patients-with-hodgkin-lymphoma/>[retrieved on Feb. 1, 2023] Jan. 25, 2016.

(56) References Cited

OTHER PUBLICATIONS

Ahmad et al. (2012) "scFv antibody: principles and clinical application," *Clinical and Developmental Immunology* 2012:1-16.
Akbar et al. (2021) "A compact vocabulary of paratope-epitope interactions enables predictability of antibody-antigen binding," *Cell Reports* 34:108856 21 pages.
Altshuler et al. (2010) "Generation of Recombinant Antibodies and Means for Increasing Their Affinity," *Biochemistry* (Moscow) 75(13):1584-1605.
Atwell et al. (1989) "Stable Heterodimers from Remodeling the Domain Interface of a Homodimer using a Phage Display Library," J Mol Biol 270:26-35.
Averdam et al. (2009) "A Novel System of Polymorphic and Diverse NK Cell Receptors in Primates," *PLoS Genetics* 5(10):e1000688.
Baek et al. (2014) "Construction of a Large Synthetic Human Fab Antibody Library on Yeast Cell Surface by Optimized Yeast Mating," J Microbial Biotechnol 24(3):408-420.
Bendayan (1995) Possiblities of False Immunocytochemical Results Generated by The Use of Monoclonal Antibodies: The Example of the Anti-proinsulin Antibody, *J. Histochem. Cytochem.* 43(9):881-886.
Berenbaum (1977) "Synergy, additivism and antagonism in immunosuppression," Clin. Exp. Immunol. 28:1-18.
Berenbaum (1989) "What is Synergy?" Pharmacological Reviews 41:93-141.
Bogen et al. (2021) "Design of a Trispecific Checkpoint Inhibitor and Natural Killer Cell Engager Based on a 2+1 Common Light Chain Antibody Architecture," Frontiers in Immunology 12:16 pages.
Boltz (2011) "Bi-specific Aptamers mediating Tumour Cell Lysis," Dissertation, M.Sc. Molekulare Biotechnologie, Technische Universität Darmstadt, pp. 1-133.
Bost et al. (1988) "Antibodies Against a Peptide Sequence Within the HIV Envelope Protein Crossreacts with Human Interleukin-2," *Immunological Investigations* 17(6&7):577-586.
Bostrom, et al. (2009) "Improving Antibody Binding Affinity and Specificity for Therapeutic Development," *Methods and Protocols* 525:353-376.
Bowen et al. (2016) "Revisiting the Immunoglobulin Intramolecular Signaling Hypothesis," *Trends Immunol.* 37(11):721-723.
Branca et al. (2018) "Nature Biotechnology's academic spinouts of 2017," Nature Biotechnology 36(4):297-306.
Briney et al. (2019) "Commonality despite exceptional diversity in the baseline human antibody repertoire," Nature 566:393 (19 pages).
Brinkmann et al. (2017) "The making of bispecific antibodies," MABS 9(2):182-212.
Brown et al. (1996) "Tolerance of single, but not multiple, amino acid replacements in antibody VH CDR 2: a means of minimizing B cell wastage from somatic hypermutation?," Journal of Immunology, 156: 3285-3291.
Bruhns et al. (2009) "Specificity and affinity of human FCγ receptors and their polymorphic variants for human IgG subclasses," *Blood* 113(16):3716-3724.
Bryceson et al. (2006) "Synergy among receptors on resting NK cells for the activation of natural cytotoxicity and cytokine secretion," *Blood* 107(1):159-166.
Busfield et al. (2014) "Targeting of acute myeloid leukemia in vitro and in vivo with an anti-CD123 mAb engineered for optimal ADCC," *Leukemia* 28(11): 2213-2221.
Cai et al. (2014) "Autonomous Stimulation of Cancer Cell Plasticity by the Human NKG2D Lymphocyte Receptor Coexpressed with Its Ligands on Cancer Cells," *PLOS ONE* 9(10):e108942.
Casset et al. (2003) "A peptide mimetic of an anti-CD4 monoclonal antibody by rational design," *Biochemical and Biophysical Research Communications* 307:198-205.
Chan et al. (2010) "Therapeutic antibodies for autoimmunity and inflammation," Nature Reviews 10:301-316.

Chen et al. (1995) "Enhancement and destruction of antibody function by somatic mutation: unequal occurrence is controlled by V gene combinatorial associations," *The EMBO Journal* 14(12):2784-2794.
Chen et al. (1999) "Selection and Analysis of an Optimized Anti-VEGF Antibody: Crystal Structure of an Affinity-matured Fab in Complex with Antigen," *J. Mol. Biol.* 293:865-881.
Chen X. et al. (2013) "Fusion protein linkers: property, design and functionality" Advanced drug delivery reviews, 65(10):1357-1369.
Cho et al. (2010) "Delivery of NKG2D Ligand Using an Anti-HER2 Antibody-NKG2D Ligand Fusion Protein Results in an Enhanced Innate and Adaptive Antitumor Response," *Cancer Research* 70(24):10121-10130.
Choi et al. (2013) "A Heterodimeric Fc-Based Bispecific Antibody Simultaneously Targeting VEGFR-2 and Met Exhibits Potent Antitumor Activity," Mol Cancer Ther. 12(12):2748-2759.
Choi et al. (2015) "Crystal structures of immunoglobulin Fc heterodimers reveal the molecular basis for heterodimer formation," Molecular Immunology 65(2):377-83.
Choi et al. (2015) "Engineering of Immunoglobulin Fc Heterodimers Using Yeast Surface-Displayed Combinatorial Fc Library Screening," PloS One. Dec. 16, 2015; 10(12);e0145349; pp. 1-20.
Chu et al. (2014) "Immunotherapy with Long-Lived Anti-CD123 x Anti-CD3 Bispecific Antibodies Stimulates Potent T Cell-Mediated Killing of Human AML Cell Lines and of CD123+ Cells in Monkeys: A Potential Therapy for Acute Myelogenous Leukemia 11," *Blood* 124(21):2316.
Colman P. M. (1994) "Effects of amino acid sequence changes on antibody-antigen interactions" Research in Immunology 145(1):33-36.
Cunningham et al. (1969) "Subgroups of Amino Acid Sequences in the Variable Regions of Immunoglobulin Heavy Chains," Proc Natl Acad Sci USA 64(3):997-1003.
Dahlberg et al. (2015) "Natural Killer Cell-Based Therapies Targeting Cancer: Possible Strategies to Gain and sustain Anti-Tumor Activity" Frontiers In Immunology 6(Article 605):19 pages.
Dasgupta et al. (2005) "Inhibition of NK Cell Activity through TGF-β1 by Down-Regulation of NKG2D in a Murine Model of Head and Neck Cancer," J Immunol 175(8):5541-5550.
Davis et al. (2010) "SEEDbodies: Fusion Proteins Based on Strand-Exchange Engineered Domain (SEED) CH3 Heterodimers in an Fc Analogue Platform for Asymmetric Binders or Immunofusions and Bispecific Antibodies," Protein Eng Des Sel 23(4):195-202.
De Pascalis et al. (2002) "Grafting of "Abbreviated" Complementarity-Determining Regions Containing Specificity-Determining Residues Essential for Ligand Contact to Engineer a Less Immunogenic Humanized Monoclonal Antibody," *The Journal of Immunology* 169:3076-3084.
Demaria et al. (2021) "Natural killer cell engagers in cancer immunotherapy: Next generation of immuno-oncology treatments," Eur. J. Immunol. 51:1934-1942.
Dickopf et al. (2020) "Format and geometries matter: Structure-based design defines the functionality of bispecific antibodies," *Computational and Structural Biotechnology Journal* 18:1221-1227.
Ding et al. (2018) "Fusion Proteins of NKG2D/NKG2DL in Cancer Immunotherapy," *International Journal of Molecular Sciences* 19(1):177.
Edwards et al. (2003) "The Remarkable Flexibility of the Human Antibody Repertoire; Isolation of Over One Thousand Different Antibodies to a Single Protein, BLyS," *J. Mol. Biol.* 334:103-118.
El-Amine et al. (2002) "In vivo induction of tolerance by an Ig peptide is not affected by the deletion of FcR or a mutated IgG Fc fragment," *International Immunology* 14(7):761-766.
Elliott et al. (2014) "Antiparallel conformation of knob and hole aglycosylated half-antibody homodimers is mediated by a CH2—CH3 hydrophobic interaction", J. Mol. Biol., 426(9):1947-57.
Felices et al. (2016) "Generation of BiKEs and TriKEs to Improve NK cell-Mediated Targeting of Tumor Cells," Natural Killer Cells: Methods and Protocols, Methods in Molecular Biology 1441:333-346.

(56) References Cited

OTHER PUBLICATIONS

Feng et al. (2011) "Design, Expression and Characterization of a Soluble Single-Chain Functional Human Neonatal Fc Receptor," Protein Expr Purif 79(1):66-71.

Feng et al., (2020) "NKG2D-Fc fusion protein promotes antitumor immunity through the depletion of immunosuppressive cells," Cancer Immunol. Immunother. 69(10):2147-2155.

Gantke et al. (2016) "Trispecific Antibodies for Selective CD16A-Directed NK-Cell Engagement in Multiple Myeloma," Blood 128(22):4513.

Gantke et al. (2017) "Trispecific antibodies for CD16A-directed NK cell engagement and dual- targeting of tumor cells," Protein Engineering, Design & Selection 38(9):673-684.

Gauthier et al. (2019) "Multifunctional Natural Killer Cell Engagers Targeting NKp46 Trigger Protective Tumor Immunity," Cell 177(7):1701-1713.

Germain et al. (2005) "MHC Class I-Related Chain a Conjugated to Antitumor antibodies Can Sensitize Tumor Cells to Specific Lysis by Natural Killer Cells," *Clinical Cancer Research US* 11(20):7516-7522.

Germain et al. (2008) "Redirecting NK cells mediated tumor cell lysis by a new recombinant bifunctional protein," *Protein Engineering, Design & Selection* 21(11):665-672.

Giuliani et al. (2017) "Activation of NK cells and disruption of PD-L1/PD-1 axis: two different ways for lenalidomide to block myeloma progression," Oncotarget 8(14):24031-24044.

Glas et al. (1997) "Analysis of rearranged immunoglobulin heavy chain variable region genes obtained from a bone marrow transplant (BMT) recipient," *Clinical & Experimental Immunology* 107(2):372-380.

Gleason et al. (2012) "Bispecific and Trispecific Killer Cell Engagers Directly Activate Human NK Cells through CD16 Signaling and Induce Cytotoxicity and Cytokine Production," *Molecular Cancer Therapeutics* 11(12):2674-2684.

Gleason et al. (2014) "CD16xCD33 bispecific killer cell engager (BiKE) activates NK cells against primary MDS and MDSC CD33+ targets," *Blood* 123(19):3016-3026.

Goel et al. (2004) "Plasticity within the Antigen-Combining Site May Manifest as Molecular Mimicry in the Humoral Immune Response," *The Journal of Immunology* 173(12):7358-7367.

Gonzales, et al. (2005) "Minimizing the Immunogenicity of Antibodies for Clinical Application," *Tumor Biol.* 26(1):31-43.

Gooden et al. (2012) "Infiltrating CTLs are bothered by HLA-E on tumors," OncoImmunology, 1(1):92-93.

Gunasekaran et al. (2010) "Enhancing Antibody Fc Heterodimer Formation through Electrostatic Steering Effects: Applications to Bispecific Molecules and Monovalent IgG," J Biol Chem 285(25):19637-46.

Ha et al. (2016) "Immunoglobulin Fc Heterodimer Platform Technology: From Design to Applications in Therapeutic Antibodies and Proteins," Front Immunol. 7:394, 16 pages.

Han et al. (2018) "Control of triple-negative breast cancer using ex vivo self-enriched, constimulated NKG2D CAR T cells," 11:92 13 pages.

Hasegawa et al. (2017) "Single amino acid substitution in LC-CDR1 induces Russell body phenotype that attenuates cellular protein synthesis through eIF2α phosphorylation and thereby downregulates IgG secretion despite operational secretory pathway traffic," MABS 9(5):854-873.

Henry et al. (2004) "A Prostate-Specific Membrane Antigen-Targeted Monoclonal Antibody-Chemotherapeutic Conjugate Designed for the Treatment of Prostate Cancer," Cancer Research 64:7995-8001.

Henry et al. (2017) "Stability-Diversity Tradeoffs Impose Fundamental Constraints on Selection of Synthetic Human $V_H/V_L$ Single-Domain Antibodies from In Vitro Display Libraries," *Frontiers in Immunology*, 8:1-15.

Herold et al. (2017) "Determinants of the assembly and function of antibody variable domains," Scientific Reports, 7:12276.

Hezareh et al. (2001) "Effector Function Activities of a Panel of Mutants of a Broadly Neutralizing Antibody against Human Immunodeficiency Virus Type 1," *Journal of Virology* 75(24):12161-12168.

Hlavacek et al. 1999 "Steric Effects on Multivalent Ligand-Receptor Binding: Exclusion of Ligand Sites by Bound Cell Surface Receptors," *Biophysical Journal* 76:3031-3043.

Holliger et al. (2005) "Engineered antibody fragments and the rise of single domains," Nat Biotechnol 23(9): 1126-36.

Hoseini et al. (2017) "Acute myeloid leukemia targets for bispecific antibodies," *Blood Cancer Journal* 7(2):e522 (12 pages).

Jachimowicz et al. (2011) "Induction of In Vitro and In Vivo NK Cell Cytotoxicity Using High-Avidity Immunoligands Targeting Prostate-Specific Membrane Antigen in Prostate Carcinoma," *Mol Cancer Thera*, 10(6):1036-1045.

Janeway et al. (1997) Chapter 3, Structure of the Antibody Molecule and Immunoglobulin Genes, *Immunology Third Edition, Garland Publishing Inc.*, 3:1-3:11.

Jonnalagadda et al. (2015) "Chimeric Antigen Receptors With Mutated IgG4 Fc Spacer Avoid Fc Receptor Binding and Improve T Cell Persistence and Antitumor Efficacy," *Molecular Therapy* 23(4):757-768.

Junttila et al. (2014) "Antitumor Efficacy of a Bispecific Antibody That Targets HER2 and Activates T Cells," *Cancer Research* 74(19):5561-5571.

Kanyavuz et al. (2019) "Breaking the law: unconventional strategies for antibody diversification," *Nature Reviews Immunology* 19(6):355-368.

Katano et al. (2015) "Predominant Development of Mature and Functional Human NK Cells in a Novel Human IL-2-Producing Transgenic NOG Mouse" J. Immunol. 194(7):3513-3525.

Kaur et al. (2015) "Applications of In Vitro-In Vivo Correlations in Generic Drug Development: Case Studies," *The AAPS Journal* 17(4):1035-1039; doi: 10.1208/s12248-015-9765-1.

Kellner et al. (2012) "Fusion proteins between ligands for NKG2D and CD20-directed single-chain variable fragments sensitize lymphoma cells for natural killer cell-mediated lysis and enhance antibody-dependent cellular cytotoxicity," Leukemia 26:830-834.

Kellner et al. (2013) "Promoting natural killer cell functions by recombinant immunoligands mimicking an induced self phenotype," Oncoimmunology 2(6):e24481.

Kellner et al. (2016) "Enhancing natural killer cell-mediated lysis of lymphoma cells by combining therapeutic antibodies with CD20-specific immunoligands engaging NKG2D or NKp30," *OncoImmunology* 5(1):e1058459-1-e1058459-12.

Khan et al. (2014) "Adjustable Locks and Flexible Keys: Plasticity of Epitope-Paratope Interactions in Germline Antibodies," J. Immunol 192:5398-5405.

Kijanka et al. (2013) "Rapid optical imaging of human breast tumour xenografts using anti-HER2 VHHs site-directly conjugated to IRDye 800CW for image-guided surgery," *Eur J Nucl Med Mol Imaging* 40:1718-1729.

Kim et al. (2014) "Mutational approaches to improve the biophysical properties of human single-domain antibodies," *Biochimica et Biophysica Acta*, 1844:1983-2001.

Kjellev et al. (2007) "Inhibition of NKG2D receptor function by antibody therapy attenuates transfer-induced colitis in SCID mice," *Eur. J. Immunol.* 37:1397-1406.

Klein et al. (2012) "Progress in overcoming the chain association issue in bispecific; heterodimeric IgG antibodies," mAbs 4(6):653-663.

Kluge et al. (2017) "EGFR/CD16A TandAbs are efficacious NK-cell engagers with favorable biological properties which potently kill EGFR(+) tumors with and without Ras mutation," Cancer Research 77(13 Suppl.):Abstract 3641.

Koerner et al. (2015) "Induction of NK and T Cell Immune Responses Against Leukemia Cells By Bispecific NKG2D-CD16 and -CD3 Fusion Proteins," Blood 126(23):2558, Abstract 606 (2 pages).

Kranz et al. (1981) "Restricted reassociation of heavy and light chains from hapten-specific monoclonal antibodies," *Pro. Natl. Acad. Sci. USA* 78(9):5807-5811.

(56) References Cited

OTHER PUBLICATIONS

Krieg et al. (2005) "Functional Analysis of B and T Lymphocyte Attenuator Engagement on CD4+ and CD8+ T Cells," *The Journal of Immunology* 175(10):6420-6427.
Kunik, et al. (2012) "Structural consensus among antibodies defines the antigen binding site," *PLoS Comput Biol.* 8(2):e1002388.
Kwong et al. (2008) "Generation, affinity maturation, and characterization of a human anti-human NKG2D monoclonal antibody with dual antagonistic and agonistic activity," *Journal of Molecular Biology* 384(5):1143-1156.
Lamminmäki et al. (2001) "Crystal Structure of a Recombinant Anti-estradiol Fab Fragment in Complex with 17β-Estradiol," *The Journal of Biological Chemistry* 276(39):36687-36694.
Lewis et al. (2014) "Generation of bispecific IgG antibodies by structure-based design of an orthogonal Fab interface," Nat Biotechnol 32(2):191-98.
Lin et al. (2011) "Improved affinity of a chicken single-chain antibody to avian infectious bronchitis virus by site-directed mutagenesis of complementarity-determining region H3," *African Journal of Biotechnology* 10(79):18294-18303.
Lin et al. (2013) "CD4+ NKG2D+ T cells induce NKG2D down-regulation in natural killer cells in CD86-RAE-1 E transgenic mice," *Immunology* 141(3):401-415.
Lippow et al. (2007) "Computational design of antibody-affinity improvement beyond in vivo maturation," *Nature Biotechnology* 25(10):1171-1176.
Liu et al. (2017) "Fc engineering for Developing Therapeutic Bispecific Antibodies and Novel Scaffolds," *Frontiers in Immunology* 8(38):1-15.
Lloyd et al. (2009) "Modelling the human immune response: performance of a 1011 human antibody repertoire against a broad panel of therapeutically relevant antigens," *Protein Engineering, Design and Selection* 22(3):159-168.
Lo et al. (2021) "Conformational epitope matching and prediction based on protein surface spiral features," *BMC Genomics* 22(Suppl 2):116 16 pages.
Long et al. (2013) "Controlling NK Cell Responses: Integration of Signals for Activation and Inhibition," Annu Rev Immunol. 2013 ; 31: 10.1146/annurev-immunol-020711-075005.
Lund et al. (1996) "Multiple interactions of IgG with its core oligosaccharide can modulate recognition by complement and human Fc gamma receptor I and influence the synthesis of its oligosaccharide chains," *J. Immunol* 157:4963-4969.
MacCallum et al. (1996) "Antibody-antigen Interactions: Contact Analysis and Binding Site Topography," *J. Mol. Biol.* 262:732-745.
Madlener et al. (2010) "A Bispecific Protein Targeting the NKG2D Receptor on Natural Killer Cells: In Vitro and In Vivo activity of ULBP2-CEA," *Blood* 116(21):2095.
Maeda et al. (2015) "New antibody modification technology and its application to antibody drugs," Farumashia 51(5):424-428.
Maeda Y. et al. (1997) "Engineering of Functional Chimeric Protein G-Vargula Luciferase" Analytical biochemistry, 249(2):147-152.
Mandelboim et al. (1999) "Human CD16 as a lysis receptor mediating direct natural killer cell cytotoxicity," *PNAS USA* 96(10):5640-5644; doi: 10.1073/pnas.96.10.5640.
Mariuzza et al. (1987) "The Structural Basis of Antigen-Antibody Recognition," *Ann. Rev. Biophys. Chem.* 16:139:59.
Marks et al. (2020) "How repertoire data are changing antibody science," *J. Biol. Chem.* 295(29):9823-9837.
McCarthy et al. (2001) "Altering the fine specificity of an anti-Legionella single chain antibody by a single amino acid insertion," *Journal of Immunological Methods* 251:137-149.
McWilliams, et al. (2016) "Targeting the Tumor Evasion Interaction of NKG2A and Its Ligand HLA-E Increases Natural-Killer Cell Activity in Chronic Lymphocytic Leukemia," Blood 1289-1291.
Merchant et al. (1998), "An efficient route to human bispecific IgG," Nature Biotechnology 16, 677-681 doi : 10.1038/nbt0798-677.
Miller et al. (2003) "Design, Construction, and in Vitro Analyses of Multivalent Antibodies," J Immunol 170(9):4854-61.
Miller et al. (2018) "Annual Review of Cancer Biology Natural Killer Cells in Cancer Immunotherapy," *Annu. Rev. Cancer Biol.* 8(3):77-103.
Miller et al. 2019 "Natural Killer Cells in Cancer Immunotherapy," Ann. Rev. Cancer Biol. 3:77-103.
Mimoto et al. (2014) "Crystal structure of a novel asymmetrically engineered Fc variant with improved affinity for FcγRs," Mo/ Immunol 58(1):132-38.
Moore et al. (2011) "A novel bispecific antibody format enables simultaneous bivalent and monovalent co-engagement of distinct target antigens," mAbs 3:6, 546-557; Nov./Dec. 2011, Landes Bioscience, DOI: 10.4161/mabs.3.6.18123.
Morris "Epitope Mapping of Protein Antigens by Competition ELISA," The Protein Protocols Handbook, Totowa, NJ, Humana Press, (Jan. 1, 1996):595-600.
Morvan et al. (2016)."NK cells and cancer: you can teach innate cells new tricks" *Nat Rev Cancer* 16(1):7-19.
Muda et al. (2011) "Therapeutic assessment of SEED: a new engineered antibody platform designed to generate mono- and bispecific antibodies," Protein Eng Des Se/ 24(5):447-54.
Muller et al. (2015) "Trastuzumab emtansine (T-DM1) renders HER2+ breast cancer highly susceptible to CTLA-4/PD-1 blockade," Sci. Transl. Med. 7(315):1-14.
Muntasell et al. (2017) "Interplay between Natural Killer Cells and Anti-HER2 Antibodies:Perspectives for Breast Cancer Immunotherapy," *Front. Immunol.* 8:1544, doi: 10.3389/fimmu.2017.01544, 15 pages.
Muntasell et al. (2017) "Targeting NK-cell checkpoints for cancer immunotherapy," Current Opinion in Immunology 45:73-81.
Myers et al. (2021) "Exploring the NK cell platform for cancer immunotherapy," Nature Reviews Clinical Oncology 18(2):85-100.
Nagasaki et al. (2014) "Interleukin-6 released by colon cancer-associated fibroblasts is critical for tumour angiogenesis: anti-interleukin-6 receptor antibody suppressed angiogenesis and inhibited tumour-stroma interaction," *British Journal of Cancer* 110(2):469-478.
Nie et al. (2020) "Biology drives the discovery of bispecific antibodies as innovative therapeutics," Antibody Therapeutics 3(1):18-62.
Notice of Opposition for Colombia Patent Application No. NC2020/0010345 dated Dec. 16, 2020.
Notice of Opposition for Colombia Patent Application No. NC2020/0016028 dated Apr. 26, 2021.
Padlan et al. (1989) "Structure of an antibody-antigen complex: Crystal structure of the HyHEL-10 Fab-lysozyme complex," *Pro. Natl. Acad. Sci. USA* 86:5938-5942.
Pakula et al. (1989) "Genetic Analysis of Protein Stability and Function," *Annu. Rev. Genet.* 23:289-310.
Parsons et al. (2016) "NKG2D Acts as a Co-Receptor for Natural Killer Cell-Mediated Anti-HIV-1 Antibody-Dependent Cellular Cytotoxicity," AIDS Research and Human Retroviruses 32(10-11) 1089-1096.
Paul et al. (1993) "Fundamental Immunology," (textbook) 292-295.
Petricevic et al. (2013) "Trastuzumab mediates antibody-dependent cell-mediated cytotoxicity and phagocytosis to the same extent in both adjuvant and metastatic HER2/neu breast cancer patients," *Journal of Translational Medicine* 11(307).
Piche-Nicholas et al. (2018) "Changes in complementarity-determining regions significantly alter IgG binding to the neonatal Fc receptor (FcRn) and pharmacokinetics," *MABS* 10(1)81-94.
Poosaria et al. (2017) "Computational de novo Design of Antibodies binding to a Peptide with High Affinity," 114(6):1331-1342.
Portolano et al. (1993) "Lack of promiscuity in autoantigen-specific H and L chain combinations as revealed by human H and L chain roulette," *J. Immunol.* 15(30):880-887.
Powers et al. (2016) "Abstract 1407: FPA 144, a therapeutic monoclonal antibody targeting the FGFR2b receptor, promotes antibody dependent cell-mediated cytotoxicity and stimulates sensitivity to PD-1 in the 4T1 syngeneic tumor model," *Cancer Research* (4 pages).
Raab et al. (2014) "Fc-Optimized NKG2D-Fc Constructs Induce NK Cell Antibody-Dependent Cellular Cytotoxicity Against Breast Cancer Cells Independently of HER2/neu Expression Status," *Journal of Immunology* 193(8):4261-72.

(56) References Cited

OTHER PUBLICATIONS

Rabia et al. (2018) "Understanding and overcoming trade-offs between antibody affinity, specificity, stability and solubility" Biochem Eng J. 137:365-374.
Raulet (2003) "Roles of the NKG2D immunoreceptor and its ligands," *Nature: Reviews Immunology* 3:781-790; doi: 10.1038/nri1199.
Ridgway et al. (1996) "Knobs-into-Holes' engineering of antibody Ch3 domains for heavy chain heterodimerization," Protein Engineering 9(7):617-21.
Roda-Navarro et al. (2020) "Understanding the Spatial Topology of Artificial Immunological Synapses Assembled in T Cell-Redirecting Strategies: A Major Issue in Cancer Immunotherapy," *Frontiers in Cell and Developmental Biology* 7:1-5.
Roell et al. (2017) "An Introduction to Terminology and Methodology of Chemical Synergy—Perspectives from Across Disciplines," *Frontiers in Pharmacology: Cancer Molecular Targets and Therapeutics* 8:1-11.
Roell et al. (2017) "An Introduction to Terminology and Methoodology of Chemical Synergy—Perspectives from Across Disciplines," *Frontiers in Pharmacology: Cancer Molecular Targets and Therapeutics* 8:1-11.
Romee et al. (2013) "NK cell CD16 surface expression and function is regulated by a disintegrin and metalloprotease-17 (ADAM17)," *Blood* 121(18):3599-608.
Rosano et al. (2014) "Recombinant protein expression in *Escherichia coli:* advances and challenges" Frontiers in Microbiology 5(172):17 pages.
Rothe et al. (2013) "The Bispecific Immunoligand ULBP2-aCEA Redirects Natural Killer Cells to Tumor Cells and Reveals Potent Anti-Tumor Activity Against Colon Carcinoma," *Int. J. Cancer* 134(12):2829-2840.
Rudikoff et al. (1982) "Single amino acid substitution altering antigen-binding specificity," *Pro. Natl. Acad. Sci USA* 79:1979-1983.
Safdari Y et al. (2013) "Antibody humanization methods-a review and update" Biotechnology and Genetic Engineering Reviews, 29(2):175-186.
Sazinsky et al. (2008) "Aglycosylated immunoglobulin $G_1$ variants productively engage activating Fc receptors," *Proceedings of the National Academy of Sciences* 105(51)20167-20172.
Schroeder et al. (2010) "Structure and Function of Immunoglobulins," *J Allergy Clin Immunol* 125:S41-S52 (24 pages).
Schuster et al. (2015) "Immunotherapy with the trifunctional anti-CD20 x anti-CD3 antibody FBTA05 (Lymphomun) in paediatric high-risk patients with recurrent CD20-positive B cell malignancies," *British Journal of Haematology* 169(1):90-102.
Shen J. et al. (2006) "Single variable domain-IgG fusion: a novel recombinant approach to Fc domain-containing bispecific antibodies" Journal of Biological Chemistry, 281(16):10706-10714.
Shum et al. (2002) "Conservation and Variation in Human and Common Chimpanzee CD94 and NKG2 Genes," *The Journal of Immunology* 168:240-252.
Siena et al. (2010) "Reduced Incidence of Infusion-Related Reactions in Metastatic Colorectal Cancer During Treatment With Cetuximab Plus Irinotecan With Combined Corticosteroid and Antihistamine Premedication," *Cancer* 116(7):1827-1837.
Singer et al. (1998) "Genes and Genomes," Moscow, "Mir" 1:63-64.
Smits et al. (2016) "Designing multivalent proteins based on natural killer cell receptors and their ligands as immunotherapy for cancer," *Expert Opinion on Biological Therapy* 16(9):1105-1112.
Sondermann et al. (2000) "The 3.2-Å crystal structure of the human IgG1 Fc fragment-Fc[gamma]RIII complex," Nature 406(6793):267-273.
Spear et al. (2013) "NKG2D ligands as therapeutic targets," *Cancer Immunology* 13(2):8.
Spiess et al. (2015) "Alternative molecular formats and therapeutic applications for bispecific antibodies," Molecular Immunology 67:95-106.

Stamova et al. (2011) "Simultaneous engagement of the activatory receptors NKG2D and CD3 for retargeting of effector cells to CD33-positive malignant cells," *Leukemia* 25:1053-1056.
Steigerwald et al. (2009) "Human IgG1 antibodies antagonizing activating receptor NKG2D on natural killer cells," mAbs 1(2):115-127.
Stein et al. (2012) "Natural Killer (NK)- and T-Cell Engaging Antibody-Derived Therapeutics," *Antibodies* 1:88-123.
Steinbacher et al. (2015) "An Fc-optimized NKG2D-immunoglobulin G fusion protein for induction of natural killer cell reactivity against leukemia," *International Journal of Cancer* 136(5):1073-1084.
Strong (2002) "Asymmetric ligand recognition by the activating natural killer cell receptor NKG2D, a symmetric homodimer," *Molecular Immunology* 38(14):1029-1037.
Strop et al. (2012) "Generating Bispecific Human IgG1 and IgG2 Antibodies from Any Antibody Pair," J Mol Biol 420:204-19.
Sulea et al. (2018) "Application of Assisted Design of Antibody and Protein Therapeutics (ADAPT) improves efficacy of a *Clostridium difficile* toxin A single-domain antibody," 8:2260 11 pages.
Tallarida (2000) "Drug Synergism and Dose Effect Analysis," Ed. Chapman & Hall pp. 1-71.
Tarantino et al. (2020) "HER2-Low Breast Cancer: Pathological and Clinical Landscape," Journal of Clinical Oncology 38(17):1951-1963.
Tay et al. (2016) "TriKEs and BiKEs join CARs on the cancer immunotherapy highway," *Human Vaccines & Immunotherapeutics* 12(11):2790-2796.
Teplyakov A. et al. (2014) "Antibody modeling assessment II. Structures and models" Proteins: Structure, Function, and Bioinformatics, 82(8):1563-1582.
Thakur et al. (2018) "Bispecific antibody based therapeutics: Strengths and challenges," Blood Review 32:339-347.
Torres M. et al. (2008) "The immunoglobulin constant region contributes to affinity and specificity" Trends in immunology, 29(2):91-97.
Trivedi et al. (2017) "Clinical pharmacology and translational aspects of bispecific antibodies," Clin. Transl. Sci., 10:147-162.
Vajda et al. (2021) "Progress toward improved understanding of antibody maturation," *Current Opinion in Structural Biology* 67:226-231.
Vajdos et al. (2002) "Comprehensive Functional Maps of the Antigen-binding Site of an Anti-ErbB2 Antibody Obtained with Shotgun Scanning Mutagenesis," *J. Mol. Biol.* 320:415-428.
Vaks et al. (2018) "Design Principles for Bispecific IgGs, Opportunities and Pitfalls of Artificial Disulfide Bonds," *Antibodies* 7(27):1-28.
Vallera et al. (2016) "IL 15 Trispecific Killer Engagers (TriKE) Make Natural Killer Cells Specific to CD33+ Targets While Also Inducing Persistence, In Vivo Expansion, and Enhanced Function," *Clin Cancer Res,* 22(14):3440-50.
Van de Winkel et al. (1993) "Human IgG Fc receptor heterogeneity: molecular aspects and clinical implications," Immunology Today 14(5):215-221.
Vidarsson et al. (2014) "IgG subclasses and allotypes: from structure to effector functions," Front. Immunol. 5:520, 17 pages.
Von Kreudenstein et al. (2013) "Improving Biophysical Properties of a Bispecific Antibody Scaffold to Aid Developability: Quality by Molecular Design," mAbs 5(5):646-54.
Von Kreudenstein et al. (2014), "Protein Engineering and the Use of Molecular Modeling and Simulation: The Case of Heterodimeric Fc Engineering," Methods 65(1):77-94.
Von Strandmann et al. (2006) "A novel bispecific protein (ULBP2-BB4) targeting the NKG2D receptor on natural killer (NK) cells and CD138 activates NK cells and has potent antitumor activity against human multiple myeloma in vitro and in vivo," *Blood* 107(5):1955-1962.
Vyas et al. (2016) "Mono- and dual-targeting triplebodies activate natural killer cells and have anti-tumor activity in vitro and in vivo against chronic lymphocytic leukemia," Oncoimmunology 5(9):p. e1211220.

(56) References Cited

OTHER PUBLICATIONS

Wang et al. (2016) "A bispecific protein rG7S-MICA recruits natural killer cells and enhances NKG2D-mediated immunosurveillance against hepatocellular carcinoma," Cancer Letters 372(2):166-178.
Wang et al. (2018) "IgG Fc engineering to modulate antibody effector functions," Protein Cell 9(1):63-73.
Ward et al. (1989) "Binding activities of a epertoire of single immunoglobulin variable domains secreted from Escherichia coli," Nature 341:544-546.
Wark et al. (2006) "Latest technologies for the enhancement of antibody affinity", Advanced Drug Delivery Reviews 58(5-6):657-670.
Weiss-Steider et al. (2011) "Expression of MICA, MICB and NKG2D in human leukemic myelomonocytic and cervical cancer cells," Journal of Experimental & Clinical Cancer Research 30(1):37.
Wensveen et al. (2018) "NKG2D: A Master Regulator of Immune Cell Responsiveness," Frontiers in Immunology 9(Article 411):8 pages.
Whalen et al. (2023) "Engaging natural killer cells for cancer therapy via NKG2D, CD16A and other receptors," 15(1) 15 pages.
Wikipedia: "Trifunctional antibody Feb. 1, 2018",, Jan. 2, 2018 (Feb. 1, 2018), pp. 1-4, XP093016568, Retrieved from the Internet: URL:https://en.wikipedia.org/w/index.php?title=Trifunctional antibody8 oldid=818265015.
Wranik et al. (2012) "LUZ-Y, a novel platform for the mammalian cell production of full-length IgG-bispecific antibodies," J Biol Chem 287(52):43331-9.
Wu et al. (1999) "Humanization of a Murine Monoclonal Antibody by Simultaneous Optimization of Framework and CDR Residues," J. Mol. Biol. 294:151-162.
Xie et al. (2005) "A new format of bispecific antibody: highly efficient heterodimerization, expression and tumor cell lysis," J Immunol Methods 296(1):95-101.
Xie et al. (2015) "VEGFR2 targeted antibody fused with MICA stimultes NKG2D mediated immunosurveillance and exhibits potent anti-tumor activity against breast cancer," Oncotarget 7(13):16455-16471.
Xu et al. (2014) "Production of bispecific antibodies in "knobs-into-holes" using a cell-free expression system," mAbs 7(1)231-242.
Xu et al. (2019) "A VEGFR2-MICA bispecific antibody activates tumor-infiltrating lymphocytes and exhibits potent anti-tumor efficacy in mice," Cancer Immunology Immunotherapy 68(9):1429-1441.
Yan et al. (2014) "Construction of a synthetic phage-displayed Nanobody library with CDR3 regions randomized by trinucleotide cassettes for diagnostic applications," Journal of Translational Medicine 12:343 (12 pages).
Yang et al. (2017) "Bispecific Antibodies as a Development Platform for New Concepts and Treatment Strategies" Int. J. Mol. Sci. 18(48) 21 pages.
Yeap et al. (2016) "CD16 is indispensable for antibody dependent cellular cytotoxicity by human monocytes," Scientific Reports 6:34310.
Young et al. (1995) "Thermal stabilization of a single-chain Fv antibody fragment by introduction of a disulphide bond," FEBS Letters 377(2):135-139.
Zhang et al. (2021) "Bispecific antibody-mediated redirection of NKG2D-CAR natural killer cells facilitates dual targeting and enhances antitumor activity," Journal for Immuno Therapy of Cancer; 9:e002980 (24 pages). doi:10.1136/jitc-2021-002980.
Zhou et al. (1995) "Characterization of human homologue of 4-1BB and its ligand, " Immunology Letters 45:67-73.
U.S. Appl. No. 16/639,150, filed Feb. 14, 2020.
U.S. Appl. No. 18/501,413, filed Nov. 3, 2023.
U.S. Appl. No. 16/971,098, filed Aug. 19, 2020.
U.S. Appl. No. 17/045,015, filed Oct. 2, 2020.
U.S. Appl. No. 17/929,282, filed Sep. 1, 2022.
U.S. Appl. No. 17/287,849, filed Apr. 22, 2021.
U.S. Appl. No. 17/920,174, filed Oct. 20, 2022.
U.S. Appl. No. 18/062,453, filed Dec. 6, 2022.
Bartlett et al. (2007) "Lenalidomide and pomalidomide strongly enhance tumor cell killing in vitro during antibody-dependent cellular cytotoxicity (ADCC) mediated by trastuzumab, cetuximab and rituximab," American Society of Clinical Oncology, 25(18S) (19 pages).
Hilpert et al. (2012) "Comprehensive analysis of NKG2D ligand expression and release in leukemia: implications for NKG2D-mediated NK cell responses," J Immunol. 189(3):1360-71.
Jorge Flavio Mendoza Rincón (2014) "El receptor NKG2D en la frontera de la inmunovigilancia y la carcinogénesis," Publicación Científica en Ciencias Biomédicas 2(21):237-43.
Kim et al. (1995) "Evidence That the Hinge Region Plays a Role in Maintaining Serum Levels of the Murine IgG1 Molecule," Molecular Immunology 32(7):467-475.
Novus Biologicals, 2015, "CD-16: Find me on macrophages, neutrophils and NK cells," https://www.novusbio.com/antibody-news/antibodies/cd16-find-me-on-macrophages-neutrophils-and-nk-cells.
Watanabe et al. (2014) NKG2D functions as an activating receptor on natural killer cells in the common marmoset (Callithrix jacchus) International Immunology 26(11):597-606.
Watzl et al. (2010) "Signal Transduction During Activation and Inhibition of Natural Killer Cells", Curr Protoc Immunol., 90(1):11.9B1-11.9B.17.
Written Opinion for International Application No. PCT/US2018/017470 dated Apr. 24, 2018.
Written Opinion for International Application No. PCT/US2018/034223 dated Aug. 30, 2018.
Wu et al. (2011), "Lenalidomide enhances antibody-dependent cellular cytotoxicity of solid tumor cells in vitro: influence of host immune and tumor markers," Cancer Immunology, Immunotherapy, Springer, 60(1):61-73.
Yang et al. (2017) "Enhancing NK cell-mediated cytotoxicity to cisplatin-resistant lung cancer cells via MEK/Erk signaling inhibition," Nature Scientific Reports, 7:7958 (13 pages).
U.S. Appl. No. 16/483,330, filed Aug. 2, 2019, U.S. Pat. No. 11,834,506, Dec. 5, 2023.
U.S. Appl. No. 18/482,629, filed Oct. 6, 2023.
U.S. Appl. No. 16/484,936, filed Aug. 9, 2019.
U.S. Appl. No. 16/486,921, filed Aug. 19, 2019.
U.S. Appl. No. 16/486,569, filed Aug. 16, 2019, U.S. Pat. No. 11,884,732, Jan. 30, 2024.
U.S. Appl. No. 18/541,475, filed Dec. 15, 2023.
U.S. Appl. No. 18/304,652, filed Apr. 21, 2023.
U.S. Appl. No. 17/095,238, filed Nov. 11, 2020.
U.S. Appl. No. 18/107,292, filed Feb. 8, 2023.
U.S. Appl. No. 16/615,261, filed Nov. 20, 2019.
U.S. Appl. No. 16/635,079, filed Jan. 29, 2020.
U.S. Appl. No. 18/442,190, filed Feb. 15, 2024.
U.S. Appl. No. 18/108,961, filed Feb. 13, 2023.
U.S. Appl. No. 16/645,613, filed Mar. 9, 2020.
U.S. Appl. No. 16/967,216, filed Aug. 4, 2020, U.S. Pat. No. 11,884,733, Jan. 30, 2024.
U.S. Appl. No. 18/501,413, filed Nov. 3, 2023, U.S. Pat. No. 11,939,384, Mar. 26, 2024.
U.S. Appl. No. 18/501,419, filed Nov. 3, 2023.
U.S. Appl. No. 18/501,427, filed Nov. 3, 2023.
U.S. Appl. No. 17/058,335, filed Nov. 24, 2020.
U.S. Appl. No. 16/967,218, filed Aug. 4, 2020.
U.S. Appl. No. 18/149,965, filed Jan. 4, 2023.
U.S. Appl. No. 18/150,040, filed Jan. 4, 2023.
U.S. Appl. No. 17/055,792, filed Nov. 16, 2020.
U.S. Appl. No. 17/265,876, filed Feb. 4, 2021.
U.S. Appl. No. 17/543,628, filed Dec. 6, 2021.
U.S. Appl. No. 17/266,349, filed Feb. 5, 2021.
U.S. Appl. No. 17/265,879, filed Feb. 4, 2021.
U.S. Appl. No. 17/266,966, filed Feb. 8, 2021.
U.S. Appl. No. 16/971,104, filed Aug. 19, 2020.
U.S. Appl. No. 17/682,367, filed Feb. 28, 2022.
U.S. Appl. No. 17/769,160, filed Apr. 14, 2022.
U.S. Appl. No. 18/003,308, filed Dec. 23, 2022.
U.S. Appl. No. 17/308,691, filed May 5, 2021.
U.S. Appl. No. 18/622,766, filed Mar. 29, 2024.

(56) References Cited

OTHER PUBLICATIONS

U.S. Appl. No. 18/166,769, filed Feb. 9, 2023.
U.S. Appl. No. 18/177,847, filed Mar. 3, 2023.
U.S. Appl. No. 18/366,876, filed Aug. 8, 2023.
Absolute Antibody, 2023, Anti-NKG2D [ADI-27749 (A49)] Standard Size Ab03079-3.0, 1 page.
Bendayan et al. (1995) "Possibilities of False Immunocytochemical Results Generated by The Use of Monoclonal Antibodies: The Example of the Anti-proinsulin Antibody," *J. Histochem. Cytochem.* 43:881-886.
Bryceson et al. (2006) "Activation, coactivation, and costimulation of resting human natural killer cells Immunological Reviews," 214:73-91.
Chen et al. (2017) "Targeting FLT3 by Chimeric Antigen Receptor T Cells for the Treatment of Acute Myeloid Leukemia," Leukemia 31(8):1830-1834.
Davis et al. (1999) "Therapy of B-Cell Lymphoma with Anti-CD20 Antibodies Can Result in the Loss of CD20 Antigen Expression," *Clinical Cancer Research* 5:611-615.
Davis et al. (2017) "Natural killer cells unleashed: Checkpoint receptor blockade and BIKE/TriKE utilization in NK-mediated anti-tumor immunotherapy," Seminars in Immunology 31:64-75.
Epling-Burnette et al. (2004) "Dysregulated NK receptor expression in patients with lymphoproliferative disease of granularlymphocytes," Blood 13(9):3431-3439.
Eruslanov et al. (2013) "Expansion of CCR8+ Inflammatory Myeloid Cells in Cancer Patients with Urothelial and Renal Carcinomas," *Clinical Cancer Research* 19(7):1670-1680.
Kennedy et al. (2002) "Incidence and nature of CD20-negative relapses following rituximab therapy in aggressive B-cell non-Hodgkin's lymphoma: a retrospective review," British Journal of Haematology 119:412-416.
Modi et al. (2022) "Trastuzumab Deruxtecan in Previously Treated HER2-Low Advanced Breast Cancer," N Engl J Med 387(1):9-20.
Plitas et al. (2016) "Regulatory T Cells Exhibit Distinct Features in Human Breast Cancer," *Immunity* 45(5):1122-1134.
Raynaud et al. (2021) "Anti-NKG2D single domain-based antibodies for the modulation of anti-tumor immune response," Oncoimmunology 10(1):e1854529-1-e1854529-14.
Stallard (2016) "New Approach Could Boost Immunotherapy for Breast Cancer," Memorial Sloan Kettering Cancer Center 1-5.
Weatherill et al. (2012) "Towards a universal disulphide stabilised single chain Fv format: importance of interchain disulphide bond location and vL-vH orientation," Protein Engineering, Design, and Selection, 25(7):321-329.

\* cited by examiner

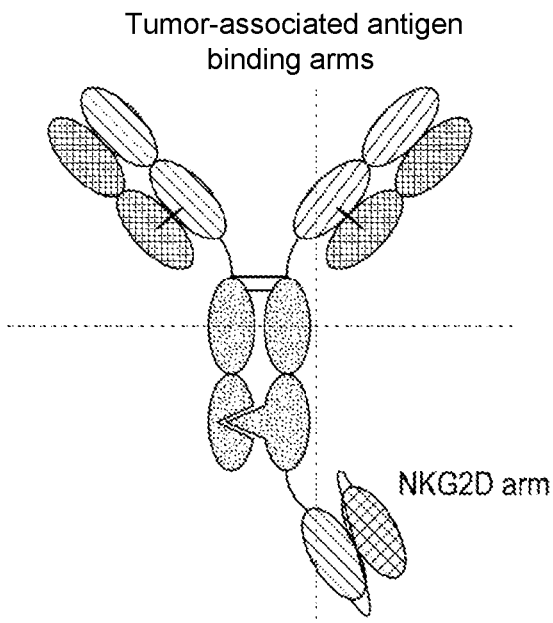
FIG. 2C
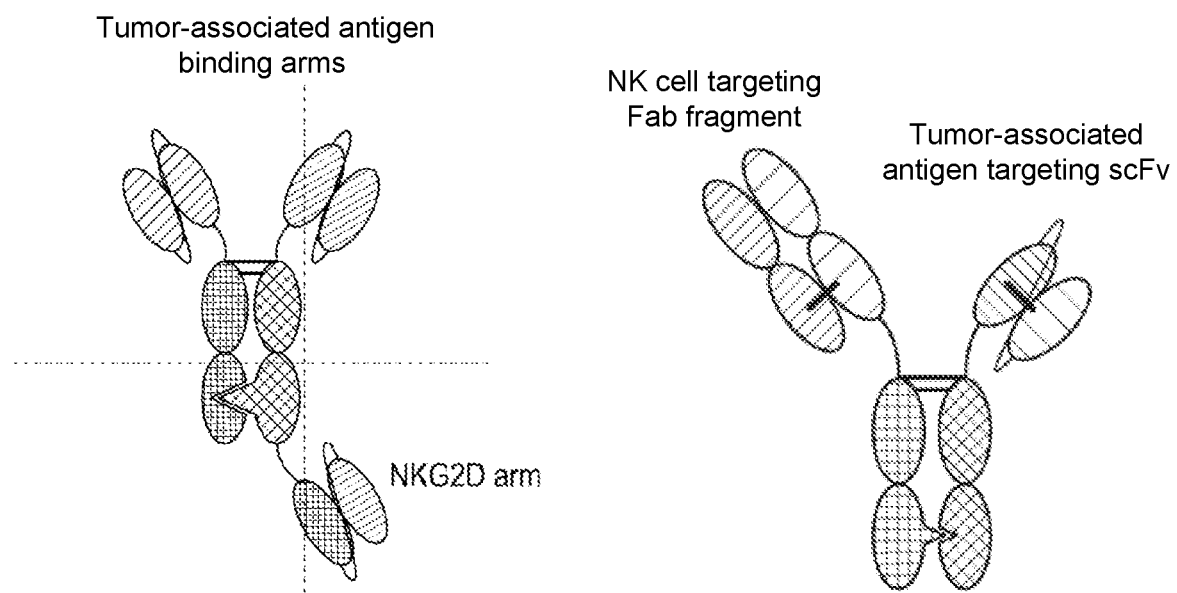
FIG. 2D  FIG. 2E

SEQUENCE LISTING

```
<160> NUMBER OF SEQ ID NOS: 205

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                85                  90                  95
Arg Ala Arg Gly Pro Trp Ser Phe Asp Pro Trp Gly Gln Gly Thr Leu
            100                 105                 110

Val Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Met Thr Gln Ser Pro Ser Thr Leu Ser Ala Ser Val Gly
1               5                  10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Ile
                85                  90                  95

Thr Phe Gly Gly Gly Thr Lys Val Glu Ile Lys
            100                 105

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ser Phe Ser Gly Tyr Tyr Trp Ser
1               5

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ile Asp His Ser Gly Ser Thr Asn Tyr Asn Pro Ser Leu Lys Ser
1               5                  10                  15

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Ala Arg Ala Arg Gly Pro Trp Ser Phe Asp Pro
1               5                   10

<210> SEQ ID NO 6
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65              70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 7
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Tyr Gly Ser Ser Pro
                85                  90                  95

Ile Thr Phe Gly Gly Gly Thr Lys Val Glu Ile Lys
            100                 105

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 8

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Tyr Thr
                85                  90                  95

Phe Gly Gly Gly Thr Lys Val Glu Ile Lys
            100                 105

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
```

```
                50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 11
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Gly Ser Trp
                20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Ser Asn Ser Tyr Tyr Thr
                 85                  90                  95

Phe Gly Gly Gly Thr Lys Val Glu Ile Lys
            100                 105

<210> SEQ ID NO 12
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
             35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
```

115

<210> SEQ ID NO 13
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Thr
                85                  90                  95

Phe Gly Gly Gly Thr Lys Val Glu Ile Lys
            100                 105

<210> SEQ ID NO 14
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Gly Phe Asp Pro Trp Gly Gln Gly Thr Leu
            100                 105                 110

Val Thr Val Ser Ser
        115

<210> SEQ ID NO 15
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Glu Leu Gln Met Thr Gln Ser Pro Ser Ser Leu Ser Ala Ser Val Gly
1               5                   10                  15

Asp Arg Val Thr Ile Thr Cys Arg Thr Ser Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Trp Ala Ser Thr Arg Glu Ser Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser Tyr Asp Ile Pro Tyr
                85                  90                  95

Thr Phe Gly Gln Gly Thr Lys Leu Glu Ile Lys
            100                 105
```

<210> SEQ ID NO 16
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115
```

<210> SEQ ID NO 17
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Gly Ser Phe Pro Ile
                 85                  90                  95

Thr Phe Gly Gly Gly Thr Lys Val Glu Ile Lys
            100                 105

<210> SEQ ID NO 18
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                 20                  25                  30

Tyr Trp Ser Trp Ile Arg Gln Pro Pro Gly Lys Gly Leu Glu Trp Ile
             35                  40                  45

Gly Glu Ile Asp His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Lys Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Asp Asp Phe Ala Thr Tyr Tyr Cys Gln Gln Ser Lys Glu Val Pro Trp
                 85                  90                  95

Thr Phe Gly Gln Gly Thr Lys Val Glu Ile Lys
            100                 105

<210> SEQ ID NO 20
```

```
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Phe Pro Thr
                85                  90                  95

Phe Gly Gly Gly Thr Lys Val Glu Ile Lys
            100                 105

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Trp Gly Ala Gly Leu Leu Lys Pro Ser Glu
1               5                   10                  15
```

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ile Tyr Pro Thr
                85                  90                  95

Phe Gly Gly Gly Thr Lys Val Glu Ile Lys
            100                 105

<210> SEQ ID NO 24
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Ala Arg Gly Pro Trp Ser Phe Asp Pro Trp Gly Gln Gly Thr Leu
        100                 105                 110

Val Thr Val Ser Ser
        115

<210> SEQ ID NO 25
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Pro Thr
                85                  90                  95

Phe Gly Gly Gly Thr Lys Val Glu Ile Lys
            100                 105

<210> SEQ ID NO 26
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 27
<211> LENGTH: 106

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gly Ser Phe Pro Thr
                85                  90                  95

Phe Gly Gly Gly Thr Lys Val Glu Ile Lys
            100                 105

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 29
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
```

```
                    20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Phe Pro Thr
                85                  90                  95

Phe Gly Gly Gly Thr Lys Val Glu Ile Lys
            100                 105

<210> SEQ ID NO 30
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 31
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe Ser Thr
```

```
                    85                  90                  95

Phe Gly Gly Gly Thr Lys Val Glu Ile Lys
            100                 105

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 33
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Thr
                85                  90                  95

Phe Gly Gly Gly Thr Lys Val Glu Ile Lys
            100                 105

<210> SEQ ID NO 34
<211> LENGTH: 117
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 34

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 35
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Phe Ile Thr
                85                  90                  95

Phe Gly Gly Gly Thr Lys Val Glu Ile Lys
            100                 105

<210> SEQ ID NO 36
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
            115

<210> SEQ ID NO 37
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Thr
                85                  90                  95

Phe Gly Gly Gly Thr Lys Val Glu Ile Lys
            100                 105

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

```
Val Thr Val Ser Ser
        115

<210> SEQ ID NO 39
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr His Ser Phe Pro Thr
                85                  90                  95

Phe Gly Gly Gly Thr Lys Val Glu Ile Lys
            100                 105

<210> SEQ ID NO 40
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 41

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Leu Tyr Ser Tyr
                85                  90                  95

Thr Phe Gly Gly Gly Thr Lys Val Glu Ile Lys
            100                 105

<210> SEQ ID NO 42
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 43
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

-continued

```
Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asp Thr Phe Ile Thr
                 85                  90                  95

Phe Gly Gly Gly Thr Lys Val Glu Ile Lys
            100                 105

<210> SEQ ID NO 44
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Asp Ser Ser Ile Arg His Ala Tyr Tyr Tyr Tyr Gly Met
            100                 105                 110

Asp Val Trp Gly Gln Gly Thr Thr Val Thr Val Ser Ser
        115                 120                 125

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Thr Phe Ser Ser Tyr Ala Ile Ser
 1               5

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Ile Ile Pro Ile Phe Gly Thr Ala Asn Tyr Ala Gln Lys Phe Gln
 1               5                  10                  15

Gly

<210> SEQ ID NO 47
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Arg Gly Asp Ser Ser Ile Arg His Ala Tyr Tyr Tyr Gly Met
1               5                   10                  15

Asp Val

<210> SEQ ID NO 48
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Ile Thr Phe Gly Gly Gly Thr Lys Val Glu Ile
            100                 105                 110

Lys

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Ser Ser Gln Ser Val Leu Tyr Ser Ser Asn Asn Lys Asn Tyr Leu
1               5                   10                  15

Ala

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Ala Ser Thr Arg Glu Ser
1               5
```

```
<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Tyr Ser Thr Pro Ile Thr
1               5

<210> SEQ ID NO 52
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Asp Arg Phe His Pro Tyr Phe Asp Tyr Trp Gly
            100                 105                 110

Gln Gly Thr Leu Val Thr Val Ser Ser
        115                 120

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Ile Ser Ser Ser Ser Tyr Tyr Trp Gly
1               5                   10

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Ile Tyr Tyr Ser Gly Ser Thr Tyr Tyr Asn Pro Ser Leu Lys Ser
1               5                   10                  15

<210> SEQ ID NO 55
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Arg Gly Ser Asp Arg Phe His Pro Tyr Phe Asp Tyr
1               5                   10

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Pro
                85                  90                  95

Thr Phe Gly Gly Gly Thr Lys Val Glu Ile Lys
            100                 105

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Gln Ser Val Ser Arg Tyr Leu Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Ala Ser Asn Arg Ala Thr
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 59

Gln Gln Phe Asp Thr Trp Pro Pro Thr
1               5

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asp His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Gly Pro Trp Ser Phe Asp Pro Trp Gly Gln Gly Thr Leu
            100                 105                 110

Val Thr Val Ser Ser
        115

<210> SEQ ID NO 61
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Glu Gln Tyr Asp Ser Tyr Pro Thr
                85                  90                  95

Phe Gly Gly Gly Thr Lys Val Glu Ile Lys
            100                 105

<210> SEQ ID NO 62
<211> LENGTH: 126
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Arg Lys Ala Ser Gly Ser Phe Tyr Tyr Tyr Tyr Gly
            100                 105                 110

Met Asp Val Trp Gly Gln Gly Thr Thr Val Thr Val Ser Ser
        115                 120                 125

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Thr Phe Ser Ser Tyr Ala Ile Ser
1               5

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ile Ile Pro Ile Phe Gly Thr Ala Asn Tyr Ala Gln Lys Phe Gln
1               5                   10                  15

Gly

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Arg Arg Gly Arg Lys Ala Ser Gly Ser Phe Tyr Tyr Tyr Tyr Gly
1               5                   10                  15

Met Asp Val

<210> SEQ ID NO 66
<211> LENGTH: 113
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 66

```
Asp Ile Val Met Thr Gln Ser Pro Asp Ser Leu Ala Val Ser Leu Gly
1               5                  10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys
```

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

```
Glu Ser Ser Gln Ser Leu Leu Asn Ser Gly Asn Gln Lys Asn Tyr Leu
1               5                  10                  15

Thr
```

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

```
Trp Ala Ser Thr Arg Glu Ser
1               5
```

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Gln Asn Asp Tyr Ser Tyr Pro Tyr Thr
1               5
```

<210> SEQ ID NO 70
<211> LENGTH: 126
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Pro Asn Tyr Gly Asp Thr Thr His Asp Tyr Tyr Tyr
            100                 105                 110

Met Asp Val Trp Gly Lys Gly Thr Thr Val Thr Val Ser Ser
        115                 120                 125

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Tyr Thr Phe Thr Ser Tyr Tyr Met His
1               5

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Ile Asn Pro Ser Gly Gly Ser Thr Ser Tyr Ala Gln Lys Phe Gln
1               5                   10                  15

Gly

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ala Arg Gly Ala Pro Asn Tyr Gly Asp Thr Thr His Asp Tyr Tyr Tyr
1               5                   10                  15

Met Asp Val

<210> SEQ ID NO 74
<211> LENGTH: 107
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Phe
                85                  90                  95

Thr Phe Gly Gly Gly Thr Lys Val Glu Ile Lys
            100                 105

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Arg Ala Ser Gln Ser Val Ser Ser Asn Leu Ala
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ala Ser Thr Arg Ala Thr
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Gln Tyr Asp Asp Trp Pro Phe Thr
1               5

<210> SEQ ID NO 78
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Thr Gly Glu Tyr Tyr Asp Thr Asp His Gly Met Asp
            100                 105                 110

Val Trp Gly Gln Gly Thr Thr Val Thr Val Ser Ser
        115                 120
```

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

```
Tyr Thr Phe Thr Gly Tyr Tyr Met His
1               5
```

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

```
Trp Ile Asn Pro Asn Ser Gly Gly Thr Asn Tyr Ala Gln Lys Phe Gln
1               5                   10                  15

Gly
```

<210> SEQ ID NO 81
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

```
Ala Arg Asp Thr Gly Glu Tyr Tyr Asp Thr Asp His Gly Met Asp Val
1               5                   10                  15

Val
```

<210> SEQ ID NO 82
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 82

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Asp Tyr Trp Pro Pro
                85                  90                  95

Thr Phe Gly Gly Gly Thr Lys Val Glu Ile Lys
            100                 105

<210> SEQ ID NO 83
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Gly
    50

<210> SEQ ID NO 84
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
    50

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic

```
                   peptide

<400> SEQUENCE: 85

Gln Gln Asp Asp Tyr Trp Pro Pro Thr
1               5

<210> SEQ ID NO 86
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser
        115                 120

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Phe Thr Phe Ser Ser Tyr Ala Met Ser
1               5

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Ile Ser Gly Ser Gly Gly Ser Thr Tyr Tyr Ala Asp Ser Val Lys
1               5                   10                  15

Gly

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 89

Ala Lys Asp Gly Gly Tyr Tyr Asp Ser Gly Ala Gly Asp Tyr
1               5                   10

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
                85                  90                  95

Thr Phe Gly Gly Gly Thr Lys Val Glu Ile Lys
            100                 105

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ala Ser Gln Gly Ile Asp Ser Trp Leu Ala
1               5                   10

<210> SEQ ID NO 92
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Ala Ser Ser Leu Gln Ser
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Gly Val Ser Tyr Pro Arg Thr

<210> SEQ ID NO 94
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Ala Gly Trp Phe Asp Pro Trp
            100                 105                 110

Gly Gln Gly Thr Leu Val Thr Val Ser Ser
        115                 120

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Phe Thr Phe Ser Ser Tyr Ser Met Asn
1               5

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Ile Ser Ser Ser Ser Ser Tyr Ile Tyr Tyr Ala Asp Ser Val Lys
1               5                   10                  15

Gly

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ala Arg Gly Ala Pro Met Gly Ala Ala Ala Gly Trp Phe Asp Pro

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys
            100                 105

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Gly Ile Ser Ser Trp Leu Ala
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ala Ala Ser Ser Leu Gln Ser
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gln Gln Gly Val Ser Phe Pro Arg Thr
1               5

<210> SEQ ID NO 102
<211> LENGTH: 125

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Ala Gly Phe Ala Tyr Gly Met Asp Tyr Tyr Tyr Met
            100                 105                 110

Asp Val Trp Gly Lys Gly Thr Thr Val Thr Val Ser Ser
        115                 120                 125

<210> SEQ ID NO 103
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 104
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40

<210> SEQ ID NO 105
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Ala Arg Glu Gly Ala Gly Phe Ala Tyr Gly Met Asp Tyr Tyr Tyr Met
1               5                   10                  15

Asp Val

<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asp Asn Trp Pro Phe
                85                  90                  95

Thr Phe Gly Gly Gly Thr Lys Val Glu Ile Lys
            100                 105

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Ala Ser Gln Ser Val Ser Ser Tyr Leu Ala
1               5                   10

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Ala Ser Asn Arg Ala Thr
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Gln Gln Ser Asp Asn Trp Pro Phe Thr
1               5
```

<210> SEQ ID NO 110
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser
        115                 120
```

<210> SEQ ID NO 111
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

```
Gln Ser Ala Leu Thr Gln Pro Ala Ser Val Ser Gly Ser Pro Gly Gln
1               5                   10                  15

Ser Ile Thr Ile Ser Cys Ser Gly Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110
```

<210> SEQ ID NO 112
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gln Val His Leu Gln Glu Ser Gly Pro Gly Leu Val Lys Pro Ser Glu
1               5                   10                  15

Thr Leu Ser Leu Thr Cys Thr Val Ser Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
        115

<210> SEQ ID NO 113
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 114
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Asn Ile Lys Asp Thr
1               5

<210> SEQ ID NO 116
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Tyr Pro Thr Asn Gly Tyr
1               5

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Trp Gly Gly Asp Gly Phe Tyr Ala Met Asp Tyr
1               5                   10

<210> SEQ ID NO 118
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60
```

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Asp Val Asn Thr Ala Val Ala
1               5

<210> SEQ ID NO 120
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser Ala Ser Phe Leu Tyr Ser
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln His Tyr Thr Thr Pro Pro Thr
1               5

<210> SEQ ID NO 122
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
        50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys

```
                        85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala
        115                 120

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Thr Phe Thr Asp Tyr
1               5

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asn Pro Asn Ser Gly Gly
1               5

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asn Leu Gly Pro Ser Phe Tyr Phe Asp Tyr
1               5                   10

<210> SEQ ID NO 126
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95
```

```
Thr Phe Gly Gln Gly Thr Lys Val Glu Ile Lys Arg
            100                 105
```

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Gln Asp Val Ser Ile Gly Val Ala
1               5
```

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Ser Ala Ser Tyr Arg Tyr Thr
1               5
```

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

```
Gln Gln Tyr Tyr Ile Tyr Pro Tyr Thr
1               5
```

<210> SEQ ID NO 130
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

```
Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
            115                 120
```

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Phe Asn Ile Lys Asp Thr
1               5

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Pro Thr Asn Gly Tyr
1               5

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Gly Gly Asp Gly Phe Tyr Ala Met Asp Tyr
1               5                   10

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Gly Gly Thr Lys Val Glu Ile Lys
            100                 105

<210> SEQ ID NO 135
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 135

Gln Asp Val Asn Thr Ala Val Ala
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Ala Ser Phe Arg Tyr Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Gln His Tyr Thr Thr Pro Pro Thr
1               5

<210> SEQ ID NO 138
<211> LENGTH: 1255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160
```

```
Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
```

-continued

```
            580                 585                 590
Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
        770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
        850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr  Arg Ser Leu
        995                 1000                1005
```

```
Leu Glu Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 139
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
```

```
            85                  90                  95
Thr Phe Gly Cys Gly Thr Lys Val Glu Ile Lys Gly Gly Gly Ser
                100                 105                 110

Gly Gly Gly Gly Ser Gly Gly Gly Ser Gly Gly Gly Gly Ser Glu
            115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
                195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser
                245

<210> SEQ ID NO 140
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
                100                 105                 110

Gly Gly Gly Gly Ser Gly Gly Gly Ser Gly Gly Gly Gly Ser Glu
            115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
                180                 185                 190
```

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
210                 215                 220

Arg Trp Gly Asp Gly Phe Tyr Ala Met Asp Tyr Trp Gly Gln Gly
225                 230                 235                 240

Thr Leu Val Thr Val Ser Ser Ala Ser Asp Lys Thr His Thr Cys Pro
                245                 250                 255

Pro Cys Pro Ala Pro Glu Leu Leu Gly Gly Pro Ser Val Phe Leu Phe
                260                 265                 270

Pro Pro Lys Pro Lys Asp Thr Leu Met Ile Ser Arg Thr Pro Glu Val
                275                 280                 285

Thr Cys Val Val Val Asp Val Ser His Glu Asp Pro Glu Val Lys Phe
290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
                340                 345                 350

Ser Asn Lys Ala Leu Pro Ala Pro Ile Glu Lys Thr Ile Ser Lys Ala
                355                 360                 365

Lys Gly Gln Pro Arg Glu Pro Arg Val Tyr Thr Leu Pro Pro Cys Arg
                370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Val Ser Asp Gly Ser
                420                 425                 430

Phe Thr Leu Tyr Ser Lys Leu Thr Val Asp Lys Ser Arg Trp Gln Gln
                435                 440                 445

Gly Asn Val Phe Ser Cys Ser Val Met His Glu Ala Leu His Asn His
                450                 455                 460

Tyr Thr Gln Lys Ser Leu Ser Leu Ser Pro Gly
465                 470                 475

<210> SEQ ID NO 141
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Met Gly Ala Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Glu Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 142
<211> LENGTH: 210
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 142

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Phe Pro Arg
                85                  90                  95

Thr Phe Gly Gly Gly Thr Lys Val Glu Ile Lys Arg Thr Val Ala Ala
            100                 105                 110

Pro Ser Pro Pro Ser Asp Glu Gln Leu Lys Ser Gly Thr Ala Ser Val
        115                 120                 125

Val Cys Leu Leu Asn Asn Phe Tyr Pro Arg Glu Ala Lys Val Gln Trp
130                 135                 140

Lys Val Asp Asn Ala Leu Gln Ser Gly Asn Ser Gln Glu Ser Val Thr
145                 150                 155                 160

Glu Gln Asp Ser Lys Asp Ser Thr Tyr Ser Leu Ser Ser Thr Leu Thr
                165                 170                 175

Leu Ser Lys Ala Asp Tyr Glu Lys His Lys Val Tyr Ala Cys Glu Val
            180                 185                 190

Thr His Gln Gly Leu Ser Ser Pro Val Thr Lys Ser Phe Asn Arg Gly
        195                 200                 205

Glu Cys
    210

<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Gly Gly Gly Ser Gly Gly Gly Ser Gly Gly Gly Gly Ser Gly
1               5                   10                  15

Gly Gly Gly Ser
            20

<210> SEQ ID NO 144
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr

```
            20                  25                  30
Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser
            115                 120

<210> SEQ ID NO 145
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255
```

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Glu Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Trp Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 146
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
            165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ser Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
            325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
            355                 360                 365

Lys Gly Gln Pro Arg Glu Pro Gln Val Cys Thr Leu Pro Pro Ser Arg
        370                 375                 380

Asp Glu Leu Thr Lys Asn Gln Val Ser Leu Ser Cys Ala Val Lys Gly
385                 390                 395                 400

Phe Tyr Pro Ser Asp Ile Ala Val Glu Trp Glu Ser Asn Gly Gln Pro
            405                 410                 415

Glu Asn Asn Tyr Lys Thr Thr Pro Pro Val Leu Asp Ser Asp Gly Ser
            420                 425                 430

Phe Phe Leu Val Ser Lys Leu Thr Val Asp Lys Ser Arg Trp Gln Gln
            435                 440                 445

Gly Asn Val Phe Ser Cys Ser Val Met His Glu Ala Leu His Asn His
        450                 455                 460

Tyr Thr Gln Lys Ser Leu Ser Leu Ser Pro Gly
465                 470                 475

<210> SEQ ID NO 147
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val

```
            35                  40                  45
Ser Ser Ile Ser Ser Ser Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ala Pro Met Gly Ala Ala Gly Trp Phe Asp Pro Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Cys Arg Asp Glu Leu Thr Lys Asn Gln Val
            355                 360                 365

Ser Leu Trp Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450
```

<210> SEQ ID NO 148
<211> LENGTH: 450
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Gly Tyr Tyr Asp Ser Gly Ala Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Arg Asp Glu Leu Thr Lys Asn Gln Val Ser
```

```
                355                 360                 365
Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 149
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asp Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Ser Tyr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 150
<211> LENGTH: 15
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 150

Gly Gly Gly Gly Ser Gly Gly Gly Ser Gly Gly Gly Ser
1               5                   10                  15

<210> SEQ ID NO 151
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(80)
<223> OTHER INFORMATION: This sequence may encompass 1-20 "Gly Gly Gly
      Ser" repeating units

<400> SEQUENCE: 151

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Ser Gly Gly Gly Ser
        35                  40                  45

Gly Gly Gly Ser Gly Gly Gly Ser Gly Gly Gly Ser Gly Gly Gly Ser
    50                  55                  60

Gly Gly Gly Ser Gly Gly Gly Ser Gly Gly Gly Ser Gly Gly Gly Ser
65                  70                  75                  80

<210> SEQ ID NO 152
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 153
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: SITE
<222> LOCATION: (1)..(80)
<223> OTHER INFORMATION: This sequence may encompass 1-20 "Gly Gly Ser
      Gly" repeating units

<400> SEQUENCE: 153

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly Gly Gly Ser Gly Gly Gly Ser Gly
        35                  40                  45

Gly Gly Ser Gly Gly Gly Ser Gly Gly Gly Ser Gly Gly Gly Ser Gly
    50                  55                  60

Gly Gly Ser Gly Gly Gly Ser Gly Gly Gly Ser Gly Gly Gly Ser Gly
65                  70                  75                  80

<210> SEQ ID NO 154
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Gly Ser Gly Gly Gly Ser Gly Gly Gly Ser Gly Gly Gly
1               5                   10                  15

Gly Ser Gly Gly Gly Ser Gly Gly Gly Ser Gly Gly Gly Gly
            20                  25                  30

Ser Gly Gly Gly Ser Gly Gly Gly Ser Gly Gly Gly Gly Ser
        35                  40                  45

Gly Gly Gly Gly Ser Gly Gly Gly Ser Gly Gly Gly Ser Gly
    50                  55                  60

Gly Gly Gly Ser Gly Gly Gly Ser Gly Gly Gly Ser Gly Gly
65                  70                  75                  80

Gly Gly Ser Gly Gly Gly Ser Gly Gly Gly Ser Gly Gly Gly
            85                  90                  95

Gly Ser Gly Gly
        100

<210> SEQ ID NO 155
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Lys Asp Gly Gly Tyr Tyr Asp Ser Gly Ala Gly Asp Tyr Trp Gly
                100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Glu Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Trp Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
    435                 440                 445

Pro Gly
    450

<210> SEQ ID NO 156
<211> LENGTH: 100
<212> TYPE: PRT
<213> ORGANISM: Artificial Sequence
```

<220> FEATURE:
<223> OTHER INFORMATION: Description of Artificial Sequence: Synthetic
      polypeptide
<220> FEATURE:
<221> NAME/KEY: SITE
<222> LOCATION: (1)..(100)
<223> OTHER INFORMATION: This sequence may encompass 1-20 "Gly Gly Ser
      Gly Gly" repeating units

<400> SEQUENCE: 156

Gly Gly Ser Gly Gly Gly Gly Ser Gly Gly Gly Ser Gly Gly Gly
1               5                   10                  15

Gly Ser Gly Gly Gly Gly Ser Gly Gly Gly Ser Gly Gly Gly Gly
            20                  25                  30

Ser Gly Gly Gly Gly Ser Gly Gly Gly Ser Gly Gly Gly Gly Ser
        35                  40                  45

Gly Gly Gly Gly Ser Gly Gly Gly Ser Gly Gly Gly Gly Ser Gly
    50                  55                  60

Gly Gly Ser Gly Gly Gly Ser Gly Gly Gly Ser Gly Gly Gly Gly
65                  70                  75                  80

Gly Gly Ser Gly Gly Gly Gly Ser Gly Gly Gly Ser Gly Gly Gly
                85                  90                  95

Gly Ser Gly Gly
        100

<210> SEQ ID NO 157
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(100)
<223> OTHER INFORMATION: This sequence may encompass 1-20 "Gly Gly Gly
      Gly Ser" repeating units

<400> SEQUENCE: 157

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly
            20                  25                  30

Gly Gly Ser Gly Gly Gly Gly Ser Gly Gly Gly Gly Ser Gly Gly
        35                  40                  45

Gly Ser Gly Gly Gly Gly Ser Gly Gly Gly Gly Ser Gly Gly Gly
    50                  55                  60

Ser Gly Gly Gly Gly Ser Gly Gly Gly Gly Ser Gly Gly Gly Ser
65                  70                  75                  80

Gly Gly Gly Gly Ser Gly Gly Gly Gly Ser Gly Gly Gly Ser Gly
                85                  90                  95

Gly Gly Gly Ser
        100

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

```
Ser Tyr Ala Ile Ser
1               5

<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Asp Ser Ser Ile Arg His Ala Tyr Tyr Tyr Gly Met Asp Val
1               5                   10                  15

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Ser Ser Tyr Tyr Trp Gly
1               5

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gly Ser Asp Arg Phe His Pro Tyr Phe Asp Tyr
1               5                   10

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Tyr Tyr Met His
1               5

<210> SEQ ID NO 163
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Ala Pro Asn Tyr Gly Asp Thr Thr His Asp Tyr Tyr Tyr Met Asp
1               5                   10                  15

Val

<210> SEQ ID NO 164
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gly Tyr Tyr Met His
1               5

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Asp Thr Gly Glu Tyr Tyr Asp Thr Asp Asp His Gly Met Asp Val
1               5                   10                  15

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ser Tyr Ala Met Ser
1               5

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Asp Gly Gly Tyr Tyr Asp Ser Gly Ala Gly Asp Tyr
1               5                   10

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ser Tyr Ser Met Asn
1               5

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Ala Pro Met Gly Ala Ala Ala Gly Trp Phe Asp Pro
```

<210> SEQ ID NO 170
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Glu Gly Ala Gly Phe Ala Tyr Gly Met Asp Tyr Tyr Met Asp Val
1               5                   10                  15

<210> SEQ ID NO 171
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Gln Gln Ser Gly Pro Glu Leu Val Lys Pro Gly Ala
    130                 135                 140

Ser Leu Lys Leu Ser Cys Thr Ala Ser Gly Phe Asn Ile Lys Asp Thr
145                 150                 155                 160

Tyr Ile His Trp Val Lys Gln Arg Pro Glu Gln Cys Leu Glu Trp Ile
                165                 170                 175

Gly Arg Ile Tyr Pro Thr Asn Gly Tyr Thr Arg Tyr Asp Pro Lys Phe
            180                 185                 190

Gln Asp Lys Ala Thr Ile Thr Ala Asp Thr Ser Ser Asn Thr Ala Tyr
        195                 200                 205

Leu Gln Val Ser Arg Leu Thr Ser Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Ala Ser Val Thr Val Ser Ser Ala
                245

<210> SEQ ID NO 172
<211> LENGTH: 15
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 172

Ala Arg Gly Ala Pro Ile Gly Ala Ala Ala Gly Trp Phe Asp Pro
1               5                   10                  15

<210> SEQ ID NO 173
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Ala Pro Ile Gly Ala Ala Ala Gly Trp Phe Asp Pro
1               5                   10

<210> SEQ ID NO 174
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Gln Gly Ala Ala Ala Gly Trp Phe Asp Pro Trp
                100                 105                 110

Gly Gln Gly Thr Leu Val Thr Val Ser Ser
        115                 120

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ala Arg Gly Ala Pro Gln Gly Ala Ala Ala Gly Trp Phe Asp Pro
1               5                   10                  15

<210> SEQ ID NO 176
<211> LENGTH: 13
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 176

Gly Ala Pro Gln Gly Ala Ala Ala Gly Trp Phe Asp Pro
1               5                   10

<210> SEQ ID NO 177
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Leu Gly Ala Ala Ala Gly Trp Phe Asp Pro Trp
            100                 105                 110

Gly Gln Gly Thr Leu Val Thr Val Ser Ser
        115                 120

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Arg Gly Ala Pro Leu Gly Ala Ala Ala Gly Trp Phe Asp Pro
1               5                   10                  15

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Ala Pro Leu Gly Ala Ala Ala Gly Trp Phe Asp Pro
1               5                   10

<210> SEQ ID NO 180
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Phe Gly Ala Ala Ala Gly Trp Phe Asp Pro Trp
            100                 105                 110

Gly Gln Gly Thr Leu Val Thr Val Ser Ser
        115                 120

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Arg Gly Ala Pro Phe Gly Ala Ala Ala Gly Trp Phe Asp Pro
1               5                   10                  15

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Ala Pro Phe Gly Ala Ala Ala Gly Trp Phe Asp Pro
1               5                   10

<210> SEQ ID NO 183
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr

```
                65                  70                  75                  80
Leu Gln Met Asn Ser Leu Arg Ala Glu Asp Thr Ala Val Tyr Tyr Cys
                        85                  90                  95

Ala Arg Gly Ala Pro Val Gly Ala Ala Ala Gly Trp Phe Asp Pro Trp
                100                 105                 110

Gly Gln Gly Thr Leu Val Thr Val Ser Ser
        115                 120

<210> SEQ ID NO 184
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Arg Gly Ala Pro Val Gly Ala Ala Ala Gly Trp Phe Asp Pro
1               5                  10                  15

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Ala Pro Val Gly Ala Ala Ala Gly Trp Phe Asp Pro
1               5                  10

<210> SEQ ID NO 186
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (102)..(102)
<223> OTHER INFORMATION: M, L, I, V, Q or F

<400> SEQUENCE: 186

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                        85                  90                  95

Ala Arg Gly Ala Pro Xaa Gly Ala Ala Ala Gly Trp Phe Asp Pro Trp
                100                 105                 110

Gly Gln Gly Thr Leu Val Thr Val Ser Ser
        115                 120
```

-continued

```
<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: M, L, I, V, Q or F

<400> SEQUENCE: 187

Ala Arg Gly Ala Pro Xaa Gly Ala Ala Ala Gly Trp Phe Asp Pro
1               5                   10                  15

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: M, L, I, V, Q or F

<400> SEQUENCE: 188

Gly Ala Pro Xaa Gly Ala Ala Ala Gly Trp Phe Asp Pro
1               5                   10

<210> SEQ ID NO 189
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
                165                 170                 175
```

```
Ala Asp Val Asn Pro Asn Ser Gly Gly Ser Ile Tyr Asn Gln Arg Phe
                180                 185                 190

Lys Gly Arg Phe Thr Leu Ser Val Asp Arg Ser Lys Asn Thr Leu Tyr
            195                 200                 205

Leu Gln Met Asn Ser Leu Arg Ala Glu Asp Thr Ala Val Tyr Tyr Cys
        210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Ala
            245
```

<210> SEQ ID NO 190
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Ala Ala Ser Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285
```

```
Val Thr Cys Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Arg Val Tyr Thr Leu Pro Pro Cys
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Val Ser Asp Gly
            420                 425                 430

Ser Phe Thr Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly
465                 470                 475

<210> SEQ ID NO 191
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
```

165                 170                 175
Ala Asp Val Asn Pro Asn Ser Gly Gly Ser Ile Tyr Asn Gln Arg Phe
                    180                 185                 190

Lys Gly Arg Phe Thr Leu Ser Val Asp Arg Ser Lys Asn Thr Leu Tyr
                195                 200                 205

Leu Gln Met Asn Ser Leu Arg Ala Glu Asp Thr Ala Val Tyr Tyr Cys
            210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Ala Ala Ser Asp Lys Thr His Thr Cys
                245                 250                 255

Pro Pro Cys Pro Ala Pro Glu Leu Leu Gly Gly Pro Ser Val Phe Leu
                260                 265                 270

Phe Pro Pro Lys Pro Lys Asp Thr Leu Met Ile Ser Arg Thr Pro Glu
                275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
                340                 345                 350

Val Ser Asn Lys Ala Leu Pro Ala Pro Ile Glu Lys Thr Ile Ser Lys
                355                 360                 365

Ala Lys Gly Gln Pro Arg Glu Pro Gln Val Cys Thr Leu Pro Pro Ser
            370                 375                 380

Arg Asp Glu Leu Thr Lys Asn Gln Val Ser Leu Ser Cys Ala Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
                420                 425                 430

Ser Phe Phe Leu Val Ser Lys Leu Thr Val Asp Lys Ser Arg Trp Gln
            435                 440                 445

Gln Gly Asn Val Phe Ser Cys Ser Val Met His Glu Ala Leu His Asn
                450                 455                 460

His Tyr Thr Gln Lys Ser Leu Ser Leu Ser Pro Gly
465                 470                 475

<210> SEQ ID NO 192
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
                20                  25                  30

Val Ala Trp Tyr Gln Gln Lys Pro Gly His Ser Pro Lys Leu Leu Ile
            35                  40                  45

```
Tyr Ser Ala Ser Phe Arg Tyr Thr Gly Val Pro Asp Arg Phe Thr Gly
    50                  55                  60
Ser Arg Ser Gly Thr Asp Phe Thr Phe Thr Ile Ser Ser Val Gln Ala
65                  70                  75                  80
Glu Asp Leu Ala Val Tyr Tyr Cys Gln Gln His Tyr Thr Thr Pro Pro
                85                  90                  95
Thr Phe Gly Cys Gly Thr Lys Val Glu Ile Lys Arg Gly Gly Gly Gly
            100                 105                 110
Ser Gly Gly Gly Gly Ser Gly Gly Gly Ser Gly Gly Gly Gly Ser
        115                 120                 125
Gln Val Gln Leu Gln Gln Ser Gly Pro Glu Leu Val Lys Pro Gly Ala
    130                 135                 140
Ser Leu Lys Leu Ser Cys Thr Ala Ser Gly Phe Asn Ile Lys Asp Thr
145                 150                 155                 160
Tyr Ile His Trp Val Lys Gln Arg Pro Glu Gln Cys Leu Glu Trp Ile
                165                 170                 175
Gly Arg Ile Tyr Pro Thr Asn Gly Tyr Thr Arg Tyr Asp Pro Lys Phe
            180                 185                 190
Gln Asp Lys Ala Thr Ile Thr Ala Asp Thr Ser Ser Asn Thr Ala Tyr
        195                 200                 205
Leu Gln Val Ser Arg Leu Thr Ser Glu Asp Thr Ala Val Tyr Tyr Cys
    210                 215                 220
Ser Arg Trp Gly Gly Asp Gly Phe Tyr Ala Met Asp Tyr Trp Gly Gln
225                 230                 235                 240
Gly Ala Ser Val Thr Val Ser Ser Ala Ala Ser Asp Lys Thr His Thr
                245                 250                 255
Cys Pro Pro Cys Pro Ala Pro Glu Leu Leu Gly Gly Pro Ser Val Phe
            260                 265                 270
Leu Phe Pro Pro Lys Pro Lys Asp Thr Leu Met Ile Ser Arg Thr Pro
        275                 280                 285
Glu Val Thr Cys Val Val Val Asp Val Ser His Glu Asp Pro Glu Val
    290                 295                 300
Lys Phe Asn Trp Tyr Val Asp Gly Val Glu Val His Asn Ala Lys Thr
305                 310                 315                 320
Lys Pro Arg Glu Glu Gln Tyr Asn Ser Thr Tyr Arg Val Val Ser Val
                325                 330                 335
Leu Thr Val Leu His Gln Asp Trp Leu Asn Gly Lys Glu Tyr Lys Cys
            340                 345                 350
Lys Val Ser Asn Lys Ala Leu Pro Ala Pro Ile Glu Lys Thr Ile Ser
        355                 360                 365
Lys Ala Lys Gly Gln Pro Arg Glu Pro Arg Val Tyr Thr Leu Pro Pro
    370                 375                 380
Cys Arg Asp Glu Leu Thr Lys Asn Gln Val Ser Leu Thr Cys Leu Val
385                 390                 395                 400
Lys Gly Phe Tyr Pro Ser Asp Ile Ala Val Glu Trp Glu Ser Asn Gly
                405                 410                 415
Gln Pro Glu Asn Asn Tyr Lys Thr Thr Pro Pro Val Leu Val Ser Asp
            420                 425                 430
Gly Ser Phe Thr Leu Tyr Ser Lys Leu Thr Val Asp Lys Ser Arg Trp
        435                 440                 445
Gln Gln Gly Asn Val Phe Ser Cys Ser Val Met His Glu Ala Leu His
    450                 455                 460
Asn His Tyr Thr Gln Lys Ser Leu Ser Leu Ser Pro Gly
```

465 470 475

<210> SEQ ID NO 193
<211> LENGTH: 477
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Pro
                85                  90                  95

Thr Phe Gly Cys Gly Thr Lys Val Glu Ile Lys Arg Gly Gly Gly Gly
            100                 105                 110

Ser Gly Gly Gly Gly Ser Gly Gly Gly Gly Ser Gly Gly Gly Gly Ser
        115                 120                 125

Gln Val Gln Leu Gln Gln Ser Gly Pro Glu Leu Val Lys Pro Gly Ala
    130                 135                 140

Ser Leu Lys Leu Ser Cys Thr Ala Ser Gly Phe Asn Ile Lys Asp Thr
145                 150                 155                 160

Tyr Ile His Trp Val Lys Gln Arg Pro Glu Gln Cys Leu Glu Trp Ile
                165                 170                 175

Gly Arg Ile Tyr Pro Thr Asn Gly Tyr Thr Arg Tyr Asp Pro Lys Phe
            180                 185                 190

Gln Asp Lys Ala Thr Ile Thr Ala Asp Thr Ser Ser Asn Thr Ala Tyr
        195                 200                 205

Leu Gln Val Ser Arg Leu Thr Ser Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Ala Ser Val Thr Val Ser Ser Ala Ala Ser Asp Lys Thr His Thr
                245                 250                 255

Cys Pro Pro Cys Pro Ala Pro Glu Leu Leu Gly Gly Pro Ser Val Phe
            260                 265                 270

Leu Phe Pro Pro Lys Pro Lys Asp Thr Leu Met Ile Ser Arg Thr Pro
        275                 280                 285

Glu Val Thr Cys Val Val Asp Val Ser His Glu Asp Pro Glu Val
    290                 295                 300

Lys Phe Asn Trp Tyr Val Asp Gly Val Glu Val His Asn Ala Lys Thr
305                 310                 315                 320

Lys Pro Arg Glu Glu Gln Tyr Asn Ser Thr Tyr Arg Val Val Ser Val
                325                 330                 335

Leu Thr Val Leu His Gln Asp Trp Leu Asn Gly Lys Glu Tyr Lys Cys
            340                 345                 350

```
Lys Val Ser Asn Lys Ala Leu Pro Ala Pro Ile Glu Lys Thr Ile Ser
            355                 360                 365

Lys Ala Lys Gly Gln Pro Arg Glu Pro Gln Val Cys Thr Leu Pro Pro
370                 375                 380

Ser Arg Asp Glu Leu Thr Lys Asn Gln Val Ser Leu Ser Cys Ala Val
385                 390                 395                 400

Lys Gly Phe Tyr Pro Ser Asp Ile Ala Val Glu Trp Glu Ser Asn Gly
            405                 410                 415

Gln Pro Glu Asn Asn Tyr Lys Thr Thr Pro Pro Val Leu Asp Ser Asp
            420                 425                 430

Gly Ser Phe Phe Leu Val Ser Lys Leu Thr Val Asp Lys Ser Arg Trp
            435                 440                 445

Gln Gln Gly Asn Val Phe Ser Cys Ser Val Met His Glu Ala Leu His
450                 455                 460

Asn His Tyr Thr Gln Lys Ser Leu Ser Leu Ser Pro Gly
465                 470                 475

<210> SEQ ID NO 194
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ala Pro Ile Gly Ala Ala Ala Gly Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240
```

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Cys Arg Asp Glu Leu Thr Lys Asn Gln Val
            355                 360                 365

Ser Leu Trp Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 195
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Cys Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

```
<210> SEQ ID NO 196
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys
            100                 105

<210> SEQ ID NO 197
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Cys Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala
        115                 120

<210> SEQ ID NO 198
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Glu Ile Lys Arg
            100                 105

<210> SEQ ID NO 199
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Cys Leu Glu Trp Ile
            35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser Ala
            115                 120

<210> SEQ ID NO 200
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
            35                  40                  45

Tyr Ser Ala Ser Phe Arg Tyr Thr Gly Val Pro Asp Arg Phe Thr Gly
    50                  55                  60

Ser Arg Ser Gly Thr Asp Phe Thr Phe Thr Ile Ser Ser Val Gln Ala
65                  70                  75                  80
```

Glu Asp Leu Ala Val Tyr Tyr Cys Gln Gln His Tyr Thr Thr Pro Pro
            85                  90                  95

Thr Phe Gly Cys Gly Thr Lys Val Glu Ile Lys Arg
            100                 105

<210> SEQ ID NO 201
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Ser Gly Ser Gly Ser Gly Ser Gly Ser Gly Ser Gly Ser Gly Ser
1               5                   10                  15

Gly Ser Gly Ser
            20

<210> SEQ ID NO 202
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 203
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gly Gly Gly Ser Gly Gly Gly Gly Ser Gly Gly Gly Gly Ser Gly
1               5                   10                  15

Gly Gly Ser
            20

<210> SEQ ID NO 204
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(40)
<223> OTHER INFORMATION: This sequence may encompass 1-20 "Gly Ser"
      repeating units

<400> SEQUENCE: 204

Gly Ser Gly Ser Gly Ser Gly Ser Gly Ser Gly Ser Gly Ser Gly Ser
1               5                   10                  15

Gly Ser Gly Ser Gly Ser Gly Ser Gly Ser Gly Ser Gly Ser Gly Ser
            20                  25                  30

```
Gly Ser Gly Ser Gly Ser Gly Ser
        35                  40

<210> SEQ ID NO 205
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(60)
<223> OTHER INFORMATION: This sequence may encompass 1-20 "Gly Gly Ser"
      repeating units

<400> SEQUENCE: 205

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser
    50                  55                  60
```

METHODS OF TREATING CANCER USING MULTI-SPECIFIC BINDING PROTEINS THAT BIND NKG2D, CD16 AND A TUMOR-ASSOCIATED ANTIGEN

CROSS-REFERENCE TO RELATED APPLICATIONS

This application claims the benefit of and priority to U.S. Provisional Patent Application No. 63/156,214, filed Mar. 3, 2021, the disclosure of which is hereby incorporated by reference in its entirety for all purposes.

SEQUENCE LISTING

The instant application contains a Sequence Listing which has been submitted electronically in ASCII format and is hereby incorporated by reference in its entirety. Said ASCII copy, created on Feb. 28, 2022, is named DFY-103US_SL.txt and is 194,767 bytes in size.

FIELD OF THE DISCLOSURE

The present disclosure relates to methods of treating cancer using multi-specific binding proteins that bind NKG2D, CD16 and a tumor-associated antigen such as HER2. In one aspect, the multi-specific binding protein is used in combination with a corticosteroid to reduce the risk of infusion-related reactions. In another aspect, the multi-specific binding protein is used to treat cancer that has low or moderate HER2 expression levels. The present disclosure also relates to pharmaceutical formulations containing the multi-specific binding proteins.

BACKGROUND

Cancer continues to be a significant health problem despite the substantial research efforts and scientific advances reported in the literature for treating this disease. Cancer immunotherapies are being developed to facilitate destruction of cancer cells using the patient's own immune system. The immune cells activated by cancer immunotherapies include T cells and natural killer (NK) cells. For example, bispecific T-cell engagers are designed to direct T cells against tumor cells, thereby rendering cytotoxicity against the tumor cells. Bispecific antibodies that bind NK cells and a tumor-associated antigen (TAA) have also been created for cancer treatment (see, e.g., WO 2016/134371).

HER2 is a transmembrane glycoprotein in the epidermal growth factor receptor family. It is a receptor tyrosine kinase and regulates cell survival, proliferation, and growth. HER2 plays an important role in human malignancies. The ERBB2 gene is amplified or overexpressed in approximately 30% of human breast cancers. Patients with HER2-overexpressing breast cancer have substantially lower overall survival rates and shorter disease-free intervals than patients whose cancer does not overexpress HER2. Moreover, overexpression of HER2 leads to increased breast cancer metastasis. Overexpression of HER2 is also known to occur in many other cancer types, including ovarian, esophageal, bladder and gastric cancer, salivary duct carcinoma, adenocarcinoma of the lung, and aggressive forms of uterine cancer, such as uterine serous endometrial carcinoma.

Multi-specific binding proteins that bind HER2 and one or more immune cell surface proteins have been studied. For example, WO 2018/152518 describes multi-specific binding proteins that bind HER2, NKG2D, and CD16. The present disclosure adds to these developments and provides clinical methods, including dosage regimens, to treat patients with specific HER2-targeting cancer immunotherapies with desired safety and efficacy. Furthermore, the present disclosure adds to the earlier developments in the field by providing formulations containing such cancer immunotherapies that are sufficiently stable and suitable for administration to patients.

SUMMARY OF THE DISCLOSURE

The present disclosure, in various embodiments, provides methods of treating cancer using a multi-specific binding protein having an antigen-binding site that binds a tumor-associated antigen such as HER2, an antigen-binding site that binds NKG2D, and an antibody Fc domain. The multi-specific binding protein can be used in combination with a corticosteroid to reduce the risk of infusion-related reactions. Alternatively, the multi-specific binding protein can be formulated at a high concentration, as disclosed herein, into a small volume, thereby allowing subcutaneous administration and reducing the risk of infusion-related reactions. The multi-specific binding protein can also be used to treat cancer that has low or moderate HER2 expression levels.

Accordingly, in one aspect, provided herein is a method of treating cancer by administering to a subject in need thereof a therapeutically effective amount of a multi-specific binding protein and a therapeutically effective amount of a corticosteroid to reduce infusion related reactions to the multi-specific binding protein. The multi-specific binding protein incorporates: (a) a first antigen-binding site that binds NKG2D; (b) a second antigen binding site that binds a tumor-associated antigen; and (c) a third antigen binding site that binds CD16. In some embodiments, the infusion related reactions include cytokine release syndrome, anaphylaxis, chills, fever/pyrexia, hypotension, hypertension, rigors, headache, dizziness, itching, sore throat, laryngeal edema, angioedema, redness/flushing, rash/urticaria, bronchospasm, tachycardia, bradycardia, auricular fibrillation, hypoxia, respiratory distress/dyspnea/shortness of breath/breathless sensation, chest tightness, nausea, vomiting, pain (e.g., chest pain, back pain), shivering, tremors, myalgia, tiredness, insomnia, asthenia, hypersensitivity, and/or diarrhea. In some embodiments, the corticosteroid is a glucocorticoid. In some embodiments, the glucocorticoid is selected from methylprednisolone, dexamethasone, hydrocortisone, prednisone, prednisolone, fluticasone, flumethasone, fluocinolone, budesonide, beclomethasone, ciclesonide, cortisone, triamcinolone, betamethasone, deflazacort, difluprednate, loteprednol, paramethasone, tixocortol, or pharmaceutically acceptable salts of any thereof. In particular embodiments, the glucocorticoid is methylprednisolone. In some embodiments the effective amount of methylprednisolone is 125 mg. In other particular embodiments, the glucocorticoid is dexamethasone.

In some embodiments, the corticosteroid is administered parenterally. In some embodiments the corticosteroid is administered intravenously. In some embodiments the corticosteroid is administered orally. In some embodiments the corticosteroid is administered prior to the administration of the multi-specific binding protein. In some embodiments the corticosteroid is administered within 6 hours prior to the administration of the multi-specific binding protein. In some embodiments, the corticosteroid is administered within 1 hour prior to the administration of the multi-specific binding protein.

In some embodiments, the method further includes administering to the subject a therapeutically effective amount of an antihistamine. In some embodiments the antihistamine is diphenhydramine. In some embodiments, the therapeutically effective amount of diphenhydramine is 40-50 mg. In some embodiments, the antihistamine is administered intravenously. In some embodiments, the antihistamine is administered within 60 minutes or within 30 minutes prior to the administration of the multi-specific binding protein.

In some embodiments, the method further includes administering to the subject a therapeutically effective amount of an antipyretic. In some embodiments, the antipyretic is acetaminophen. In some embodiments, the therapeutically effective amount of acetaminophen is 800-1000 mg. In some embodiments, the antipyretic is administered intravenously. In some embodiments, the antipyretic is administered within 60 minutes or within 30 minutes prior to the administration of the multi-specific binding protein.

In some embodiments, the tumor-associated antigen is HER2. In some embodiments, the cancer has HER2 expression level scored as 1+ or 2+.

In another aspect, the present disclosure provides a method of treating a cancer having a HER2 expression level scored as 1+ by administering a therapeutically effective amount of a multi-specific binding protein to a subject in need thereof. The multi-specific binding protein incorporates: (a) a first antigen-binding site that binds NKG2D; (b) a second antigen-binding site that binds HER2; and (c) an antibody Fc domain or a portion thereof sufficient to bind CD16, or a third antigen-binding site that binds CD16.

In another aspect, the present disclosure provides a method of treating a cancer having a HER2 expression level scored as 2+ by administering a therapeutically effective amount of a multi-specific binding protein to a subject in need thereof. The multi-specific binding protein incorporates: (a) a first antigen-binding site that binds NKG2D; (b) a second antigen-binding site that binds HER2; and (c) an antibody Fc domain or a portion thereof sufficient to bind CD16, or a third antigen-binding site that binds CD16.

In some embodiments, the cancer is a solid tumor. In some embodiments, the cancer is a locally advanced or metastatic solid tumor. In some embodiments, the cancer is selected from breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, non-small cell lung cancer (NSCLC), glioblastoma, esophageal cancer, squamous carcinoma of the skin, carcinoma of the salivary gland, biliary tract cancer, lung squamous, mesothelioma, liver cancer, sarcoma, bladder cancer, or gallbladder cancer. In particular embodiments, the cancer is urothelial bladder cancer or metastatic breast cancer.

In some embodiments, the multi-specific binding protein is administered to the subject in an initial four-week treatment cycle on day 1, day 8, and day 15. In some embodiments, the multi-specific binding protein is not administered on day 22. In some embodiments, the method further includes administering the multi-specific binding protein to the subject on day 1 and day 15 in each of one or more subsequent four-week treatment cycles after the initial treatment cycle. In some embodiments, each of the doses includes the multi-specific binding protein at an amount selected from $5.2 \times 10^{-5}$ mg/kg, $1.6 \times 10^{-4}$ mg/kg, $5.2 \times 10^{-4}$ mg/kg, $1.6 \times 10^{-3}$ mg/kg, $5.2 \times 10^{-3}$ mg/kg, $1.6 \times 10^{-2}$ mg/kg, $5.2 \times 10^{-2}$ mg/kg, $1.6 \times 10^{-1}$ mg/kg, 0.52 mg/kg, 1.0 mg/kg, 1.6 mg/kg, 5.2 mg/kg, 10 mg/kg, 20 mg/kg, or 50 mg/kg. In some embodiments, the multi-specific binding protein is administered by intravenous infusion. In some embodiments, the multi-specific binding protein is administered subcutaneously.

In some embodiments, the multi-specific binding protein is used as a monotherapy. In some embodiments, the method further includes administering to the subject an anti-PD-1 antibody. In some embodiments, the anti-PD-1 antibody is pembrolizumab. In some embodiments, 200 mg of pembrolizumab is administered on day 1 of the initial treatment cycle. In some embodiments, if the subject receives one or more subsequent treatment cycles, 200 mg of pembrolizumab is administered once every three weeks in the subsequent treatment cycles.

In some embodiments, a corticosteroid is administered to the subject on day 1 of the initial four-week cycle. In some embodiments, an antihistamine is administered to the subject on day 1 of the initial four-week cycle. In some embodiments, an analgesic is administered to the subject on day 1 of the initial four-week cycle.

In some embodiments, the multi-specific binding protein is formulated in a pharmaceutical composition that includes histidine, a sugar or sugar alcohol, and a polysorbate, at pH 5.5 to 6.5. In some embodiments, the pharmaceutical composition includes greater than 50 mg/mL of the multi-specific binding protein.

In another aspect, the present disclosure provides a method of treating cancer by administering to a subject in need thereof a pharmaceutical composition that includes: (i) greater than 50 mg/mL of a multi-specific binding protein incorporating (a) a first antigen-binding site that binds NKG2D, (b) a second antigen-binding site that binds a tumor-associated antigen, and (c) an antibody Fc domain or a portion thereof sufficient to bind CD16, or a third antigen-binding site that binds CD16; (ii) histidine; (iii) a sugar or sugar alcohol; and (iv) a polysorbate, at pH 5.5 to 6.5.

In another aspect, the present disclosure provides a method of treating cancer having a HER2 expression level scored as 1+ by administering to a subject in need thereof: (i) a pharmaceutical composition that includes: greater than 50 mg/mL of a multi-specific binding protein, histidine, a sugar or sugar alcohol, and a polysorbate, at pH 5.5 to 6.5, and (ii) a therapeutically effective amount of a corticosteroid to reduce one or more infusion-related reactions to the multi-specific binding protein. The multi-specific binding protein incorporates: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16.

In another aspect, the present disclosure provides a method of treating cancer having a HER2 expression level scored as 2+ by administering to a subject in need thereof: (i) a pharmaceutical composition containing greater than 50 mg/mL of a multi-specific binding protein, histidine, a sugar or sugar alcohol, and a polysorbate, at pH 5.5 to 6.5; and (ii) a therapeutically effective amount of a corticosteroid to reduce one or more infusion-related reactions to the multi-specific binding protein. The multi-specific binding protein incorporates: (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16.

In certain embodiments, the cancer is a solid tumor. In certain embodiments, the cancer is a locally advanced or metastatic solid tumor. In certain embodiments, the cancer is breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, non-small cell lung cancer (NSCLC), glioblastoma, esophageal cancer, squamous carcinoma of the skin, carcinoma of the salivary gland, biliary tract cancer, lung squamous, mesothelioma, liver cancer, sarcoma, bladder cancer, or gallbladder cancer. In certain embodiments, the cancer is urothelial bladder cancer or metastatic breast cancer.

In certain embodiments, the pharmaceutical composition is administered to the subject in an initial four-week treatment cycle on day 1, day 8, and day 15. In certain embodiments, the pharmaceutical composition is not administered on day 22. In certain embodiments, the method further includes administering the pharmaceutical composition to the subject on day 1 and day 15 in each of one or more subsequent four-week treatment cycles after the initial treatment cycle.

In certain embodiments, each of the administered doses of the pharmaceutical composition includes administration of the multi-specific binding protein at an amount selected from $5.2 \times 10^{-5}$ mg/kg, $1.6 \times 10^{-4}$ mg/kg, $5.2 \times 10^{-4}$ mg/kg, $1.6 \times 10^{-3}$ mg/kg, $5.2 \times 10^{-3}$ mg/kg, $1.6 \times 10^{-2}$ mg/kg, $5.2 \times 10^{-2}$ mg/kg, $1.6 \times 10^{-1}$ mg/kg, 0.52 mg/kg, 1.0 mg/kg, 1.6 mg/kg, 5.2 mg/kg, 10 mg/kg, 20 mg/kg, or 50 mg/kg. In certain embodiments, the pharmaceutical composition is administered by intravenous infusion. In certain embodiments, the multi-specific binding protein is administered subcutaneously.

In certain embodiments, the pharmaceutical composition is used as a monotherapy.

In other embodiments, the method further includes administering to the subject an anti-PD-1 antibody. In certain embodiments, the anti-PD-1 antibody is pembrolizumab. In certain embodiments, 200 mg of pembrolizumab is administered on Day 1 of the initial treatment cycle. In certain embodiments, if the subject receives one or more subsequent treatment cycles, 200 mg of pembrolizumab is administered once every three weeks in the subsequent treatment cycles.

In certain embodiments, a corticosteroid is administered to the subject on Day 1 of the initial four-week cycle. In certain embodiments, an antihistamine is administered to the subject on Day 1 of the initial four-week cycle. In certain embodiments, an antipyretic is administered to the subject on Day 1 of the initial four-week cycle.

In another aspect, the present disclosure provides a pharmaceutical composition containing greater than 50 mg/mL of a multi-specific binding protein histidine, a sugar or sugar alcohol, and a polysorbate, at pH 5.5 to 6.5. The multi-specific binding protein incorporates (a) a first antigen-binding site that binds NKG2D; (b) a second antigen-binding site that binds a tumor-associated antigen; and (c) an antibody Fc domain or a portion thereof sufficient to bind CD16, or a third antigen-binding site that binds CD16.

In some embodiments of any one of the preceding pharmaceutical compositions or methods using pharmaceutical compositions, the pharmaceutical composition contains greater than or equal to 60 mg/mL, greater than or equal to 70 mg/mL, greater than or equal to 80 mg/mL, greater than or equal to 90 mg/mL, greater than or equal to 100 mg/mL, greater than or equal to 125 mg/mL, greater than or equal to 150 mg/mL, greater than or equal to 175 mg/mL, or greater than or equal to 200 mg/mL of the multi-specific binding protein. In some embodiments, the pharmaceutical composition contains 60-250 mg/mL, 60-225 mg/mL, 60-200 mg/mL, 60-175 mg/mL, 50-150 mg/mL, 60-150 mg/mL, 60-125 mg/mL, 60-100 mg/mL, 60-90 mg/mL, 60-80 mg/mL, 60-70 mg/mL, 70-250 mg/mL, 70-225 mg/mL, 70-200 mg/mL, 70-175 mg/mL, 70-150 mg/mL, 70-150 mg/mL, 70-125 mg/mL, 70-100 mg/mL, 70-90 mg/mL, 70-80 mg/mL, 80-250 mg/mL, 80-225 mg/mL, 80-200 mg/mL, 80-175 mg/mL, 80-150 mg/mL, 80-150 mg/mL, 80-125 mg/mL, 80-100 mg/mL, 80-90 mg/mL, 90-250 mg/mL, 90-225 mg/mL, 90-200 mg/mL, 90-175 mg/mL, 90-150 mg/mL, 90-150 mg/mL, 90-125 mg/mL, 90-100 mg/mL, 100-250 mg/mL, 100-225 mg/mL, 100-200 mg/mL, 100-175 mg/mL, 100-150 mg/mL, 100-125 mg/mL, 125-250 mg/mL, 125-225 mg/mL, 125-200 mg/mL, 125-175 mg/mL, 125-150 mg/mL, 150-250 mg/mL, 150-225 mg/mL, 150-200 mg/mL, 150-175 mg/mL, 175-250 mg/mL, 175-225 mg/mL, 175-200 mg/mL, 200-250 mg/mL, or 200-225 mg/mL of the multi-specific binding protein. In some embodiments, the pharmaceutical composition contains 60 mg/mL, 70 mg/mL, 80 mg/mL, 90 mg/mL, 100 mg/mL, 125 mg/mL, 150 mg/mL, 175 mg/mL, 200 mg/mL, or 220 mg/mL of the multi-specific binding protein.

In some embodiments, the pH of the pharmaceutical composition is 5.8 to 6.2. In some embodiments, the pH of the pharmaceutical composition is 5.95 to 6.05. In some embodiments, the concentration of histidine in the pharmaceutical composition is 10 to 25 mM. In some embodiments, the concentration of histidine in the pharmaceutical composition is about 20 mM.

In some embodiments, the sugar or sugar alcohol is a disaccharide. In some embodiments, the disaccharide is sucrose. In some embodiments, the sugar or sugar alcohol is a sugar alcohol derived from a monosaccharide. In some embodiments, the sugar alcohol derived from a monosaccharide is sorbitol. In some embodiments, the concentration of the sugar or sugar alcohol in the pharmaceutical composition is 200 to 300 mM. In some embodiments, the concentration of the sugar or sugar alcohol in the pharmaceutical formulation is about 250 mM.

In some embodiments, the polysorbate is polysorbate 80. In some embodiments, the concentration of polysorbate 80 in the pharmaceutical composition is 0.005% (w/v) to 0.05% (w/v). In some embodiments, the concentration of polysorbate 80 in the pharmaceutical composition is about 0.01% (w/v). In some embodiments, the concentration of NaCl, if any, is about 10 mM or lower in the pharmaceutical formulation. In some embodiments, the concentration of NaCl, if any, is about 1 mM or lower in the pharmaceutical formulation.

In some embodiments, the first antigen-binding site includes a heavy chain variable domain with the complementarity-determining region 1 (CDR1), complementarity-determining region 2 (CDR2), and complementarity-determining region 3 (CDR3) sequences represented by the amino acid sequences of SEQ ID NOs: 168, 96, and 188, respectively, and a light chain variable domain with the CDR1, CDR2, and CDR3 sequences represented by the amino acid sequences of SEQ ID NOs: 99, 100, and 101, respectively. In some embodiments, the heavy chain variable domain has the CDR1, CDR2, and CDR3 sequences represented by the amino acid sequences of SEQ ID NOs: 168, 96, and 169, respectively; and the light chain variable domain has the CDR1, CDR2, and CDR3 sequences represented by the amino acid sequences of SEQ ID NOs: 99, 100, and 101, respectively.

In some embodiments, the heavy chain variable domain of the first antigen-binding site has an amino acid sequence at least 90% identical to SEQ ID NO:94, and the light chain variable domain has an amino acid sequence at least 90% identical to SEQ ID NO:98. In some embodiments, the heavy chain variable domain of the first antigen-binding site has the amino acid sequence of SEQ ID NO:94, and the light chain variable domain has the amino acid sequence of SEQ ID NO:98. In some embodiments, the first antigen-binding site that binds NKG2D is a Fab.

In some embodiments, the second antigen-binding site includes a heavy chain variable domain with the CDR1, CDR2, and CDR3 sequences represented by the amino acid sequences of SEQ ID NOs: 115, 116, and 117, respectively, and a light chain variable domain with the CDR1, CDR2, and CDR3 sequences represented by the amino acid sequences of SEQ ID NOs: 119, 120, and 121, respectively.

In some embodiments, the heavy chain variable domain of the second antigen-binding site has an amino acid sequence at least 90% identical to SEQ ID NO:195, and the light chain variable domain of the second antigen-binding site has an amino acid sequence at least 90% identical to SEQ ID NO:196. In some embodiments, the heavy chain variable domain of the second antigen-binding site has the amino acid sequence of SEQ ID NO:195, and the light chain variable domain of the second antigen-binding site has the amino acid sequence of SEQ ID NO:196.

In some embodiments, the second antigen-binding site is an scFv. In some embodiments, the light chain variable domain of the second antigen-binding site is linked to the heavy chain variable domain of the second antigen-binding site via a flexible linker. In some embodiments, the flexible linker has the amino acid sequence of SEQ ID NO:143.

In some embodiments, the light chain variable domain of the second antigen-binding site is positioned to the N-terminus of the heavy chain variable domain of the second antigen-binding site. In some embodiments, the heavy chain variable domain of the second antigen-binding site forms a disulfide bridge with the light chain variable domain of the second antigen-binding site. In some embodiments, the disulfide bridge is formed between C44 of the heavy chain variable domain and C100 of the light chain variable domain, the amino acid positions numbered under Kabat. In some embodiments, the cysteine residues at position 44 of the heavy chain variable domain and at position 100 of the light chain variable domain are introduced by mutating the wild-type residues to cysteine residues at these positions. In some embodiments, the scFv has the amino acid sequence of SEQ ID NO:139.

In some embodiments, the multi-specific binding protein includes an antibody Fc domain. In some embodiments, the antibody Fc domain includes a first antibody Fc polypeptide linked to the first antigen-binding site and a second antibody Fc polypeptide linked to the second antigen-binding site. In some embodiments, the first antibody Fc polypeptide is linked to the heavy chain portion of the first antigen-binding site. In some embodiments, the second antigen-binding site is linked to the second antibody Fc polypeptide via a hinge including Ala-Ser. In some embodiments, the first and second antibody Fc polypeptides each include a hinge and a CH2 domain of a human IgG1 antibody. In some embodiments, the first and second antibody Fc polypeptides each have an amino acid sequence at least 90% identical to amino acids 234-332 of a wild-type human IgG1 antibody. In some embodiments, the first and second antibody Fc polypeptides incorporate different mutations promoting heterodimerization. In some embodiments, the first antibody Fc polypeptide is a human IgG1 Fc sequence having K360E and K409W substitutions. In some embodiments, the second antibody Fc polypeptide is a human IgG1 Fc sequence having Q347R, D399V, and F405T substitutions.

In some embodiments, the multi-specific binding protein binds HER2 and includes a first polypeptide having the amino acid sequence of SEQ ID NO:141, a second polypeptide having the amino acid sequence of SEQ ID NO:140, and a third polypeptide having the amino acid sequence of SEQ ID NO:142.

In another aspect, the present disclosure provides a method of treating a HER2-overexpressing gastric cancer in a subject in need thereof by administering to the subject a multi-specific binding protein. The multi-specific binding protein incorporates: (a) a first antigen-binding site that binds NKG2D; (b) a second antigen-binding site that binds HER2; and (c) an antibody Fc domain or a portion thereof sufficient to bind CD16, or a third antigen-binding site that binds CD16.

In certain embodiments, the gastric cancer is advanced gastric cancer or cancer of the gastro-esophageal junction. In certain embodiments, the subject previously received a first line of therapy. In certain embodiments, the first line of therapy included a platinum salt and a fluoropyridine in combination with trastuzumab or a biosimilar to trastuzumab. In certain embodiments, the subject progressed after the first line of therapy. In certain embodiments, the cancer has a HER2 expression level scored as 3+ by immunohistochemistry. In other embodiments, the cancer has a HER2 expression level scored as 2+ by immunohistochemistry and HER2 gene amplification (e.g., determined by in situ hybridization).

In certain embodiments, the method of treating gastric cancer further includes administering an anti-PD-1 antibody to the subject. In certain embodiments, the anti-PD-1 antibody is nivolumab. In certain embodiments, nivolumab is administered to the subject at a dose of 120 to 600 mg. In certain embodiments, nivolumab is administered to the subject at a dose of 480 mg. In certain embodiments, nivolumab is administered once every four weeks. In certain embodiments, the multi-specific binding protein is administered in one or more four-week treatment cycles, and nivolumab is administered on Day 1 of the same treatment cycles. In certain embodiments, nivolumab is administered to the subject by intravenous infusion.

In certain embodiments, the method of treating gastric cancer further includes administering a cytoskeletal-disrupting chemotherapeutic agent to the subject. In certain embodiments, the cytoskeletal-disrupting chemotherapeutic agent is nab-paclitaxel. In certain embodiments, nab-paclitaxel is administered to the subject at a dose of 50 to 300 mg/m$^2$. In certain embodiments, nab-paclitaxel is administered to the subject at a dose of 100 mg/m$^2$. In certain embodiments, nab-paclitaxel is administered three times every four weeks. In certain embodiments, the multi-specific binding protein is administered in one or more four-week treatment cycles, and nab-paclitaxel is administered on Day 1, Day 8, and Day 15 of the same treatment cycles. In certain embodiments, nab-paclitaxel is not administered on Day 22 of the treatment cycles. In certain embodiments, nab-paclitaxel is administered to the subject by intravenous infusion.

In another aspect, the present disclosure provides a method of treating triple-negative breast cancer in a subject in need thereof by administering to the subject a multi-specific binding protein. The multi-specific binding protein incorporates: (a) a first antigen-binding site that binds NKG2D; (b) a second antigen-binding site that binds HER2;

and (c) an antibody Fc domain or a portion thereof sufficient to bind CD16, or a third antigen-binding site that binds CD16.

In certain embodiments, the subject is not eligible for treatment in combination with an anti-PD-L1 therapy or the cancer in the subject is PD-L1 negative. In certain embodiments, the subject (a) is eligible for treatment with nab-paclitaxel after failure of combination chemotherapy for metastatic disease or relapse within 6 months of adjuvant chemotherapy; (b) has a cancer that has no standard therapy or for which standard therapy has failed; or (c) has an advanced, optionally unresectable, recurrent, or metastatic triple-negative breast cancer. In certain embodiments, the triple-negative breast cancer has a PD-L1 score (CPS) less than 10 as measured by immunohistochemistry. In certain embodiments, the triple-negative breast cancer is metastatic or locally advanced. In certain embodiments, the subject has not previously received a chemotherapy or targeted systemic therapy.

In certain embodiments of the method of treating gastric cancer or triple-negative breast cancer, the multi-specific binding protein is administered on Day 1, Day 8, and Day 15 of an initial treatment cycle. In certain embodiments, the multi-specific binding protein is not administered on Day 22 of the initial treatment cycle. In certain embodiments, after the initial treatment cycle, the multi-specific binding protein is administered on Day 1 and Day 15 of one or more subsequent four-week treatment cycles. In certain embodiments, the multi-specific binding protein is administered, in each dose, at an amount selected from the group consisting of $5.2\times10^{-5}$ mg/kg, $1.6\times10^{-4}$ mg/kg, $5.2\times10^{-4}$ mg/kg, $1.6\times10^{-3}$ mg/kg, $5.2\times10^{-3}$ mg/kg, $1.6\times10^{-2}$ mg/kg, $5.2\times10^{-2}$ mg/kg, $1.6\times10^{-1}$ mg/kg, 0.52 mg/kg, 1.0 mg/kg, 1.6 mg/kg, 5.2 mg/kg, 10 mg/kg, 15 mg/kg, 20 mg/kg, and 50 mg/kg. In certain embodiments, the multi-specific binding protein is administered by intravenous infusion. In certain embodiments, the multi-specific binding protein is used as a monotherapy.

In certain embodiments, the first antigen-binding site takes the format of a Fab having a heavy chain variable domain (VH) and a light chain variable domain (VL). The VH of the Fab has complementarity-determining region 1 (CDR1), complementarity-determining region 2 (CDR2), and complementarity-determining region 3 (CDR3) sequences represented by the amino acid sequences of SEQ ID NOs: 168, 96, and 188, respectively. The VL of the Fab has CDR1, CDR2, and CDR3 sequences represented by the amino acid sequences of SEQ ID NOs: 99, 100, and 101, respectively. In certain embodiments, the VH of the Fab has CDR1, CDR2, and CDR3 sequences represented by the amino acid sequences of SEQ ID NOs: 168, 96, and 169, respectively. In certain embodiments, the VL of the Fab has CDR1, CDR2, and CDR3 sequences represented by the amino acid sequences of SEQ ID NOs: 99, 100, and 101, respectively. In certain embodiments, the VH of the Fab has an amino acid sequence at least 90% identical to SEQ ID NO:94, and the VL of the Fab has an amino acid sequence at least 90% identical to SEQ ID NO:98. In certain embodiments, the VH of the Fab has the amino acid sequence of SEQ ID NO:94, and the VL of the Fab has the amino acid sequence of SEQ ID NO:98.

In certain embodiments, the second antigen-binding site takes the format of a single chain variable fragment (scFv) having a VH and a VL. The VH of the scFv has CDR1, CDR2, and CDR3 sequences represented by the amino acid sequences of SEQ ID NOs: 115, 116, and 117, respectively. The VL of the scFv has CDR1, CDR2, and CDR3 sequences represented by the amino acid sequences of SEQ ID NOs: 119, 120, and 121, respectively. In certain embodiments, the VH of the scFv has an amino acid sequence at least 90% identical to SEQ ID NO:195, and the VL of the scFv has an amino acid sequence at least 90% identical to SEQ ID NO:196. In certain embodiments, the VH of the scFv has the amino acid sequence of SEQ ID NO:195, and the VL of the scFv has the amino acid sequence of SEQ ID NO:196. In certain embodiments, the VL of the scFv is linked to the VH of the scFv via a flexible linker, for example, a flexible linker having the amino acid sequence of SEQ ID NO:143. In certain embodiments, the VL of the scFv is positioned to the N-terminus of the VH of the scFv. In certain embodiments, the VH of the scFv forms a disulfide bridge with the VL of the scFv, for example, a disulfide bridge formed between C44 of the VH and C100 of the VL. In certain embodiments, the scFv has the amino acid sequence of SEQ ID NO:139.

In certain embodiments, the antibody Fc domain includes a first antibody Fc sequence linked to the Fab and a second antibody Fc sequence linked to the scFv. In certain embodiments, the first antibody Fc sequence is linked to the heavy chain portion of the Fab. In certain embodiments, the scFv is linked to the second antibody Fc sequence via a hinge having the amino acid sequence Ala-Ser. In certain embodiments, the first and second antibody Fc sequences each has a hinge and a CH2 domain of a human IgG1 antibody. In certain embodiments, the first and second antibody Fc sequences each has an amino acid sequence at least 90% identical to amino acids 234-332 of a wild-type human IgG1 antibody. In certain embodiments, the first and second antibody Fc sequences have different mutations that promote heterodimerization. For example, in certain embodiments, the first antibody Fc sequence is a human IgG1 Fc sequence incorporating K360E and K409W substitutions, and/or the second antibody Fc sequence is a human IgG1 Fc sequence incorporating Q347R, D399V, and F405T substitutions.

In certain embodiments, the multi-specific binding protein includes (a) a first polypeptide having the amino acid sequence of SEQ ID NO:141, (b) a second polypeptide having the amino acid sequence of SEQ ID NO:140, and (c) a third polypeptide having the amino acid sequence of SEQ ID NO:142.

In certain embodiments, the multi-specific binding protein, prior to the administration, has been formulated in a pharmaceutical composition at a concentration of 10 mg/mL to 50 mg/mL. In certain embodiments, the pharmaceutical composition contains 10 mg/mL to 25 mg/mL of the multi-specific binding protein. In certain embodiments, the pharmaceutical composition contains about 15 mg/mL of the multi-specific binding protein.

In certain embodiments, the pharmaceutical composition has a pH in the range of 5.5 to 6.5, for example, a pH of about 6.0. In certain embodiments, the pharmaceutical composition contains 5 to 50 mM histidine. In certain embodiments, the pharmaceutical composition contains 10 to 25 mM histidine. In certain embodiments, the pharmaceutical composition contains about 20 mM histidine.

In certain embodiments, the pharmaceutical composition contains 50 to 300 mM sugar or sugar alcohol (e.g., sucrose). In certain embodiments, the pharmaceutical composition contains 150 to 300 mM of the sugar or sugar alcohol. In certain embodiments, the pharmaceutical composition contains about 250 mM of the sugar or sugar alcohol.

In certain embodiments, the pharmaceutical composition contains 0.005% to 0.05% mM (w/v) polysorbate (e.g., polysorbate-80). In certain embodiments, the pharmaceutical composition contains 0.005% to 0.02% mM (w/v) of the polysorbate. In certain embodiments, the pharmaceutical composition contains about 0.01% (w/v) of the polysorbate.

In certain embodiments, the pharmaceutical composition contains (i) 10 mg/mL to 50 mg/mL of the multi-specific binding protein, (ii) 5 mM to 50 mM histidine, (iii) 50 mM to 300 mM sucrose, and (iv) 0.005% to 0.05% (w/v) polysorbate 80, at pH 5.5 to 6.5. In certain embodiments, the pharmaceutical composition contains (i) 10 mg/mL to 25 mg/mL of the multi-specific binding protein, (ii) 10 mM to 25 mM histidine, (iii) 150 mM to 300 mM sucrose, and (iv) 0.005% to 0.02% (w/v) polysorbate 80, at pH 5.5 to 6.5. In certain embodiments, the pharmaceutical composition contains (i) about 15 mg/mL of the multi-specific binding protein, (ii) about 20 mM histidine, (iii) about 250 mM sucrose, and (iv) about 0.01% (w/v) polysorbate 80, at about pH 6.0.

Other embodiments and details of the disclosure are presented herein below.

BRIEF DESCRIPTION OF THE DRAWINGS

FIGS. 2A-2E illustrate five exemplary formats of a multi-specific binding protein, e.g., a trispecific binding protein (TriNKET). As shown in FIG. 2A, either the NKG2D-binding domain or the tumor-associated antigen binding domain can take the scFv format (left arm). An antibody that contains an NKG2D targeting scFv, a tumor-associated antigen targeting Fab fragment, and a heterodimerized antibody constant region is referred herein as the F3-TriNKET. An antibody that contains a tumor-associated antigen targeting scFv, an NKG2D targeting Fab fragment, and a heterodimerized antibody constant region/domain that binds CD16 is referred herein as the F3'-TriNKET (FIG. 2E). As shown in FIG. 2B, both the NKG2D binding domain and a tumor-associated antigen binding domain can take the scFv format. FIGS. 2C to 2D are illustrations of an antibody with three antigen-binding sites, including two antigen-binding sites that bind a tumor-associated antigen, and the NKG2D-binding site fused to the heterodimerized antibody constant region. These antibody formats are referred herein as F4-TriNKET. FIG. 2C illustrates that the two tumor-associated antigen binding sites are in the Fab fragment format, and the NKG2D binding site in the scFv format. FIG. 2D illustrates that the tumor-associated antigen binding sites are in the scFv format, and the NKG2D binding site is in the scFv format. FIG. 2E represents a trispecific antibody (TriNKET) that contains a tumor-associated antigen targeting scFv, an NKG2D targeting Fab fragment, and a heterodimerized antibody constant region/domain ("CD domain") that binds CD16. The antibody format is referred herein as F3'-TriNKET. In certain exemplary multi-specific binding proteins, heterodimerization mutations on the antibody constant region include K360E and K409W on one constant domain; and Q347R, D399V and F405T on the opposite constant domain (shown as a triangular lock-and-key shape in the CD domains). The bold bar between the heavy and the light chain variable domains of the Fab fragments represents a disulfide bond.

FIG. 13A is an exemplary representation of one form of a κλ-Body; FIG. 13B is an exemplary representation of another κλ-Body.

FIG. 32A describes a trial design for a dose escalation phase. FIG. 32B describes a trial design for an efficacy expansion cohorts phase. Abbreviations used in the figures include: DL=dose level; Combo PD-1=combination therapy with pembrolizumab; PK=pharmacokinetics; PD=pharmacodynamics; HER2 HIGH=high expression of HER2 of 3+, per immunohistochemistry; MBC HER2 2+/1+ =metastatic breast cancer with medium/low expression of HER2 of 2+/1+, per immunohistochemistry; UBC 2L/3L=urothelial bladder cancer 2nd line-/3rd line treatment.

DETAILED DESCRIPTION

Definitions

Figure 1:
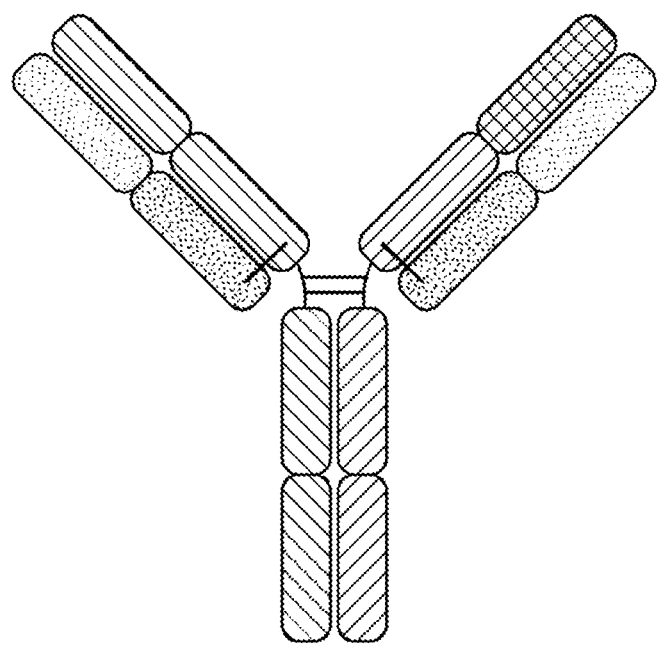
FIG. 1 is a representation of a heterodimeric, multi-specific antibody, e.g., a trispecific binding protein (TriNKET). Each arm can represent either an NKG2D binding domain or a tumor-associated antigen binding domain. In some embodiments, the NKG2D binding domain and the tumor-associated antigen binding domain can share a common light chain.

To facilitate an understanding of the present invention, a number of terms and phrases are defined below.

The terms "a" and "an" as used herein mean "one or more" and include the plural unless the context is inappropriate.

As used herein, the terms "Fab" and "scFv" refer to two different forms of protein fragments that each include an antigen-binding site. The term "antigen-binding site" refers to the part of the immunoglobulin molecule that participates in antigen binding. In human antibodies, the antigen-binding site is formed by amino acid residues of the N-terminal variable ("V") regions of the heavy ("H") and light ("L") chains, which are also called "VH" and "VL," respectively. Three highly divergent stretches within the V regions of the heavy and light chains are referred to as "hypervariable regions" which are interposed between more conserved flanking stretches known as "framework regions," or "FR." Thus the term "FR" refers to amino acid sequences which are naturally found between and adjacent to hypervariable regions in immunoglobulins. In a human antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." In certain animals, such as camels and cartilaginous fish, the antigen-binding site is formed by a single antibody chain providing a "single domain antibody." Antigen-binding sites can exist in an intact antibody, in an antigen-binding fragment of an antibody that retains the antigen-binding surface such as a Fab, or in a recombinant polypeptide such as an scFv, using a peptide linker to connect the heavy chain variable domain to the light chain variable domain in a single polypeptide. All the amino acid positions in heavy or light chain variable regions disclosed herein are numbered according to Kabat numbering, unless otherwise indicated.

The CDRs of an antigen-binding site can be determined by the methods described in Kabat et al., *J. Biol. Chem.* 252, 6609-6616 (1977) and Kabat et al., Sequences of protein of immunological interest. (1991), Chothia et al., *J. Mol. Biol.* 196:901-917 (1987), and MacCallum et al., *J. Mol. Biol.* 262:732-745 (1996). The CDRs determined under these definitions typically include overlapping or subsets of amino acid residues when compared against each other. In certain embodiments, the term "CDR" is a CDR as defined by MacCallum et al., *J. Mol. Biol.* 262:732-745 (1996) and Martin A., Protein Sequence and Structure Analysis of Antibody Variable Domains, in Antibody Engineering, Kontermann and Dubel, eds., Chapter 31, pp. 422-439, Springer-Verlag, Berlin (2001). In certain embodiments, the term "CDR" is a CDR as defined by Kabat et al., *J. Biol. Chem.* 252, 6609-6616 (1977) and Kabat et al., Sequences of protein of immunological interest. (1991). In certain embodiments, heavy chain CDRs and light chain CDRs of an antibody are defined using different conventions. For example, in certain embodiments, the heavy chain CDRs are defined according to MacCallum (supra), and the light CDRs are defined according to Kabat (supra). CDRH1, CDRH2 and CDRH3 denote the heavy chain CDRs, and CDRL1, CDRL2 and CDRL3 denote the light chain CDRs.

The term "tumor-associated antigen" or "TAA," as used herein, means any antigen including but not limited to a protein, glycoprotein, ganglioside, carbohydrate, or lipid that is associated with cancer. In certain embodiments, a tumor-associated antigen is expressed on the surface of a cell. For example, a tumor-associated antigen can be expressed on malignant cells or in the tumor microenvironment, such as on tumor-associated blood vessels, extracellular matrix, mesenchymal stroma, or immune infiltrates.

The term "HER2-overexpressing," as used herein to characterize a cancer, means HER2-positive cancer according to the ASCO/CAP HER2 testing guideline (Wolff et al., (2007) J. Clin. Oncol. 25(1):118-45) and the 2018 update (Wolff et al., (2018) J. Clin. Oncol. 36(20):2105-22). A HER2-overexpressing cancer can have a HER2 expression level scored as 3+ by immunohistochemistry, or a HER2 expression level scored as 2+ by immunohistochemistry further supported by detection of ERBB2 gene amplification (e.g., determined by in situ hybridization (ISH), chromogenic in situ hybridization (CISH), quantitative PCR, or DNA sequencing).

As used herein, the term "pharmaceutical formulation" refers to the combination of an active agent with a carrier, inert or active, making the composition especially suitable for diagnostic or therapeutic use in vivo or ex vivo.

As used herein, the terms "subject" and "patient" refer to an organism to be treated by the methods and compositions described herein. Such organisms preferably include, but are not limited to, mammals (e.g., murines, simians, equines, bovines, porcines, primates, canines, felines, and the like), and more preferably include humans.

The terms "treat," "treating," or "treatment," and other grammatical equivalents as used in this disclosure, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. The term "therapeutic benefit" refers to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route.

The term "about" refers to any minimal alteration in the concentration or amount of an agent that does not change the efficacy of the agent in preparation of a formulation and in treatment of a disease or disorder. In certain embodiments, the term "about" may include ±5%, ±10%, or ±15% of a specified numerical value or data point.

Ranges can be expressed in this disclosure as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed in this disclosure, and that each value is also disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units is also disclosed. For example, if 10 and 15 are disclosed, then 11, 12, 13, and 14 are also disclosed.

Throughout the description, where compositions are described as having, including, containing, incorporating, or comprising specific components, or where processes and methods are described as having, including, or comprising specific steps, it is intended that compositions and methods are inclusive or open-ended and do not exclude additional, unrecited components or steps. It is contemplated that, additionally, there are compositions of the present invention that consist essentially of, or consist of, the recited components, and that there are processes and methods according to the present invention that consist essentially of, or consist of, the recited steps.

As a general matter, compositions specifying a percentage are by weight unless otherwise specified. Further, if a variable is not accompanied by a definition, then the previous definition of the variable controls.

Multi-Specific Binding Proteins

The present disclosure provides pharmaceutical compositions or pharmaceutical formulations that contain a multi-specific binding protein having an antigen-binding site that binds a tumor-associated antigen such as HER2, an antigen-binding site that binds NKG2D, and an antibody Fc domain. Also provided are uses of the multi-specific binding proteins and pharmaceutical formulations in treating cancer, such as a locally advanced or metastatic solid tumor. The multi-specific binding proteins are capable of binding a target (e.g., HER2) on a cancer cell and NKG2D and CD16 on natural killer cells. Such binding brings the cancer cell into proximity with the natural killer cell, which facilitates direct and indirect destruction of the cancer cell by the natural killer cells.

The first component of the multi-specific binding proteins binds to NKG2D receptor-expressing cells, which can include but are not limited to NK cells, NKT cells, γδ T cells and CD8$^+$ αβ T cells. Upon NKG2D binding, the multi-specific binding proteins may block natural ligands, such as ULBP6 and MICA, from binding to NKG2D and activating NK cells. The second component of the multi-specific binding proteins binds to HER2-expressing cells, which can include but are limited to breast, ovarian, esophageal, bladder and gastric cancer, salivary duct carcinoma, adenocarcinoma of the lung and aggressive forms of uterine cancer, such as uterine serous endometrial carcinoma. The third component of the multi-specific binding proteins is an antibody Fc domain, which binds to cells expressing CD16 such as NK cells, macrophages, neutrophils, eosinophils, mast cells, and follicular dendritic cells.

The multi-specific binding proteins described herein can take various formats. For example, one format involves a heterodimeric, multi-specific antibody including a first immunoglobulin heavy chain, a second immunoglobulin heavy chain and an immunoglobulin light chain (FIG. 1). The first immunoglobulin heavy chain includes a first Fc (hinge-CH2-CH3) domain fused via either a linker or an antibody hinge to an Fab fragment composed of a heavy chain portion including a heavy chain variable domain and a heavy chain CH1 domain, and a light chain portion including a light chain variable domain and a light chain constant domain (CL), and the heavy chain and light chain portions of the Fab fragment pair and bind NKG2D. The second immunoglobulin heavy chain includes a second Fc (hinge-CH2-CH3) domain fused via either a linker or an antibody hinge to a single-chain variable fragment (scFv) composed of a heavy chain variable domain and light chain variable domain which pair and bind the tumor-associate antigen.

In some embodiments, the single-chain variable fragment (scFv) described above is linked to the antibody constant domain via a hinge sequence. In some embodiments, the hinge has the amino acid sequence Ala-Ser. In some other embodiments, the hinge has the amino acid sequences Ala-Ser and Thr-Lys-Gly. The hinge sequence can provide flexibility of binding to the target antigen, and balance between flexibility and optimal geometry.

In some embodiments, the single-chain variable fragment (scFv) described above includes a heavy chain variable domain and a light chain variable domain. In some embodiments, the heavy chain variable domain forms a disulfide bridge with the light chain variable domain to enhance stability of the scFv. For example, a disulfide bridge can be formed between the C44 residue of the heavy chain variable domain and the C100 residue of the light chain variable domain, the amino acid positions numbered under Kabat. For example, in some embodiments, the disulfide bridge is formed between a cysteine residue (naturally present or introduced by mutation) at position 44 (C44) of the VH of the scFv and a cysteine residue (naturally present or introduced by mutation) at position 100 (C100) of the VL of the scFv, numbered under the Kabat numbering scheme. In some embodiments, the heavy chain variable domain is linked to the light chain variable domain via a flexible linker. Any suitable linker can be used, for example, the (G4S)$_4$ linker (SEQ ID NO:143). In some embodiments of the scFv, the heavy chain variable domain is positioned at the N-terminus of the light chain variable domain. In some embodiments of the scFv, the heavy chain variable domain is positioned at the C terminus of the light chain variable domain.

Figure 2A:
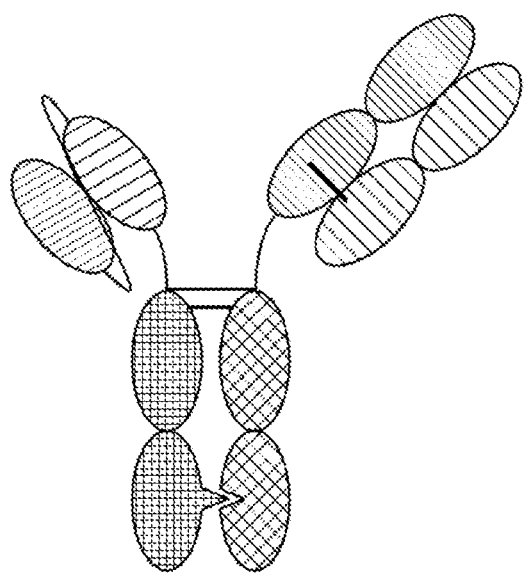
Figure 2B:
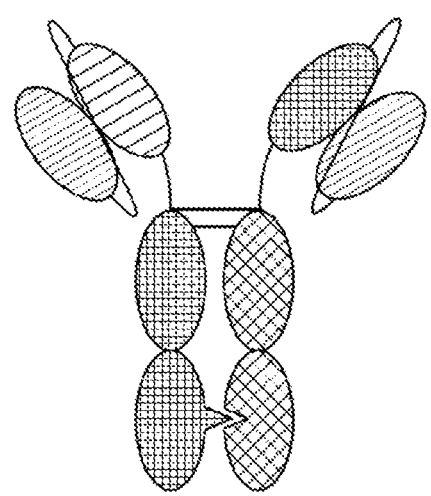
Figure 3:
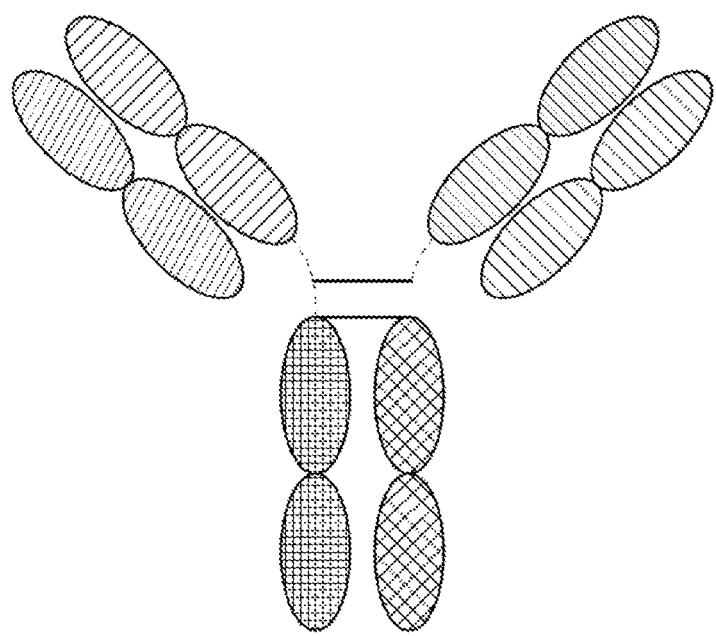
FIG. 3 is a representation of a TriNKET in the Triomab form, which is a trifunctional, bispecific antibody that maintains an IgG-like shape. This chimera consists of two half antibodies, each with one light and one heavy chain, that originate from two parental antibodies. Triomab form may be a heterodimeric construct containing ½ of rat antibody and ½ of mouse antibody.
Figure 4:
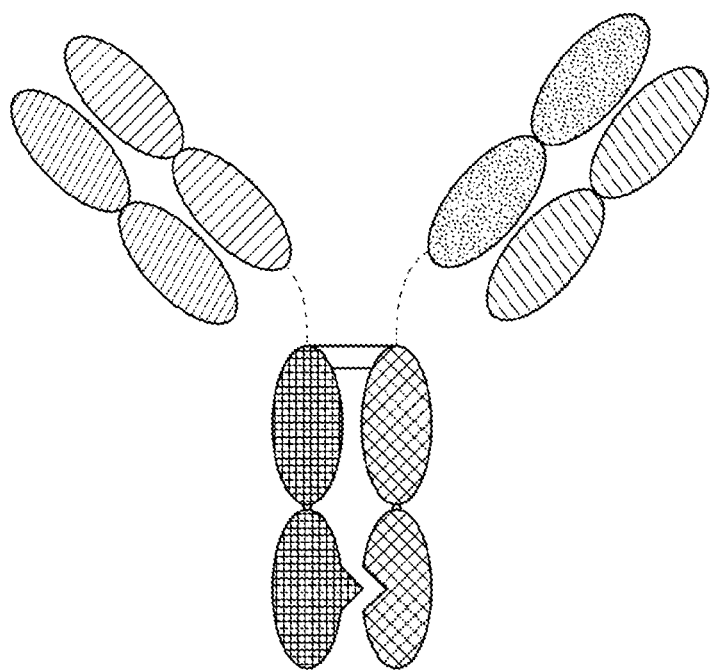
FIG. 4 is a representation of a TriNKET in the KiH Common Light Chain form, which involves the knobs-into-holes (KIHs) technology. KiH is a heterodimer containing 2 Fab fragments binding to target 1 and 2, and an Fc domain stabilized by heterodimerization mutations. TriNKET in the KiH format may be a heterodimeric construct with 2 Fab fragments binding to target 1 and target 2, containing two different heavy chains and a common light chain that pairs with both heavy chains.
Figure 5:
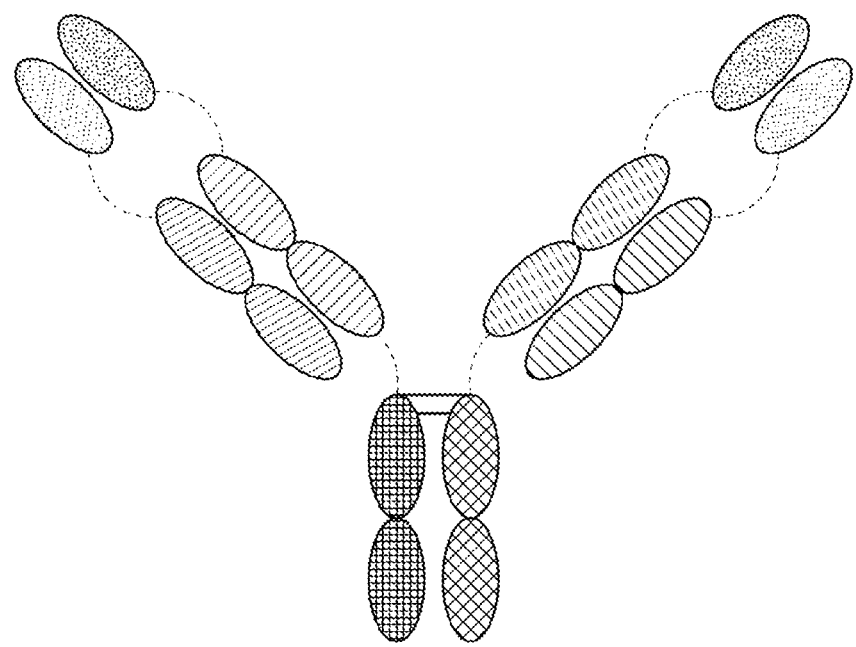
FIG. 5 is a representation of a TriNKET in the dual-variable domain immunoglobulin (DVD-Ig™) form, which combines the target-binding domains of two monoclonal antibodies via flexible naturally occurring linkers, and yields a tetravalent IgG-like molecule. DVD-Ig™ is a homodimeric construct where variable domain targeting antigen 2 is fused to the N-terminus of a variable domain of a Fab fragment targeting antigen 1. DVD-Ig™ form contains a normal Fc domain.
Figure 6:
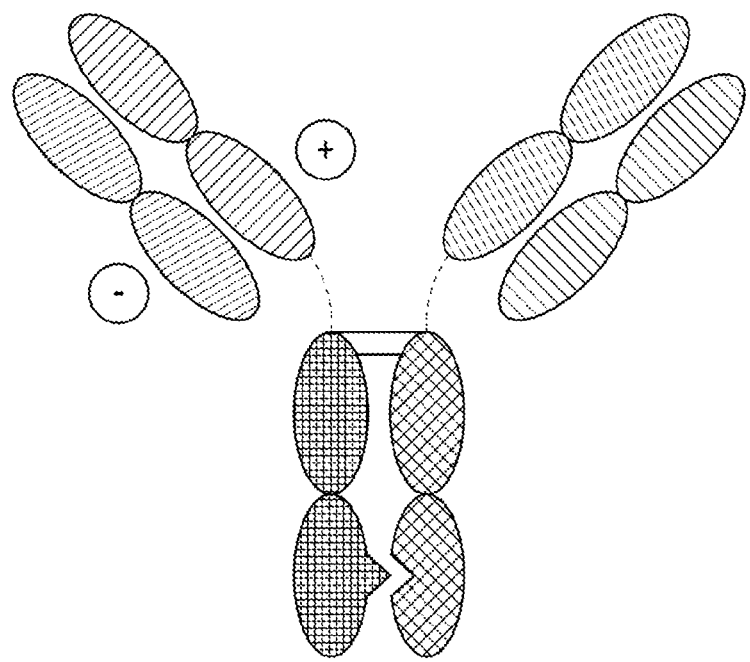
FIG. 6 is a representation of a TriNKET in the Orthogonal Fab fragment interface (Ortho-Fab) form, which is a heterodimeric construct that contains 2 Fab fragments binding to target 1 and target 2 fused to Fc. Light chain (LC)-heavy chain (HC) pairing is ensured by orthogonal interface. Heterodimerization is ensured by mutations in the Fc domain.
Figure 7:
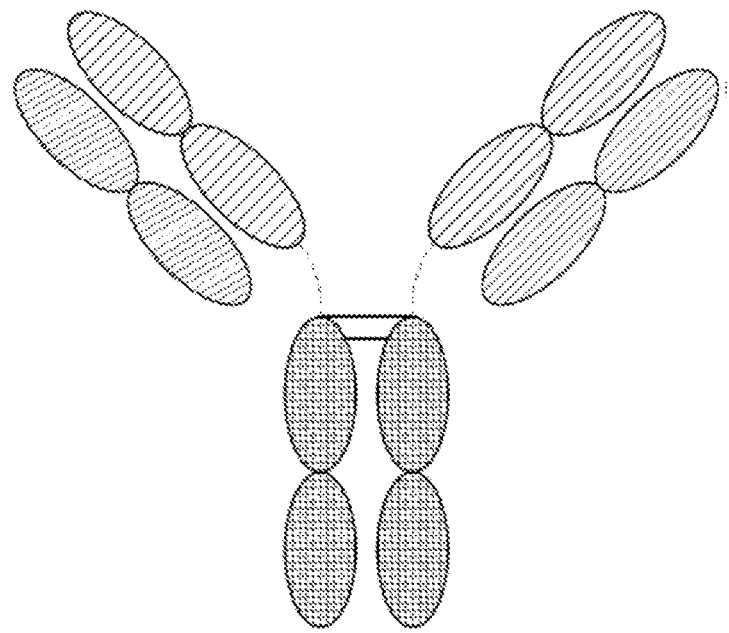
FIG. 7 is a representation of a TriNKET in the 2-in-1 Ig format.
Figure 8:
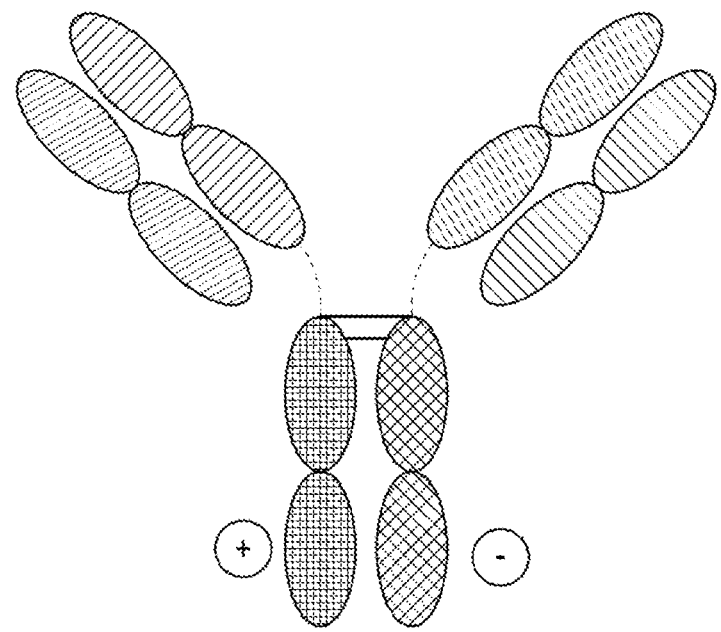
FIG. 8 is a representation of a TriNKET in the ES form, which is a heterodimeric construct containing two different Fab fragments binding to target 1 and target 2 fused to the Fc domain. Heterodimerization is ensured by electrostatic steering mutations in the Fc domain.
Figure 9:
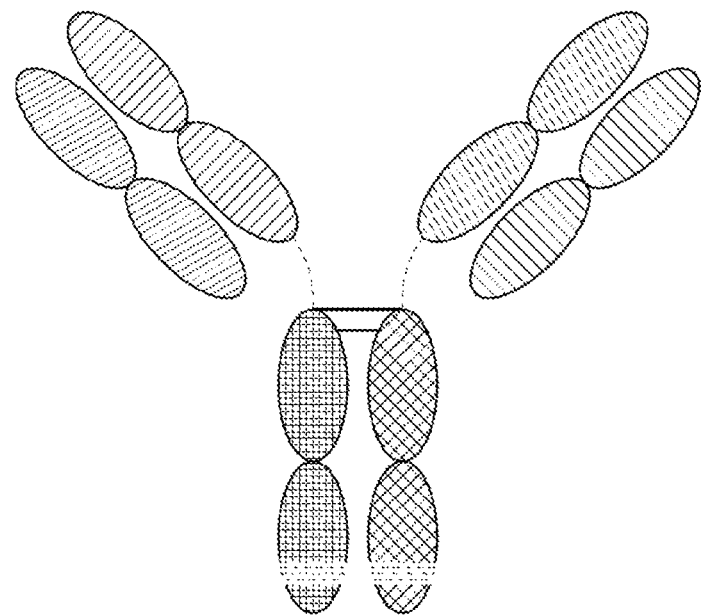
FIG. 9 is a representation of a TriNKET in the Fab Arm Exchange form: antibodies that exchange Fab fragment arms by swapping a heavy chain and attached light chain (half-molecule) with a heavy-light chain pair from another molecule, resulting in bispecific antibodies. Fab Arm Exchange form (cFae) is a heterodimer containing 2 Fab fragments binding to target 1 and 2, and an Fc domain stabilized by heterodimerization mutations.
Figure 10:
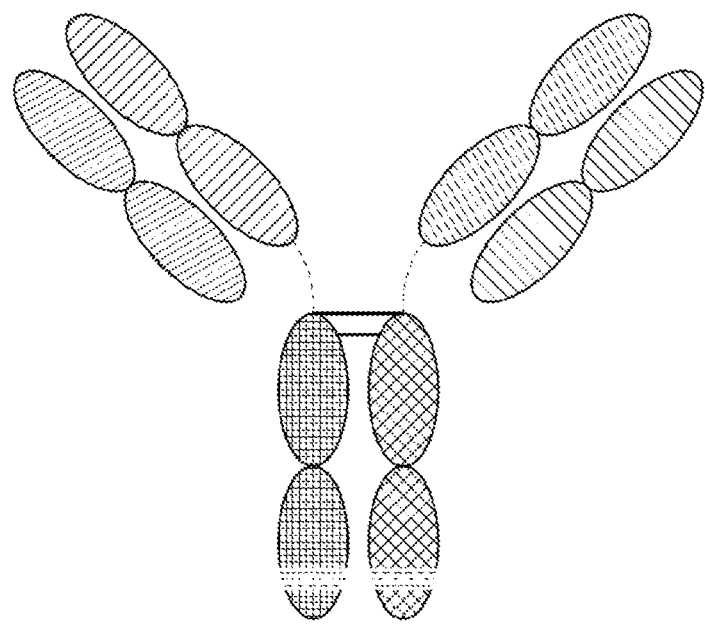
FIG. 10 is a representation of a TriNKET in the SEED Body form, which is a heterodimer containing 2 Fab fragments binding to target 1 and 2, and an Fc domain stabilized by heterodimerization mutations.
Figure 11:
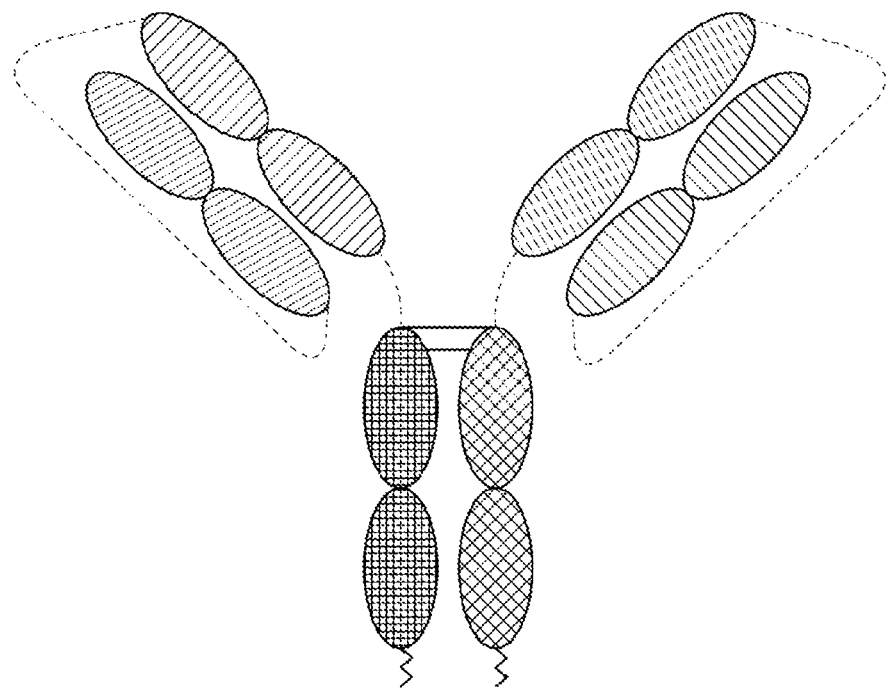
FIG. 11 is a representation of a TriNKET in the LuZ-Y form, in which a leucine zipper is used to induce heterodimerization of two different HCs. The LuZ-Y form is a heterodimer containing two different scFabs binding to target 1 and 2, fused to an Fc domain. Heterodimerization is ensured through leucine zipper motifs fused to the C-terminus of the Fc domain.
Figure 12:
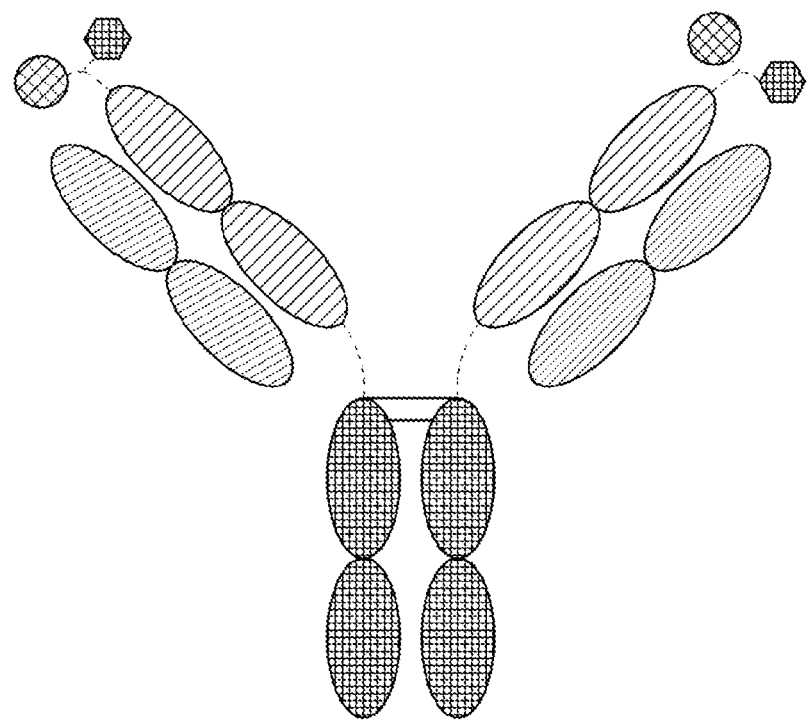
FIG. 12 is a representation of a TriNKET in the Cov-X-Body form.
Figure 13A:
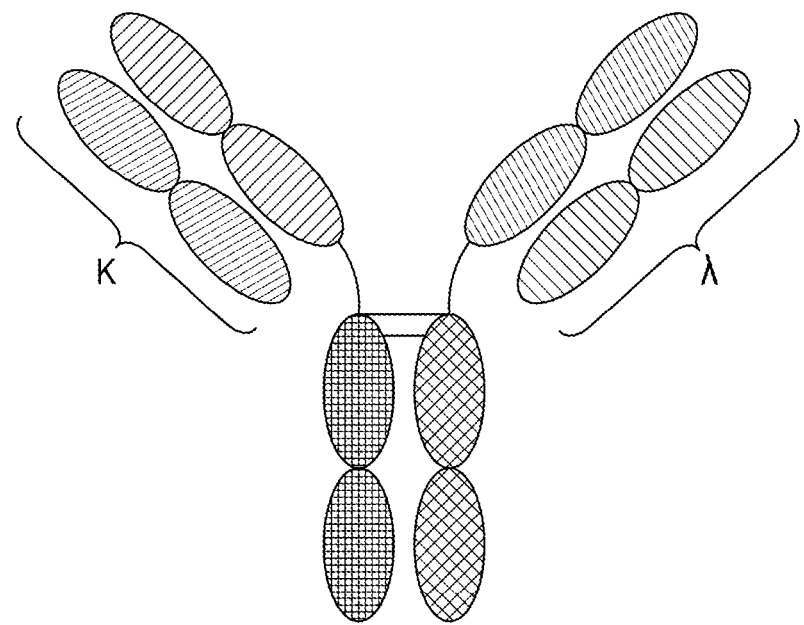
FIGS. 13A-13B are representations of TriNKETs in the κλ-Body forms, which are heterodimeric constructs with two different Fab fragments fused to a Fc domain stabilized by heterodimerization mutations: one Fab fragment targeting antigen 1 contains kappa LC, and the second Fab fragment targeting antigen 2 contains lambda LC.
Figure 13B:
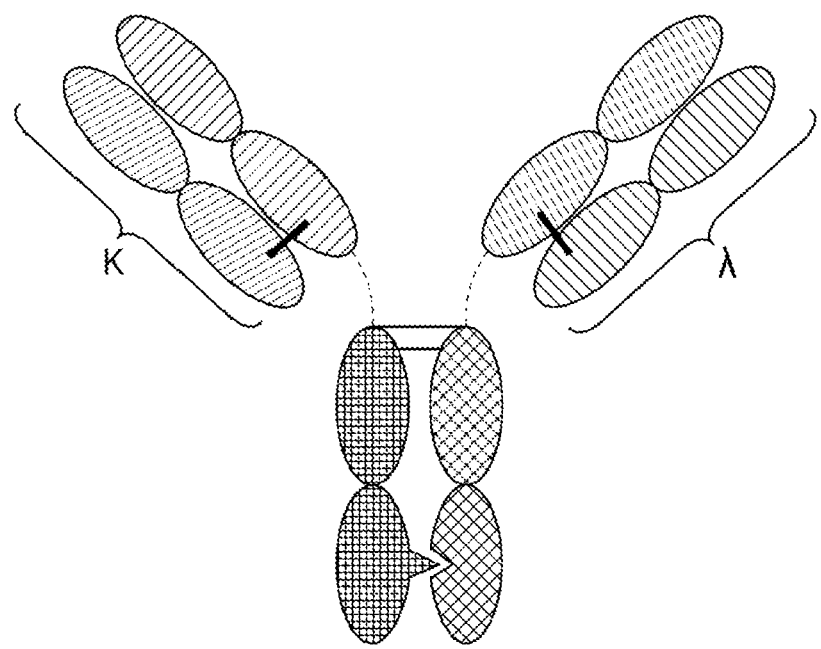
Figure 14:
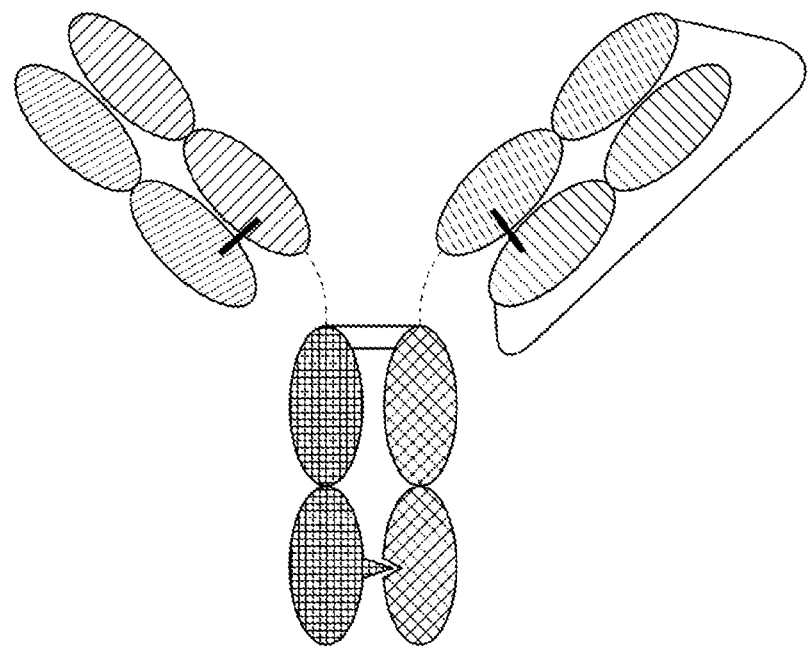
FIG. 14 is a representation of an Oasc-Fab heterodimeric construct that includes a Fab fragment binding to target 1 and an scFab binding to target 2, both of which are fused to the Fc domain. Heterodimerization is ensured by mutations in the Fc domain.
Figure 15:
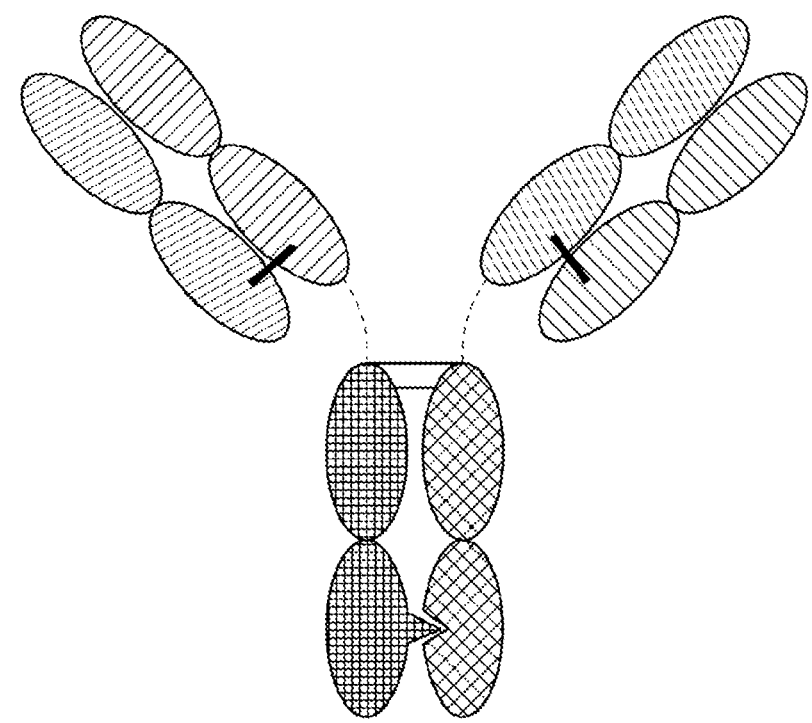
FIG. 15 is a representation of a DuetMab, which is a heterodimeric construct containing two different Fab fragments binding to antigens 1 and 2, and an Fc domain that is stabilized by heterodimerization mutations. Fab fragments 1 and 2 contain differential S—S bridges that ensure correct light chain and heavy chain pairing.
Figure 16:
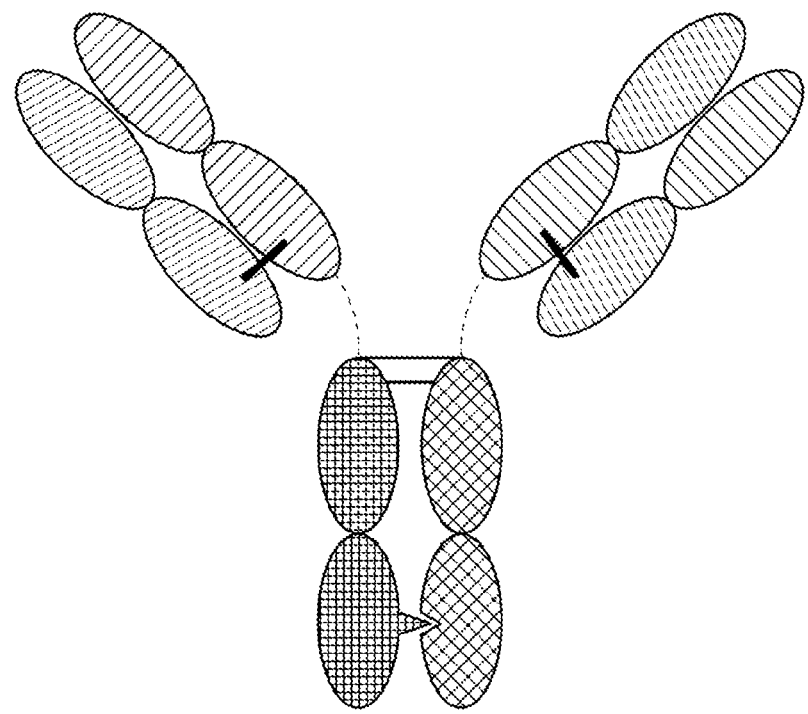
FIG. 16 is a representation of a CrossmAb, which is a heterodimeric construct with two different Fab fragments binding to targets 1 and 2, and an Fc domain stabilized by heterodimerization mutations. CL and CH1 domains, and VH and VL domains are switched, e.g., CH1 is fused in-line with VL, and CL is fused in-line with VH.
Figure 17:
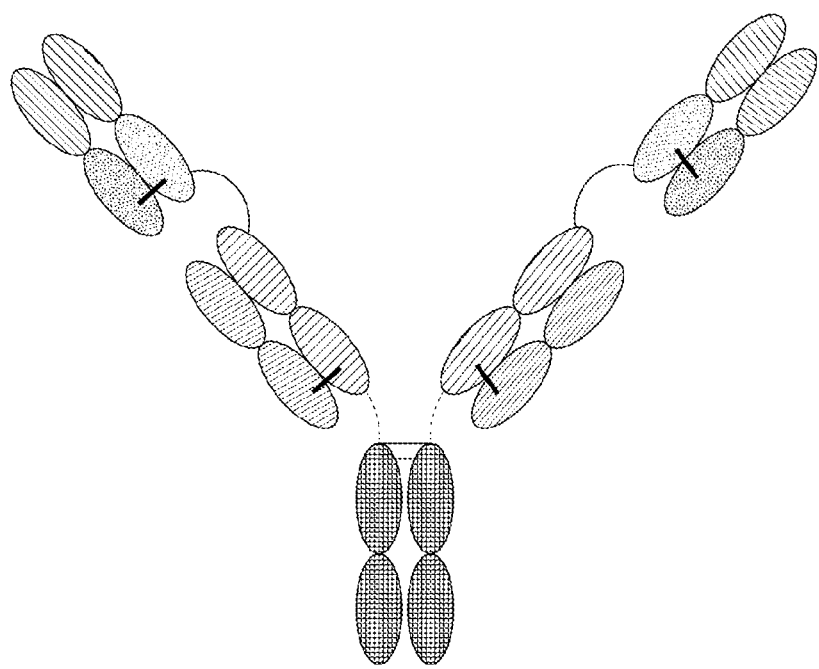
FIG. 17 is a representation of a Fit-Ig, which is a homodimeric construct where a Fab fragment binding to antigen 2 is fused to the N-terminus of HC of a Fab fragment that binds to antigen 1. The construct contains a wild-type Fc domain.

The multi-specific binding proteins described herein can further include one or more additional antigen-binding sites. The additional antigen-binding site(s) may be fused to the C-terminus of the constant region CH2 domain or to the C-terminus of the constant region CH3 domain, optionally via a linker sequence. In certain embodiments, the additional antigen-binding site(s) takes the form of a single-chain variable region (scFv) that is optionally disulfide-stabilized, resulting in a tetravalent or trivalent multi-specific binding protein. For example, a multi-specific binding protein includes an NKG2D-binding site, a TAA-binding site, a third antigen-binding site that binds a TAA, and an antibody constant region or a portion thereof sufficient to bind CD16, or a fourth antigen-binding site that binds CD16. Any one of these antigen-binding sites can either take the form of an Fab or an scFv, such as the scFv described above. In some embodiments, the third antigen-binding site binds a different TAA. In some embodiments, the third antigen-binding site binds to the same TAA, and the exemplary formats are shown in FIGS. 2C and 2D. Accordingly, the multi-specific binding proteins can provide bivalent engagement of the TAA. In certain embodiments, bivalent engagement of the TAA by the multi-specific proteins can stabilize the TAA on the cancer cell surface, and enhance cytotoxicity of NK cells towards the cancer cells. Bivalent engagement of the TAA by the multi-specific proteins can confer stronger binding of the multi-specific proteins to the cancer cells, thereby facilitating a stronger cytotoxic response of NK cells towards the cancer cells, especially towards cancer cells expressing a low level of the TAA.

Within the Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

In some embodiments, the antibody constant domain includes a CH2 domain and a CH3 domain of an IgG antibody, for example, a human IgG1 antibody. In some embodiments, mutations are introduced in the antibody constant domain to enable heterodimerization with another antibody constant domain. For example, if the antibody constant domain is derived from the constant domain of a human IgG1, the antibody constant domain can have an amino acid sequence at least 90% identical to amino acids 234-332 of a human IgG1 antibody that differs at one or more positions selected from Q347, Y349, L351, S354, E356, E357, K360, Q362, S364, T366, L368, K370, N390, K392, T394, D399, S400, D401, F405, Y407, K409, T411, and K439. All the amino acid positions in an Fc domain or hinge region disclosed herein are numbered according to EU numbering.

In some embodiments, the antibody constant domain can have an amino acid sequence at least 90% identical to amino acids 234-332 of a human IgG1 antibody that differs by one or more substitutions selected from Q347E, Q347R, Y349S, Y349K, Y349T, Y349D, Y349E, Y349C, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390D, N390E, K392L, K392M, K392V, K392F, K392D, K392E, T394F, D399R, D399K, D399V, S400K, S400R, D401K, F405A, F405T, Y407A, Y407I, Y407V, K409F, K409W, K409D, T411D, T411E, K439D, and K439E.

Individual components of the multi-specific binding proteins are described in more detail below.

NKG2D-Binding Site

Upon binding to the NKG2D receptor and CD16 receptor on natural killer cells and a TAA on cancer cells, the multi-specific binding proteins can engage more than one kind of NK-activating receptor, and may block the binding of natural ligands to NKG2D. In certain embodiments, the multi-specific binding proteins can agonize NK cells in humans. In some embodiments, the multi-specific binding proteins can agonize NK cells in humans and in other species such as rodents and cynomolgus monkeys.

Table 1 lists peptide sequences of heavy chain variable domains and light chain variable domains that, in combination, can bind to NKG2D. In some embodiments, the heavy chain variable domain and the light chain variable domain are arranged in Fab format. These NKG2D binding domains can vary in their binding affinity to NKG2D, nevertheless, they all activate human NK cells. Unless indicated otherwise, the CDR sequences provided in Table 1 are determined under Kabat.

TABLE 1

Exemplary NKG2D-Binding Sites

| Clones | Heavy chain variable domain amino acid sequence | Light chain variable domain amino acid sequence |
|---|---|---|
| ADI-27705 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 1) CDR1 (SEQ ID NO: 3)- GSFSGYYWS CDR2 (SEQ ID NO: 4)- EIDHSGSTNYNPSLKS CDR3 (SEQ ID NO: 5)- ARARGPWSFDP | DIQMTQSPSTLSASVGDRVTITC RASQSISSWLAWYQQKPGKAPK LLIYKASSLESGVPSRFSGSGSG TEFTLTISSLQPDDFATYYCQQY NSYPITFGGGTKVEIK (SEQ ID NO: 2) |
| ADI-27724 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 6) | EIVLTQSPGTLSLSPGERATLSCR ASQSVSSSYLAWYQQKPGQAPR LLIYGASSRATGIPDRFSGSGSG TDFTLTISRLEPEDFAVYYCQQY GSSPITFGGGTKVEIK (SEQ ID NO: 7) |
| ADI-27740 (A40) | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 7) | DIQMTQSPSTLSASVGDRVTITC RASQSIGSWLAWYQQKPGKAP KLLIYKASSLESGVPSRFSGSGS GTEFTLTISSLQPDDFATYYCQQ YHSFYTFGGGTKVEIK (SEQ ID NO: 9) |
| ADI-27741 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 10) | DIQMTQSPSTLSASVGDRVTITC RASQSIGSWLAWYQQKPGKAP KLLIYKASSLESGVPSRFSGSGS GTEFTLTISSLQPDDFATYYCQQ SNSYYTFGGGTKVEIK (SEQ ID NO: 11) |

TABLE 1-continued

Exemplary NKG2D-Binding Sites

| Clones | Heavy chain variable domain amino acid sequence | Light chain variable domain amino acid sequence |
| --- | --- | --- |
| ADI-27743 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 12) | DIQMTQSPSTLSASVGDRVTITC RASQSISSWLAWYQQKPGKAPK LLIYKASSLESGVPSRFSGSGSG TEFTLTISSLQPDDFATYYCQQY NSYPTFGGGTKVEIK (SEQ ID NO: 13) |
| ADI-28153 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWGFDPWGQGTLVTVSS (SEQ ID NO: 14) | ELQMTQSPSSLSASVGDRVTITC RTSQSISSYLNWYQQKPGQPPK LLIYWASTRESGVPDRFSGSGSG TDFTLTISSLQPEDSATYYCQQS YDIPYTFGQGTKLEIK (SEQ ID NO: 15) |
| ADI-28226 (C26) | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 16) | DIQMTQSPSTLSASVGDRVTITC RASQSISSWLAWYQQKPGKAPK LLIYKASSLESGVPSRFSGSGSG TEFTLTISSLQPDDFATYYCQQY GSFPITFGGGTKVEIK (SEQ ID NO: 17) |
| ADI-28154 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 18) | DIQMTQSPSTLSASVGDRVTITC RASQSISSWLAWYQQKPGKAPK LLIYKASSLESGVPSRFSGSGSG TDFTLTISSLQPDDFATYYCQQS KEVPWTFGQGTKVEIK (SEQ ID NO: 19) |
| ADI-29399 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 20) | DIQMTQSPSTLSASVGDRVTITC RASQSISSWLAWYQQKPGKAPK LLIYKASSLESGVPSRFSGSGSG TEFTLTISSLQPDDFATYYCQQY NSFPTFGGGTKVEIK (SEQ ID NO: 21) |
| ADI-29401 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 22) | DIQMTQSPSTLSASVGDRVTITC RASQSIGSWLAWYQQKPGKAP KLLIYKASSLESGVPSRFSGSGS GTEFTLTISSLQPDDFATYYCQQ YDIYPTFGGGTKVEIK (SEQ ID NO: 23) |
| ADI-29403 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 24) | DIQMTQSPSTLSASVGDRVTITC RASQSISSWLAWYQQKPGKAPK LLIYKASSLESGVPSRFSGSGSG TEFTLTISSLQPDDFATYYCQQY DSYPTFGGGTKVEIK (SEQ ID NO: 25) |
| ADI-29405 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 26) | DIQMTQSPSTLSASVGDRVTITC RASQSISSWLAWYQQKPGKAPK LLIYKASSLESGVPSRFSGSGSG TEFTLTISSLQPDDFATYYCQQY GSFPTFGGGTKVEIK (SEQ ID NO: 27) |
| ADI-29407 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 28) | DIQMTQSPSTLSASVGDRVTITC RASQSISSWLAWYQQKPGKAPK LLIYKASSLESGVPSRFSGSGSG TEFTLTISSLQPDDFATYYCQQY QSFPTFGGGTKVEIK (SEQ ID NO: 29) |
| ADI-29419 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 30) | DIQMTQSPSTLSASVGDRVTITC RASQSISSWLAWYQQKPGKAPK LLIYKASSLESGVPSRFSGSGSG TEFTLTISSLQPDDFATYYCQQY SSFSTFGGGTKVEIK (SEQ ID NO: 31) |

TABLE 1-continued

Exemplary NKG2D-Binding Sites

| Clones | Heavy chain variable domain amino acid sequence | Light chain variable domain amino acid sequence |
|---|---|---|
| ADI-29421 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 32) | DIQMTQSPSTLSASVGDRVTITC RASQSISSWLAWYQQKPGKAPK LLIYKASSLESGVPSRFSGSGSG TEFTLTISSLQPDDFATYYCQQY ESYSTFGGGTKVEIK (SEQ ID NO: 33) |
| ADI-29424 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 34) | DIQMTQSPSTLSASVGDRVTITC RASQSISSWLAWYQQKPGKAPK LLIYKASSLESGVPSRFSGSGSG TEFTLTISSLQPDDFATYYCQQY DSFITFGGGTKVEIK (SEQ ID NO: 35) |
| ADI-29425 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 36) | DIQMTQSPSTLSASVGDRVTITC RASQSISSWLAWYQQKPGKAPK LLIYKASSLESGVPSRFSGSGSG TEFTLTISSLQPDDFATYYCQQY QSYPTFGGGTKVEIK (SEQ ID NO: 37) |
| ADI-29426 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 38) | DIQMTQSPSTLSASVGDRVTITC RASQSIGSWLAWYQQKPGKAP KLLIYKASSLESGVPSRFSGSGS GTEFTLTISSLQPDDFATYYCQQ YHSFPTFGGGTKVEIK (SEQ ID NO: 39) |
| ADI-29429 | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 40) | DIQMTQSPSTLSASVGDRVTITC RASQSIGSWLAWYQQKPGKAP KLLIYKASSLESGVPSRFSGSGS GTEFTLTISSLQPDDFATYYCQQ YELYSYTFGGGTKVEIK (SEQ ID NO: 41) |
| ADI-29447 (F47) | QVQLQQWGAGLLKPSETLSLTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTVSS (SEQ ID NO: 42) | DIQMTQSPSTLSASVGDRVTITC RASQSISSWLAWYQQKPGKAPK LLIYKASSLESGVPSRFSGSGSG TEFTLTISSLQPDDFATYYCQQY DTFITFGGGTKVEIK (SEQ ID NO: 43) |
| ADI-27727 | QVQLVQSGAEVKKPGSSVKVSCKA SGGTFSSYAISWVRQAPGQGLEWM GGIIPIFGTANYAQKFQGRVTITADE STSTAYMELSSLRSEDTAVYYCAR GDSSIRHAYYYYGMDVWGQGTTV TVSS (SEQ ID NO: 44) CDR1 (SEQ ID NO: 45)- GTFSSYAIS (non-Kabat) or SYAIS (SEQ ID NO: 158) CDR2 (SEQ ID NO: 46)- GIIPIFGTANYAQKFQG CDR3 (SEQ ID NO: 47)- ARGDSSIRHAYYYYGMDV (non-Kabat) or GDSSIRHAYYYYGMDV (SEQ ID NO: 159) | DIVMTQSPDSLAVSLGERATINC KSSQSVLYSSNNKNYLAWYQQ KPGQPPKLLIYWASTRESGVPD RFSGSGSGTDFTLTISSLQAEDV AVYYCQQYYSTPITFGGGTKVE IK (SEQ ID NO: 48) CDR1 (SEQ ID NO: 49)- KSSQSVLYSSNNKNYLA CDR2 (SEQ ID NO: 50)- WASTRES CDR3 (SEQ ID NO: 51)- QQYYSTPIT |
| ADI-29443 (F43) | QLQLQESGPGLVKPSETLSLTCTVS GGSISSSSYYWGWIRQPPGKGLEWI GSIYYSGSTYYNPSLKSRVTISVDTS KNQFSLKLSSVTAADTAVYYCARG SDRFHPYFDYWGQGTLVTVSS (SEQ ID NO: 52) CDR1 (SEQ ID NO: 53)- GSISSSSYYWG (non-Kabat) or SSSYYWG (SEQ ID NO: 160) CDR2 (SEQ ID NO: 54)- SIYYSGSTYYNPSLKS CDR3 (SEQ ID NO: 55)- ARGSDRFHPYFDY (non-Kabat) or GSDRFHPYFDY (SEQ ID NO: 161) | EIVLTQSPATLSLSPGERATLSCR ASQSVSRYLAWYQQKPGQAPR LLIYDASNRATGIPARFSGSGSG TDFTLTISSLEPEDFAVYYCQQF DTWPPTFGGGTKVEIK (SEQ ID NO: 56) CDR1 (SEQ ID NO: 57)- RASQSVSRYLA CDR2 (SEQ ID NO: 58)- DASNRAT CDR3 (SEQ ID NO: 59)- QQFDTWPPT |

TABLE 1-continued

Exemplary NKG2D-Binding Sites

| Clones | Heavy chain variable domain amino acid sequence | Light chain variable domain amino acid sequence |
|---|---|---|
| ADI-29404 (F04) | QVQLQQWGAGLLKPSETLSTCAV YGGSFSGYYWSWIRQPPGKGLEWI GEIDHSGSTNYNPSLKSRVTISVDTS KNQFSLKLSSVTAADTAVYYCARA RGPWSFDPWGQGTLVTSS (SEQ ID NO: 60) | DIQMTQSPSTLSASVGDRVTITC RASQSISSWLAWYQQKPGKAPK LLIYKASSLESGVPSRFSGSGSG TEFTLTISSLQPDDFATYYCEQY DSYPTFGGGTKVEIK (SEQ ID NO: 61) |
| ADI-28200 | QVQLVQSGAEVKKPGSSVKVSCKA SGGTFSSYAISWVRQAPGQGLEWM GGIIPIFGTANYAQKFQGRVTITADE STSTAYMELSSLRSEDTAVYYCAR RGRKASGSFYYYGMDVWGQGTT VTVSS (SEQ ID NO: 62) CDR1 (SEQ ID NO: 63)- GTFSSYAIS (non-Kabat) or SYAIS (SEQ ID NO: 158) CDR2 (SEQ ID NO: 64)-GIIPIFGTANYAQKFQG CDR3 (SEQ ID NO: 65)- ARRGRKASGSFYYYYGMDV | DIVMTQSPDSLAVSLGERATINC ESSQSLLNSGNQKNYLTWYQQ KPGQPPKPLIYWASTRESGVPD RFSGSGSGTDFTLTISSLQAEDV AVYYCQNDYSYPYTFGQGTKL EIK (SEQ ID NO: 66) CDR1 (SEQ ID NO: 67)- ESSQSLLNSGNQKNYLT CDR2 (SEQ ID NO: 68)- WASTRES CDR3 (SEQ ID NO: 69)- QNDYSYPYT |
| ADI-29379 (E79) | QVQLVQSGAEVKKPGASVKVSCK ASGYTFTSYYMHWVRQAPGQGLE WMGIINPSGGSTSYAQKFQGRVTM TRDTSTSTVYMELSSLRSEDTAVYY CARGAPNYGDTTHDYYYMDVWG KGTTVTVSS (SEQ ID NO: 70) CDR1 (SEQ ID NO: 71)- YTFTSYYMH (non-Kabat) or SYYMH (SEQ ID NO: 162) CDR2 (SEQ ID NO: 72)- IINPSGGSTSYAQKFQG CDR3 (SEQ ID NO: 73)- ARGAPNYGDTTHDYYYMDV (non-Kabat) or GAPNYGDTTHDYYYMDV (SEQ ID NO: 163) | EIVMTQSPATLSVSPGERATLSC RASQSVSSNLAWYQQKPGQAP RLLIYGASTRATGIPARFSGSGS GTEFTLTISSLQSEDFAVYYCQQ YDDWPFTFGGGTKVEIK (SEQ ID NO: 74) CDR1 (SEQ ID NO: 75)- RASQSVSSNLA CDR2 (SEQ ID NO: 76)- GASTRAT CDR3 (SEQ ID NO: 77)- QQYDDWPFT |
| ADI-29463 (F63) | QVQLVQSGAEVKKPGASVKVSCK ASGYTFTGYYMHWVRQAPGQGLE WMGWINPNSGGTNYAQKFQGRVT MTRDTSISTAYMELSRLRSDDTAV YYCARDTGEYYDTDDHGMDVWG QGTTVTVSS (SEQ ID NO: 78) CDR1 (SEQ ID NO: 79)- YTFTGYYMH (non-Kabat) or GYYMH (SEQ ID NO: 164) CDR2 (SEQ ID NO: 80)- WINPNSGGTNYAQKFQG CDR3 (SEQ ID NO: 81)- ARDTGEYYDTDDHGMDV (non-Kabat) or DTGEYYDTDDHGMDV (SEQ ID NO: 165) | EIVLTQSPGTLSLSPGERATLSCR ASQSVSSNLAWYQQKPGQAPR LLIYGASTRATGIPARFSGSGSG TEFTLTISSLQSEDFAVYYCQQD DYWPPTFGGGTKVEIK (SEQ ID NO: 82) CDR1 (SEQ ID NO: 75)- RASQSVSSNLA CDR2 (SEQ ID NO: 76)- GASTRAT CDR3 (SEQ ID NO: 85)- QQDDYWPPT |
| ADI-27744 (A44) | EVQLLESGGGLVQPGGSLRLSCAAS GFTFSSYAMSWVRQAPGKGLEWV SAISGSGGSTYYADSVKGRFTISRD NSKNTLYLQMNSLRAEDTAVYYC AKDGGYYDSGAGDYWGQGTLVTV SS (SEQ ID NO: 86) CDR1 (SEQ ID NO: 87)- FTFSSYAMS (non-Kabat) or SYAMS (SEQ ID NO: 166) CDR2 (SEQ ID NO: 88)- AISGSGGSTYYADSVKG CDR3 (SEQ ID NO: 89)- AKDGGYYDSGAGDY (non-Kabat) or DGGYYDSGAGDY (SEQ ID NO: 167) | DIQMTQSPSSVSASVGDRVTITC RASQGIDSWLAWYQQKPGKAP KLLIYAASSLQSGVPSRFSGSGS GTDFTLTISSLQPEDFATYYCQQ GVSYPRTFGGGTKVEIK (SEQ ID NO: 90) CDR1 (SEQ ID NO: 91)- RASQGIDSWLA CDR2 (SEQ ID NO: 92)- AASSLQS CDR3 (SEQ ID NO: 93)- QQGVSYPRT |

TABLE 1-continued

Exemplary NKG2D-Binding Sites

| Clones | Heavy chain variable domain amino acid sequence | Light chain variable domain amino acid sequence |
|---|---|---|
| ADI-27749 (A49) | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPMGAAAGWFDPWGQGTLVT VSS (SEQ ID NO: 94) CDR1 (SEQ ID NO: 95)- FTFSSYSMN (non-Kabat) or SYSMN (SEQ ID NO: 168) CDR2 (SEQ ID NO: 96)- SISSSSSYIYYADSVKG CDR3 (SEQ ID NO: 97)- ARGAPMGAAAGWFDP (non-Kabat) or GAPMGAAAGWFDP (SEQ ID NO: 169) | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 98) CDR1 (SEQ ID NO: 99)- RASQGISSWLA CDR2 (SEQ ID NO: 100)- AASSLQS CDR3 (SEQ ID NO: 101)- QQGVSFPRT |
| ADI-29378 (E78) | QVQLVQSGAEVKKPGASVKVSCK ASGYTFTSYYMHWVRQAPGQGLE WMGIINPSGGSTSYAQKFQGRVTM TRDTSTSTVYMELSSLRSEDTAVYY CAREGAGFAYGMDYYYMDVWGK GTTVTVSS (SEQ ID NO: 102) CDR1 (SEQ ID NO: 71)- YTFTSYYMH (non-Kabat) or SYYMH (SEQ ID NO: 162) CDR2 (SEQ ID NO: 72)- IINPSGGSTSYAQKFQG CDR3 (SEQ ID NO: 105)- AREGAGFAYGMDYYYMDV (non-Kabat) or EGAGFAYGMDYYYMDV (SEQ ID NO: 170) | EIVLTQSPATLSLSPGERATLSCR ASQSVSSYLAWYQQKPGQAPR LLIYDASNRATGIPARFSGSGSG TDFTLTISSLEPEDFAVYYCQQS DNWPFTFGGGTKVEIK (SEQ ID NO: 106) CDR1 (SEQ ID NO: 107)- RASQSVSSYLA CDR2 (SEQ ID NO: 108)- DASNRAT CDR3 (SEQ ID NO: 109)- QQSDNWPFT |
| A49MI | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPIGAAAGWFDPWGQGTLVT VSS (SEQ ID NO: 144) CDR1 (SEQ ID NO: 95)- FTFSSYSMN (non-Kabat) or SYSMN (SEQ ID NO: 168) CDR2 (SEQ ID NO: 96)- SISSSSSYIYYADSVKG CDR3: (non-Kabat) ARGAPIGAAAGWFDP (SEQ ID NO: 172) or GAPIGAAAGWFDP (SEQ ID NO: 173) | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 98) CDR1 (SEQ ID NO: 99)- RASQGISSWLA CDR2 (SEQ ID NO: 100)- AASSLQS CDR3 (SEQ ID NO: 101)- QQGVSFPRT |
| A49MQ | EVQLVESGGGLVKPGGSLRLSCAA SGFTFSSYSMNWVRQAPGKGLEW VSSISSSSSYIYYADSVKGRFTISRD NAKNSLYLQMNSLRAEDTAVYYC ARGAPQGAAAGWFDPWGQGTLVT VSS (SEQ ID NO: 174) CDR1 (SEQ ID NO: 95)- FTFSSYSMN (non-Kabat) or SYSMN (SEQ ID NO: 168) CDR2 (SEQ ID NO: 96)- SISSSSSYIYYADSVKG CDR3 (non-Kabat) (SEQ ID NO: 175)- ARGAPQGAAAGWFDP or CDR3 (SEQ ID NO: 176)- GAPQGAAAGWFDP | DIQMTQSPSSVSASVGDRVTITC RASQGISSWLAWYQQKPGKAP KLLIYAASSLQSGVPSRFSGSGS GTDFTLTISSLQPEDFATYYCQQ GVSFPRTFGGGTKVEIK (SEQ ID NO: 98) CDR1 (SEQ ID NO: 99)- RASQGISSWLA CDR2 (SEQ ID NO: 100)- AASSLQS CDR3 (SEQ ID NO: 101)- QQGVSFPRT |

TABLE 1-continued

Exemplary NKG2D-Binding Sites

| Clones | Heavy chain variable domain amino acid sequence | Light chain variable domain amino acid sequence |
|---|---|---|
| A49ML | EVQLVESGGGLVKPGGSLRLSCAA<br>SGFTFSSYSMNWVRQAPGKGLEW<br>VSSISSSSSYIYYADSVKGRFTISRD<br>NAKNSLYLQMNSLRAEDTAVYYC<br>ARGAPLGAAAGWFDPWGQGTLVT<br>VSS<br>(SEQ ID NO: 177)<br>CDR1 (SEQ ID NO: 95)-<br>FTFSSYSMN (non-Kabat) or SYSMN<br>(SEQ ID NO: 168)<br>CDR2 (SEQ ID NO: 96)-<br>SISSSSSYIYYADSVKG<br>CDR3 (non-Kabat) (SEQ ID NO: 178)-<br>ARGAPLGAAAGWFDP or CDR3<br>(SEQ ID NO: 179)-<br>GAPLGAAAGWFDP | DIQMTQSPSSVSASVGDRVTITC<br>RASQGISSWLAWYQQKPGKAP<br>KLLIYAASSLQSGVPSRFSGSGS<br>GTDFTLTISSLQPEDFATYYCQQ<br>GVSFPRTFGGGTKVEIK<br>(SEQ ID NO: 98)<br>CDR1 (SEQ ID NO: 99)-<br>RASQGISSWLA<br>CDR2 (SEQ ID NO: 100)-<br>AASSLQS<br>CDR3 (SEQ ID NO: 101)-<br>QQGVSFPRT |
| A49MF | EVQLVESGGGLVKPGGSLRLSCAA<br>SGFTFSSYSMNWVRQAPGKGLEW<br>VSSISSSSSYIYYADSVKGRFTISRD<br>NAKNSLYLQMNSLRAEDTAVYYC<br>ARGAPFGAAAGWFDPWGQGTLVT<br>VSS<br>(SEQ ID NO: 180)<br>CDR1 (SEQ ID NO: 95)-<br>FTFSSYSMN (non-Kabat) or SYSMN<br>(SEQ ID NO: 168)<br>CDR2 (SEQ ID NO: 96)-<br>SISSSSSYIYYADSVKG<br>CDR3 (non-Kabat) (SEQ ID NO: 181)-<br>ARGAPFGAAAGWFDP or CDR3<br>(SEQ ID NO: 182)-<br>GAPFGAAAGWFDP | DIQMTQSPSSVSASVGDRVTITC<br>RASQGISSWLAWYQQKPGKAP<br>KLLIYAASSLQSGVPSRFSGSGS<br>GTDFTLTISSLQPEDFATYYCQQ<br>GVSFPRTFGGGTKVEIK<br>(SEQ ID NO: 98)<br>CDR1 (SEQ ID NO: 99)-<br>RASQGISSWLA<br>CDR2 (SEQ ID NO: 100)-<br>AASSLQS<br>CDR3 (SEQ ID NO: 101)-<br>QQGVSFPRT |
| A49MV | EVQLVESGGGLVKPGGSLRLSCAA<br>SGFTFSSYSMNWVRQAPGKGLEW<br>VSSISSSSSYIYYADSVKGRFTISRD<br>NAKNSLYLQMNSLRAEDTAVYYC<br>ARGAPVGAAAGWFDPWGQGTLVT<br>VSS<br>(SEQ ID NO: 183)<br>CDR1 (SEQ ID NO: 95)-<br>FTFSSYSMN (non-Kabat) or SYSMN<br>(SEQ ID NO: 168)<br>CDR2 (SEQ ID NO: 96)-<br>SISSSSSYIYYADSVKG<br>CDR3 (non-Kabat) (SEQ ID NO: 184)-<br>ARGAPVGAAAGWFDP or CDR3<br>(SEQ ID NO: 185)-<br>GAPVGAAAGWFDP | DIQMTQSPSSVSASVGDRVTITC<br>RASQGISSWLAWYQQKPGKAP<br>KLLIYAASSLQSGVPSRFSGSGS<br>GTDFTLTISSLQPEDFATYYCQQ<br>GVSFPRTFGGGTKVEIK<br>(SEQ ID NO: 98)<br>CDR1 (SEQ ID NO: 99)-<br>RASQGISSWLA<br>CDR2 (SEQ ID NO: 100)-<br>AASSLQS<br>CDR3 (SEQ ID NO: 101)-<br>QQGVSFPRT |
| A49-consensus | EVQLVESGGGLVKPGGSLRLSCAA<br>SGFTFSSYSMNWVRQAPGKGLEW<br>VSSISSSSSYIYYADSVKGRFTISRD<br>NAKNSLYLQMNSLRAEDTAVYYC<br>ARGAPXGAAAGWFDPWGQGTLVT<br>VSS, wherein X is M, L, I, V,<br>Q, or F (SEQ ID NO: 186)<br>CDR1 (SEQ ID NO: 95)-<br>FTFSSYSMN (non-Kabat) or SYSMN<br>(SEQ ID NO: 168)<br>CDR2 (SEQ ID NO: 96)-<br>SISSSSSYIYYADSVKG<br>CDR3 (non-Kabat)<br>(SEQ ID NO: 187)-<br>ARGAPXGAAAGWFDP or CDR3<br>(SEQ ID NO: 188)-<br>GAPXGAAAGWFDP, wherein X is M,<br>L, I, V, Q, or F | DIQMTQSPSSVSASVGDRVTITC<br>RASQGISSWLAWYQQKPGKAP<br>KLLIYAASSLQSGVPSRFSGSGS<br>GTDFTLTISSLQPEDFATYYCQQ<br>GVSFPRTFGGGTKVEIK<br>(SEQ ID NO: 98)<br>CDR1 (SEQ ID NO: 99)-<br>RASQGISSWLA<br>CDR2 (SEQ ID NO: 100)-<br>AASSLQS<br>CDR3 (SEQ ID NO: 101)-<br>QQGVSFPRT |

TABLE 1-continued

Exemplary NKG2D-Binding Sites

| Clones | Heavy chain variable domain amino acid sequence | Light chain variable domain amino acid sequence |
| --- | --- | --- |
| NKG2D binder in U.S. Pat. No. 9,273,136 | QVQLVESGGGLVKPGGSLRLSCAA SGFTFSSYGMHWVRQAPGKGLEWV AFIRYDGSNKYYADSVKGRFTISR DNSKNTLYLQMNSLRAEDTAVYY CAKDRGLGDGTYFDYWGQGTTVT VSS (SEQ ID NO: 110) | QSALTQPASVSGSPGQSITISCS GSSSNIGNNAVNWYQQLPGKAPK LLIYYDDLLPSGVSDRFSGSKSG TSAFLAISGLQSEDEADYYCAA WDDSLNGPVFGGGTKLTVL (SEQ ID NO: 111) |
| NKG2D binder in U.S. Pat. No. 7,879,985 | QVHLQESGPGLVKPSETLSLTCTVS DDSISSYYWSWIRQPPGKGLEWIGH ISYSGSANYNPSLKSRVTISVDTSKN QFSLKLSSVTAADTAVYYCANWD DAFNIWGQGTMVTVSS (SEQ ID NO: 112) | EIVLTQSPGTLSLSPGERATLSC RASQSVSSSYLAWYQQKPGQAPR LLIYGASSRATGIPDRFSGSGSG TDFTLTISRLEPEDFAVYYCQQY GSSPWTFGQGTKVEIK (SEQ ID NO: 113) |

In some embodiments, the Fab includes a heavy chain variable domain related to SEQ ID NO:94 and a light chain variable domain related to SEQ ID NO:98. For example, the heavy chain variable domain of the Fab can be at least 90% (e.g., 90%, 91%, 92%, 93%, 94%, 95%, 96%, 97%, 98%, 99%, or 100%) identical to SEQ ID NO:94, and/or incorporate amino acid sequences identical to the CDR1 (SEQ ID NO:95 or 168), CDR2 (SEQ ID NO:96), and CDR3 (SEQ ID NO:97 or 169) sequences of SEQ ID NO:94. Similarly, the light chain variable domain of the Fab can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO:101) sequences of SEQ ID NO:98.

In some embodiments, the Fab includes a heavy chain variable domain related to SEQ ID NO:144 and a light chain variable domain related to SEQ ID NO:98. For example, the heavy chain variable domain of the Fab can be at least 90% (e.g., 90%, 91%, 92%, 93%, 94%, 95%, 96%, 97%, 98%, 99%, or 100%) identical to SEQ ID NO:144, and/or incorporate amino acid sequences identical to the CDR1 (SEQ ID NO:95 or 168), CDR2 (SEQ ID NO:96), and CDR3 (SEQ ID NO:172 or 173) sequences of SEQ ID NO:144. Similarly, the light chain variable domain of the Fab can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO:101) sequences of SEQ ID NO:98.

In some embodiments, the Fab includes a heavy chain variable domain related to SEQ ID NO:174 and a light chain variable domain related to SEQ ID NO:98. For example, the heavy chain variable domain of the Fab can be at least 90% (e.g., 90%, 91%, 92%, 93%, 94%, 95%, 96%, 97%, 98%, 99%, or 100%) identical to SEQ ID NO:174, and/or incorporate amino acid sequences identical to the CDR1 (SEQ ID NO:95 or 168), CDR2 (SEQ ID NO:96), and CDR3 (SEQ ID NO:175 or 176) sequences of SEQ ID NO:174. Similarly, the light chain variable domain of the Fab can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO:101) sequences of SEQ ID NO:98.

In some embodiments, the Fab includes a heavy chain variable domain related to SEQ ID NO:177 and a light chain variable domain related to SEQ ID NO:98. For example, the heavy chain variable domain of the Fab can be at least 90% (e.g., 90%, 91%, 92%, 93%, 94%, 95%, 96%, 97%, 98%, 99%, or 100%) identical to SEQ ID NO:177, and/or incorporate amino acid sequences identical to the CDR1 (SEQ ID NO:95 or 168), CDR2 (SEQ ID NO:96), and CDR3 (SEQ ID NO:178 or 179) sequences of SEQ ID NO:177. Similarly, the light chain variable domain of the Fab can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO:101) sequences of SEQ ID NO:98.

In some embodiments, the Fab includes a heavy chain variable domain related to SEQ ID NO:180 and a light chain variable domain related to SEQ ID NO:98. For example, the heavy chain variable domain of the Fab can be at least 90% (e.g., 90%, 91%, 92%, 93%, 94%, 95%, 96%, 97%, 98%, 99%, or 100%) identical to SEQ ID NO:180, and/or incorporate amino acid sequences identical to the CDR1 (SEQ ID NO:95 or 168), CDR2 (SEQ ID NO:96), and CDR3 (SEQ ID NO:181 or 182) sequences of SEQ ID NO:180. Similarly, the light chain variable domain of the Fab can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO:101) sequences of SEQ ID NO:98.

In some embodiments, the Fab includes a heavy chain variable domain related to SEQ ID NO:183 and a light chain variable domain related to SEQ ID NO:98. For example, the heavy chain variable domain of the Fab can be at least 90% (e.g., 90%, 91%, 92%, 93%, 94%, 95%, 96%, 97%, 98%, 99%, or 100%) identical to SEQ ID NO:183, and/or incorporate amino acid sequences identical to the CDR1 (SEQ ID NO:95 or 168), CDR2 (SEQ ID NO:96), and CDR3 (SEQ ID NO:184 or 185) sequences of SEQ ID NO:183. Similarly, the light chain variable domain of the Fab can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO:101) sequences of SEQ ID NO:98.

In some embodiments, the Fab includes a heavy chain variable domain related to SEQ ID NO:186 and a light chain variable domain related to SEQ ID NO:98. For example, the heavy chain variable domain of the Fab can be at least 90% (e.g., 90%, 91%, 92%, 93%, 94%, 95%, 96%, 97%, 98%, 99%, or 100%) identical to SEQ ID NO:186, and/or incorporate amino acid sequences identical to the CDR1 (SEQ ID NO:95 or 168), CDR2 (SEQ ID NO:96), and CDR3 (SEQ ID NO:187 or 188) sequences of SEQ ID NO:186. Similarly, the light chain variable domain of the Fab can be at least 90% (e.g., 90%, 91%, 92%, 93%, 94%, 95%, 96%, 97%, 98%, 99%, or 100%) identical to SEQ ID NO:98, and/or incorporate amino acid sequences identical to the CDR1 (SEQ ID NO:99), CDR2 (SEQ ID NO:100), and CDR3 (SEQ ID NO:101) sequences of SEQ ID NO:98.

In some embodiments, the Fab includes a heavy chain variable domain related to SEQ ID NO:86 and a light chain variable domain related to SEQ ID NO:90. For example, the heavy chain variable domain of the Fab can be at least 90% (e.g., 90%, 91%, 92%, 93%, 94%, 95%, 96%, 97%, 98%, 99%, or 100%) identical to SEQ ID NO:86, and/or incorporate amino acid sequences identical to the CDR1 (SEQ ID NO:87 or 166), CDR2 (SEQ ID NO:88), and CDR3 (SEQ ID NO:89 or 167) sequences of SEQ ID NO:86. Similarly, the light chain variable domain of the Fab can be at least 90% (e.g., 90%, 91%, 92%, 93%, 94%, 95%, 96%, 97%, 98%, 99%, or 100%) identical to SEQ ID NO:90, and/or incorporate amino acid sequences identical to the CDR1 (SEQ ID NO:91), CDR2 (SEQ ID NO:92), and CDR3 (SEQ ID NO:93) sequences of SEQ ID NO:90.

In some embodiments, the Fab includes a heavy chain variable domain related to SEQ ID NO:102 and a light chain variable domain related to SEQ ID NO:106. For example, the heavy chain variable domain of the Fab can be at least 90% (e.g., 90%, 91%, 92%, 93%, 94%, 95%, 96%, 97%, 98%, 99%, or 100%) identical to SEQ ID NO:102, and/or incorporate amino acid sequences identical to the CDR1 (SEQ ID NO:71 or 162), CDR2 (SEQ ID NO:72), and CDR3 (SEQ ID NO:105 or 170) sequences of SEQ ID NO:102. Similarly, the light chain variable domain of the Fab can be at least 90% (e.g., 90%, 91%, 92%, 93%, 94%, 95%, 96%, 97%, 98%, 99%, or 100%) identical to SEQ ID NO:106, and/or incorporate amino acid sequences identical to the CDR1 (SEQ ID NO:107), CDR2 (SEQ ID NO:108), and CDR3 (SEQ ID NO:109) sequences of SEQ ID NO:106.

In some embodiments, the Fab includes a heavy chain variable domain related to SEQ ID NO:70 and a light chain variable domain related to SEQ ID NO:74. For example, the heavy chain variable domain of the Fab can be at least 90% (e.g., 90%, 91%, 92%, 93%, 94%, 95%, 96%, 97%, 98%, 99%, or 100%) identical to SEQ ID NO:70, and/or incorporate amino acid sequences identical to the CDR1 (SEQ ID NO:71 or 162), CDR2 (SEQ ID NO:72), and CDR3 (SEQ ID NO:73 or 163) sequences of SEQ ID NO:70. Similarly, the light chain variable domain of the Fab can be at least 90% (e.g., 90%, 91%, 92%, 93%, 94%, 95%, 96%, 97%, 98%, 99%, or 100%) identical to SEQ ID NO:74, and/or incorporate amino acid sequences identical to the CDR1 (SEQ ID NO:75), CDR2 (SEQ ID NO:76), and CDR3 (SEQ ID NO:77) sequences of SEQ ID NO:74.

In some embodiments, the Fab includes a heavy chain variable domain related to SEQ ID NO:70 and a light chain variable domain related to SEQ ID NO:74. For example, the heavy chain variable domain of the Fab can be at least 90% (e.g., 90%, 91%, 92%, 93%, 94%, 95%, 96%, 97%, 98%, 99%, or 100%) identical to SEQ ID NO:70, and/or incorporate amino acid sequences identical to the CDR1 (SEQ ID NO:71 or 162), CDR2 (SEQ ID NO:72), and CDR3 (SEQ ID NO:73 or 163) sequences of SEQ ID NO:70. Similarly, the light chain variable domain of the Fab can be at least 90% (e.g., 90%, 91%, 92%, 93%, 94%, 95%, 96%, 97%, 98%, 99%, or 100%) identical to SEQ ID NO:74, and/or incorporate amino acid sequences identical to the CDR1 (SEQ ID NO:75), CDR2 (SEQ ID NO:76), and CDR3 (SEQ ID NO:77) sequences of SEQ ID NO:74.

In some embodiments, the Fab includes a heavy chain variable domain related to SEQ ID NO:78 and a light chain variable domain related to SEQ ID NO:82. For example, the heavy chain variable domain of the Fab can be at least 90% (e.g., 90%, 91%, 92%, 93%, 94%, 95%, 96%, 97%, 98%, 99%, or 100%) identical to SEQ ID NO:78, and/or incorporate amino acid sequences identical to the CDR1 (SEQ ID NO:79 or 164), CDR2 (SEQ ID NO:80), and CDR3 (SEQ ID NO:81 or 165) sequences of SEQ ID NO:78. Similarly, the light chain variable domain of the Fab can be at least 90% (e.g., 90%, 91%, 92%, 93%, 94%, 95%, 96%, 97%, 98%, 99%, or 100%) identical to SEQ ID NO:82, and/or incorporate amino acid sequences identical to the CDR1 (SEQ ID NO:75), CDR2 (SEQ ID NO:76), and CDR3 (SEQ ID NO:77) sequences of SEQ ID NO:82.

The multi-specific binding proteins can bind to NKG2D-expressing cells, which include but are not limited to NK cells, γδ T cells and CD8$^+$αβ T cells. Upon NKG2D binding, the multi-specific binding proteins may block natural ligands, such as ULBP6 and MICA, from binding to NKG2D and activating NK cells.

In certain embodiments, the Fab or the multi-specific binding protein binds to NKG2D with an affinity of $K_D$ of 2 nM to 120 nM, e.g., 2 nM to 110 nM, 2 nM to 100 nM, 2 nM to 90 nM, 2 nM to 80 nM, 2 nM to 70 nM, 2 nM to 60 nM, 2 nM to 50 nM, 2 nM to 40 nM, 2 nM to 30 nM, 2 nM to 20 nM, 2 nM to 10 nM, about 15 nM, about 14 nM, about 13 nM, about 12 nM, about 11 nM, about 10 nM, about 9 nM, about 8 nM, about 7 nM, about 6 nM, about 5 nM, about 4.5 nM, about 4 nM, about 3.5 nM, about 3 nM, about 2.5 nM, about 2 nM, about 1.5 nM, about 1 nM, between about 0.5 nM to about 1 nM, about 1 nM to about 2 nM, about 2 nM to 3 nM, about 3 nM to 4 nM, about 4 nM to about 5 nM, about 5 nM to about 6 nM, about 6 nM to about 7 nM, about 7 nM to about 8 nM, about 8 nM to about 9 nM, about 9 nM to about 10 nM, about 1 nM to about 10 nM, about 2 nM to about 10 nM, about 3 nM to about 10 nM, about 4 nM to about 10 nM, about 5 nM to about 10 nM, about 6 nM to about 10 nM, about 7 nM to about 10 nM, or about 8 nM to about 10 nM.

In certain embodiments, the Fab binds to NKG2D with a $K_D$ of 2 nM to 120 nM, as measured by surface plasmon resonance. In certain embodiments, the multi-specific binding protein binds to NKG2D with a $K_D$ of 2 nM to 120 nM, as measured by surface plasmon resonance. In certain embodiments, the Fab binds to NKG2D with a $K_D$ of 10 nM to 62 nM, as measured by surface plasmon resonance. In certain embodiments, the multi-specific binding protein binds to NKG2D with a $K_D$ of 10 nM to 62 nM, as measured by surface plasmon resonance.

In some embodiments, the Fab described above is linked to an antibody Fc polypeptide. In some embodiments, the heavy chain portion of the Fab is linked to the N-terminus of an antibody Fc polypeptide.

TAA-Binding Site

Tumor-associated antigens (TAAs) that can be targeted by the multi-specific binding protein include but are not limited to ANO1, BCMA, EpCAM, CAIX, CEA, CCR4, CD2, CD123, CD133, CD19, CD20, CD22, CD25, CD30, CD33, CD37, CD38, CD40, CD52, CD70, CLAUDIN-18.2, DLL3, EGFR/ERBB1, GD2, IGF1R, HER2/ERBB2, HER3/ERBB3, HER4/ERBB4, MUC1, cMET, SLAMF7, PSMA, mesothelin, MICA, MICB, TRAILR1, TRAILR2, TROP2, MAGE-A3, B7.1, B7.2, CTLA4, PD1, 5T4, GPNMB, FR-alpha, PAPP-A, FLT3, GPC3, CXCR4, ROR1, ROR2, HLA-E, PD-L1, VLA4, CD44, CD13, CD15, CD47, CLL1, CD81, CD23, CD79a, CD79b, CD80, CRLF2, SLAMF7, CD138, CA125, NaPi2b, Nectin4, ADAMS, ADAMS, SLC44A4, CA19-9, LILRB1, LILRB2, LILRB3, LILRB4, LILRB5, ULRA 1, LILRA2, LILRA3, ULRA4, LILRA5, and ULRA6, CCR8, CD7, CTLA4, CX3CR1, ENTPD1, HAVCR2, IL-1R2, PDCD1LG2, TIGIT, TNFRSF4, TNFRSF8, TNFRSF9, GEM, NT5E, TNFRSF18, MUC1, P-cadherin, Plexin-A1, TNFRSF10B, STEAP1, CDCP1, PTK7, Axl, erbB-3, EDNRB, Tyrp1, CD14, CD163, CSF3R, Siglec-9, ITGAM, VISTA, B7-H4 (VTCN1), CCR1, LRRC25, PTAFR, SIRPB1, TLR2, TLR4, CD300LB, ATP1A3, CCR5, MUC1 (or MUC1-C), Plexin-A1, TNFRSF10B, STEAP1, CDCP1, PTK7, AXL, EDNRB, OLR1, and TYRP1.

In certain embodiments, the tumor-associated antigen is HER2. Table 2 lists amino acid sequences of heavy chain variable domains and light chain variable domains that, in combination, can bind to HER2. In certain embodiments, an antigen-binding site that binds HER2 takes the format of an scFv.

TABLE 2

Exemplary HER2-Binding Sites

| Clones | Heavy chain variable domain amino acid sequence | Light chain variable domain amino acid sequence |
|---|---|---|
| Trastuzumab | EVQLVESGGGLVQPGGSLRLSCA ASGFNIKDTYIHWVRQAPGKGLE WVARIYPTNGYTRYADSVKGRFT ISADTSKNTAYLQMNSLRAEDTA VYYCSRWGGDGFYAMDYWGQG TLVTVSS (SEQ ID NO: 114) CDR1(SEQ ID NO: 115)-GFNIKDT CDR2 (SEQ ID NO: 116)-YPTNGY CDR3 (SEQ ID NO: 117)- WGGDGFYAMDY | DIQMTQSPSSLSASVGDRVTITCR ASQDVNTAVAWYQQKPGKAPK LLIYSASFLYSGVPSRFSGSRSGT DFTLTISSLQPEDFATYYCQQHY TTPPTFGQGTKVEIK (SEQ ID NO: 118) CDR1(SEQ ID NO: 119)- QDVNTAVA CDR2 (SEQ ID NO: 120)- SASFLYS CDR3 (SEQ ID NO: 121)- QQHYTTPPT |
| Trastuzumab (VH and VL in scFv construct) | EVQLVESGGGLVQPGGSLRLSCA ASGFNIKDTYIHWVRQAPGKCLE WVARIYPTNGYTRYADSVKGRFT ISADTSKNTAYLQMNSLRAEDTA VYYCSRWGGDGFYAMDYWGQG TLVTVSS (SEQ ID NO: 195) CDR1(SEQ ID NO: 115)-GFNIKDT CDR2 (SEQ ID NO: 116)-YPTNGY CDR3 (SEQ ID NO: 117)- WGGDGFYAMDY | DIQMTQSPSSLSASVGDRVTITC RASQDVNTAVAWYQQKPGKAPK LLIYSASFLYSGVPSRFSGSRSGT DFTLTISSLQPEDFATYYCQQHY TTPPTFGCGTKVEIK (SEQ ID NO: 196) CDR1(SEQ ID NO: 119)- QDVNTAVA CDR2 (SEQ ID NO: 120)- SASFLYS CDR3 (SEQ ID NO: 121)- QQHYTTPPT |
| Trastuzumab -scFv | DIQMTQSPSSLSASVGDRVTITCRASQDVNTAVAWYQQKPGKAPKLLI YSASFLYSGVPSRFSGSRSGTDFTLTISSLQPEDFATYYCQQHYTTPP TFGCGTKVEIKGGGGSGGGGSGGGGSGGGGSEVQLVESGGGLVQPGGS LRLSCAASGFNIKDTYIHWVRQAPGKCLEWVARIYPTNGYTRYADSVK GRFTISADTSKNTAYLQMNSLRAEDTAVYYCSRWGGDGFYAMDYWG QGTLVTVSS (SEQ ID NO: 139) | |
| Pertuzumab | EVQLVESGGGLVQPGGSLRLSCA ASGFTFTDYTMDWVRQAPGKGL EWVADVNPNSGGSIYNQRFKGRF TLSVDRSKNTLYLQMNSLRAEDT AVYYCARNLGPSFYFDYWGQGT LVTVSSA (SEQ ID NO: 122) CDR1 (SEQ ID NO: 123)-GFTFTDY CDR2 (SEQ ID NO: 124)-NPNSGG CDR3 (SEQ ID NO: 125)- NLGPSFYFDY | DIQMTQSPSSLSASVGDRVTITCK ASQDVSIGVAWYQQKPGKAPKL LIYSASYRYTGVPSRFSGSGSGTD FTLTISSLQPEDFATYYCQQYYIY PYTFGQGTKVEIKR (SEQ ID NO: 126) CDR1 (SEQ ID NO: 127)- QDVSIGVA CDR2 (SEQ ID NO: 128)- SASYRYT CDR3 (SEQ ID NO: 129)- QQYYIYPYT |
| Pertuzumab (VH and VL in scFv construct) | EVQLVESGGGLVQPGGSLRLSCA ASGFTFTDYTMDWVRQAPGKGL EWVADVNPNSGGSIYNQRFKGRF TLSVDRSKNTLYLQMNSLRAEDT AVYYCARNLGPSFYFDYWGQGT LVTVSSA (SEQ ID NO: 197) CDR1 (SEQ ID NO: 123)-GFTFTDY CDR2 (SEQ ID NO: 124)-NPNSGG CDR3 (SEQ ID NO: 125)- NLGPSFYFDY | DIQMTQSPSSLSASVGDRVTITCK ASQDVSIGVAWYQQKPGKAPKL LIYSASYRYTGVPSRFSGSGSGTD FTLTISSLQPEDFATYYCQQYYIY PYTFGCGTKVEIKR (SEQ ID NO: 198) CDR1 (SEQ ID NO: 127)- QDVSIGVA CDR2 (SEQ ID NO: 128)- SASYRYT CDR3 (SEQ ID NO: 129)- QQYYIYPYT |

TABLE 2-continued

Exemplary HER2-Binding Sites

| Clones | Heavy chain variable domain amino acid sequence | Light chain variable domain amino acid sequence |
|---|---|---|
| Pertuzumab scFv | | DIQMTQSPSSLSASVGDRVTITCKASQDVSIGVAWYQQKPGKAPKLLI YSASYRYTGVPSRFSGSGSGTDFTLTISSLQPEDFATYYCQQYYIYPY TFGCGTKVEIKRGGGGSGGGGSGGGGSGGGGSEVQLVESGGGLVQPGG SLRLSCAASGFTFTDYTMDWVRQAPGKCLEWVADVNPNSGGSIYNQRF KGRFTLSVDRSKNTLYLQMNSLRAEDTAVYYCARNLGPSFYFDYWG QGTLVTVSSA (SEQ ID NO: 189) |
| MGAH22 (US 8,802,093) | QVQLQQSGPELVKPGASLKLSCT ASGFNIKDTYIHWVKQRPEQGLE WIGRIYPTNGYTRYDPKFQDKATI TADTSSNTAYLQVSRLTSEDTAV YYCSRWGGDGFYAMDYWGQGA SVTVSS (SEQ ID NO: 130) CDR1 (SEQ ID NO: 131)-GFNIKDT CDR2 (SEQ ID NO: 132)-YPTNGY CDR3 (SEQ ID NO: 133)- WGGDGFYAMDY | DIVMTQSHKFMSTSVGDRVSITC KASQDVNTAVAWYQQKPGHSP KLLIYSASFRYTGVPDRFTGSRSG TDFTFTISSVQAEDLAVYYCQQH YTTPPTFGGGTKVEIK (SEQ ID NO: 134) CDR1 (SEQ ID NO: 135)- QDVNTAVA CDR2 (SEQ ID NO: 136)- SASFRYT CDR3 (SEQ ID NO: 137)- QQHYTTPPT |
| MGAH22 (VH and VL in scFv construct) | QVQLQQSGPELVKPGASLKLSCT ASGFNIKDTYIHWVKQRPEQCLE WIGRIYPTNGYTRYDPKFQDKATI TADTSSNTAYLQVSRLTSEDTAV YYCSRWGGDGFYAMDYWGQGA SVTVSSA (SEQ ID NO: 199) CDR1 (SEQ ID NO: 131)-GFNIKDT CDR2 (SEQ ID NO: 132)-YPTNGY CDR3 (SEQ ID NO: 133)- WGGDGFYAMDY | DIVMTQSHKFMSTSVGDRVSITC KASQDVNTAVAWYQQKPGHSP KLLIYSASFRYTGVPDRFTGSRSG TDFTFTISSVQAEDLAVYYCQQH YTTPPTFGCGTKVEIKR (SEQ ID NO: 200) CDR1 (SEQ ID NO: 135)- QDVNTAVA CDR2 (SEQ ID NO: 136)- SASFRYT CDR3 (SEQ ID NO: 137)- QQHYTTPPT |
| MGAH22 scFv | | DIVMTQSHKFMSTSVGDRVSITCKASQDVNTAVAWYQQKPGHSPKLL IYSASFRYTGVPDRFTGSRSGTDFTFTISSVQAEDLAVYYCQQHYTT PPTFGCGTKVEIKRGGGGSGGGGSGGGGSGGGGSQVQLQQSGPELVK PGASLKLSCTASGFNIKDTYIHWVKQRPEQCLEWIGRIYPTNGYTRY DPKFQDKATITADTSSNTAYLQVSRLTSEDTAVYYCSRWGGDGFYAM DYWGQGASVTVSSA (SEQ ID NO: 171) |

Alternatively, novel antigen-binding sites that can bind to HER2 can be identified by screening for binding to the amino acid sequence defined by SEQ ID NO:138 or a mature extracellular fragment thereof.

(SEQ ID NO: 138)
MELAALCRWGLLLALLPPGAASTQVCTGTDMKLRLP

ASPETHLDMLRHLYQGCQVVQGNLELTYLPTNASL

SFLQDIQEVQGYVLIAHNQVRQVPLQRLRIVRGTQ

LFEDNYALAVLDNGDPLNNTTPVTGASPGGLRELQ

LRSLTEILKGGVLIQRNPQLCYQDTILWKDIFHKN

NQLALTLIDTNRSRACHPCSPMCKGSRCWGESSED

CQSLTRTVCAGGCARCKGPLPTDCCHEQCAAGCTG

PKHSDCLACLHFNHSGICELHCPALVTYNTDTFES

MPNPEGRYTFGASCVTACPYNYLSTDVGSCTLVCP

LHNQEVTAEDGTQRCEKCSKPCARVCYGLGMEHLR

EVRAVTSANIQEFAGCKKIFGSLAFLPESFDGDPA

-continued

SNTAPLQPEQLQVFETLEEITGYLYISAWPDSLPD

LSVFQNLQVIRGRILHNGAYSLTLQGLGISWLGLR

SLRELGSGLALIHHNTHLCFVHTVPWDQLFRNPHQ

ALLHTANRPEDECVGEGLACHQLCARGHCWGPGPT

QCVNCSQFLRGQECVEECRVLQGLPREYVNARHCL

PCHPECQPQNGSVTCFGPEADQCVACAHYKDPPFC

VARCPSGVKPDLSYMPIWKFPDEEGACQPCPINCT

HSCVDLDDKGCPAEQRASPLTSIISAVVGILLVVV

LGVVFGILIKRRQQKIRKYTMRRLLQETELVEPLT

PSGAMPNQAQMRILKETELRKVKVLGSGAFGTVYK

GIWIPDGENVKIPVAIKVLRENTSPKANKEILDEA

YVMAGVGSPYVSRLLGICLTSTVQLVTQLMPYGCL

LDHVRENRGRLGSQDLLNWCMQIAKGMSYLEDVRL

VHRDLAARNVLVKSPNHVKITDFGLARLLDIDETE

-continued

YHADGGKVPIKWMALESILRRRFTHQSDVWSYGVT

VWELMTFGAKPYDGIPAREIPDLLEKGERLPQPPI

CTIDVYMIMVKCWMIDSECRPRFRELVSEFSRMAR

DPQRFVVIQNEDLGPASPLDSTFYRSLLEDDDMGD

LVDAEEYLVPQQGFFCPDPAPGAGGMVHHRHRSSS

TRSGGGDLTLGLEPSEEEAPRSPLAPSEGAGSDVF

DGDLGMGAAKGLQSLPTHDPSPLQRYSEDPTVPLP

SETDGYVAPLTCSPQPEYVNQPDVRPQPPSPREGP

LPAARPAGATLERPKTLSPGKNGVVKDVFAFGGAV

ENPEYLTPQGGAAPQPHPPPAFSPAFDNLYYWDQD

PPERGAPPSTFKGTPTAENPEYLGLDVPV

In some embodiments, the scFv includes a heavy chain variable domain related to SEQ ID NO:195 and a light chain variable domain related to SEQ ID NO:196. For example, the heavy chain variable domain of the scFv can be at least 90% (e.g., 90%, 91%, 92%, 93%, 94%, 95%, 96%, 97%, 98%, 99%, or 100%) identical to SEQ ID NO:195, and/or incorporate amino acid sequences identical to the CDR1 (SEQ ID NO:115), CDR2 (SEQ ID NO:116), and CDR3 (SEQ ID NO:117) sequences of SEQ ID NO:195. Similarly, the light chain variable domain of the scFv can be at least 90% (e.g., 90%, 91%, 92%, 93%, 94%, 95%, 96%, 97%, 98%, 99%, or 100%) identical to SEQ ID NO:196, and/or incorporate amino acid sequences identical to the CDR1 (SEQ ID NO:119), CDR2 (SEQ ID NO:120), and CDR3 (SEQ ID NO:121) sequences of SEQ ID NO:196. In some embodiments, the scFv has the amino acid sequence of SEQ ID NO:139.

In some embodiments, the scFv includes a heavy chain variable domain related to SEQ ID NO:197 and a light chain variable domain related to SEQ ID NO:198. For example, the heavy chain variable domain of the scFv can be at least 90% (e.g., 90%, 91%, 92%, 93%, 94%, 95%, 96%, 97%, 98%, 99%, or 100%) identical to SEQ ID NO:197, and/or incorporate amino acid sequences identical to the CDR1 (SEQ ID NO:123), CDR2 (SEQ ID NO:124), and CDR3 (SEQ ID NO:125) sequences of SEQ ID NO:197. Similarly, the light chain variable domain of the scFv can be at least 90% (e.g., 90%, 91%, 92%, 93%, 94%, 95%, 96%, 97%, 98%, 99%, or 100%) identical to SEQ ID NO:198, and/or incorporate amino acid sequences identical to the CDR1 (SEQ ID NO:127), CDR2 (SEQ ID NO:128), and CDR3 (SEQ ID NO:129) sequences of SEQ ID NO:198. In some embodiments, the scFv has the amino acid sequence of SEQ ID NO:189.

In some embodiments, the scFv includes a heavy chain variable domain related to SEQ ID NO:199 and a light chain variable domain related to SEQ ID NO:200. For example, the heavy chain variable domain of the scFv can be at least 90% (e.g., 90%, 91%, 92%, 93%, 94%, 95%, 96%, 97%, 98%, 99%, or 100%) identical to SEQ ID NO:199, and/or incorporate amino acid sequences identical to the CDR1 (SEQ ID NO:131), CDR2 (SEQ ID NO:132), and CDR3 (SEQ ID NO:133) sequences of SEQ ID NO:199. Similarly, the light chain variable domain of the scFv can be at least 90% (e.g., 90%, 91%, 92%, 93%, 94%, 95%, 96%, 97%, 98%, 99%, or 100%) identical to SEQ ID NO:200, and/or incorporate amino acid sequences identical to the CDR1 (SEQ ID NO:135), CDR2 (SEQ ID NO:136), and CDR3 (SEQ ID NO:137) sequences of SEQ ID NO:200. In some embodiments, the scFv has the amino acid sequence of SEQ ID NO:171.

The scFv described above includes a heavy chain variable domain and a light chain variable domain. In some embodiments, the heavy chain variable domain forms a disulfide bridge with the light chain variable domain to enhance stability of the scFv. For example, a disulfide bridge can be formed between the C44 residue of the heavy chain variable domain and the C100 residue of the light chain variable domain, the amino acid positions numbered under Kabat. For example, in some embodiments, the disulfide bridge is formed between a cysteine residue (naturally present or introduced by mutation) at position 44 (C44) of the VH of the scFv and a cysteine residue (naturally present or introduced by mutation) at position 100 (C100) of the VL of the scFv, numbered under the Kabat numbering scheme.

The VH and VL of the scFv can be positioned in various orientations. In certain embodiments, the VL is positioned N-terminal to the VH. In certain embodiments, the VL is positioned C-terminal to the VH.

The VH and VL of the scFv can be connected via a linker, e.g., a peptide linker. In certain embodiments, the peptide linker is a flexible linker. Regarding the amino acid composition of the linker, peptides are selected with properties that confer flexibility, do not interfere with the structure and function of the other domains of the proteins of the present invention, and resist cleavage from proteases. For example, glycine and serine residues generally provide protease resistance. In certain embodiments, the VL is positioned N-terminal to the VH and is connected to the VH via a linker.

The length of the linker (e.g., flexible linker) can be "short," e.g., 0, 1, 2, 3, 4, 5, 6, 7, 8, 9, 10, 11 or 12 amino acid residues, or "long," e.g., at least 13 amino acid residues. In certain embodiments, the linker is 10-50, 10-40, 10-30, 10-25, 10-20, 15-50, 15-40, 15-30, 15-25, 15-20, 20-50, 20-40, 20-30, or 20-25 amino acid residues in length.

In certain embodiments, the linker includes a $(GS)_n$ (SEQ ID NO:204), $(GGS)_n$ (SEQ ID NO:205), $(GGGS)_n$(SEQ ID NO:151), $(GGSG)_n$(SEQ ID NO:153), $(GGSGG)_n$(SEQ ID NO:156), and $(GGGGS)_n$(SEQ ID NO:157) sequence, wherein n is 1, 2, 3, 4, 5, 6, 7, 8, 9, 10, 11, 12, 13, 14, 15, 16, 17, 18, 19, or 20. In certain embodiments, the linker includes an amino acid sequence selected from SEQ ID NO:143, SEQ ID NO:201, SEQ ID NO:202, SEQ ID NO:103, SEQ ID NO:104, SEQ ID NO:83, SEQ ID NO:84, SEQ ID NO:150, SEQ ID NO:152, and SEQ ID NO:154, as listed in Table 3.

TABLE 3

Exemplary Linkers

| SEQ ID | Amino Acid Sequence |
| --- | --- |
| SEQ ID NO: 201 | GSGSGSGSGSGSGSGSGSGS |
| SEQ ID NO: 202 | GGSGGSGGSGGSGGSGGSGGSGGSGGSGGS |
| SEQ ID NO: 103 | GGGSGGGSGGGSGGGSGGGSGGGSGGGSGGGSGGGSGGGS |

TABLE 3-continued

Exemplary Linkers

| SEQ ID | Amino Acid Sequence |
|---|---|
| SEQ ID NO: 104 | GGSGGGSGGGSGGGSGGGSGGGSGGGSGGGSGGGSGGGSG |
| SEQ ID NO: 83 | GGSGGGSGGGSGGGSGGGSGGGSGGGSGGGSGGGSGGGSGG GGSGGGGSGG |
| SEQ ID NO: 84 | GGGGSGGGGSGGGGSGGGGSGGGGSGGGGSGGGGSGGGGS GGGGSGGGGS |
| SEQ ID NO: 143 | GGGGSGGGGSGGGGSGGGGS |
| SEQ ID NO: 150 | GGGGSGGGGSGGGGS |
| SEQ ID NO: 152 | GGGGSGGGGSGGGGSGGGGSGGGGSGGGGSGGGGSGGGGS GGGGSGGGGSGGGGSGGGGSGGGGSGGGGSGGGGSGGGGS GGGGSGGGGSGGGGSGGGGS |
| SEQ ID NO: 154 | GGSGGGSGGGSGGGSGGGSGGGSGGGSGGGSGGGSGGGSGG GGSGGGSGGGSGGGSGGGSGGGSGGGSGGGSGGGSGGGSGG GGSGGGSGGGSGGGSGG |

In specific embodiments, the light chain variable domain is linked to the N-terminus of the heavy chain variable domain via a flexible linker, e.g., the (G4S)$_4$ linker (SEQ ID NO:143).

In some embodiments, the scFv described above is linked to an antibody Fc polypeptide via a hinge sequence. In some embodiments, the hinge includes the amino acid sequence Ala-Ser. In some other embodiments, the hinge includes the amino acid sequences Ala-Ser and Thr-Lys-Gly. The hinge sequence can provide flexibility of binding to the target antigen and balance between flexibility and optimal geometry.

Fc Domain

The antibody Fc domain of the multi-specific binding protein includes a first antibody Fc polypeptide linked to the Fab and a second antibody Fc polypeptide linked to the scFv. The two antibody Fc polypeptides pair and form a dimer that binds CD16.

Within the antibody Fc domain, CD16 binding is mediated by the hinge region and the CH2 domain. For example, within human IgG1, the interaction with CD16 is primarily focused on amino acid residues Asp 265-Glu 269, Asn 297-Thr 299, Ala 327-Ile 332, Leu 234-Ser 239, and carbohydrate residue N-acetyl-D-glucosamine in the CH2 domain (see, Sondermann et al., Nature, 406 (6793):267-273). Based on the known domains, mutations can be selected to enhance or reduce the binding affinity to CD16, such as by using phage-displayed libraries or yeast surface-displayed cDNA libraries, or can be designed based on the known three-dimensional structure of the interaction.

The assembly of heterodimeric antibody heavy chains can be accomplished by expressing two different antibody heavy chain sequences in the same cell, which may lead to the assembly of homodimers of each antibody heavy chain as well as assembly of heterodimers.

Promoting the preferential assembly of heterodimers can be accomplished by incorporating different mutations in the CH3 domain of each antibody heavy chain constant region as shown in U.S. Ser. No. 13/494,870, U.S. Ser. No. 16/028,850, U.S. Ser. No. 11/533,709, U.S. Ser. No. 12/875,015, U.S. Ser. No. 13/289,934, U.S. Ser. No. 14/773,418, U.S. Ser. No. 12/811,207, U.S. Ser. No. 13/866,756, U.S. Ser. No. 14/647,480, and U.S. Ser. No. 14/830,336. For example, mutations can be made in the CH3 domain based on human IgG1 through incorporating distinct pairs of amino acid substitutions within a first polypeptide and a second polypeptide that allow these two chains to selectively heterodimerize with each other. The positions of amino acid substitutions illustrated below are all numbered according to the EU index as in Kabat.

In one scenario, an amino acid substitution in the first polypeptide replaces the original amino acid with a larger amino acid, selected from arginine (R), phenylalanine (F), tyrosine (Y) or tryptophan (W), and at least one amino acid substitution in the second polypeptide replaces the original amino acid(s) with a smaller amino acid(s), chosen from alanine (A), serine (S), threonine (T), or valine (V), such that the larger amino acid substitution (a protuberance) fits into the surface of the smaller amino acid substitutions (a cavity). For example, one polypeptide can incorporate a T366W substitution, and the other can incorporate three substitutions including T366S, L368A, and Y407V.

An antibody heavy chain variable domain of the invention can optionally be coupled to an amino acid sequence at least 90% identical to an antibody constant region, such as an IgG constant region including hinge, CH2 and CH3 domains with or without a CH1 domain. In some embodiments, the amino acid sequence of the constant region is at least 90% identical to a human antibody constant region, such as a human IgG1 constant region, an IgG2 constant region, IgG3 constant region, or IgG4 constant region. In some other embodiments, the amino acid sequence of the constant region is at least 90% identical to an antibody constant region from another mammal, such as rabbit, dog, cat, mouse, or horse. One or more mutations can be incorporated into the constant region as compared to human IgG1 constant region, for example at Q347, Y349, L351, S354, E356, E357, K360, Q362, S364, T366, L368, K370, N390, K392, T394, D399, S400, D401, F405, Y407, K409, T411 and/or K439. Exemplary substitutions include, for example, Q347E, Q347R, Y349S, Y349K, Y349T, Y349D, Y349E, Y349C, T350V, L351K, L351D, L351Y, S354C, E356K, E357Q, E357L, E357W, K360E, K360W, Q362E, S364K, S364E, S364H, S364D, T366V, T366I, T366L, T366M, T366K, T366W, T366S, L368E, L368A, L368D, K370S, N390E, N390S, K392L, K392M, K392V, K392F, K392D, K392E, T394F, T394W, D399R, D399K, D399V, S400K, S400R, D401K, F405A, F405T, Y407A, Y407I, Y407V, K409F, K409W, K409D, T411D, T411E, K439D, and K439E. All the amino acid positions in an Fc domain or hinge region disclosed herein are numbered according to EU numbering.

In certain embodiments, mutations that can be incorporated into the CH1 of a human IgG1 constant region may be at amino acid V125, F126, P127, T135, T139, A140, F170, P171, and/or V173. In certain embodiments, mutations that can be incorporated into the Cκ of a human IgG1 constant region may be at amino acid E123, F116, S176, V163, S174, and/or T164.

Amino acid substitutions could be selected from the following sets of substitutions shown in Table 4.

TABLE 4

Exemplary Fc Substitutions that Promote Heterodimerization

| | First Polypeptide | Second Polypeptide |
|---|---|---|
| Set 1 | S364E/F405A | Y349K/T394F |
| Set 2 | S364H/D401K | Y349T/T411E |
| Set 3 | S364H/T394F | Y349T/F405A |

TABLE 4-continued

Exemplary Fc Substitutions that Promote Heterodimerization

|  | First Polypeptide | Second Polypeptide |
|---|---|---|
| Set 4 | S364E/T394F | Y349K/F405A |
| Set 5 | S364E/T411E | Y349K/D401K |
| Set 6 | S364D/T394F | Y349K/F405A |
| Set 7 | S364H/F405A | Y349T/T394F |
| Set 8 | S364K/E357Q | L368D/K370S |
| Set 9 | L368D/K370S | S364K |
| Set 10 | L368E/K370S | S364K |
| Set 11 | K360E/Q362E | D401K |
| Set 12 | L368D/K370S | S364K/E357L |
| Set 13 | K370S | S364K/E357Q |
| Set 14 | F405L | K409R |
| Set 15 | K409R | F405L |

Alternatively, amino acid substitutions could be selected from the following sets of substitutions shown in Table 5.

TABLE 5

Exemplary Fc Substitutions that Promote Heterodimerization

|  | First Polypeptide | Second Polypeptide |
|---|---|---|
| Set 1 | K409W | D399V/F405T |
| Set 2 | Y349S | E357W |
| Set 3 | K360E | Q347R |
| Set 4 | K360E/K409W | Q347R/D399V/F405T |
| Set 5 | Q347E/K360E/K409W | Q347R/D399V/F405T |
| Set 6 | Y349S/K409W | E357W/D399V/F405T |

Alternatively, amino acid substitutions could be selected from the following sets of substitutions shown in Table 6.

TABLE 6

Exemplary Fc Substitutions that Promote Heterodimerization

|  | First Polypeptide | Second Polypeptide |
|---|---|---|
| Set 1 | T366K/L351K | L351D/L368E |
| Set 2 | T366K/L351K | L351D/Y349E |
| Set 3 | T366K/L351K | L351D/Y349D |
| Set 4 | T366K/L351K | L351D/Y349E/L368E |
| Set 5 | T366K/L351K | L351D/Y349D/L368E |
| Set 6 | E356K/D399K | K392D/K409D |

Alternatively, at least one amino acid substitution in each polypeptide chain could be selected from Table 7.

TABLE 7

Exemplary Fc Substitutions that Promote Heterodimerization

| First Polypeptide | Second Polypeptide |
|---|---|
| L351Y, D399R, D399K, S400K, S400R, Y407A, Y407I, Y407V | T366V, T366I, T366L, T366M, N390D, N390E, K392L, K392M, K392V, K392F K392D, K392E, K409F, K409W, T411D and T411E |

Alternatively, at least one amino acid substitution could be selected from the following sets of substitutions in Table 8, where the position(s) indicated in the First Polypeptide column is replaced by any known negatively-charged amino acid, and the position(s) indicated in the Second Polypeptide Column is replaced by any known positively-charged amino acid.

TABLE 8

Exemplary Fc Positions for Substitutions

| First Polypeptide | Second Polypeptide |
|---|---|
| K392, K370, K409, or K439 | D399, E356, or E357 |

Alternatively, at least one amino acid substitution could be selected from the following sets of substitutions in Table 9, where the position(s) indicated in the First Polypeptide column is replaced by any known positively-charged amino acid, and the position(s) indicated in the Second Polypeptide Column is replaced by any known negatively-charged amino acid.

TABLE 9

Exemplary Fc Positions for Substitutions

| First Polypeptide | Second Polypeptide |
|---|---|
| D399, E356, or E357 | K409, K439, K370, or K392 |

Alternatively, amino acid substitutions could be selected from the following sets in Table 10.

TABLE 10

Exemplary Fc Substitutions that Promote Heterodimerization

| First Polypeptide | Second Polypeptide |
|---|---|
| T350V, L351Y, F405A, and Y407V | T350V, T366L, K392L, and T394W |

When selecting Fc substitutions, a skilled person would appreciate that the first polypeptide and the second polypeptide in Tables 4-10 may correspond to the first antibody Fc polypeptide and the second antibody Fc polypeptide, respectively. Alternatively, the first polypeptide and the second polypeptide in Tables 4-10 may correspond to the second antibody Fc polypeptide and the first antibody Fc polypeptide, respectively.

In some embodiments, the amino acid sequence of one polypeptide chain of the antibody constant region differs from the amino acid sequence of an IgG1 constant region at position T366, and the amino acid sequence of the other polypeptide chain of the antibody constant region differs from the amino acid sequence of an IgG1 constant region at one or more positions selected from T366, L368 and Y407.

In some embodiments, the amino acid sequence of one polypeptide chain of the antibody constant region differs from the amino acid sequence of an IgG1 constant region at one or more positions selected from T366, L368 and Y407, and the amino acid sequence of the other polypeptide chain of the antibody constant region differs from the amino acid sequence of an IgG1 constant region at position T366.

In some embodiments, the amino acid sequence of one polypeptide chain of the antibody constant region differs from the amino acid sequence of an IgG1 constant region at one or more positions selected from E357, K360, Q362, S364, L368, K370, T394, D401, F405, and T411, and the amino acid sequence of the other polypeptide chain of the antibody constant region differs from the amino acid sequence of an IgG1 constant region at one or more positions selected from Y349, E357, S364, L368, K370, T394, D401, F405 and T411.

In some embodiments, the amino acid sequence of one polypeptide chain of the antibody constant region differs from the amino acid sequence of an IgG1 constant region at one or more positions selected from Y349, E357, S364, L368, K370, T394, D401, F405 and T411, and the amino acid sequence of the other polypeptide chain of the antibody constant region differs from the amino acid sequence of an IgG1 constant region at one or more positions selected from E357, K360, Q362, S364, L368, K370, T394, D401, F405, and T411.

In some embodiments, the amino acid sequence of one polypeptide chain of the antibody constant region differs from the amino acid sequence of an IgG1 constant region at one or more positions selected from L351, D399, S400 and Y407, and the amino acid sequence of the other polypeptide chain of the antibody constant region differs from the amino acid sequence of an IgG1 constant region at one or more positions selected from T366, N390, K392, K409 and T411.

In some embodiments, the amino acid sequence of one polypeptide chain of the antibody constant region differs from the amino acid sequence of an IgG1 constant region at one or more positions selected from T366, N390, K392, K409 and T411, and the amino acid sequence of the other polypeptide chain of the antibody constant region differs from the amino acid sequence of an IgG1 constant region at one or more positions selected from L351, D399, S400 and Y407.

In some embodiments, the amino acid sequence of one polypeptide chain of the antibody constant region differs from the amino acid sequence of an IgG1 constant region at one or more positions selected from Q347, Y349, K360, and K409, and the amino acid sequence of the other polypeptide chain of the antibody constant region differs from the amino acid sequence of an IgG1 constant region at one or more positions selected from Q347, E357, D399 and F405.

In some embodiments, the amino acid sequence of one polypeptide chain of the antibody constant region differs from the amino acid sequence of an IgG1 constant region at one or more positions selected from Q347, E357, D399 and F405, and the amino acid sequence of the other polypeptide chain of the antibody constant region differs from the amino acid sequence of an IgG1 constant region at one or more positions selected from Y349, K360, Q347 and K409.

In some embodiments, the amino acid sequence of one polypeptide chain of the antibody constant region differs from the amino acid sequence of an IgG1 constant region at one or more positions selected from K370, K392, K409 and K439, and the amino acid sequence of the other polypeptide chain of the antibody constant region differs from the amino acid sequence of an IgG1 constant region at one or more positions selected from D356, E357 and D399.

In some embodiments, the amino acid sequence of one polypeptide chain of the antibody constant region differs from the amino acid sequence of an IgG1 constant region at one or more positions selected from D356, E357 and D399, and the amino acid sequence of the other polypeptide chain of the antibody constant region differs from the amino acid sequence of an IgG1 constant region at one or more positions selected from K370, K392, K409 and K439.

In some embodiments, the amino acid sequence of one polypeptide chain of the antibody constant region differs from the amino acid sequence of an IgG1 constant region at one or more positions selected from L351, E356, T366 and D399, and the amino acid sequence of the other polypeptide chain of the antibody constant region differs from the amino acid sequence of an IgG1 constant region at one or more positions selected from Y349, L351, L368, K392 and K409.

In some embodiments, the amino acid sequence of one polypeptide chain of the antibody constant region differs from the amino acid sequence of an IgG1 constant region at one or more positions selected from Y349, L351, L368, K392 and K409, and the amino acid sequence of the other polypeptide chain of the antibody constant region differs from the amino acid sequence of an IgG1 constant region at one or more positions selected from L351, E356, T366 and D399.

In some embodiments, the amino acid sequence of one polypeptide chain of the antibody constant region differs from the amino acid sequence of an IgG1 constant region by K360E and K409W substitutions, and the amino acid sequence of the other polypeptide chain of the antibody constant region differs from the amino acid sequence of an IgG1 constant region by Q347R, D399V and F405T substitutions.

In some embodiments, the amino acid sequence of one polypeptide chain of the antibody constant region differs from the amino acid sequence of an IgG1 constant region by Q347R, D399V and F405T substitutions, and the amino acid sequence of the other polypeptide chain of the antibody constant region differs from the amino acid sequence of an IgG1 constant region by K360E and K409W substitutions.

In some embodiments, the amino acid sequence of one polypeptide chain of the antibody constant region differs from the amino acid sequence of an IgG1 constant region by a T366W substitution, and the amino acid sequence of the other polypeptide chain of the antibody constant region differs from the amino acid sequence of an IgG1 constant region by T366S, T368A, and Y407V substitutions.

In some embodiments, the amino acid sequence of one polypeptide chain of the antibody constant region differs from the amino acid sequence of an IgG1 constant region by T366S, T368A, and Y407V substitutions, and the amino acid sequence of the other polypeptide chain of the antibody constant region differs from the amino acid sequence of an IgG1 constant region by a T366W substitution.

In some embodiments, the amino acid sequence of one polypeptide chain of the antibody constant region differs from the amino acid sequence of an IgG1 constant region by T350V, L351Y, F405A, and Y407V substitutions, and the amino acid sequence of the other polypeptide chain of the antibody constant region differs from the amino acid sequence of an IgG1 constant region by T350V, T366L, K392L, and T394W substitutions.

In some embodiments, the amino acid sequence of one polypeptide chain of the antibody constant region differs from the amino acid sequence of an IgG1 constant region by T350V, T366L, K392L, and T394W substitutions, and the amino acid sequence of the other polypeptide chain of the antibody constant region differs from the amino acid sequence of an IgG1 constant region by T350V, L351Y, F405A, and Y407V substitutions.

Alternatively, or additionally, the structural stability of a hetero-multimeric protein may be increased by introducing an S354C substitution on either of the first or second polypeptide chain, and a Y349C substitution on the opposing polypeptide chain, which forms an artificial disulfide bridge within the interface of the two polypeptides. In some embodiments, the amino acid sequence of one polypeptide chain of the antibody constant region differs from the amino acid sequence of an IgG1 constant region by an S354C substitution, and the amino acid sequence of the other polypeptide chain of the antibody constant region differs from the amino acid sequence of an IgG1 constant region by a Y349C substitution.

When selecting Fc substitutions, a skilled person would appreciate that the "one polypeptide chain" and "the other polypeptide chain" of an antibody constant region described above may correspond to the first antibody Fc polypeptide and the second antibody Fc polypeptide, respectively. Alternatively, the "one polypeptide chain" and "the other polypeptide chain" of an antibody constant region described above may correspond to the second antibody Fc polypeptide and the first antibody Fc polypeptide, respectively.

Exemplary Multi-Specific Binding Proteins

Listed below are examples of TriNKETs that include a HER2-binding scFv and an NKG2D-binding Fab each linked to an antibody constant region, and antibody constant regions incorporating mutations that enable heterodimerization of two Fc polypeptide chains. The scFv includes a heavy chain variable domain (VH) and a light chain variable domain (VL) derived from an anti-HER2 antibody (e.g., trastuzumab), and further includes substitution of Cys for the amino acid residues at position 100 of the VL and position 44 of the VH, thereby facilitating formation of a disulfide bridge between the VH and VL of the scFv. The VL is linked N-terminal to the VH via a (G4S)$_4$ linker (SEQ ID NO:143), and the VH is linked N-terminal to an Fc via an Ala-Ser linker. The Ala-Ser linker is included at the elbow hinge region sequence to balance between flexibility and optimal geometry. In certain embodiments, an additional sequence, Thr-Lys-Gly, can be added N-terminal or C-terminal to the Ala-Ser sequence at the hinge. As used herein to describe these exemplary TriNKETs, the Fc domain includes an antibody hinge, CH2, and CH3.

Accordingly, each of the TriNKETs described below have the following three polypeptide chains:

Chain A, including from N-terminus to C-terminus: a VH of an NKG2D-binding Fab, a CH1, and an antibody Fc polypeptide;

Chain B, including from N-terminus to C-terminus: a VL of a HER2-binding scFv, a (G4S)$_4$ linker (SEQ ID NO:143), a VH of the HER2-binding scFv, an Ala-Ser linker, and an antibody Fc polypeptide; and Chain C, including from N-terminus to C-terminus: a VL of the NKG2D-binding Fab, and a light chain constant domain (CL).

The amino acid sequences of exemplary TriNKETs are summarized in Table 11.

In certain embodiments, a multi-specific binding protein of the present disclosure includes a first polypeptide chain, a second polypeptide chain, and a third polypeptide chain, having the amino acid sequences of Chain A, Chain B, and Chain C, respectively, of a TriNKET disclosed in Table 11.

In an exemplary embodiment, the antibody Fc polypeptide linked to the NKG2D-binding Fab fragment incorporates the mutations of Q347R, D399V, and F405T, and the antibody Fc polypeptide linked to the HER2 scFv incorporates matching mutations K360E and K409W for forming a heterodimer. In another exemplary embodiment, the antibody Fc polypeptide linked to the NKG2D-binding Fab fragment incorporates knob mutations T366S, L368A, and Y407V, and the antibody Fc polypeptide linked to the HER2-binding scFv incorporates a "hole" mutation T366W. In an exemplary embodiment, the antibody Fc polypeptide linked to the NKG2D-binding Fab fragment includes an S354C substitution in the CH3 domain, which forms a disulfide bond with a Y349C substitution on the antibody Fc polypeptide linked to the HER2-binding scFv.

TABLE 11

Exemplary Multi-Specific Binding Proteins

| TriNKET Construct | NKG2D Binding Fab | HER2 Binding scFv | Human IgG1 Fc | Chain A | Chain B | Chain C |
|---|---|---|---|---|---|---|
| A49-F3'-TriNKET-Trastuzumab | A49 | Trastuzumab | EW-RVT | SEQ ID NO: 141 | SEQ ID NO: 140 | SEQ ID NO: 142 |
| A49-F3'-KiH-TriNKET-Trastuzumab | A49 | Trastuzumab | KiH | SEQ ID NO: 147 | SEQ ID NO: 146 | SEQ ID NO: 142 |
| A49-F3'-TriNKET-Pertuzumab | A49 | Pertuzumab | EW-RVT | SEQ ID NO: 141 | SEQ ID NO: 190 | SEQ ID NO: 142 |
| A49-F3'-KiH-TriNKET-Pertuzumab | A49 | Pertuzumab | KiH | SEQ ID NO: 147 | SEQ ID NO: 191 | SEQ ID NO: 142 |
| A49-F3'-TriNKET-MGAH22 | A49 | MGAH22 | EW-RVT | SEQ ID NO: 141 | SEQ ID NO: 192 | SEQ ID NO: 142 |
| A49-F3'-KiH-TriNKET-MGAH22 | A49 | MGAH22 | KiH | SEQ ID NO: 147 | SEQ ID NO: 193 | SEQ ID NO: 142 |
| A49MI-F3'-TriNKET-Trastuzumab | A49MI | Trastuzumab | EW-RVT | SEQ ID NO: 145 | SEQ ID NO: 140 | SEQ ID NO: 142 |
| A49MI-F3'-KiH-TriNKET-Trastuzumab | A49MI | Trastuzumab | KiH | SEQ ID NO: 194 | SEQ ID NO: 146 | SEQ ID NO: 142 |
| A49MI-F3'-TriNKET-Pertuzumab | A49MI | Pertuzumab | EW-RVT | SEQ ID NO: 145 | SEQ ID NO: 190 | SEQ ID NO: 142 |
| A49MI-F3'-KiH-TriNKET-Pertuzumab | A49MI | Pertuzumab | KiH | SEQ ID NO: 194 | SEQ ID NO: 191 | SEQ ID NO: 142 |
| A49MI-F3'-TriNKET-MGAH22 | A49MI | MGAH22 | EW-RVT | SEQ ID NO: 145 | SEQ ID NO: 192 | SEQ ID NO: 142 |
| A49MI-F3'-KiH-TriNKET-MGAH22 | A49MI | MGAH22 | KiH | SEQ ID NO: 194 | SEQ ID NO: 193 | SEQ ID NO: 142 |
| A44-F3'-TriNKET-Trastuzumab | A44 | Trastuzumab | EW-RVT | SEQ ID NO: 155 | SEQ ID NO: 140 | SEQ ID NO: 149 |
| A44-F3'-KiH-TriNKET-Trastuzumab | A44 | Trastuzumab | KiH | SEQ ID NO: 148 | SEQ ID NO: 146 | SEQ ID NO: 149 |
| A44-F3'-TriNKET-Pertuzumab | A44 | Pertuzumab | EW-RVT | SEQ ID NO: 155 | SEQ ID NO: 190 | SEQ ID NO: 149 |
| A44-F3'-KiH-TriNKET-Pertuzumab | A44 | Pertuzumab | KiH | SEQ ID NO: 148 | SEQ ID NO: 191 | SEQ ID NO: 149 |
| A44-F3'-TriNKET-MGAH22 | A44 | MGAH22 | EW-RVT | SEQ ID NO: 155 | SEQ ID NO: 192 | SEQ ID NO: 149 |

TABLE 11-continued

Exemplary Multi-Specific Binding Proteins

| TriNKET Construct | NKG2D Binding Fab | HER2 Binding scFv | Human IgG1 Fc | Chain A | Chain B | Chain C |
|---|---|---|---|---|---|---|
| A44-F3'-KiH-TriNKET-MGAH22 | A44 | MGAH22 | KiH | SEQ ID NO: 148 | SEQ ID NO: 193 | SEQ ID NO: 149 |

Specific TriNKETs and their polypeptide chains are described in more detail below. In the amino acid sequences, (G$_4$S)$_4$ (SEQ ID NO:143) and Ala-Ser linkers are bold-underlined; Cys residues in the scFv that form disulfide bridges are bold-italic-underlined; Fc heterodimerization mutations are bold-underlined; and CDR sequences under Kabat are underlined.

For example, a TriNKET of the present disclosure is A49-F3'-TriNKET-Trastuzumab. A49-F3'-TriNKET-Trastuzumab includes a single-chain variable fragment (scFv) (SEQ ID NO:139) derived from trastuzumab that binds HER2, linked via a hinge including Ala-Ser to a first antibody Fc polypeptide; and an NKG2D-binding Fab fragment derived from A49 linked to a second antibody Fc polypeptide. The Fab fragment includes a heavy chain portion having a heavy chain variable domain (SEQ ID NO:94) and a CH1 domain, and a light chain portion having a light chain variable domain (SEQ ID NO:98) and a light chain constant domain. The heavy chain variable domain is connected to the CH1 domain, and the CH1 domain is connected to the second antibody Fc polypeptide. A49-F3'-TriNKET-Trastuzumab includes three polypeptides having the sequences of SEQ ID NO:140, SEQ ID NO:141, and SEQ ID NO:142.

SEQ ID NO:140 represents the full sequence of the HER2-binding scFv linked to the first antibody Fc polypeptide via a hinge including Ala-Ser (scFv-Fc). The first antibody Fc polypeptide includes Q347R, D399V, and F405T substitutions for heterodimerization and an S354C substitution for forming a disulfide bond with a Y349C substitution in SEQ ID NO:141 as described below. The scFv (SEQ ID NO:139) includes a heavy chain variable domain of trastuzumab connected to the N-terminus of a light chain variable domain of trastuzumab via a (G$_4$S)$_4$ linker (SEQ ID NO:143), the scFv represented as VL-(G$_4$S)$_4$-VH ("(G$_4$S)$_4$" is represented by SEQ ID NO:143). The heavy and the light variable domains of the scFv are also connected through a disulfide bridge between C100 of VL and C44 of VH, as a result of Q100C and G44C substitutions in the VL and VH, respectively.

Trastuzumab scFv
(SEQ ID NO: 139)
DIQMTQSPSSLSASVGDRVTITCRASQDVNTAVAWYQQKPGKAPKLLI

YSASFLYSGVPSRFSGSRSGTDFTLTISSLQPEDFATYYCQQHYTTPP

TFGCGTKVEIKGGGGSGGGGSGGGGSGGGGSEVQLVESGGGLVQPGGS

LRLSCAASGFNIKDTYIHWVRQAPGKCLEWVARIYPTNGYTRYADSVK

GRFTISADTSKNTAYLQMNSLRAEDTAVYYCSRWGGDGFYAMDYWGQG

TLVTVSS

Trastuzumab scFv-Fc (RVT)
(SEQ ID NO: 140)
DIQMTQSPSSLSASVGDRVTITCRASQDVNTAVAWYQQKPGKAPKLLI

YSASFLYSGVPSRFSGSRSGTDFTLTISSLQPEDFATYYCQQHYTTPP

TFGCGTKVEIKGGGGSGGGGSGGGGSGGGGSEVQLVESGGGLVQPGGS

LRLSCAASGFNIKDTYIHWVRQAPGKCLEWVARIYPTNGYTRYADSVK

GRFTISADTSKNTAYLQMNSLRAEDTAVYYCSRWGGDGFYAMDYWGQG

TLVTVSSASDKTHTCPPCPAPELLGGPSVFLFPPKPKDTLMISRTPEV

TCVVVDVSHEDPEVKFNWYVDGVEVHNAKTKPREEQYNSTYRVVSVLT

VLHQDWLNGKEYKCKVSNKALPAPIEKTISKAKGQPREPRVYTLPPCR

DELTKNQVSLTCLVKGFYPSDIAVEWESNGQPENNYKTTPPVLVSDGS

FTLYSKLTVDKSRWQQGNVFSCSVMHEALHNHYTQKSLSLSPG

SEQ ID NO:141 represents the heavy chain portion of the Fab fragment, which includes a heavy chain variable domain (SEQ ID NO:94) of an NKG2D-binding site and a CH1 domain, connected to the second antibody Fc polypeptide. The antibody Fc polypeptide in SEQ ID NO:141 includes a Y349C substitution in the CH3 domain, which forms a disulfide bond with an S354C substitution on the Fc polypeptide in SEQ ID NO:140. In SEQ ID NO:141, the antibody Fc polypeptide also includes K360E and K409W substitutions for heterodimerization with the Fc in SEQ ID NO:140.

A49 VH
(SEQ ID NO: 94)
EVQLVESGGGLVKPGGSLRLSCAASGFTFSSYSMNWVRQAPGKGLEWVS

SISSSSSYIYYADSVKGRFTISRDNAKNSLYLQMNSLRAEDTAVYYCAR

GAPMGAAAGWFDPWGQGTLVTVSS

A49 VH-CH1-Fc (EW)
(SEQ ID NO: 141)
EVQLVESGGGLVKPGGSLRLSCAASGFTFSSYSMNWVRQAPGKGLEWVS

SISSSSSYIYYADSVKGRFTISRDNAKNSLYLQMNSLRAEDTAVYYCAR

GAPMGAAAGWFDPWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

```
                                              -continued
AKGQPREPQVCTLPPSRDELTENQVSLTCLVKGFYPSDIAVEWESNGQP
       -                -

ENNYKTTPPVLDSDGSFFLYSWLTVDKSRWQQGNVFSCSVMHEALHNHY
                     -

TQKSLSLSPG
```

SEQ ID NO:142 represents the light chain portion of the Fab fragment including a light chain variable domain (SEQ ID NO:98) of an NKG2D-binding site and a light chain constant domain.

```
A49 VL
                                                 (SEQ ID NO: 98)
DIQMTQSPSSVSASVGDRVTITCRASQGISSWLAWYQQKPGKAPKLLIY
                       ----------------

AASSLQSGVPSRFSGSGSGTDFTLTISSLQPEDFATYYCQQGVSFPRTF
----                                   ---------

GGGTKVEIK

A49 VL-LC
                                                (SEQ ID NO: 142)
DIQMTQSPSSVSASVGDRVTITCRASQGISSWLAWYQQKPGKAPKLLIY

AASSLQSGVPSRFSGSGSGTDFTLTISSLQPEDFATYYCQQGVSFPRTF

GGGTKVEIKRTVAAPSPPSDEQLKSGTASVVCLLNNFYPREAKVQWKVD

NALQSGNSQESVTEQDSKDSTYSLSSTLTLSKADYEKHKVYACEVTHQG

LSSPVTKSFNRGEC
```

Another TriNKET of the present disclosure is A49MI-F3'-TriNKET-Trastuzumab. A49MI-F3'-TriNKET-Trastuzumab includes the same HER2-binding scFv (SEQ ID NO:139) as in A49-F3'-TriNKET-Trastuzumab linked via a hinge including Ala-Ser to an antibody Fc polypeptide; and an NKG2D-binding Fab fragment derived from A49MI linked to a second antibody Fc polypeptide. The Fab fragment includes a heavy chain portion including a heavy chain variable domain (SEQ ID NO:144) and a CH1 domain, and a light chain portion including a light chain variable domain (SEQ ID NO:98) and a light chain constant domain. The heavy chain variable domain is connected to the CH1 domain, and the CH1 domain is connected to the second antibody Fc polypeptide. A49MI-F3'-TriNKET-Trastuzumab includes three polypeptides having the sequences of SEQ ID NO:140 (as in A49-F3'-TriNKET-Trastuzumab), SEQ ID NO:145, and SEQ ID NO:142 (as in A49-F3'-TriNKET-Trastuzumab).

SEQ ID NO:145 represents a heavy chain portion of the Fab fragment, which includes a heavy chain variable domain (SEQ ID NO:144) of an NKG2D-binding site and a CH1 domain, connected to the first antibody Fc polypeptide. In SEQ ID NO:144, a methionine in the CDR3 of SEQ ID NO:94 has been substituted by isoleucine (M→I substitution; shown within a third bracket H in SEQ ID NO:144 and SEQ ID NO:145). The antibody Fc polypeptide in SEQ ID NO:145 includes a Y349C substitution in the CH3 domain, which forms a disulfide bond with an S354C substitution in the antibody Fc polypeptide in SEQ ID NO:140. In SEQ ID NO:145, the antibody Fc polypeptide also includes K360E and K409W substitutions.

```
A49MI VH
                                                (SEQ ID NO: 144)
EVQLVESGGGLVKPGGSLRLSCAASGFTFSSYSMNWVRQAPGKGLEWV
                               --------

SSISSSSSYIYYADSVKGRFTISRDNAKNSLYLQMNSLRAEDTAVYYC
```

```
                                              -continued
ARGAP[I]GAAAGWFDPWGQGTLVTVSS
    ---

A49MI VH-CH1-Fc (EW)
                                                (SEQ ID NO: 145)
EVQLVESGGGLVKPGGSLRLSCAASGFTFSSYSMNWVRQAPGKGLEWV

SSISSSSSYIYYADSVKGRFTISRDNAKNSLYLQMNSLRAEDTAVYYC

ARGAP[I]GAAAGWFDPWGQGTLVTVSSASTKGPSVFPLAPSSKSTSG

GTAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAPE

LLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALP

APIEKTISKAKGQPREPQVCTLPPSRDELTENQVSLTCLVKGFYPSDI
                     -         -

AVEWESNGQPENNYKTTPPVLDSDGSFFLYSWLTVDKSRWQQGNVFSC
                                  -

SVMHEALHNHYTQKSLSLSPG
```

Another TriNKET of the present disclosure is A49-F3'-KiH-TriNKET-Trastuzumab. KiH refers to the knobs-into-holes (KiH) Fc technology, which involves engineering of the CH3 domains to create either a "knob" or a "hole" in each heavy chain to promote heterodimerization. The concept behind the KiH Fc technology was to introduce a "knob" in one CH3 domain (CH3A) by substitution of a small residue with a bulky one (e.g., $T366W_{CH3A}$ in EU numbering). To accommodate the "knob," a complementary "hole" surface was created on the other CH3 domain (CH3B) by replacing the closest neighboring residues to the knob with smaller ones (e.g., $T366S/L368A/Y407V_{CH3B}$). The "hole" mutation was optimized by structure-guided phage library screening (Atwell S, Ridgway J B, Wells J A, Carter P., Stable heterodimers from remodeling the domain interface of a homodimer using a phage display library, *J. Mol. Biol.* (1997) 270(1):26-35). X-ray crystal structures of KiH Fc variants (Elliott J M, Ultsch M, Lee J, Tong R, Takeda K, Spiess C, et al., Antiparallel conformation of knob and hole aglycosylated half-antibody homodimers is mediated by a CH2-CH3 hydrophobic interaction. *J. Mol. Biol.* (2014) 426(9):1947-57; Mimoto F, Kadono S, Katada H, Igawa T, Kamikawa T, Hattori K. Crystal structure of a novel asymmetrically engineered Fc domain variant with improved affinity for FcγRs. *Mol. Immunol.* (2014) 58(1): 132-8) demonstrated that heterodimerization is thermodynamically favored by hydrophobic interactions driven by steric complementarity at the inter-CH3 domain core interface, whereas the knob-knob and the hole-hole interfaces do not favor homodimerization owing to steric hindrance and disruption of the favorable interactions, respectively.

A49-F3'-KiH-TriNKET-Trastuzumab includes the same HER2-binding scFv (SEQ ID NO:139) as in A49-F3'-TriNKET-Trastuzumab linked via a hinge including Ala-Ser to a first antibody Fc polypeptide incorporating the "hole" substitutions of T366S, L368A, and Y407V; and the same NKG2D-binding Fab fragment as in A49-F3'-TriNKET-Trastuzumab, the CH1 domain of which is connected to a second antibody Fc polypeptide incorporating the "knob" substitution of T366W. A49-F3'-KiH-TriNKET-Trastuzumab includes three polypeptides having the sequences of SEQ ID NO:146, SEQ ID NO:147, and SEQ ID NO:142 (as in A49-F3'-TriNKET-Trastuzumab).

SEQ ID NO:146 represents the full sequence of the HER2-binding scFv (SEQ ID NO:139) linked to the first antibody Fc polypeptide via a hinge including Ala-Ser (scFv-Fc). The first antibody Fc polypeptide includes T366S, L368A, and Y407V substitutions for heterodimerization and an S354C substitution for forming a disulfide bond with a Y349C substitution in SEQ ID NO:147 as described below.

```
Trastuzumab scFv-Fc (KiH)
                                          (SEQ ID NO: 146)
DIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTF

GCGTKVEIKGGGGSGGGGSGGGGSGGGGSEVQLVESGGGLVQPGGSLRL

SCAASGFNIKDTYIHWVRQAPGKCLEWVARIYPTNGYTRYADSVKGRFT

ISADTSKNTAYLQMNSLRAEDTAVYYCSRWGGDGFYAMDYWGQGTLVTV

SSASDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPAPIEKTISKAKGQPREPQVCTLPPSRDELTKNQV

SLSCAVKGFYPSDIAVEWESNGQPENNYKTTPPVLDSDGSFFLVSKLTV

DKSRWQQGNVFSCSVMHEALHNHYTQKSLSLSPG
```

SEQ ID NO:147 represents the heavy chain portion of a Fab fragment having a heavy chain variable domain (SEQ ID NO:94) of an NKG2D-binding site derived from A49 and a CH1 domain, connected to the second antibody Fc polypeptide. The antibody Fc polypeptide in SEQ ID NO:147 includes an S354C substitution, which forms a disulfide bond with a Y349C substitution in the CH3 domain of the first antibody Fc polypeptide. In SEQ ID NO:147, the antibody Fc polypeptide also includes a T366W substitution.

```
A49 VH-CH1-Fc (KiH)
                                          (SEQ ID NO: 147)
EVQLVESGGGLVKPGGSLRLSCAASGFTFSSYSMNWVRQAPGKGLEWVS

SISSSSSYIYYADSVKGRFTISRDNAKNSLYLQMNSLRAEDTAVYYCAR

GAPMGAAAGWFDPWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPCRDELTKNQVSLWCLVKGFYPSDIAVEWESNGQP

ENNYKTTPPVLDSDGSFFLYSKLTVDKSRWQQGNVFSCSVMHEALHNHY

TQKSLSLSPG
```

Another TriNKET of the present disclosure is A49MI-F3'-KiH-TriNKET-Trastuzumab. A49MI-F3'-KiH-TriNKET-Trastuzumab includes the same HER2-binding scFv (SEQ ID NO:139) as in A49-F3'-TriNKET-Trastuzumab linked via a hinge including Ala-Ser to a first antibody Fc polypeptide incorporating the "hole" substitutions of T366S, L368A, and Y407V; and the same NKG2D-binding Fab fragment as in A49MI-F3'-TriNKET-Trastuzumab, the CH1 domain of which is connected to a second antibody Fc polypeptide incorporating the "knob" substitution of T366W. A49MI-F3'-KiH-TriNKET-Trastuzumab includes three polypeptides having the sequences of SEQ ID NO:146 (as in A49-F3'-KiH-TriNKET-Trastuzumab), SEQ ID NO:194, and SEQ ID NO:142 (as in A49-F3'-TriNKET-Trastuzumab).

SEQ ID NO:194 represents the heavy chain portion of a Fab fragment having a heavy chain variable domain (SEQ ID NO:144) of an NKG2D-binding site derived from A49MI and a CH1 domain, connected to the second antibody Fc polypeptide. The antibody Fc polypeptide in SEQ ID NO:194 includes an S354C substitution, which forms a disulfide bond with a Y349C substitution in the CH3 domain of the first antibody Fc polypeptide. In SEQ ID NO:194, the antibody Fc polypeptide also includes a T366W substitution.

```
A49MI VH-CH1-Fc (KiH)
                                          (SEQ ID NO: 194)
EVQLVESGGGLVKPGGSLRLSCAASGFTFSSYSMNWVRQAPGKGLEWVS

SISSSSSYIYYADSVKGRFTISRDNAKNSLYLQMNSLRAEDTAVYYCAR

GAPIGAAAGWFDPWGQGTLVTVSSASTKGPSVFPLAPSSKSTSGGTAAL

GCLVKDYFPEPVTVSWNSGALTSGVHTFPAVLQSSGLYSLSSVVTVPSS

SLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISK

AKGQPREPQVYTLPPCRDELTKNQVSLWCLVKGFYPSDIAVEWESNGQP

ENNYKTTPPVLDSDGSFFLYSKLTVDKSRWQQGNVFSCSVMHEALHNHY

TQKSLSLSPG
```

Another exemplary TriNKET of the present disclosure is A44-F3'-TriNKET-Trastuzumab. A44-F3'-TriNKET-Trastuzumab includes the same HER2-binding scFv (SEQ ID NO:139) as in A49-F3'-TriNKET-Trastuzumab linked via a hinge including Ala-Ser to a first antibody Fc polypeptide; and an NKG2D-binding Fab fragment derived from A44 linked to a second antibody Fc polypeptide. The Fab fragment includes a heavy chain portion having a heavy chain variable domain (SEQ ID NO:86) and a CH1 domain, and a light chain portion having a light chain variable domain (SEQ ID NO:90) and a light chain constant domain. The heavy chain variable domain is connected to the CH1 domain, and the CH1 domain is connected to the second antibody Fc polypeptide. A44-F3'-TriNKET-Trastuzumab includes three polypeptides having the sequences of SEQ ID NO:140 (as in A49-F3'-TriNKET-Trastuzumab), SEQ ID NO:155, and SEQ ID NO:149.

SEQ ID NO:155 represents a heavy chain variable domain (SEQ ID NO:86) of an NKG2D-binding site derived from A44, connected to the second antibody Fc polypeptide. The antibody Fc polypeptide in SEQ ID NO:155 includes a Y349C substitution in the CH3 domain, which forms a disulfide bond with an S354C substitution on the first antibody Fc polypeptide. In SEQ ID NO:155, the antibody Fc polypeptide also includes K360E and K409W substitutions.

```
A44VH
                                          (SEQ ID NO: 86)
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

DGGYYDSGAGDYWGQGTLVTVSS
```

A44 VH-CH1-Fc (EW)
(SEQ ID NO: 155)
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

DGGYYDSGAGDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQV<u>C</u>TLPPSRD<u>E</u>LTENQVSLTCLVKGFYPSDIAVEWESNGQPE

NNYKTTPPVLDSDGSFFLYSWLTVDKSRWQQGNVFSCSVMHEALHNHYT

QKSLSLSPG

SEQ ID NO:149 represents the light chain portion of the Fab fragment including a light chain variable domain (SEQ ID NO:90) of an NKG2D-binding site and a light chain constant domain.

A44VL
(SEQ ID NO: 90)
DIQMTQSPSSVSASVGDRVTITC<u>RASQGIDSWLA</u>WYQQKPGKAPKLLIY

<u>AASSLQS</u>GVPSRFSGSGSGTDFTLTISSLQPEDFATYYC<u>QQGVSYPRTF</u>

<u>GGG</u>TKVEIK

A44 VL-CL
(SEQ ID NO: 149)
DIQMTQSPSSVSASVGDRVTITC<u>RASQGIDSWLA</u>WYQQKPGKAPKLLIY

<u>AASSLQS</u>GVPSRFSGSGSGTDFTLTISSLQPEDFATYYC<u>QQGVSYPRTF</u>

<u>GGG</u>TKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Another exemplary TriNKET of the present disclosure is A44-F3'-KiH-TriNKET-Trastuzumab. A44-F3'-KiH-TriNKET-Trastuzumab includes the same HER2-binding scFv (SEQ ID NO:139) as in A49-F3'-TriNKET-Trastuzumab linked via a hinge including Ala-Ser to a first antibody Fc polypeptide incorporating the "hole" substitutions of T366S, L368A, and Y407V; and the same NKG2D-binding Fab fragment as in A44-F3'-TriNKET-Trastuzumab, the CH1 domain of which is connected to a second antibody Fc polypeptide incorporating the "knob" substitution of T366W. A44-F3'-KiH-TriNKET-Trastuzumab includes three polypeptides having the sequences of SEQ ID NO:146 (as in A49-F3'-KiH-TriNKET-Trastuzumab), SEQ ID NO:148, and SEQ ID NO:149 (as in A44-F3'-TriNKET-Trastuzumab).

SEQ ID NO:148 represents a heavy chain variable domain (SEQ ID NO:86) of an NKG2D-binding site derived from A44, connected to the second antibody Fc polypeptide. The antibody Fc polypeptide in SEQ ID NO:148 includes a Y349C substitution in the CH3 domain, which forms a disulfide bond with an S354C substitution on the first antibody Fc polypeptide. In SEQ ID NO:148, the antibody Fc polypeptide also includes a T366W substitution.

A44 VH-CH1-Fc (KiH)
(SEQ ID NO: 148)
EVQLLESGGGLVQPGGSLRLSCAASGFTFSSYAMSWVRQAPGKGLEWVS

AISGSGGSTYYADSVKGRFTISRDNSKNTLYLQMNSLRAEDTAVYYCAK

DGGYYDSGAGDYWGQGTLVTVSSASTKGPSVFPLAPSSKSTSGGTAALG

CLVKDYFPEPVTVSWNSGALTSGVHTFPAVLQSSGLYSLSSVVTVPSSS

LGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKA

KGQPREPQVYTLPP<u>C</u>RDELTKNQVSL<u>W</u>CLVKGFYPSDIAVEWESNGQPE

NNYKTTPPVLDSDGSFFLYSKLTVDKSRWQQGNVFSCSVMHEALHNHYT

QKSLSLSPG

Another TriNKET of the present disclosure is A49-F3'-TriNKET-Pertuzumab. A49-F3'-TriNKET-Pertuzumab includes an scFv (SEQ ID NO:189) derived from pertuzumab that binds HER2, linked via a hinge including Ala-Ser to a first antibody Fc polypeptide; and the same NKG2D-binding Fab fragment as in A49-F3'-TriNKET-Trastuzumab, the CH1 domain of which is connected to a second antibody Fc polypeptide. The first antibody Fc polypeptide incorporates Q347R, D399V, and F405T substitutions, and the second antibody Fc polypeptide incorporates K360E and K409W substitutions. A49-F3'-TriNKET-Pertuzumab includes three polypeptides, having the sequences of SEQ ID NO:190, SEQ ID NO:141 (as in A49-F3'-TriNKET-Trastuzumab), and SEQ ID NO:142 (as in A49-F3'-TriNKET-Trastuzumab).

SEQ ID NO:190 represents the full sequence of the HER2-binding scFv linked to the first antibody Fc polypeptide via a hinge including Ala-Ser (scFv-Fc). The first antibody Fc polypeptide incorporates Q347R, D399V, and F405T substitutions for heterodimerization and an S354C substitution for forming a disulfide bond with a Y349C substitution in SEQ ID NO:141 as described above. The scFv (SEQ ID NO:189) includes a heavy chain variable domain of pertuzumab connected to the N-terminus of a light chain variable domain of pertuzumab via a $(G_4S)_4$ linker (SEQ ID NO:143), the scFv represented as VL-$(G_4S)_4$-VH ("$(G_4S)_4$" is represented by SEQ ID NO:143). The heavy and the light variable domains of the scFv are also connected through a disulfide bridge between C100 of VL and C44 of VH, as a result of Q100C and G44C substitutions in the VL and VH, respectively.

Pertuzumab scFv
(SEQ ID NO: 189)
DIQMTQSPSSLSASVGDRVTITCKAS<u>QDVSIGVA</u>WYQQKPGKAPKLLIY <u>SASYRYT</u>GVPSRFSGSGSGTDFTLTISSLQPEDFATYYC<u>QQYYIYPYTF</u>

G<u>C</u>TKVEIKR<u>GGGGSGGGGSGGGGSGGGGS</u>EVQLVESGGGLVQPGGSLR

LSCAASG<u>FTFTDYTMD</u>WVRQAPGK<u>C</u>LEWVAD<u>VNPNSGGS</u>IYNQRFKGRF

TLSVDRSKNTLYLQMNSLRAEDTAVYYCAR<u>NLGPSFYFDY</u>WGQGTLVTV

SSA

Pertuzumab scFv-Fc
(SEQ ID NO: 190)
DIQMTQSPSSLSASVGDRVTITCKAS<u>QDVSIGVA</u>WYQQKPGKAPKLLIY <u>SASYRYT</u>GVPSRFSGSGSGTDFTLTISSLQPEDFATYYC<u>QQYYIYPYTF</u>

```
GCGTKVEIKRGGGGSGGGGSGGGGSGGGGSEVQLVESGGGLVQPGGSLR

LSCAASGFTFTDYTMDWVRQAPGKCLEWVADVNPNSGGSIYNQRFKGRF

TLSVDRSKNTLYLQMNSLRAEDTAVYYCARNLGPSFYFDYWGQGTLVTV

SSAASDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPRVYTLPPCRDELTKNQ

VSLTCLVKGFYPSDIAVEWESNGQPENNYKTTPPVLVSDGSFTLYSKLT

VDKSRWQQGNVFSCSVMHEALHNHYTQKSLSLSPG
```

Another exemplary TriNKET of the present disclosure is A49MI-F3'-TriNKET-Pertuzumab. A49MI-F3'-TriNKET-Pertuzumab includes the same HER2-binding scFv (SEQ ID NO:189) as in A49-F3'-TriNKET-Pertuzumab linked via a hinge including Ala-Ser to a first antibody Fc polypeptide; and the same NKG2D-binding Fab fragment as in A49MI-F3'-TriNKET-Trastuzumab, the CH1 domain of which is connected to a second antibody Fc polypeptide. The first antibody Fc polypeptide incorporates Q347R, D399V, and F405T substitutions, and the second antibody Fc polypeptide incorporates K360E and K409W substitutions. A49MI-F3'-TriNKET-Pertuzumab includes three polypeptides having the sequences of SEQ ID NO:190 (as in A49-F3'-KiH-TriNKET-Pertuzumab), SEQ ID NO:145 (as in A49MI-F3'-TriNKET-Trastuzumab), and SEQ ID NO:142 (as in A49-F3'-TriNKET-Trastuzumab).

Another exemplary TriNKET of the present disclosure is A49-F3'-KiH-TriNKET-Pertuzumab. A49-F3'-KiH-TriNKET-Pertuzumab includes the same HER2-binding scFv (SEQ ID NO:189) as in A49-F3'-TriNKET-Pertuzumab linked via a hinge including Ala-Ser to a first antibody Fc polypeptide; and the same NKG2D-binding Fab fragment as in A49-F3'-TriNKET-Trastuzumab, the CH1 domain of which is connected to a second antibody Fc polypeptide. The first antibody Fc polypeptide incorporates the "hole" substitutions of T366S, L368A, and Y407V, and the second antibody Fc polypeptide incorporates the "knob" substitution of T366W. A49-F3'-KiH-TriNKET-Pertuzumab includes three polypeptides, having the sequences of SEQ ID NO:191, SEQ ID NO:147 (as in A49-F3'-KiH-TriNKET-Trastuzumab), and SEQ ID NO:142 (as in A49-F3'-TriNKET-Trastuzumab).

SEQ ID NO:191 represents the full sequence of the HER2-binding scFv (SEQ ID NO:189) linked to the first antibody Fc polypeptide via a hinge including Ala-Ser (scFv-Fc). The first antibody Fc polypeptide incorporates T366S, L368A, and Y407V substitutions for heterodimerization and an S354C substitution for forming a disulfide bond with a Y349C substitution in SEQ ID NO:191 as described above.

```
Pertuzumab scFv-Fc (KiH)
                                       (SEQ ID NO: 191)
DIQMTQSPSSLSASVGDRVTITCKASQDVSIGVAWYQQKPGKAPKLLIY

SASYRYTGVPSRFSGSGSGTDFTLTISSLQPEDFATYYCQQYYIYPYTF

GCGTKVEIKRGGGGSGGGGSGGGGSGGGGSEVQLVESGGGLVQPGGSLR

LSCAASGFTFTDYTMDWVRQAPGKCLEWVADVNPNSGGSIYNQRFKGRF

TLSVDRSKNTLYLQMNSLRAEDTAVYYCARNLGPSFYFDYWGQGTLVTV

SSAASDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVCTLPPSRDELTKNQ

VSLSCAVKGFYPSDIAVEWESNGQPENNYKTTPPVLDSDGSFFLVSKLT

VDKSRWQQGNVFSCSVMHEALHNHYTQKSLSLSPG
```

Another exemplary TriNKET of the present disclosure is A49MI-F3'-KiH-TriNKET-Pertuzumab. A49MI-F3'-KiH-TriNKET-Pertuzumab includes the same HER2-binding scFv (SEQ ID NO:189) as in A49-F3'-TriNKET-Pertuzumab linked via a hinge including Ala-Ser to a first antibody Fc polypeptide; and the same NKG2D-binding Fab fragment as in A49MI-F3'-TriNKET-Trastuzumab, the CH1 domain of which is connected to a second antibody Fc polypeptide. The first antibody Fc polypeptide incorporates the "hole" substitutions of T366S, L368A, and Y407V, and the second antibody Fc polypeptide incorporates the "knob" substitution of T366W. A49MI-F3'-KiH-TriNKET-Pertuzumab includes three polypeptides having the sequences of SEQ ID NO:191 (as in A49-F3'-KiH-TriNKET-Pertuzumab), SEQ ID NO:194 (as in A49MI-F3'-KiH-TriNKET-Trastuzumab), and SEQ ID NO:142 (as in A49-F3'-TriNKET-Trastuzumab).

Another exemplary TriNKET of the present disclosure is A44-F3'-TriNKET-Pertuzumab. A44-F3'-TriNKET-Pertuzumab includes the same HER2-binding scFv (SEQ ID NO:189) as in A49-F3'-TriNKET-Pertuzumab linked via a hinge including Ala-Ser to a first antibody Fc polypeptide; and the same NKG2D-binding Fab fragment as in A44-F3'-TriNKET-Trastuzumab, the CH1 domain of which is connected to a second antibody Fc polypeptide. The first antibody Fc polypeptide incorporates Q347R, D399V, and F405T substitutions, and the second antibody Fc polypeptide incorporates K360E and K409W substitutions. A44-F3'-TriNKET-Pertuzumab includes three polypeptides having the sequences of SEQ ID NO:190 (as in A49-F3'-KiH-TriNKET-Pertuzumab), SEQ ID NO:155 (as in A44-F3'-TriNKET-Trastuzumab), and SEQ ID NO:149 (as in A44-F3'-TriNKET-Trastuzumab).

Another exemplary TriNKET of the present disclosure is A44-F3'-KiH-TriNKET-Pertuzumab. A44-F3'-KiH-TriNKET-Pertuzumab includes the same HER2-binding scFv (SEQ ID NO:189) as in A49-F3'-TriNKET-Pertuzumab linked via a hinge including Ala-Ser to a first antibody Fc polypeptide; and the same NKG2D-binding Fab fragment as in A44-F3'-TriNKET-Trastuzumab, the CH1 domain of which is connected to a second antibody Fc polypeptide. The first antibody Fc polypeptide incorporates the "hole" substitutions of T366S, L368A, and Y407V, and the second antibody Fc polypeptide incorporates the "knob" substitution of T366W. A44-F3'-KiH-TriNKET-Pertuzumab includes three polypeptides having the sequences of SEQ ID NO:191 (as in A49-F3'-KiH-TriNKET-Pertuzumab), SEQ ID NO:148 (as in A44-F3'-KiH-TriNKET-Trastuzumab), and SEQ ID NO:149 (as in A44-F3'-TriNKET-Trastuzumab).

Another TriNKET of the present disclosure is A49-F3'-TriNKET-MGAH22. A49-F3'-TriNKET-MGAH22 includes an scFv (SEQ ID NO:171) derived from MGAH22 that binds HER2, linked via a hinge including Ala-Ser to a first antibody Fc polypeptide; and the same NKG2D-binding Fab fragment as in A49-F3'-TriNKET-Trastuzumab, the CH1 domain of which is connected to a second antibody Fc polypeptide. The first antibody Fc polypeptide incorporates Q347R, D399V, and F405T substitutions, and the second antibody Fc polypeptide linked to the Fab fragment incorporates K360E and K409W substitutions. A49-F3'-TriNKET-MGAH22 includes three polypeptides having the sequences of SEQ ID NO:192, SEQ ID NO:141 (as in A49-F3'-TriNKET-Trastuzumab), and SEQ ID NO:142 (as in A49-F3'-TriNKET-Trastuzumab).

SEQ ID NO:192 represents the full sequence of the HER2-binding scFv linked to the first antibody Fc polypeptide via a hinge including Ala-Ser (scFv-Fc). The first antibody Fc domain incorporates Q347R, D399V, and F405T substitutions for heterodimerization and an S354C substitution for forming a disulfide bond with a Y349C substitution in SEQ ID NO:141 as described above. The scFv (SEQ ID NO:171) includes a heavy chain variable domain of pertuzumab connected to the N-terminus of a light chain variable domain of pertuzumab via a (G4S)4 linker (SEQ ID NO:143), the scFv represented as VL-(G4S)4-VH ("(G4S)4" is represented by SEQ ID NO:143). The heavy and light variable domains of the scFv are also connected through a disulfide bridge between C100 of VL and C44 of VH, as a result of G100C and G44C substitutions in the VL and VH, respectively.

MGAH22 scFv
(SEQ ID NO: 171)
DIVMTQSHKFMSTSVGDRVSITCKAS<u>QDVNTAVA</u>WYQQKPGHSPKLLIY

<u>SASFRYT</u>GVPDRFTGSRSGTDFTFTISSVQAEDLAVYYC<u>QQHYTTPPTF</u>

G<u>C</u>GTKVEIKR<u>GGGGSGGGGSGGGGSGGGGS</u>QVQLQQSGPELVKPGASLK

LSCTAS<u>GFNIKDTYIH</u>WVKQRPEQ<u>C</u>LEWIGRI<u>YPTNGY</u>TRYDPKFQDKA

TITADTSSNTAYLQVSRLTSEDTAVYYCSR<u>WGGDGFYAMDY</u>WGQGASVT

VSSA

MGAH22 scFv-Fc
(SEQ ID NO: 192)
DIVMTQSHKFMSTSVGDRVSITCKAS<u>QDVNTAVA</u>WYQQKPGHSPKLLIY

<u>SASFRYT</u>GVPDRFTGSRSGTDFTFTISSVQAEDLAVYYC<u>QQHYTTPPTF</u>

G<u>C</u>GTKVEIKR<u>GGGGSGGGGSGGGGSGGGGS</u>QVQLQQSGPELVKPGASLK

LSCTAS<u>GFNIKDTYIH</u>WVKQRPEQ<u>C</u>LEWIGRI<u>YPTNGY</u>TRYDPKFQDKA

TITADTSSNTAYLQVSRLTSEDTAVYYCSR<u>WGGDGFYAMDY</u>WGQGASVT

VSSA<u>AS</u>DKTHTCPPCPAPELLGGPSVFLFPPKPKDTLMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREP<u>R</u>VYTLP<u>EC</u>RDELTKN

QVSLTCLVKGFYPSDIAVEWESNGQPENNYKTTPPVL<u>V</u>SDGSF<u>T</u>LYSKL

TVDKSRWQQGNVFSCSVMHEALHNHYTQKSLSLSPG

Another TriNKET of the present disclosure is A49MI-F3'-TriNKET-MGAH22. A49MI-F3'-TriNKET-MGAH22 includes the same HER2-binding scFv (SEQ ID NO:171) as in A49-F3'-TriNKET-MGAH22 linked via a hinge including Ala-Ser to a first antibody Fc polypeptide; and the same NKG2D-binding Fab fragment as in A49MI-F3'-TriNKET-Trastuzumab, the CH1 domain of which is connected to a second antibody Fc polypeptide. The first antibody Fc polypeptide incorporates Q347R, D399V, and F405T substitutions, and the second antibody Fc polypeptide incorporates K360E and K409W substitutions. A49MI-F3'-KiH-TriNKET-MGAH22 includes three polypeptides, having the sequences of SEQ ID NO:192 (as in A49-F3'-TriNKET-MGAH22), SEQ ID NO:145 (as in A49MI-F3'-TriNKET-Trastuzumab), and SEQ ID NO:142 (as in A49-F3'-TriNKET-Trastuzumab).

Another TriNKET of the present disclosure is A49-F3'-KiH-TriNKET-MGAH22. A49-F3'-KiH-TriNKET-MGAH22 includes the same HER2-binding scFv (SEQ ID NO:171) as in A49-F3'-TriNKET-MGAH22 linked via a hinge including Ala-Ser to a first antibody Fc polypeptide; and the same NKG2D-binding Fab fragment as in A49-F3'-TriNKET-Trastuzumab, the CH1 domain of which is connected to a second antibody Fc polypeptide. The first antibody Fc polypeptide incorporates the "hole" substitutions of T366S, L368A, and Y407V, and the second antibody Fc polypeptide linked to the Fab fragment incorporates the "knob" substitution of T366W. A49-F3'-KiH-TriNKET-MGAH22 includes three polypeptides having the sequences of SEQ ID NO:193, SEQ ID NO:147 (as in A49-F3'-KiH-TriNKET-Trastuzumab), and SEQ ID NO:142 (as in A49-F3'-TriNKET-Trastuzumab).

SEQ ID NO:193 represents the full sequence of the HER2-binding scFv (SEQ ID NO:171) linked to the first antibody Fc polypeptide via a hinge including Ala-Ser (scFv-Fc). The first antibody Fc polypeptide incorporates T366S, L368A, and Y407V substitutions for heterodimerization and an S354C substitution for forming a disulfide bond with a Y349C substitution in SEQ ID NO:147 as described above.

MGAH22 scFv-Fc (KiH)
(SEQ ID NO: 193)
DIVMTQSHKFMSTSVGDRVSITCKAS<u>QDVNTAVA</u>WYQQKPGHSPKLLIY

<u>SASFRYT</u>GVPDRFTGSRSGTDFTFTISSVQAEDLAVYYC<u>QQHYTTPPTF</u>

G<u>C</u>GTKVEIKR<u>GGGGSGGGGSGGGGSGGGGS</u>QVQLQQSGPELVKPGASLK

LSCTAS<u>GFNIKDTYIH</u>WVKQRPEQ<u>C</u>LEWIGRI<u>YPTNGY</u>TRYDPKFQDKA

TITADTSSNTAYLQVSRLTSEDTAVYYCSR<u>WGGDGFYAMDY</u>WGQGASVT

VSSA<u>AS</u>DKTHTCPPCPAPELLGGPSVFLFPPKPKDTLMISRTPEVTCVV

VDVSHEDPEVKFNWYVDGVEVHNAKTKPREEQYNSTYRVVSVLTVLHQD

WLNGKEYKCKVSNKALPAPIEKTISKAKGQPREPQV<u>C</u>TLPPSRDELTKN

QVSL<u>SC</u>AVKGFYPSDIAVEWESNGQPENNYKTTPPVLDSDGSFFL<u>V</u>SKL

TVDKSRWQQGNVFSCSVMHEALHNHYTQKSLSLSPG

Another exemplary TriNKET of the present disclosure is A49MI-F3'-KiH-TriNKET-MGAH22. A49MI-F3'-KiH-TriNKET-MGAH22 includes the same HER2-binding scFv (SEQ ID NO:171) as in A49-F3'-TriNKET-MGAH22 linked via a hinge including Ala-Ser to a first antibody Fc polypeptide; and the same NKG2D-binding Fab fragment as in A49MI-F3'-TriNKET-Trastuzumab, the CH1 domain of which is connected to a second antibody Fc polypeptide. The first antibody Fc polypeptide incorporates the "hole" substitutions of T366S, L368A, and Y407V, and the second antibody Fc polypeptide incorporates the "knob" substitution of T366W. A49MI-F3'-KiH-TriNKET-MGAH22 includes three polypeptides having the sequences of SEQ ID NO:193 (as in A49-F3'-KiH-TriNKET-MGAH22), SEQ ID NO:194 (as in A49MI-F3'-KiH-TriNKET-Trastuzumab), and SEQ ID NO:142 (as in A49-F3'-TriNKET-Trastuzumab).

Another exemplary TriNKET of the present disclosure is A44-F3'-TriNKET-MGAH22. A44-F3'-TriNKET-MGAH22 includes the same HER2-binding scFv (SEQ ID NO:171) as in A49-F3'-TriNKET-MGAH22 linked via a hinge including Ala-Ser to a first antibody Fc polypeptide; and the same NKG2D-binding Fab fragment as in A44-F3'-TriNKET-Trastuzumab, the CH1 domain of which is connected to a second antibody Fc polypeptide. The first antibody Fc polypeptide incorporates Q347R, D399V, and F405T substitutions, and the second antibody Fc polypeptide incorporates K360E and K409W substitutions. A44-F3'-TriNKET-MGAH22 includes three polypeptides having the sequences of SEQ ID NO:192 (as in A49-F3'-TriNKET-MGAH22), SEQ ID NO:155 (as in A44-F3'-TriNKET-Trastuzumab), and SEQ ID NO:149 (as in A44-F3'-TriNKET-Trastuzumab).

Another exemplary TriNKET of the present disclosure is A44-F3'-KiH-TriNKET-MGAH22. A44-F3'-KiH-TriNKET-MGAH22 includes the same HER2-binding scFv (SEQ ID NO:171) as in A49-F3'-TriNKET-MGAH22 linked via a hinge including Ala-Ser to a first antibody Fc polypeptide; and the same NKG2D-binding Fab fragment as in A44-F3'-TriNKET-Trastuzumab, the CH1 domain of which is connected to a second antibody Fc polypeptide. The first antibody Fc polypeptide incorporates the "hole" substitutions of T366S, L368A, and Y407V, and the second antibody Fc polypeptide incorporates the "knob" substitution of T366W. A44-F3'-KiH-TriNKET-MGAH22 includes three polypeptides having the sequences of SEQ ID NO:193 (as in A49-F3'-KiH-TriNKET-MGAH22), SEQ ID NO:148 (as in A44-F3'-KiH-TriNKET-Trastuzumab), and SEQ ID NO:149 (as in A44-F3'-TriNKET-Trastuzumab).

In certain embodiments, a TriNKET of the present disclosure is identical to one of the exemplary TriNKETs described above that includes the EW-RVT Fc mutations, except that the antibody Fc polypeptide linked to the NKG2D-binding Fab fragment incorporates the substitutions of Q347R, D399V, and F405T, and the antibody Fc polypeptide linked to the HER2-binding scFv incorporates matching substitutions K360E and K409W for forming a heterodimer. In certain embodiments, a TriNKET of the present disclosure is identical to one of the exemplary TriNKETs described above that includes the KiH Fc mutations, except that the antibody Fc polypeptide linked to the NKG2D-binding Fab fragment incorporates the "hole" substitutions of T366S, L368A, and Y407V, and the antibody Fc polypeptide linked to the HER2-binding scFv incorporates the "knob" substitution of T366W for forming a heterodimer.

In certain embodiments, a TriNKET of the present disclosure is identical to one of the exemplary TriNKETs described above, except that the antibody Fc polypeptide linked to the NKG2D-binding Fab fragment includes an S354C substitution in the CH3 domain, and the antibody Fc polypeptide linked to the HER2-binding scFv includes a matching Y349C substitution in the CH3 domain for forming a disulfide bond.

As described in International Application No. PCT/US2019/045561, the multi-specific binding proteins disclosed herein are effective in reducing tumor growth and killing cancer cells in in vitro assays and animal models. For example, A49-F3'-TriNKET-Trastuzumab is superior to trastuzumab in inducing NK cell-mediated cytotoxicity against various human cancer cell lines, such as 786-0 cells that express low levels of HER2 (HER2+), H661 cells that express moderate levels of HER2 (HER2++), and SkBr3 cells that express high levels of HER2 (HER2+++). Furthermore, the multi-specific binding proteins do not significantly induce NK-mediated killing of healthy non-cancerous human cells (e.g., human cardiomyocytes).

Specific embodiments of a multi-specific binding protein useful in any of the methods of treatment and formulations disclosed herein are described below.

In some embodiments, the first antigen-binding site that binds NKG2D includes a heavy chain variable domain (VH) with complementarity-determining region 1 (CDR1), complementarity-determining region 2 (CDR2), and complementarity-determining region 3 (CDR3) having the amino acid sequences of SEQ ID NOs: 168, 96, and 188, respectively; and a light chain variable domain (VL) with CDR1, CDR2, and CDR3 having the amino acid sequences of SEQ ID NOs: 99, 100, and 101, respectively. In some embodiments, the first antigen-binding site that binds NKG2D includes a VH with an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:94, and a VL with an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:98. In some embodiments, the first antigen-binding site that binds NKG2D is a Fab.

In some embodiments, the second antigen-binding site that binds HER2 includes a VH with CDR1, CDR2, and CDR3 having the amino acid sequences of SEQ ID NOs: 115, 116, and 117, respectively; and a VL with CDR1, CDR2, and CDR3 having the amino acid sequences of SEQ ID NOs: 119, 120, and 121, respectively. In some embodiments, the second antigen-binding site that binds HER2 includes a VH with an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:195, and a VL with an amino acid sequence at least 90% (e.g., at least 91%, at least 92%, at least 93%, at least 94%, at least 95%, at least 96%, at least 97%, at least 98%, at least 99%, or 100%) identical to the amino acid sequence of SEQ ID NO:196. In some embodiments, the second antigen-binding site that binds HER2 is a single chain variable fragment (scFv). In some embodiments, the VL of the scFv is linked to the VH of the scFv via a flexible linker. In some embodiments, the flexible linker has the amino acid sequence of SEQ ID NO:143. In some embodiments, the VL of the scFv is positioned to the N-terminus of the VH of the scFv. In some embodiments, the VH of the scFv forms a disulfide bridge with the VL of the scFv (e.g., between residues C44 of the VH of the scFv and C100 of the VL of the scFv). In some embodiments, the scFv has the amino acid sequence of SEQ ID NO:139.

In some embodiments, the antibody Fc domain comprises a first antibody Fc sequence linked to the Fab that binds NKG2D and a second antibody Fc sequence linked to the scFv that binds HER2. In some embodiments, the first antibody Fc sequence is linked to the heavy chain portion of the Fab. In some embodiments, the scFv is linked to the second antibody Fc sequence via a hinge comprising Ala-Ser. In some embodiments, the first and second antibody Fc sequences each comprise a hinge and a CH2 domain of a human IgG1 antibody. In some embodiments, the first and second antibody Fc sequences each comprise an amino acid sequence at least 90% identical to amino acids 234-332 of a wild-type human IgG1 antibody. In some embodiments, the first and second antibody Fc sequences comprise different mutations that promote heterodimerization. In some embodiments, the first antibody Fc sequence is a human IgG1 Fc sequence comprising K360E and K409W substitutions. In some embodiments, the second antibody Fc sequence is a human IgG1 Fc sequence comprising Q347R, D399V, and F405T substitutions.

In some embodiments, the multi-specific binding protein includes a first polypeptide, second polypeptide, and third polypeptide having amino acid sequences of SEQ ID NO:141, SEQ ID NO:140, and SEQ ID NO:142, respectively.

Production of Multi-Specific Binding Proteins

The multi-specific binding proteins described above can be made using recombinant DNA technology well known to a skilled person in the art. For example, a first nucleic acid sequence encoding the first immunoglobulin heavy chain can be cloned into a first expression vector; a second nucleic acid sequence encoding the second immunoglobulin heavy chain can be cloned into a second expression vector; a third nucleic acid sequence encoding the immunoglobulin light chain can be cloned into a third expression vector; and the first, second, and third expression vectors can be stably transfected together into host cells to produce the multimeric proteins.

A skilled person in the art would appreciate that during production and/or storage of proteins, N-terminal glutamate (E) or glutamine (Q) can be cyclized to form a lactam (e.g., spontaneously or catalyzed by an enzyme present during production and/or storage). Accordingly, in some embodiments where the N-terminal residue of an amino acid sequence of a polypeptide is E or Q, a corresponding amino acid sequence with the E or Q replaced with pyroglutamate is also contemplated herein.

A skilled person in the art would also appreciate that during protein production and/or storage, the C-terminal lysine (K) of a protein can be removed (e.g., spontaneously or catalyzed by an enzyme present during production and/or storage). Such removal of K is often observed with proteins that include an Fc domain at their C-termini. Accordingly, in some embodiments where the C-terminal residue of an amino acid sequence of a polypeptide (e.g., an antibody Fc polypeptide) is K, a corresponding amino acid sequence with the K removed is also contemplated herein.

To achieve the highest yield of the multi-specific binding protein, different ratios of the first, second, and third expression vector can be explored to determine the optimal ratio for transfection into the host cells. After transfection, single clones can be isolated for cell bank generation using methods known in the art, such as limited dilution, ELISA, FACS, microscopy, or Clonepix.

Clones can be cultured under conditions suitable for bio-reactor scale-up and maintained expression of the multi-specific binding protein. The multi-specific binding proteins can be isolated and purified using methods known in the art including centrifugation, depth filtration, cell lysis, homogenization, freeze-thawing, affinity purification, gel filtration, ion exchange chromatography, hydrophobic interaction exchange chromatography, and mixed-mode chromatography.

Pharmaceutical Formulations

The present disclosure also provides pharmaceutical compositions and pharmaceutical formulations that contain a multi-specific binding protein disclosed herein (e.g., A49-F3'-TriNKET-Trastuzumab) at a concentration of greater than 50 mg/mL. The pharmaceutical formulation contains one or more excipients and is maintained at a certain pH. The term "excipient," as used herein, means any non-therapeutic agent added to the formulation to provide a desired physical or chemical property, for example, pH, osmolarity, viscosity, clarity, color, isotonicity, odor, sterility, stability, rate of dissolution or release, adsorption, or penetration.

Excipients and pH

The one or more excipients in the pharmaceutical composition or pharmaceutical formulation of the present invention contains a buffering agent. The term "buffering agent," as used herein, refers to one or more components that when added to an aqueous solution is able to protect the solution against variations in pH when adding acid or alkali, or upon dilution with a solvent. In addition to phosphate buffers, glycinate, carbonate, citrate, histidine buffers and the like can be used, in which case, sodium, potassium or ammonium ions can serve as counterion.

In certain embodiments, the buffer or buffer system includes at least one buffer that has a buffering range that overlaps fully or in part with the range of pH 5.5-7.4. In certain embodiments, the buffer has a pKa of about 6.0±0.5. In certain embodiments, the buffer contains a histidine buffer. In certain embodiments, the histidine is present at a concentration of 5 to 100 mM, 10 to 100 mM, 15 to 100 mM, 20 to 100 mM, 5 to 50 mM, 10 to 50 mM, 15 to 100 mM, 20 to 100 mM, 5 to 25 mM, 10 to 25 mM, 15 to 25 mM, 20 to 25 mM, 5 to 20 mM, 10 to 20 mM, or 15 to 20 mM. In certain embodiments, the histidine is present at a concentration of 5 mM, 10 mM, 15 mM, 20 mM, 25 mM, or 50 mM. In certain embodiments, the histidine is present at a concentration of 20 mM.

The pharmaceutical composition or pharmaceutical formulation disclosed herein may have a pH of 5.5 to 6.5. For example, in certain embodiments, the pharmaceutical composition or pharmaceutical formulation has a pH of 5.5 to 6.5 (i.e., 6.0±0.5), 5.6 to 6.4 (i.e., 6.0±0.4), 5.7 to 6.3 (i.e., 6.0±0.3), 5.8 to 6.2 (i.e., 6.0±0.2), 5.9 to 6.1 (i.e., 6.0±0.1), or 5.95 to 6.05 (i.e., 6.0±0.05). In certain embodiments, the pharmaceutical composition or pharmaceutical formulation has a pH of 5.5, 5.6, 5.7, 5.8, 5.9, 6.0, 6.1, 6.2, 6.3, 6.4, or 6.5. In certain embodiments, the pharmaceutical composition or pharmaceutical formulation has a pH of 6.0. Under the rules of scientific rounding, a pH greater than or equal to 5.95 and smaller than or equal to 6.05 is rounded as 6.0.

In certain embodiments, the buffer system of the pharmaceutical composition or pharmaceutical formulation contains histidine at 10 to 25 mM, at a pH of 6.0±0.2. In certain embodiments, the buffer system of the pharmaceutical composition or pharmaceutical formulation contains histidine at 20 mM, at a pH of 6.0±0.2. In certain embodiments, the buffer system of the pharmaceutical composition or pharmaceutical formulation contains histidine at 10 to 25 mM, at a pH of 6.0±0.05. In certain embodiments, the buffer system of the pharmaceutical composition or pharmaceutical formulation contains histidine at 20 mM, at a pH of 6.0±0.05.

The one or more excipients in the pharmaceutical composition or pharmaceutical formulation disclosed herein may further contains a sugar or sugar alcohol. Sugars and sugar alcohols are useful in pharmaceutical composition or pharmaceutical formulations as a thermal stabilizer. In certain embodiments, the pharmaceutical composition or pharmaceutical formulation contains a sugar, for example, a monosaccharide (glucose, xylose, or erythritol), a disaccharide (e.g., sucrose, trehalose, maltose, or galactose), or an oligosaccharide (e.g., stachyose). In specific embodiments, the pharmaceutical composition or pharmaceutical formulation contains sucrose. In certain embodiments, the pharmaceutical composition contains a sugar alcohol, for example, a sugar alcohol derived from a monosaccharide (e.g., mannitol, sorbitol, or xylitol), a sugar alcohol derived from a disaccharide (e.g., lactitol or maltitol), or a sugar alcohol derived from an oligosaccharide. In specific embodiments, the pharmaceutical composition or pharmaceutical formulation contains sorbitol.

The amount of the sugar or sugar alcohol contained within the formulation can vary depending on the specific circumstances and intended purposes for which the formulation is used. In certain embodiments, the pharmaceutical composition or pharmaceutical formulation contains 50 to 300 mM, 50 to 250 mM, 100 to 300 mM, 100 to 250 mM, 150 to 300 mM, 150 to 250 mM, 200 to 300 mM, 200 to 250 mM, or 250 to 300 mM of the sugar or sugar alcohol. In certain embodiments, the pharmaceutical composition or pharmaceutical formulation contains 50 mM, 75 mM, 100 mM, 125 mM, 150 mM, 200 mM, 250 mM, or 300 mM of the sugar or sugar alcohol. In specific embodiments, the pharmaceutical composition or pharmaceutical formulation contains 250 mM of the sugar or sugar alcohol (e.g., sucrose or sorbitol).

The one or more excipients in the pharmaceutical composition or pharmaceutical formulation disclosed herein further contains a surfactant. The term "surfactant," as used herein, refers to a surface active molecule containing both a hydrophobic portion (e.g., alkyl chain) and a hydrophilic portion (e.g., carboxyl and carboxylate groups). Surfactants are useful in pharmaceutical composition or pharmaceutical formulations for reducing aggregation of a therapeutic protein. Surfactants suitable for use in the pharmaceutical composition or pharmaceutical formulations are generally non-ionic surfactants and include, but are not limited to, polysorbates (e.g. polysorbates 20 or 80); poloxamers (e.g. poloxamer 188); sorbitan esters and derivatives; Triton; sodium laurel sulfate; sodium octyl glycoside; lauryl-, myristyl-, linoleyl-, or stearyl-sulfobetadine; lauryl-, myristyl-, linoleyl- or stearyl-sarcosine; linoleyl-, myristyl-, or cetyl-betaine; lauramidopropyl-cocamidopropyl-, linoleami-dopropyl-, myristamidopropyl-, palmidopropyl-, or isoste-aramidopropylbetaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethylene glycol, polypropyl glycol, and copolymers of ethylene and propylene glycol (e.g., Pluronics, PF68 etc.). In certain embodiments, the surfactant is a polysorbate. In certain embodiments, the surfactant is polysorbate 80.

The amount of a non-ionic surfactant contained within the pharmaceutical composition or pharmaceutical formulation of the present invention may vary depending on the specific properties desired of the formulation, as well as the particular circumstances and purposes for which the formulations are intended to be used. In certain embodiments, the pharmaceutical composition or pharmaceutical formulation contains 0.005% to 0.5%, 0.005% to 0.2%, 0.005% to 0.1%, 0.005% to 0.05%, 0.005% to 0.02%, 0.005% to 0.01%, 0.01% to 0.5%, 0.01% to 0.2%, 0.01% to 0.1%, 0.01% to 0.05%, or 0.01% to 0.02% of the non-ionic surfactant (e.g., polysorbate 80). In certain embodiments, the pharmaceutical composition or pharmaceutical formulation contains 0.005%, 0.01%, 0.02%, 0.03%, 0.04%, 0.05%, 0.06%, 0.07%, 0.08%, 0.09%, 0.1%, 0.15%, 0.2%, 0.25%, 0.3%, 0.35%, 0.4%, 0.45%, or 0.5% of the non-ionic surfactant (e.g., polysorbate 80). The concentrations of non-ionic surfactant are provided as % (w/v) values.

In certain embodiments, the pharmaceutical composition or pharmaceutical formulation is isotonic. An "isotonic" formulation is one which has essentially the same osmotic pressure as human blood. Isotonic formulations generally have an osmotic pressure from about 250 to 350 mOsmol/kgH$_2$O. Isotonicity can be measured using a vapor pressure or ice-freezing type osmometer. In certain embodiments, the osmolarity of the pharmaceutical composition or pharmaceutical formulation is 250 to 350 mOsmol/kgH$_2$O. In certain embodiments, the osmolarity of the pharmaceutical composition or pharmaceutical formulation is 300 to 350 mOsmol/kgH$_2$O.

Substances such as a sugar, a sugar alcohol, and NaCl can be included in the pharmaceutical composition or pharmaceutical formulation for desired osmolarity. In certain embodiments, the concentration of NaCl in the pharmaceutical composition or pharmaceutical formulation, if any, is equal to or lower than 10 mM, 9 mM, 8 mM, 7 mM, 6 mM, 5 mM, 4 mM, 3 mM, 2 mM, 1 mM, 0.5 mM, 0.1 mM, 50 µM, 10 µM, 5 µM, or 1 µM. In certain embodiments, the concentration of NaCl in the pharmaceutical composition or pharmaceutical formulation is below the detection limit. In certain embodiments, no NaCl is added when preparing the pharmaceutical composition or pharmaceutical formulation.

The pharmaceutical composition or pharmaceutical formulation disclosed herein may further include one or more other substances, such as a bulking agent or a preservative. A "bulking agent" is a compound which adds mass to a lyophilized mixture and contributes to the physical structure of the lyophilized cake (e.g., facilitates the production of an essentially uniform lyophilized cake which maintains an open pore structure). Illustrative bulking agents include mannitol, glycine, polyethylene glycol and sorbitol. The lyophilized formulations of the present invention may contain such bulking agents. A preservative reduces bacterial action and may, for example, facilitate the production of a multi-use (multiple-dose) formulation.

The multi-specific binding protein can be formulated in the pharmaceutical composition or pharmaceutical formulation at high concentrations, for example, greater than 50 mg/mL. In certain embodiments, the pharmaceutical composition or pharmaceutical formulation contains greater than or equal to 60 mg/mL, greater than or equal to 70 mg/mL, greater than or equal to 80 mg/mL, greater than or equal to 90 mg/mL, greater than or equal to 100 mg/mL, greater than or equal to 125 mg/mL, greater than or equal to 150 mg/mL, greater than or equal to 175 mg/mL, or greater than or equal to 200 mg/mL of the multi-specific binding protein. In certain embodiments, the pharmaceutical composition or pharmaceutical formulation contains 60-250 mg/mL, 60-225 mg/mL, 60-200 mg/mL, 60-175 mg/mL, 50-150 mg/mL, 60-150 mg/mL, 60-125 mg/mL, 60-100 mg/mL, 60-90 mg/mL, 60-80 mg/mL, 60-70 mg/mL, 70-250 mg/mL, 70-225 mg/mL, 70-200 mg/mL, 70-175 mg/mL, 70-150 mg/mL, 70-150 mg/mL, 70-125 mg/mL, 70-100 mg/mL, 70-90 mg/mL, 70-80 mg/mL, 80-250 mg/mL, 80-225 mg/mL, 80-200 mg/mL, 80-175 mg/mL, 80-150 mg/mL, 80-150 mg/mL, 80-125 mg/mL, 80-100 mg/mL, 80-90 mg/mL, 90-250 mg/mL, 90-225 mg/mL, 90-200 mg/mL, 90-175 mg/mL, 90-150 mg/mL, 90-150 mg/mL, 90-125 mg/mL, 90-100 mg/mL, 100-250 mg/mL, 100-225 mg/mL, 100-200 mg/mL, 100-175 mg/mL, 100-150 mg/mL, 100-125 mg/mL, 125-250 mg/mL, 125-225 mg/mL, 125-200 mg/mL, 125-175 mg/mL, 125-150 mg/mL, 150-250 mg/mL, 150-225 mg/mL, 150-200 mg/mL, 150-175 mg/mL, 175-250 mg/mL, 175-225 mg/mL, 175-200 mg/mL, 200-250 mg/mL, or 200-225 mg/mL of the multi-specific binding protein. In certain embodiments, the pharmaceutical composition or pharmaceutical formulation contains 60 mg/mL, 70 mg/mL, 80 mg/mL, 90 mg/mL, 100 mg/mL, 125 mg/mL, 150 mg/mL, 175 mg/mL, 200 mg/mL, or 220 mg/mL of the multi-specific binding protein.

Exemplary Formulations

In certain embodiments, the pharmaceutical composition or pharmaceutical formulation of the present invention contains the multi-specific binding protein, histidine, a sugar or sugar alcohol (e.g., sucrose or sorbitol), and a polysorbate (e.g., polysorbate 80), at pH 5.5 to 6.5.

In certain embodiments, the pharmaceutical composition or pharmaceutical formulation contains 10 to 250 mg/mL of the multi-specific binding protein, 10 to 25 mM of histidine, 200 to 300 mM of a sugar or sugar alcohol (e.g., sucrose or sorbitol), and 0.005% to 0.05% of a polysorbate (e.g., polysorbate 80), at pH 5.5 to 6.5. In certain embodiments, the pharmaceutical composition or pharmaceutical formulation contains 10 to 250 mg/mL of the multi-specific binding protein, 20 mM of histidine, 250 mM of a sugar or sugar alcohol (e.g., sucrose or sorbitol), and 0.01% of a polysorbate (e.g., polysorbate 80), at pH 5.5 to 6.5. In certain embodiments, the pharmaceutical composition or pharmaceutical formulation contains 10 to 250 mg/mL of the multi-specific binding protein, 20 mM of histidine, 250 mM of a sugar or sugar alcohol (e.g., sucrose or sorbitol), and 0.01% of a polysorbate (e.g., polysorbate 80), at pH 5.8 to 6.2. In certain embodiments, the pharmaceutical composition or pharmaceutical formulation contains 10 to 250 mg/mL of the multi-specific binding protein, 20 mM of histidine, 250 mM of a sugar or sugar alcohol (e.g., sucrose or sorbitol), and 0.01% of a polysorbate (e.g., polysorbate 80), at pH 5.95 to 6.05.

In certain embodiments, the pharmaceutical composition or pharmaceutical formulation contains 10 to 250 mg/mL of the multi-specific binding protein, 10 to 25 mM of histidine, 200 to 300 mM of sucrose, and 0.005% to 0.05% of polysorbate 80, at pH 5.5 to 6.5. In certain embodiments, the pharmaceutical composition or pharmaceutical formulation contains 10 to 250 mg/mL of the multi-specific binding protein, 20 mM of histidine, 250 mM of sucrose, and 0.01% of polysorbate 80, at pH 5.5 to 6.5. In certain embodiments, the pharmaceutical composition or pharmaceutical formulation contains 10 to 250 mg/mL of the multi-specific binding protein, 20 mM of histidine, 250 mM of sucrose, and 0.01% of polysorbate 80, at pH 5.8 to 6.2. In certain embodiments, the pharmaceutical composition or pharmaceutical formulation contains 10 to 250 mg/mL of the multi-specific binding protein, 20 mM of histidine, 250 mM of sucrose, and 0.01% of polysorbate 80, at pH 5.95 to 6.05.

In certain embodiments, the pharmaceutical composition or pharmaceutical formulation contains 10 to 250 mg/mL of the multi-specific binding protein, 10 to 25 mM of histidine, 200 to 300 mM of sorbitol, and 0.005% to 0.05% of polysorbate 80, at pH 5.5 to 6.5. In certain embodiments, the pharmaceutical composition or pharmaceutical formulation contains 10 to 250 mg/mL of the multi-specific binding protein, 20 mM of histidine, 250 mM of sorbitol, and 0.01% of polysorbate 80, at pH 5.5 to 6.5. In certain embodiments, the pharmaceutical composition or pharmaceutical formulation contains 10 to 250 mg/mL of the multi-specific binding protein, 20 mM of histidine, 250 mM of sorbitol, and 0.01% of polysorbate 80, at pH 5.8 to 6.2. In certain embodiments, the pharmaceutical composition or pharmaceutical formulation contains 10 to 250 mg/mL of the multi-specific binding protein, 20 mM of histidine, 250 mM of sorbitol, and 0.01% of polysorbate 80, at pH 5.95 to 6.05.

In certain embodiments, the pharmaceutical composition or pharmaceutical formulation contains 10 to 50 mg/mL of the multi-specific binding protein, 5 mM to 50 mM of histidine, 50 mM to 300 mM sucrose, and about 0.005% to 0.05% (w/v) of polysorbate 80, at pH 5.5 to 6.5. In certain embodiments, the pharmaceutical composition or pharmaceutical formulation contains 10 to 25 mg/mL of the multi-specific binding protein, 10 mM to 25 mM of histidine, 150 mM to 300 mM sucrose, and about 0.005% to 0.02% (w/v) of polysorbate 80, at pH 5.8 to 6.2. In certain embodiments, the pharmaceutical composition or pharmaceutical formulation contains about 15 mg/mL of the multi-specific binding protein, about 20 mM of histidine, about 250 mM sucrose, and about 0.01% (w/v) of polysorbate 80, at about pH 6.0.

Stability of the Multi-Specific Binding Protein

The pharmaceutical compositions or pharmaceutical formulations disclosed herein exhibit high levels of stability. A pharmaceutical formulation is stable when the multi-specific binding protein within the formulation retains an acceptable degree of physical property, chemical structure, and/or biological function after storage under defined conditions.

Stability can be measured by determining the percentage of the multi-specific binding protein in the formulation that remains in a native conformation after storage for a defined amount of time at a defined temperature. The percentage of a protein in a native conformation can be determined by, for example, size exclusion chromatography (e.g., size exclusion high performance liquid chromatography), where a protein in the native conformation is not aggregated (eluted in a high molecular weight fraction) or degraded (eluted in a low molecular weight fraction). In certain embodiments, more than 95%, 96%, 97%, 98%, or 99% of the multi-specific binding protein has native conformation, as determined by size-exclusion chromatography, after incubation at 4° C. for 3 weeks. In certain embodiments, more than 90%, 91%, 92%, 93%, 94%, 95%, 96%, 97%, 98%, or 99% of the multi-specific binding protein has native conformation, as determined by size-exclusion chromatography, after incubation at 50° C. for 3 weeks. In certain embodiments, less than 0.5%, 0.6%, 0.7%, 0.8%, 0.9%, or 1% of the multi-specific binding protein forms a high molecular weight complex (i.e., having a higher molecular weight than the native protein), as determined by size-exclusion chromatography, after incubation at 4° C. for 3 weeks. In certain embodiments, less than 1%, 2%, 3%, 4%, or 5% of the multi-specific binding protein form a high molecular weight complex (i.e., having a higher molecular weight than the native protein), as determined by size-exclusion chromatography, after incubation at 50° C. for 3 weeks. In certain embodiments, less than 0.5%, 0.6%, 0.7%, 0.8%, 0.9%, or 1% of the multi-specific binding protein is degraded (i.e., having a lower molecular weight than the native protein), as determined by size-exclusion chromatography, after incubation at 4° C. for 3 weeks. In certain embodiments, less than 1%, 1.5%, 2%, 2.5%, or 3% of the multi-specific binding protein is degraded (i.e., having a lower molecular weight than the native protein), as determined by size-exclusion chromatography, after incubation at 50° C. for 3 weeks.

Stability can also be measured by determining the percentage of multi-specific binding protein present in a more acidic fraction ("acidic form") relative to the main fraction of protein ("main charge form"). While not wishing to be bound by theory, deamidation of a protein may cause it to become more negatively charged and thus more acidic relative to the non-deamidated protein (see, e.g., Robinson, Protein Deamidation, (2002) PNAS 99(8):5283-88). The percentage of the acidic form of a protein can be determined by ion exchange chromatography (e.g., cation exchange high performance liquid chromatography) or imaged capillary isoelectric focusing (icIEF). In certain embodiments, at least 50%, 60%, 70%, 80%, or 90% of the multi-specific binding protein in the pharmaceutical composition or pharmaceutical formulation is in the main charge form after incubation at 4° C. for 3 weeks. In certain embodiments, at least 15%, 20%, 25%, 30%, 40%, 50%, 60%, 70%, 80%, or 90% of the multi-specific binding protein in the pharmaceutical composition or pharmaceutical formulation is in the main charge form after incubation at 50° C. for 3 weeks. In certain embodiments, no more than 10%, 20%, 30%, 40%, or 50% of the multi-specific binding protein in the pharmaceutical composition or pharmaceutical formulation is in an acidic form after incubation at 4° C. for 3 weeks. In certain embodiments, no more than 10%, 20%, 30%, 40%, 50%, 60%, 70%, 75%, 80%, or 85% of the multi-specific binding protein in the pharmaceutical composition or pharmaceutical formulation is in an acidic form after incubation at 50° C. for 3 weeks.

Stability can also be measured by determining the purity of the multi-specific binding protein by electrophoresis after denaturing the protein with sodium dodecyl sulfate (SDS). The protein sample can be denatured in the presence or absence of an agent that reduces protein disulfide bonds (e.g., β-mercaptoethanol). In certain embodiments, the purity of the multi-specific binding protein in the pharmaceutical composition or pharmaceutical formulation, as measured by capillary electrophoresis after denaturing the protein sample under reducing conditions (e.g., in the presence of β-mercaptoethanol), is at least 95%, 96%, 97%, 98%, or 99% after incubation at 4° C. for 3 weeks. In certain embodiments, the purity of the multi-specific binding protein in the pharmaceutical composition or pharmaceutical formulation, as measured by capillary electrophoresis after denaturing the protein sample under reducing conditions (e.g., in the presence of β-mercaptoethanol), is at least 90%, 91%, 92%, 93%, 94%, 95%, 96%, 97%, 98%, or 99% after incubation at 50° C. for 3 weeks. In certain embodiments, the purity of the multi-specific binding protein in the pharmaceutical composition or pharmaceutical formulation, as measured by capillary electrophoresis after denaturing the protein sample under non-reducing conditions, is at least 95%, 96%, 97%, 98%, or 99% after incubation at 4° C. for 3 weeks. In certain embodiments, the purity of the multi-specific binding protein in the pharmaceutical composition or pharmaceutical formulation, as measured by capillary electrophoresis after denaturing the protein sample under non-reducing conditions, is at least 85%, 86%, 87%, 88%, 89%, 90%, 91%, 92%, 93%, 94%, 95%, 96%, 97%, 98%, or 99% after incubation at 50° C. for 3 weeks.

Stability can also be measured by determining the parameters of a protein solution by dynamic light scattering. The Z-average and polydispersity index (PDI) values indicate the average diameter of particles in a solution and these measures increase when aggregates are present in the solution. The monomer % Pd value indicates the spread of different monomers detected, where lower values indicate a monodispere solution, which is preferred. The monomer size detected by DLS is useful in confirming that the main population is monomer and to characterize any higher order aggregates that may be present. In certain embodiments, the Z-average value of the pharmaceutical composition or pharmaceutical formulation does not increase by more than 5%, 10%, or 15% after incubation at 4° C. for 3 weeks. In certain embodiments, the Z-average value of the pharmaceutical composition or pharmaceutical formulation does not increase by more than 5%, 10%, 15%, 20%, or 25% after incubation at 50° C. for 3 weeks. In certain embodiments, the PDI value of the pharmaceutical composition or pharmaceutical formulation does not increase by more than 10%, 20%, 30%, 40%, or 50% after incubation at 4° C. for 3 weeks. In certain embodiments, the PDI value of the pharmaceutical composition or pharmaceutical formulation does not increase by more than 2-fold, 3-fold, 4-fold, or 5-fold after incubation at 50° C. for 3 weeks.

Exemplary methods to determine stability of the multi-specific binding protein in the pharmaceutical composition or pharmaceutical formulation are described in Example 1 of the present disclosure. Additionally, stability of the protein can be assessed by measuring the binding affinity of the multi-specific binding protein to its targets or the biological activity of the multi-specific binding protein in certain in vitro assays, such as the NK cell activation assays and cytotoxicity assays described in WO 2018/152518.

Dosage Forms

The pharmaceutical composition or pharmaceutical formulation can be prepared and stored as a liquid formulation or a lyophilized form. In certain embodiments, the pharmaceutical composition or pharmaceutical formulation is a liquid formulation for storage at 2-8° C. (e.g., 4° C.) or a frozen formulation for storage at −20° C. or lower. The sugar or sugar alcohol in the formulation is used as a lyoprotectant.

Prior to pharmaceutical use, the pharmaceutical composition or pharmaceutical formulation can be diluted or reconstituted in an aqueous carrier suitable for the route of administration. Other exemplary carriers include sterile water for injection (SWFI), bacteriostatic water for injection (BWFI), a pH buffered solution (e.g., phosphate-buffered saline), sterile saline solution, Ringer's solution, or dextrose solution. For example, when prepared for intravenous administration, the pharmaceutical composition or pharmaceutical formulation can be diluted in a 0.9% sodium chloride (NaCl) solution, or a 0.9% NaCl solution and 0.01% polysorbate 80. In certain embodiments, the diluted pharmaceutical composition or pharmaceutical formulation is isotonic and suitable for administration by intravenous infusion.

The pharmaceutical composition or pharmaceutical formulation contains the multi-specific binding protein at a concentration suitable for storage. In certain embodiments, the pharmaceutical composition or pharmaceutical formulation contains the multi-specific binding protein at a concentration of 10-50 mg/mL, 10-40 mg/mL, 10-30 mg/mL, 10-25 mg/mL, 10-20 mg/mL, 10-15 mg/mL, 15-50 mg/mL, 15-40 mg/mL, 15-30 mg/mL, 15-25 mg/mL, 15-20 mg/mL, 20-50 mg/mL, 20-40 mg/mL, 20-30 mg/mL, 20-25 mg/mL, 30-50 mg/mL, 30-40 mg/mL, or 40-50 mg/mL. In certain embodiments, the pharmaceutical composition or pharmaceutical formulation contains the multi-specific binding protein at a concentration of 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 25 mg/mL, 30 mg/mL, 35 mg/mL, 40 mg/mL, 45 mg/mL, or 50 mg/mL.

In certain embodiments, the pharmaceutical composition or pharmaceutical formulation is packaged in a container (e.g., a vial, bag, pen, or syringe). In certain embodiments, the formulation may be a lyophilized formulation or a liquid formulation. In certain embodiments, the amount of multi-specific binding protein in the container is suitable for administration as a single dose. In certain embodiments, the amount of multi-specific binding protein in the container is suitable for administration in multiple doses. In certain embodiments, the pharmaceutical composition or pharmaceutical formulation contains 0.1 to 2000 mg of the multi-specific binding protein. In certain embodiments, the pharmaceutical composition or pharmaceutical formulation contains 1 to 2000 mg, 10 to 2000 mg, 20 to 2000 mg, 50 to 2000 mg, 100 to 2000 mg, 200 to 2000 mg, 500 to 2000 mg, 1000 to 2000 mg, 0.1 to 1000 mg, 1 to 1000 mg, 10 to 1000 mg, 20 to 1000 mg, 50 to 1000 mg, 100 to 1000 mg, 200 to 1000 mg, 500 to 1000 mg, 0.1 to 500 mg, 1 to 500 mg, 10 to 500 mg, 20 to 500 mg, 50 to 500 mg, 100 to 500 mg, 200 to 500 mg, 0.1 to 200 mg, 1 to 200 mg, 10 to 200 mg, 20 to 200 mg, 50 to 200 mg, 100 to 200 mg, 0.1 to 100 mg, 1 to 100 mg, 10 to 100 mg, 20 to 100 mg, 50 to 100 mg, 0.1 to 50 mg, 1 to 50 mg, 10 to 50 mg, 20 to 50 mg, 0.1 to 20 mg, 1 to 20 mg, 10 to 20 mg, 0.1 to 10 mg, 1 to 10 mg, or 0.1 to 1 mg of the multi-specific binding protein. In certain embodiments, the pharmaceutical composition or pharmaceutical formulation contains 0.1 mg, 1 mg, 2 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 400 mg, 500 mg, 600 mg, 700 mg, 800 mg, 900 mg, 1000 mg, 1500 mg, or 2000 mg of the multi-specific binding protein.

Therapeutic Uses

Combinational Use with Corticosteroids

In one aspect, the present disclosure provides a method of treating cancer, the method including administering to a subject in need thereof a therapeutically effective amount of a multi-specific binding protein, pharmaceutical composition, or pharmaceutical formulation disclosed herein (administered as a monotherapy or in a combination therapy) and a therapeutically effective amount of a corticosteroid to reduce one or more infusion-related reactions to the multi-specific binding protein, pharmaceutical composition, or pharmaceutical formulation. The present disclosure also provides a multi-specific binding protein, pharmaceutical composition, or pharmaceutical formulation disclosed herein (administered as a monotherapy or in a combination therapy) for use in a method of treating cancer in combination with a therapeutically effective amount of a corticosteroid to reduce one or more infusion-related reactions to the multi-specific binding protein, pharmaceutical composition, or pharmaceutical formulation. In a combination therapy, the multi-specific binding protein, pharmaceutical composition, or pharmaceutical formulation disclosed herein can be combined with an immunotherapy, such as an anti-PD-1 antibody (e.g., nivolumab, pembrolizumab), and/or a chemotherapy, such as a cytoskeletal-disrupting chemotherapeutic agent (e.g., paclitaxel, nab-paclitaxel, docetaxel).

The corticosteroids that are useful in the present invention generally include steroids produced by the adrenocortex, such as glucocorticoids and mineralocorticoids, and synthetic analogs and derivatives of naturally occurring corticosteroids having anti-inflammatory activity. In certain embodiments, the corticosteroid is a glucocorticoid. Glucocorticoids bind the glucocorticoid receptor and reduce inflammation by inhibiting the immune response. In certain embodiments, the corticosteroid is a mineralocorticoid. Mineral corticoids bind the mineralocorticoid receptor and act to regulate $Na^+/K^+$ concentrations in the serum. Some corticosteroids can have both glucocorticoid and mineralocorticoid functions. Examples of corticosteroids are disclosed in U.S. Pat. No. 10,799,599. In certain embodiments, the corticosteroid used in the method disclosed herein is selected from methylprednisolone, dexamethasone, hydrocortisone, prednisone, prednisolone, fluticasone, flumethasone, fluocinolone, budesonide, beclomethasone, ciclesonide, cortisone, triamcinolone, betamethasone, deflazacort, difluprednate, loteprednol, paramethasone, tixocortol, aldosterone, cloprednol, cortivazol, deoxycortone, desonide, desoximetasone, difluorocortolone, fluclorolone, fludrocortisone, flunisolide, fluocinonide, fluocortin butyl, fluorocortisone, fluorocortolone, fluorometholone, flurandrenolone, halcinonide, iconiethasone, meprednisone, mometasone, rofleponide, RPR 106541, and their respective pharmaceutically acceptable derivatives, such beclomethasone dipropionate (anhydrous of monohydrate), beclomethasone monopropionate, dexamethasone 21-isonicotinate, fluticasone propionate, icomethasone enbutate, tixocortol 21-pivalate, and triamcinolone acetonide, and pharmaceutically acceptable salts and/or derivatives thereof.

In certain embodiments, the glucocorticoid is methylprednisolone. Exemplary effective amounts of methylprednisolone can be in the range of 8 to 200 mg, 20 to 200 mg, 25 to 200 mg, 50 to 200 mg, 75 to 200 mg, 100 to 200 mg, 125 to 200 mg, 150 to 200 mg, 175 to 200 mg, 25 to 175 mg, 50 to 175 mg, 75 to 175 mg, 100 to 175 mg, 125 to 175 mg, 150 to 175 mg, 20 to 150 mg, 25 to 150 mg, 50 to 150 mg, 75 to 150 mg, 100 to 150 mg, 125 to 150 mg, 25 to 125 mg, 50 to 125 mg, 75 to 125 mg, 100 to 125 mg, 25 to 100 mg, 50 to 100 mg, 75 to 100 mg, 25 to 75 mg, 50 to 75 mg, 25 to 50 mg, about 25 mg, about 50 mg, about 75 mg, about 100 mg, about 125 mg, about 150 mg, about 175 mg, or about 200 mg. In certain embodiments, the effective amount of methylprednisolone is about 125 mg. In certain embodiments, the effective amount of methylprednisolone by oral administration is 8 mg, 16 mg 32 mg, 48 mg, 64 mg, 80 mg, 96 mg, or 120 mg.

In certain embodiments, the glucocorticoid is dexamethasone. Exemplary effective amounts of dexamethasone can be in the range of 8-200 mg, 20-200 mg, 50-200 mg, 100-200 mg, 20-150 mg, 50-150 mg, 50-100 mg, or 100-150 mg. In certain embodiments, the effective amount of dexamethasone by intravenous administration is 20 mg, 30 mg, 40 mg, 50 mg, 60 mg, 70 mg, 80 mg, 90 mg, 100 mg, 125 mg, or 150 mg. In certain embodiments, the effective amount of dexamethasone by oral administration is 8 mg, 16 mg, 32 mg, 48 mg, 64 mg, 80 mg, 96 mg, or 120 mg.

In certain embodiments, the corticosteroid is administered parenterally. In certain embodiments, the corticosteroid is administered intravenously. In certain embodiments, the corticosteroid is administered orally.

The corticosteroid can be administered prior to, simultaneously with, or subsequent to the administration of the multi-specific binding protein. In certain embodiments, the corticosteroid is administered within 6 hours, within 5 hours, within 4 hours, within 3 hours, within 2 hours, within 1 hour, within 30 minutes, within 15 minutes, or immediately prior to the administration of the multi-specific binding protein (e.g., prior to the beginning of the administration of the multi-specific binding protein). In certain embodiments, the corticosteroid is administered within 1 hour prior to the administration of the multi-specific binding protein (e.g., prior to the beginning of the administration of the multi-specific binding protein). In certain embodiments, the corticosteroid is administered simultaneously with the administration of the multi-specific binding protein. In certain embodiments, the corticosteroid and the multi-specific binding protein are diluted into a single pharmaceutical composition administered to the subject. In certain embodiments, the duration of administration of the corticosteroid and the duration of administration of the multi-specific binding protein completely or partially overlap. In certain embodiments, the corticosteroid is administered within 2 hours, 1 hour, or 30 minutes subsequent to the administration of the multi-specific binding protein (e.g., subsequent to the beginning of the administration of the multi-specific binding protein).

In certain embodiments, the corticosteroid is administered on day 1 of the first cycle (i.e., in combination with the first dose of the multi-specific binding protein). In certain embodiments, the corticosteroid is administered only on day 1 of the first cycle (i.e., in combination with the first dose of the multi-specific binding protein). In certain embodiments, the corticosteroid is further administered if an infusion-related reaction persists or recurs. In certain embodiments, infusion-related reactions include a persistent rash, diarrhea, colitis, autoimmune hepatitis, arthritis, glomerulonephritis, cardiomyopathy, or uveitis or another inflammatory eye conditions.

In certain embodiments, the corticosteroid (e.g., methylprednisolone) is administered 30 to 90 min., 40 to 90 min., 50 to 90 min., 60 to 90 min., 70 to 90 min., 80 to 90 min., 30 to 80 min., 40 to 80 min., 50 to 80 min., 60 to 80 min., 70 to 80 min., 30 to 70 min., 40 to 70 min., 50 to 70 min., 60 to 70 min., 30 to 60 min., 40 to 60 min., 50 to 60 min., 30 to 50 min., 40 to 50 min., 30 to 40 min., about 30 min., about 40 min., about 50 min., about 60 min., about 70 min., about 80 min., or about 90 min., prior to administration of the multi-specific binding protein, pharmaceutical composition, or pharmaceutical formulation disclosed herein.

In certain embodiments, subjects receive premedication treatment including about 125 mg of methylprednisolone administered intravenously within 60 minutes of administration of the multi-specific binding protein, pharmaceutical composition, or pharmaceutical formulation disclosed herein. In certain embodiments, premedication treatment further includes intravenous or oral administration of 40 to 50 mg diphenhydramine and 800 to 1000 mg of acetaminophen 30 to 60 minutes prior to administration of the multi-specific binding protein, pharmaceutical composition, or pharmaceutical formulation disclosed herein. In certain embodiments, about 1.6, 5.2, 10, 15, or 20 mg/kg of multi-specific binding protein (e.g., A49-F3'-TriNKET-Trastuzumab) is administered to the subject after pre-medication treatment.

Exemplary infusion-related reactions to a multi-specific binding protein disclosed herein include cytokine release syndrome, anaphylaxis, chills, fever/pyrexia, hypotension, hypertension, rigors, headache, dizziness, itching, sore throat, laryngeal edema, angioedema, redness/flushing, rash/urticaria, bronchospasm, tachycardia, bradycardia, auricular fibrillation, hypoxia, respiratory distress/dyspnea/shortness of breath/breathless sensation, chest tightness, nausea, vomiting, pain (e.g., chest pain, back pain), shivering, tremors, myalgia, tiredness, insomnia, asthenia, hypersensitivity, and diarrhea. Clinical presentations of cytokine release syndrome are described in Shimabukuro-Vornhagen et al., include but are not limited to fever (e.g., high fever), fatigue, headache, rash, arthralgia, myalgia, hypotension, vasopressor-requiring circulatory shock, vascular leakage, disseminated intravascular coagulation, and multi-organ system failure. In certain embodiments, the co-administration of the corticosteroid reduces one or more of the infusion-related reactions in the subject.

Combinational Use with Antihistamines

An antihistamine can be used to avoid or mitigate an allergic response (e.g., anaphylaxis) to the multi-specific binding protein. Accordingly, in certain embodiments, the method further includes administering to the subject a therapeutically effective amount of an antihistamine. Exemplary antihistamines are disclosed in U.S. Pat. No. 10,898,693. In certain embodiments, the antihistamine used in the method disclosed herein is selected from crivastine, azelastine, bilastine, brompheniramine, buclizine, bromodiphenhydramine, carbinoxamine, cetirizine, cyclizine, chlorpheniramine, chlorodiphenhydramine, clemastine, cromolyn, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocetirizine, loratadine, nedocromil, olopatadine, phenindamine, pheniramine, phenyltoloxamine, promethazine, pyrilamine, rupatadine, tripelennamine, triprolidine, and combinations thereof. In certain embodiments, the antihistamine is diphenhydramine. In certain embodiments, the therapeutically effective amount of diphenhydramine is 10 to 100 mg, 20 to 100 mg, 30 to 100 mg, 40 to 100 mg, 50 to 100 mg, 60 to 100 mg, 70 to 100 mg, 80 to 100 mg, 90 to 100 mg, 10 to 90 mg, 20 to 90 mg, 30 to 90 mg, 40 to 90 mg, 50 to 90 mg, 60 to 90 mg, 70 to 90 mg, 80 to 90 mg, 10 to 80 mg, 20 to 80 mg, 30 to 80 mg, 40 to 80 mg, 50 to 80 mg, 60 to 80 mg, 70 to 80 mg, 10 to 70 mg, 20 to 70 mg, 30 to 70 mg, 40 to 70 mg, 50 to 70 mg, 60 to 70 mg, 10 to 60 mg, 20 to 60 mg, 30 to 60 mg, 40 to 60 mg, 50 to 60 mg, 10 to 50 mg, 20 to 50 mg, 30 to 50 mg, 40 to 50 mg, 20 to 40 mg, 30 to 40 mg, 20 to 30 mg, about 20 mg, about 30 mg, about 40 mg, about 50 mg, about 60 mg, about 70 mg, about 80 mg, about 90 mg, or about 100 mg. In certain embodiments, the therapeutically effective amount of diphenhydramine is 40 to 50 mg.

In certain embodiments, the antihistamine is administered parenterally. In certain embodiments, the antihistamine is administered intravenously. In certain embodiments, the antihistamine is administered orally.

The antihistamine can be administered prior to, simultaneously with, or subsequent to the administration of the multi-specific binding protein, pharmaceutical composition, or pharmaceutical formulation disclosed herein. In certain embodiments, the antihistamine is administered within 2 hours, within 1.5 hours, within 1 hour (60 minutes), within 45 minutes, within 30 minutes, within 15 minutes, or immediately prior to the administration of the multi-specific binding protein (e.g., prior to the beginning of the administration of the multi-specific binding protein), pharmaceutical composition, or pharmaceutical formulation disclosed herein. In certain embodiments, the antihistamine is administered with every dose of the multi-specific binding protein.

In certain embodiments, the antihistamine (e.g., diphenhydramine) is administered 30 to 90 min., 40 to 90 min., 50 to 90 min., 60 to 90 min., 70 to 90 min., 80 to 90 min., 30 to 80 min., 40 to 80 min., 50 to 80 min., 60 to 80 min., 70 to 80 min., 30 to 70 min., 40 to 70 min., 50 to 70 min., 60 to 70 min., 30 to 60 min., 40 to 60 min., 50 to 60 min., 30 to 50 min., 40 to 50 min., 30 to 40 min., about 30 min., about 40 min., about 50 min., about 60 min., about 70 min., about 80 min., or about 90 min., prior to administration of the multi-specific binding protein, pharmaceutical composition, or pharmaceutical formulation disclosed herein.

In certain embodiments, a subject receives premedication treatment including 40 to 50 mg of diphenhydramine administered intravenously or orally 30 to 60 minutes prior to administration of the multi-specific binding protein, pharmaceutical composition, or pharmaceutical formulation disclosed herein. In certain embodiments, premedication treatment further includes intravenous or oral administration of 800 to 100 mg acetaminophen prior to administration of the multi-specific binding protein, pharmaceutical composition, or pharmaceutical formulation disclosed herein.

Where the method of treatment disclosed herein includes multiple doses (e.g., five or more doses) of the multi-specific binding protein, in certain embodiments, the antihistamine is administered with the first dose, the first two doses, the first three doses, the first four doses, or the first five doses of the multi-specific binding protein.

Combinational Use with Analgesics and Antipyretics

An analgesic can be used to relieve pain as a result of the administration of the multi-specific binding protein, pharmaceutical composition, or pharmaceutical formulation disclosed herein, whether administered as a monotherapy or as a combination therapy with an anti-PD-1 antibody (e.g., nivolumab or pembrolizumab) or a cytoskeletal-disrupting chemotherapeutic agent. Accordingly, in certain embodiments, the method further includes administering to the subject a therapeutically effective amount of an analgesic. Exemplary analgesics are disclosed in U.S. Patent Application Publication No. 2015/0342989 and U.S. Pat. No. 10,899,834. In certain embodiments, the analgesic used in the method disclosed herein is selected from acetaminophen, salicylamide, salicyl salicylate, methyl salicylate, magnesium salicylate, faislamine, ethenzamide, diflunisal, choline magnesium salicylate, benorylate/benorilatem and amoxiprin, acetylsalicylate, ceciafenac, acemetacin, alclofenac, bromfenac, diclofenac, etodolac, indomethacin, nabumetone, oxametacin, progiumetacin, sulindac, tolmetin, iminoprofen, benoxaprofen, carproten, dexihuprofen, dexketoprofen, fenbufen, fenoprofen, flunoxaprofen, flurbiprofen, ibuprofen, ibuproxam, indoprofen, ketoprofen, ketorolac, loxoprofen, naproxen, oxaprozin, pirprofen, suprofen, tiaprofenic acid, mefenamic acid, flutenamic acid, meciofenamic acid, toffenamic acid, droxicam, lornoxicam, meloxicam, piroxicam, tenoxicam, dipyrone, azapropazone, ciofezone, kebuzone, metamizole, mofebutazone, oxyphenbutazone, phenazone, phenylbutazone, sulfinpyrazone, decoxib, rofecoxib, parecoxib, etoricoxib, codeine, dihydrocodeine, morphine or a morphine derivative or pharmaceutically acceptable salt thereof, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, and pentazocine, and pharmaceutically acceptable salts thereof. In certain embodiments, the analgesic is acetaminophen. In certain embodiments, the therapeutically effective amount of acetaminophen is in the range of 325-1000 mg, 400-1000 mg, 500-1000 mg, 600-1000 mg, 700-1000 mg, 800-1000 mg, 900-1000 mg, 325-800 mg, 400-800 mg, 500-800 mg, 600-800 mg, 700-800 mg, 325-600 mg, 400-600 mg, or 500-600 mg. In certain embodiments, the effective amount of acetaminophen is 325 mg, 500 mg, 650 mg, 700 mg, 800 mg, 900 mg, or 1000 mg.

In certain embodiments, the analgesic is administered parenterally. In certain embodiments, the analgesic is administered intravenously. In certain embodiments, the analgesic is administered orally.

The analgesic can be administered prior to, simultaneously with, or subsequent to the administration of the multi-specific binding protein, pharmaceutical composition, or pharmaceutical formulation disclosed herein. In certain embodiments, the analgesic is administered within 2 hours, within 1.5 hours, within 1 hour (60 minutes), within 45 minutes, within 30 minutes, within 15 minutes, or immediately prior to the administration of the multi-specific binding protein (e.g., prior to the beginning of the administration of the multi-specific binding protein). In certain embodiments, the analgesic is administered simultaneously with the administration of the multi-specific binding protein. In certain embodiments, the analgesic and the multi-specific binding protein are diluted into a single pharmaceutical composition administered to the subject. In certain embodiments, the analgesic (e.g., acetaminophen) is administered with every dose of the multi-specific binding protein.

In certain embodiments, the analgesic (e.g., acetaminophen) is administered 30 to 90 min., 40 to 90 min., 50 to 90 min., 60 to 90 min., 70 to 90 min., 80 to 90 min., 30 to 80 min., 40 to 80 min., 50 to 80 min., 60 to 80 min., 70 to 80 min., 30 to 70 min., 40 to 70 min., 50 to 70 min., 60 to 70 min., 30 to 60 min., 40 to 60 min., 50 to 60 min., 30 to 50 min., 40 to 50 min., 30 to 40 min., about 30 min., about 40 min., about 50 min., about 60 min., about 70 min., about 80 min., or about 90 min., prior to administration of the multi-specific binding protein, pharmaceutical composition, or pharmaceutical formulation disclosed herein.

In certain embodiments, the duration of administration of the analgesic and the duration of administration of the multi-specific binding protein completely or partially overlap. In certain embodiments, the analgesic is administered within 2 hours, 1 hour, or 30 minutes subsequent to the administration of the multi-specific binding protein (e.g., subsequent to the beginning of the administration of the multi-specific binding protein).

An antipyretic can be used to prevent or reduce fever as a result of the administration of the multi-specific binding protein, pharmaceutical composition, or pharmaceutical formulation disclosed herein, whether administered as a monotherapy or as a combination therapy with an anti-PD-1 antibody (e.g., nivolumab or pembrolizumab) or a cytoskeletal-disrupting chemotherapeutic agent. Accordingly, in certain embodiments, the method further includes administering to the subject a therapeutically effective amount of an antipyretic. Exemplary antipyretics are disclosed in U.S. Patent Application Publication No. 2015/0342989. In certain embodiments, the antipyretic used in the method disclosed herein is selected from acetaminophen, salicylamide, salicyl salicylate, methyl salicylate, magnesium salicylate, faislamine, ethenzamide, diflunisal, choline magnesium salicylate, benorylate/benorilatem and amoxiprin, acetylsalicylate, ceclofenac, acemetacin, alclofenac, bromfenac, diclofenac, etodolac, indomethacin, nabumetone, oxametacin, proglumetacin, sulindac, tolmetin, iminoprofen, benoxaprofen, carprofen, dexibuprofen, dexketoprofen, fenbufen, fenoprofen, flunoxaprofen, flurbiprofen, ibuprofen, ibuproxam, indoprofen, ketoprofen, ketorolac, loxoprofen, naproxen, oxaprozin, pirprofen, suprofen, tiaprofenic acid, mefenamic acid, flufenamic acid, meclofenamic acid, tolfenamic acid, droxicam, lornoxicam, meloxicam, piroxicam, tenoxicam, dipyrone, azapropazone, clofezone, kebuzone, metamizole, mofebutazone, oxyphenbutazone, phenazone, phenylbutazone, sulfinpyrazone, decoxib, rofecoxib, parecoxib, and etoricoxib. In certain embodiments, the antipyretic is acetaminophen. In certain embodiments, the therapeutically effective amount of acetaminophen is in the range of 325-1000 mg, 400-1000 mg, 500-1000 mg, 600-1000 mg, 700-1000 mg, 800-1000 mg, 900-1000 mg, 325-800 mg, 400-800 mg, 500-800 mg, 600-800 mg, 700-800 mg, 325-600 mg, 400-600 mg, or 500-600 mg. In certain embodiments, the effective amount of acetaminophen is 325 mg, 500 mg, 650 mg, 700 mg, 800 mg, 900 mg, or 1000 mg.

In certain embodiments, the antipyretic is administered parenterally. In certain embodiments, the antipyretic is administered intravenously. In certain embodiments, the antipyretic is administered orally.

The antipyretic can be administered prior to, simultaneously with, or subsequent to the administration of the multi-specific binding protein. In certain embodiments, the antipyretic is administered within 2 hours, 1.5 hours, 1 hour (60 minutes), 45 minutes, 30 minutes, or 15 minutes prior to the administration of the multi-specific binding protein (e.g., prior to the beginning of the administration of the multi-specific binding protein). In certain embodiments, the antipyretic is administered simultaneously with the administration of the multi-specific binding protein. In certain embodiments, the antipyretic and the multi-specific binding protein are diluted into a single pharmaceutical composition administered to the subject. In certain embodiments, the duration of administration of the antipyretic and the duration of administration of the multi-specific binding protein completely or partially overlap. In certain embodiments, the antipyretic is administered within 2 hours, 1 hour, or 30 minutes subsequent to the administration of the multi-specific binding protein (e.g., subsequent to the beginning of the administration of the multi-specific binding protein). In certain embodiments, the antipyretic (e.g., acetaminophen) is administered with every dose of the multi-specific binding protein.

The antipyretic can be administered prior to, simultaneously with, or subsequent to the administration of the multi-specific binding protein, pharmaceutical composition, or pharmaceutical formulation disclosed herein. In certain embodiments, the analgesic (e.g., acetaminophen) is administered 30 to 90 min., 40 to 90 min., 50 to 90 min., 60 to 90 min., 70 to 90 min., 80 to 90 min., 30 to 80 min., 40 to 80 min., 50 to 80 min., 60 to 80 min., 70 to 80 min., 30 to 70 min., 40 to 70 min., 50 to 70 min., 60 to 70 min., 30 to 60 min., 40 to 60 min., 50 to 60 min., 30 to 50 min., 40 to 50 min., 30 to 40 min., about 30 min., about 40 min., about 50 min., about 60 min., about 70 min., about 80 min., or about 90 min., prior to administration of the multi-specific binding protein, pharmaceutical composition, or pharmaceutical formulation disclosed herein.

In certain embodiments, subjects receive premedication treatment including 800 to 1000 mg of acetaminophen administered intravenously or orally 30 to 60 minutes prior to administration of the multi-specific binding protein, pharmaceutical composition, or pharmaceutical formulation disclosed. In certain embodiments, premedication treatment further includes intravenous or oral administration of 40 to 50 mg diphenhydramine prior to administration of the multi-specific binding protein, pharmaceutical composition, or pharmaceutical formulation disclosed.

Dosage Regimens

In certain embodiments, the method includes administering to a subject in need thereof a multi-specific binding protein, pharmaceutical composition, or pharmaceutical formulation disclosed herein (e.g., A49-F3'-TriNKET-Trastuzumab) in an initial four-week treatment cycle on day 1, day 8, and day 15. In certain embodiments, the multi-specific binding protein, pharmaceutical composition, or pharmaceutical formulation is administered to the subject only on these three days in the initial four-week treatment cycle. In specific embodiments, the multi-specific binding protein, pharmaceutical composition, or pharmaceutical formulation is not administered to the subject on day 22. This regimen is a dose intensification schedule, which is designed to reach maximal saturation of the target as early as possible during the course of the treatment while minimizing the infusion burden for the patient.

In certain embodiments, the method further includes administering to the subject the multi-specific binding protein, pharmaceutical composition, or pharmaceutical formulation on Day 1 and Day 15 in each of one or more subsequent four-week treatment cycles after the initial treatment cycle. In certain embodiments, the multi-specific binding protein, pharmaceutical composition, or pharmaceutical formulation is administered to the subject only on these two days in each subsequent four-week treatment cycle. In specific embodiments, the multi-specific binding protein, pharmaceutical composition, or pharmaceutical formulation is not administered to the subject on day 8 or day 22. The subsequent treatment cycles, in which the subject receives administration of the multi-specific binding protein, pharmaceutical composition, or pharmaceutical formulation once every two weeks, are designed to maintain a certain level of the multi-specific binding protein, pharmaceutical composition, or pharmaceutical formulation in the subject. In certain embodiments, the subject receives at least 1, 2, 3, 4, 5, 6, 7, 8, 9, 10, 11, 12, 13, 14, or 15 subsequent treatment cycles. In certain embodiments, the subject receives subsequent treatment cycles until regression of the cancer.

In certain embodiments, the method includes administering to a subject in need thereof a multi-specific binding protein, pharmaceutical composition, or pharmaceutical formulation disclosed herein (e.g., A49-F3'-TriNKET-Trastuzumab) as a monotherapy. In certain embodiments, the method includes administering the multi-specific binding protein, pharmaceutical composition, or pharmaceutical formulation disclosed herein (e.g., A49-F3'-TriNKET-Trastuzumab) intravenously as a one hour infusion in four-week treatment cycles.

In certain embodiments, the method includes administering to a subject in need thereof a multi-specific binding protein, pharmaceutical composition, or pharmaceutical formulation disclosed herein (e.g., A49-F3'-TriNKET-Trastuzumab) over a 45 to 75 min., 50 to 75 min., 55 to 75 min., 60 to 75 min., 65 to 75 min., 70 to 75 min., 45 to 70 min., 50 to 70 min., 55 to 70 min., 60 to 70 min., 65 to 70 min., 45 to 65 min., 50 to 65 min., 55 to 65 min., 60 to 65 min., 45 to 60 min., 50 to 60 min., 55 to 60 min., 45 to 135 min., 60 to 135 min., 75 to 135 min., 90 to 135 min., 105 to 135 min., 120 to 135 min., 45 to 120 min., 60 to 120 min., 75 to 120 min., 90 to 120 min., 105 to 120 min., 45 to 105 min., 60 to 105 min., 75 to 105 min., 90 to 105 min., 45 to 90 min., 60 to 90 min., 75 to 90 min., 45 to 75 min., 60 to 75 min., 45 to 60 min., about 45 min., about 50 min., about 55 min., about 60 min., about 65 min., about 70 min., about 75 min., about 90 min., about 105 min., or about 120 min. period.

In certain embodiments, one or more doses of the multi-specific binding protein, pharmaceutical composition, or pharmaceutical formulation in the initial and subsequent treatment cycles contain 0.1-20 mg/kg, 0.1-10 mg/kg, 0.1-5 mg/kg, 0.1-2 mg/kg, 0.1-1 mg/kg, 0.1-0.5 mg/kg, 0.1-0.2 mg/kg, 0.2-20 mg/kg, 0.2-10 mg/kg, 0.2-5 mg/kg, 0.2-2 mg/kg, 0.2-1 mg/kg, 0.2-0.5 mg/kg, 0.5-20 mg/kg, 0.5-10 mg/kg, 0.5-5 mg/kg, 0.5-2 mg/kg, 0.5-1 mg/kg, 1-20 mg/kg, 1-10 mg/kg, 1-5 mg/kg, or 1-2 mg/kg of the multi-specific binding protein relative to the body weight of the subject. In certain embodiments, one or more doses of the multi-specific binding protein, pharmaceutical composition, or pharmaceutical formulation in the initial and subsequent treatment cycles contain 0.1 mg/kg, 0.15 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg of the multi-specific binding protein relative to the body weight of the subject.

In certain embodiments, each of the doses of the multi-specific binding protein, pharmaceutical composition, or pharmaceutical formulation in the initial and subsequent treatment cycles contain 0.1-20 mg/kg, 0.1-10 mg/kg, 0.1-5 mg/kg, 0.1-2 mg/kg, 0.1-1 mg/kg, 0.1-0.5 mg/kg, 0.1-0.2 mg/kg, 0.2-20 mg/kg, 0.2-10 mg/kg, 0.2-5 mg/kg, 0.2-2 mg/kg, 0.2-1 mg/kg, 0.2-0.5 mg/kg, 0.5-20 mg/kg, 0.5-10 mg/kg, 0.5-5 mg/kg, 0.5-2 mg/kg, 0.5-1 mg/kg, 1-20 mg/kg, 1-10 mg/kg, 1-5 mg/kg, or 1-2 mg/kg of the multi-specific binding protein relative to the body weight of the subject. In certain embodiments, each of the doses of the multi-specific binding protein, pharmaceutical composition, or pharmaceutical formulation in the initial and subsequent treatment cycles contain a same amount in the range of 0.1-20 mg/kg, 0.1-10 mg/kg, 0.1-5 mg/kg, 0.1-2 mg/kg, 0.1-1 mg/kg, 0.1-0.5 mg/kg, 0.1-0.2 mg/kg, 0.2-20 mg/kg, 0.2-10 mg/kg, 0.2-5 mg/kg, 0.2-2 mg/kg, 0.2-1 mg/kg, 0.2-0.5 mg/kg, 0.5-20 mg/kg, 0.5-10 mg/kg, 0.5-5 mg/kg, 0.5-2 mg/kg, 0.5-1 mg/kg, 1-20 mg/kg, 1-10 mg/kg, 1-5 mg/kg, or 1-2 mg/kg of the multi-specific binding protein relative to the body weight of the subject.

In certain embodiments, each of the doses in the initial and subsequent treatment cycles contain 0.1 mg/kg, 0.15 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg of the multi-specific binding protein. In certain embodiments, each of the doses in the initial and subsequent treatment cycles contains 0.1 mg/kg, 0.15 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg of the multi-specific binding protein.

In certain embodiments, each of the doses in the initial and subsequent treatment cycles contains $5.2 \times 10^{-5}$ mg/kg, $1.6 \times 10^{-4}$ mg/kg, $5.2 \times 10^{-4}$ mg/kg, $1.6 \times 10^{-3}$ mg/kg, $5.2 \times 10^{-3}$ mg/kg, $1.6 \times 10^{-2}$ mg/kg, $5.2 \times 10^{-2}$ mg/kg, $1.6 \times 10^{-1}$ mg/kg, 0.52 mg/kg, 1.6 mg/kg, 5.2 mg/kg, 10 mg/kg, or 20 mg/kg of the multi-specific binding protein. In certain embodiments, each of the doses in the initial and subsequent treatment cycles contains $5.2 \times 10^{-5}$ mg/kg, $1.6 \times 10^{-4}$ mg/kg, $5.2 \times 10^{-4}$ mg/kg, $1.6 \times 10^{-3}$ mg/kg, $5.2 \times 10^{-3}$ mg/kg, $1.6 \times 10^{-2}$ mg/kg, $5.2 \times 10^{-2}$ mg/kg, $1.6 \times 10^{-1}$ mg/kg, 0.52 mg/kg, 1 mg/kg, 1.6 mg/kg, 5.2 mg/kg, 10 mg/kg, 20 mg/kg, or 50 mg/kg of the multi-specific binding protein.

In certain embodiments, the multi-specific binding protein, pharmaceutical composition, or pharmaceutical formulation is administered intravenously. For example, in certain embodiments, the multi-specific binding protein, pharmaceutical composition, or pharmaceutical formulation is administered by intravenous infusion, e.g., with a prefilled bag, a prefilled pen, or a prefilled syringe. In certain embodiments, the multi-specific binding protein, in a pharmaceutical composition or pharmaceutical formulation disclosed herein, is diluted prior to administration. For example, in certain embodiments, the pharmaceutical composition or pharmaceutical formulation is diluted with sodium chloride and is administered intravenously from a 250 ml saline bag. The intravenous infusion may be for about one hour (e.g., 50 to 80 minutes). In certain embodiments, the bag is connected to a channel including a tube and/or a needle.

In certain embodiments, the multi-specific binding protein, pharmaceutical composition, or pharmaceutical formulation is administered subcutaneously. For example, in certain embodiments, the multi-specific binding protein, pharmaceutical composition, or pharmaceutical formulation is administered by subcutaneous injection using a syringe or an auto-injector. In certain embodiments, the multi-specific binding protein, pharmaceutical composition, or pharmaceutical formulation is administered by subcutaneous injection at the abdomen, arm, or thigh. In specific embodiments, the pharmaceutical composition or pharmaceutical formulation suitable for subcutaneous administration contains the multi-specific binding protein at a concentration greater than 50 mg/mL as described in the Pharmaceutical Formulations subsection above. In certain embodiments, the pharmaceutical composition or pharmaceutical formulation contains greater than or equal to 60 mg/mL, greater than or equal to 70 mg/mL, greater than or equal to 80 mg/mL, greater than or equal to 90 mg/mL, greater than or equal to 100 mg/mL, greater than or equal to 125 mg/mL, greater than or equal to 150 mg/mL, greater than or equal to 175 mg/mL, or greater than or equal to 200 mg/mL of the multi-specific binding protein. In certain embodiments, the pharmaceutical composition or pharmaceutical formulation contains 60-250 mg/mL, 60-225 mg/mL, 60-200 mg/mL, 60-175 mg/mL, 50-150 mg/mL, 60-150 mg/mL, 60-125 mg/mL, 60-100 mg/mL, 60-90 mg/mL, 60-80 mg/mL, 60-70 mg/mL, 70-250 mg/mL, 70-225 mg/mL, 70-200 mg/mL, 70-175 mg/mL, 70-150 mg/mL, 70-150 mg/mL, 70-125 mg/mL, 70-100 mg/mL, 70-90 mg/mL, 70-80 mg/mL, 80-250 mg/mL, 80-225 mg/mL, 80-200 mg/mL, 80-175 mg/mL, 80-150 mg/mL, 80-150 mg/mL, 80-125 mg/mL, 80-100 mg/mL, 80-90 mg/mL, 90-250 mg/mL, 90-225 mg/mL, 90-200 mg/mL, 90-175 mg/mL, 90-150 mg/mL, 90-150 mg/mL, 90-125 mg/mL, 90-100 mg/mL, 100-250 mg/mL, 100-225 mg/mL, 100-200 mg/mL, 100-175 mg/mL, 100-150 mg/mL, 100-125 mg/mL, 125-250 mg/mL, 125-225 mg/mL, 125-200 mg/mL, 125-175 mg/mL, 125-150 mg/mL, 150-250 mg/mL, 150-225 mg/mL, 150-200 mg/mL, 150-175 mg/mL, 175-250 mg/mL, 175-225 mg/mL, 175-200 mg/mL, 200-250 mg/mL, or 200-225 mg/mL of the multi-specific binding protein. In certain embodiments, the pharmaceutical composition or pharmaceutical formulation contains 60 mg/mL, 70 mg/mL, 80 mg/mL, 90 mg/mL, 100 mg/mL, 125 mg/mL, 150 mg/mL, 175 mg/mL, 200 mg/mL, or 220 mg/mL of the multi-specific binding protein.

Cancers Suitable for Treatment

The multi-specific binding protein, pharmaceutical composition, or pharmaceutical formulation disclosed herein can be used to treat various types of cancer. In certain embodiments, the cancer is a solid tumor. In certain other embodiments, the cancer is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, or uterine cancer. In yet other embodiments, the cancer is a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, Bartholin gland carcinoma, basal cell carcinoma, biliary cancer, bone cancer, bone marrow cancer, bronchial cancer, bronchial gland carcinoma, carcinoid, cholangiocarcinoma, chondrosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, intraepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor.

In certain embodiments, the cancer is a hematologic malignancy. In certain embodiments, the hematologic malignancy is leukemia. In certain embodiments, the leukemia is acute myeloid leukemia (AML), acute lymphoblastic leukemia (ALL), myelodysplasia, myelodysplastic syndromes, acute T-lymphoblastic leukemia, acute promyelocytic leukemia, chronic myelomonocytic leukemia, or myeloid blast crisis of chronic myeloid leukemia.

In specific embodiments, the types of cancer that can be treated with the multi-specific binding protein, pharmaceutical composition, or pharmaceutical formulation disclosed herein, where the second antigen-binding site of the multi-specific binding protein binds HER2, include but are not limited to breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, NSCLC, glioblastoma, esophageal cancer, squamous carcinoma of the skin, carcinoma of the salivary gland, biliary tract cancer, lung squamous, mesothelioma, liver cancer, sarcoma, bladder cancer, and gallbladder cancer. In certain embodiments, the cancer is a solid tumor. In certain embodiments, the cancer is a locally advanced or metastatic solid tumor. In certain embodiments, the cancer is gastric cancer (e.g., HER2 high or HER2 3+). In certain embodiments, the cancer is urothelial bladder cancer (e.g., urothelial bladder cancer expressing HER2). In certain embodiments, the cancer is metastatic breast cancer (e.g., metastatic triple negative breast cancer). In certain embodiments, the cancer is a solid tumor (e.g., HER2 high or HER2 3+).

Disclosed herein, in various embodiments, is a method of treating a HER2-overexpressing gastric cancer in a subject in need thereof, including administering an effective amount of a multi-specific binding protein or a pharmaceutical formulation disclosed herein. In certain embodiments, the cancer has a HER2 expression level scored as 3+ by immunohistochemistry. In other embodiments, the cancer has a HER2 expression level scored as 2+ by immunohistochemistry and HER2 gene amplification (e.g., determined by in situ hybridization).

Also disclosed herein, in various embodiments, is a method of treating a HER2-overexpressing gastric cancer in a subject in need thereof, including administering an anti-PD-1 antibody (e.g., nivolumab) and an effective amount of a multi-specific binding protein or a pharmaceutical formulation disclosed herein. In certain embodiments, the cancer has a HER2 expression level scored as 3+ by immunohistochemistry. In other embodiments, the cancer has a HER2 expression level scored as 2+ by immunohistochemistry and HER2 gene amplification (e.g., determined by in situ hybridization).

Also disclosed herein, in various embodiments, is a method of treating a HER2-overexpressing gastric cancer in a subject in need thereof, including administering nab-paclitaxel and an effective amount of a multi-specific binding protein or a pharmaceutical formulation disclosed herein. In certain embodiments, the cancer has a HER2 expression level scored as 3+ by immunohistochemistry. In other embodiments, the cancer has a HER2 expression level scored as 2+ by immunohistochemistry and HER2 gene amplification (e.g., determined by in situ hybridization).

Also disclosed herein, in various embodiments, is a method of treating a HER2-overexpressing gastric cancer in a subject in need thereof, including administering (e.g. via intravenous infusion) an effective amount of a multi-specific binding protein or a pharmaceutical formulation disclosed herein, in combination with nivolumab, and further in combination with nab-paclitaxel. In certain embodiments, the gastric cancer has a HER2 expression level scored as 3+ by immunohistochemistry. In other embodiments, the gastric cancer has a HER2 expression level scored as 2+ by immunohistochemistry and HER2 gene amplification (e.g., determined by in situ hybridization).

Disclosed herein, in various embodiments, is a method of treating metastatic triple negative breast cancer (TNBC) in a subject in need thereof, including administering an effective amount of a multi-specific binding protein or a pharmaceutical formulation disclosed herein.

In certain embodiments, the subject treated by the method disclosed herein has a HER2-positive cancer. Methods of determining HER2 expression in a cancer include but are not limited to immunohistochemistry (IHC). Anti-HER2 antibodies (e.g., Ventana 4B5 antibody and Bond Oracle CB11 antibody) have been approved by the FDA for detecting HER2, and immunohistochemistry kits (e.g., HercepTest™) are commercially available. The level of HER2 expression in a tumor sample, as detected by immunohistochemistry, can be quantified and scored as 1+, 2+, or 3+ according to the ASCO/CAP guideline (Wolff et al., (2007) J. Clin. Oncol. 25(1):118-45) and the 2018 update (Wolff et al., (2018) J. Clin. Oncol. 36(20):2105-22). Under the 2018

ASCO/CAP guideline, a cancer or tumor is scored as HER2 3+ if in a sample, circumferential membrane staining of HER2 is complete, intense and in >10% of tumor cells, which is readily appreciated using a low power objective and observed within a homogeneous and contiguous invasive cell population. A cancer or tumor is scored as HER2 2+ if weak to moderate complete membrane staining of HER2 is observed in >10% of tumor cells in a sample. A cancer or tumor is scored as HER2 1+ if incomplete membrane staining of HER2 is faint or barely perceptible and in >10% of tumor cells in a sample. A cancer or tumor is scored as HER2 negative if no HER2 staining is observed or membrane staining is incomplete and is faint or barely perceptible and in ≤10% of tumor cells. Where a cancer or tumor is scored as HER2 2+ in this initial IHC assessment, a reflex test (same specimen using ISH) or a new test (new specimen if available, using IHC or ISH) must be ordered. Based on the result of the reflex test or the new test, the cancer or tumor may be re-scored as HER2 3+ or 1+.

It is understood that ERBB2 gene amplification is generally correlated with HER2 overexpression. Determining whether ERBB2 gene is amplified in a cancer tissue sample may help reduce false-positive results from immunohistochemistry of the same sample (see, e.g., Sarode et al., (2015) Arch. Pathol. Lab. Med. 139:922-28). Accordingly, in certain embodiments, the cancer or tumor in the subject has been assessed by ERBB2 gene amplification. In certain embodiments, the cancer or tumor harbors ERBB2 gene amplification, for example, an average ERBB2 gene copy number greater than or equal to 4.0 signals per cell (e.g., greater than or equal to 6.0 signals per cell). In certain embodiments, the cancer or tumor (e.g., a HER2 1+ cancer or tumor) has an average ERBB2 gene copy number less than 4.0 signals per cell. In certain embodiments, the cancer or tumor (e.g., a HER2 1+ cancer or tumor) does not have ERBB2 gene amplification. Methods of detecting gene amplification include but are not limited to fluorescent in situ hybridization (FISH), chromogenic in situ hybridization (CISH), quantitative PCR, and DNA sequencing. In certain embodiments, ERBB2 gene amplification is determined by FISH. In certain embodiments, ERBB2 gene amplification is determined by DNA sequencing (e.g., deep sequencing).

New technologies can be employed to assess HER2 levels in patient samples. For example, the automated quantitative analysis technology can quantitatively assess HER2 expression by measuring the intensity of antibody-conjugated fluorophores. The HERmark technology measures HER2 expression through a proximity-based release of antibody-bound fluorescent tags. The quantitative IHC technology converts antibody/antigen complexes into red dots, subsequently counted to quantify HER2 expression. The time-resolved fluorescence energy transfer technology enables assessment of HER2 expression through the detection of fluorescence emitted by two fluorophores in close proximity. The quantitative real-time polymerase chain reaction technology enables quantitative measurement of the amount of HER2 mRNA in a sample. The flow cytometry technology enables measurement of the number of HER2 proteins on the surface of a cell. These assays can complement the results of the IHC or FISH assays, thereby obtaining more accurate assessment of the HER2 level in the cancer or tumor.

For example, in certain embodiments, the cancer or tumor can be assessed by flow cytometry. As described in Example 5 below, Molecules of Equivalent Soluble Fluorochrome (MESF) beads with manufacturer predetermined fluorophore amounts can be used to generate a calibration curve. This calibration curve can be used to correlate the geometric mean fluorescence intensity (MFI) of a given cell population to standardized molecules numbers. The reagent detecting the HER2 proteins can be a protein that binds HER2 (e.g., a HER2 TriNKET disclosed herein) coupled with a fluorophore. Where the sample is a cell line, the geometric mean of the number of HER2 proteins on the cells can be determined. Cell lines with determined levels of HER2 can then be used as references, e.g., in an IHC assay, to determine the level of HER2 in tumor samples. In fact, SKBR3, MDA-MB-175 and MDA-MB-231 cell lines are used as references to set level 3, level 1 and level 0 staining intensity for the HercepTest. In certain embodiments, a cell line having a geometric mean of 500,000 or more (e.g., 600,000 or more, 700,000 or more, 800,000 or more, or 900,000 or more) HER2 proteins on each cell corresponds to the cells that have complete, intense circumferential membrane staining of HER2 in a HER2 3+ sample; a cell line having a geometric mean of 75,000 to 499,999 (e.g., 80,000 to 499,999, 90,000 to 499,999, 100,000 to 499,999, 110,000 to 499,999, 120,000 to 499,999, 85,000 to 399,999, 90,000 to 399,999, 100,000 to 399,999, 110,000 to 399,999, 115,000 to 399,999, 120,000 to 399,999, 85,000 to 299,999, 90,000 to 299,999, 95,000 to 299,999, 100,000 to 299,999, 105,000 to 299,999, 110,000 to 299,999, 85,000 to 199,999, 90,000 to 199,999, 95,000 to 199,999, 100,000 to 199,999, 105,000 to 199,999, or 110,000 to 199,999,) HER2 proteins on each cell corresponds to the cells that have weak to moderate complete membrane staining of HER2 in a HER2 2+ sample; a cell line having a geometric mean of 10,000 to 74,999 (e.g., 11,000 to 74,999, 11,000 to 69,999, 11,000 to 64,999, 11,000 to 59,999, or 11,000 to 54,999) HER2 proteins on each cell corresponds to the cells that have faint or barely perceptible, incomplete membrane staining of HER2 in a HER2 1+ sample. A cell line having a geometric mean of less than 10,000 (e.g., 9000 or less, 8000 or less, 7000 or less, 6000 or less, 5000 or less, 4000 or less) HER2 proteins on each cell corresponds to negative membrane staining in a HER2 0 sample. According to the 2018 ASCO/CAP guideline, more than 10% of tumor cells in a sample must meet the required HER2 level threshold.

In certain embodiments, the subject treated by the method disclosed herein has a cancer or tumor (e.g., any one of the types of cancer disclosed in the preceding three paragraphs) with HER2 level scored as 1+, 2+, or 3+. In certain embodiments, the subject treated by the method disclosed herein has a cancer or tumor (e.g., any one of the types of cancer disclosed in the preceding three paragraphs) with HER2 level scored as 1+ or 2+. In certain embodiments, the subject treated by the method disclosed herein has a cancer or tumor (e.g., any one of the types of cancer disclosed in the preceding three paragraphs) with HER2 level scored as 2+ or 3+. In certain embodiments, the subject treated by the method disclosed herein has a cancer or tumor (e.g., any one of the types of cancer disclosed in the preceding three paragraphs) with HER2 level scored as 1+. In certain embodiments, the subject treated by the method disclosed herein has a cancer or tumor (e.g., any one of the types of cancer disclosed in the preceding three paragraphs) with HER2 level scored as 2+. In certain embodiments, the subject treated by the method disclosed herein has a cancer or tumor (e.g., any one of the types of cancer disclosed in the preceding three paragraphs) with HER2 level scored as 3+. In certain embodiments, the HER2 level is determined by immunohistochemistry (e.g., HercepTest™). In certain embodiments, the subject treated by the method disclosed herein has a tumor that shows HER2 expression at least as a faint/barely perceptible membrane staining detected in at least or more than 10% of the tumor cells. In certain embodiments, the subject treated by the method disclosed herein has a tumor that shows HER2 expression at least as a weak to moderate complete membrane staining detected in at least or more than 10% of the tumor cells. In certain embodiments, the subject treated by the method disclosed herein has a tumor that shows HER2 expression at least as a strong complete membrane staining detected in at least or more than 10% of the tumor cells.

In certain embodiments, the subject treated by the method disclosed herein has a cancer or tumor with a HER2 level scored as 1+, and the cancer or tumor is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, uterine cancer, a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, Bartholin gland carcinoma, basal cell carcinoma, biliary cancer, bone cancer, bone marrow cancer, bronchial cancer, bronchial gland carcinoma, carcinoid, cholangiocarcinoma, chondrosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, intraepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor. In certain embodiments, the subject treated by the method disclosed herein has a cancer or tumor with a HER2 level scored as 1+, and the cancer or tumor is a hematologic malignancy such as leukemia, acute myeloid leukemia (AML), acute lymphoblastic leukemia (ALL), myelodysplasia, myelodysplastic syndromes, acute T-lymphoblastic leukemia, acute promyelocytic leukemia, chronic myelomonocytic leukemia, or myeloid blast crisis of chronic myeloid leukemia. In certain embodiments, the subject treated by the method disclosed herein has a cancer or tumor with a HER2 level scored as 1+, and the cancer or tumor is breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, NSCLC, glioblastoma, esophageal cancer, squamous carcinoma of the skin, carcinoma of the salivary gland, biliary tract cancer, lung squamous, mesothelioma, liver cancer, sarcoma, bladder cancer, gallbladder cancer, urothelial bladder cancer, or metastatic breast cancer. In certain embodiments, the subject treated by the method disclosed herein has a cancer or tumor with a HER2 level scored as 1+, and the cancer or tumor is a solid tumor, such as a locally advanced or metastatic solid tumor. In certain embodiments, the cancer or tumor is a triple negative breast cancer with a HER2 level scored as 1+. In certain embodiments, the cancer or tumor is positive for a hormone receptor (i.e., positive for estrogen receptor, progesterone receptor, or both) and negative for HER2 (e.g., as assessed by IHC). According to the 2018 ASCO/CAP HER2 testing guideline update, breast cancer is considered HER2 negative in cases of IHC 0 and 1+ results, or IHC 2+ with a negative ISH assay. Thus, in certain embodiments, the cancer or tumor is a triple negative breast cancer negative for estrogen receptor and progesterone receptor (e.g., as assessed by IHC) with a HER2 level scored as IHC 1+. In certain embodiments, the cancer or tumor is a hormone receptor positive breast cancer (e.g., as assessed by IHC) with a HER2 level scored as IHC 1+. In certain embodiments, the HER2 1+ cancer or tumor has an average ERBB2 gene copy number less than 4.0 signals per cell. In certain embodiments, the HER2 1+ cancer or tumor does not have ERBB2 gene amplification.

In certain embodiments, the subject treated by the method disclosed herein has a cancer or tumor with a HER2 level scored as 2+, and the cancer or tumor is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, uterine cancer, a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, Bartholin gland carcinoma, basal cell carcinoma, biliary cancer, bone cancer, bone marrow cancer, bronchial cancer, bronchial gland carcinoma, carcinoid, cholangiocarcinoma, chondrosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, intraepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor. In certain embodiments, the subject treated by the method disclosed herein has a cancer or tumor with a HER2 level scored as 2+, and the cancer or tumor is a hematologic malignancy such as leukemia, acute myeloid leukemia (AML), acute lymphoblastic leukemia (ALL), myelodysplasia, myelodysplastic syndromes, acute T-lymphoblastic leukemia, acute promyelocytic leukemia, chronic myelomonocytic leukemia, or myeloid blast crisis of chronic myeloid leukemia. In certain embodiments, the subject treated by the method disclosed herein has a cancer or tumor with a HER2 level scored as 2+, and the cancer or tumor is breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, NSCLC, glioblastoma, esophageal cancer, squamous carcinoma of the skin, carcinoma of the salivary gland, biliary tract cancer, lung squamous, mesothelioma, liver cancer, sarcoma, bladder cancer, gallbladder cancer, urothelial bladder cancer, or metastatic breast cancer. In certain embodiments, the subject treated by the method disclosed herein has a cancer or tumor with a HER2 level scored as 2+, and the cancer or tumor is a solid tumor, such as a locally advanced or metastatic solid tumor. In certain embodiments, the cancer or tumor is a triple negative breast cancer with a HER2 level scored as IHC 2+ with a negative ISH assay. In certain embodiments, the cancer or tumor is a hormone receptor positive breast cancer (e.g., as assessed by IHC) with a HER2 level scored as IHC 2+ with a negative ISH assay. In certain embodiments, the HER2 2+ cancer or tumor has an average ERBB2 gene copy number less than 4.0 signals per cell. In certain embodiments, the HER2 2+ cancer or tumor does not have ERBB2 gene amplification.

In certain embodiments, the subject treated by the method disclosed herein has a cancer or tumor with a HER2 level that is not high (i.e., scored as 1+ or 2+), and the cancer or tumor is brain cancer, bladder cancer, breast cancer, cervical cancer, colon cancer, colorectal cancer, endometrial cancer, esophageal cancer, leukemia, lung cancer, liver cancer, melanoma, ovarian cancer, pancreatic cancer, prostate cancer, rectal cancer, renal cancer, stomach cancer, testicular cancer, uterine cancer, a vascularized tumor, squamous cell carcinoma, adenocarcinoma, small cell carcinoma, melanoma, glioma, neuroblastoma, sarcoma (e.g., an angiosarcoma or chondrosarcoma), larynx cancer, parotid cancer, biliary tract cancer, thyroid cancer, acral lentiginous melanoma, actinic keratoses, acute lymphocytic leukemia, acute myeloid leukemia, adenoid cystic carcinoma, adenomas, adenosarcoma, adenosquamous carcinoma, anal canal cancer, anal cancer, anorectum cancer, astrocytic tumor, Bartholin gland carcinoma, basal cell carcinoma, biliary cancer, bone cancer, bone marrow cancer, bronchial cancer, bronchial gland carcinoma, carcinoid, cholangiocarcinoma, chondrosarcoma, choroid plexus papilloma/carcinoma, chronic lymphocytic leukemia, chronic myeloid leukemia, clear cell carcinoma, connective tissue cancer, cystadenoma, digestive system cancer, duodenum cancer, endocrine system cancer, endodermal sinus tumor, endometrial hyperplasia, endometrial stromal sarcoma, endometrioid adenocarcinoma, endothelial cell cancer, ependymal cancer, epithelial cell cancer, Ewing's sarcoma, eye and orbit cancer, female genital cancer, focal nodular hyperplasia, gallbladder cancer, gastric antrum cancer, gastric fundus cancer, gastrinoma, glioblastoma, glucagonoma, heart cancer, hemangioblastomas, hemangioendothelioma, hemangiomas, hepatic adenoma, hepatic adenomatosis, hepatobiliary cancer, hepatocellular carcinoma, Hodgkin's disease, ileum cancer, insulinoma, intraepithelial neoplasia, intraepithelial squamous cell neoplasia, intrahepatic bile duct cancer, invasive squamous cell carcinoma, jejunum cancer, joint cancer, Kaposi's sarcoma, pelvic cancer, large cell carcinoma, large intestine cancer, leiomyosarcoma, lentigo maligna melanomas, lymphoma, male genital cancer, malignant melanoma, malignant mesothelial tumors, medulloblastoma, medulloepithelioma, meningeal cancer, mesothelial cancer, metastatic carcinoma, mouth cancer, mucoepidermoid carcinoma, multiple myeloma, muscle cancer, nasal tract cancer, nervous system cancer, neuroepithelial adenocarcinoma nodular melanoma, non-epithelial skin cancer, non-Hodgkin's lymphoma, oat cell carcinoma, oligodendroglial cancer, oral cavity cancer, osteosarcoma, papillary serous adenocarcinoma, penile cancer, pharynx cancer, pituitary tumors, plasmacytoma, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous cell carcinoma, striated muscle cancer, submesothelial cancer, superficial spreading melanoma, T cell leukemia, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, VIPoma, vulva cancer, well differentiated carcinoma, or Wilms tumor. In certain embodiments, the subject treated by the method disclosed herein has a cancer or tumor with a HER2 level that is not high (i.e., scored as 1+ or 2+), and the cancer or tumor is a hematologic malignancy such as leukemia, acute myeloid leukemia (AML), acute lymphoblastic leukemia (ALL), myelodysplasia, myelodysplastic syndromes, acute T-lymphoblastic leukemia, acute promyelocytic leukemia, chronic myelomonocytic leukemia, or myeloid blast crisis of chronic myeloid leukemia. In certain embodiments, the subject treated by the method disclosed herein has a cancer or tumor with a HER2 level scored that is not high (e.g., scored as 1+ or 2+), and the cancer or tumor is breast cancer, thyroid cancer, gastric cancer, renal cell carcinoma, adenocarcinoma of the lung, prostate cancer, cholangiocarcinoma, uterine cancer, pancreatic cancer, colorectal cancer, ovarian cancer, cervical cancer, head and neck cancer, NSCLC, glioblastoma, esophageal cancer, squamous carcinoma of the skin, carcinoma of the salivary gland, biliary tract cancer, lung squamous, mesothelioma, liver cancer, sarcoma, bladder cancer, gallbladder cancer, urothelial bladder cancer, and metastatic breast cancer. In certain embodiments, the subject treated by the method disclosed herein has a cancer or tumor with a HER2 level scored that is not high (i.e., scored as 1+ or 2+), and the cancer or tumor is a solid tumor, such as a locally advanced or metastatic solid tumor. In certain embodiments, the cancer or tumor is a triple negative breast cancer with a HER2 level scored as IHC 1+, or IHC 2+ with a negative ISH assay. In certain embodiments, the cancer or tumor is a hormone receptor positive breast cancer (e.g., as assessed by IHC) with a HER2 level scored as IHC 1+, or IHC 2+ with a negative ISH assay. In certain embodiments, the cancer or tumor with a HER2 level score that is not high (i.e., scored as 1+ or 2+) has an average ERBB2 gene copy number less than 4.0 signals per cell. In certain embodiments, the cancer or tumor with a HER2 level score that is not high (i.e., scored as 1+ or 2+) does not have ERBB2 gene amplification.

In certain embodiments, the subject treated in accordance with the methods disclosed herein has not received prior therapy for treating the cancer. In certain embodiments, the subject treated in accordance with the methods disclosed herein has not received prior chemotherapy or immunotherapy for treating the cancer. In certain embodiments, the subject treated in accordance with the methods disclosed herein has received a prior therapy (e.g., a chemotherapy or immunotherapy) but continues to experience cancer progression despite the prior therapy. In certain embodiments, the subject treated in accordance with the methods disclosed herein has experienced cancer regression after receiving a prior therapy (e.g., a chemotherapy or immunotherapy), but later experienced cancer relapse. In certain embodiments, the subject treated in accordance with the methods disclosed herein is intolerant to a prior therapy (e.g., a chemotherapy or immunotherapy).

In certain embodiments, the subject treated in accordance with the methods disclosed herein meets one or more of the inclusion criteria of a clinical trial cohort (e.g., the accelerated titration cohort, the "3+3" dose escalation cohort, the safety/PK/PD expansion cohorts, the urothelial bladder cancer (UBC) cohort, the metastatic breast cancer (MBC) cohort, the Basket solid tumors with high HER2 expression (HER2 3+) cohort, or the Combination therapy with pembrolizumab cohort) described in Example 3. In certain embodiments, the subject treated in accordance with the methods disclosed herein meets all the inclusion criteria of a clinical trial cohort (e.g., the accelerated titration cohort, the "3+3" dose escalation cohort, the safety/PK/PD expansion cohorts, the UBC cohort, the MBC cohort, the Basket solid tumors with high HER2 expression (HER2 3+) cohort, or the Combination therapy with pembrolizumab cohort) described in Example 3.

In certain embodiments, provide herein are methods of treating cancer in a subject having one or more (e.g., all) of the following characteristics:
histologically or cytologically proven locally advanced or metastatic solid tumors, for which no standard therapy exists, or standard therapy has failed;
primary tumors having documented HER2 expression detected by immunohistochemistry;
detectable erbb2 amplification and/or erbb2 activating mutations in a tumor biopsy;
histologically or cytologically proven locally advanced or metastatic solid tumors for which no standard therapy exists, or standard therapy has failed;
has HER2-expressing tumors (at least 1+ at the time of screening) as determined by immunohistochemistry using a CLIA accredited (or equivalent) method;
has disease measurable with at least one unidimensional measurable lesion by RECIST 1.1;
ECOG performance status of 0 or 1 at study entry and an estimated life expectancy of at least 3 months;
baseline left ventricular ejection fraction (LVEF)≥55% as measured by echocardiography or multigated acquisition (MUGA) scan;
adequate hematological function defined by white blood cell (WBC) count ≥3×10$^9$/L with absolute neutrophil count (ANC)≥1.5×10$^9$/L, lymphocyte count ≥0.5×10$^9$/L, platelet count ≥75×10$^9$/L, and hemoglobin ≥9 g/dL (may have been transfused);
adequate hepatic function defined by a total bilirubin level ≤1.5×the upper limit of normal (ULN), an aspartate aminotransferase (AST) level ≤2.5×ULN, and an alanine aminotransferase (ALT) level ≤2.5×ULN or, for patients with documented metastatic disease to the liver, AST and ALT levels ≤5×ULN; and/or
adequate renal function defined by an estimated creatinine clearance >50 mL/min according to the Cockcroft-Gault formula.

In certain embodiments, provide herein are methods of treating cancer in a subject having one or more (e.g., all) of the following characteristics:
is eligible to receive nivolumab per its label for a malignancy of epithelial origin; or has a tumor that does not have a standard therapy or standard therapy has failed; and
has received anti-PD-1 or anti-PD-L1 as a previous line of therapy; or has not received anti-PD-1 or anti-PD-L1 as a previous line of therapy and has experienced a grade 3 or 4 drug-related toxicity or a grade 2 drug related toxicity impacting the lungs or the neurological system, related to the prior anti-PD-1 or anti-PD-L1 therapy.

In certain embodiments, provide herein are methods of treating cancer in a subject having one or more (e.g., all) of the following characteristics:
is eligible to receive nab-paclitaxel per its label after failure of combination therapy for metastatic disease or relapse within 6 months of adjuvant chemotherapy, and has not been exposed to taxanes within the last six months;
has a tumor that has no standard therapy or standard therapy has failed; or has an advanced (unresectable/recurrent/metastatic) triple negative breast cancer (TNBC).

In certain embodiments, provide herein are methods of treating a subject having urothelial bladder cancer (UBC) and one or more (e.g., all) of the following characteristics:
- histologically or cytologically documented locally advanced or metastatic transitional cell carcinoma of the urothelium (including renal pelvis, ureters, urinary urothelial, urethra);
- radiographic disease progression after the subject's last line of therapy;
- received treatment with one (and no more than one) platinum-containing regimen (e.g., platinum plus another agent such as gemcitabine, methotrexate, vinblastine, doxorubicin, etc.) for inoperable locally advanced or metastatic urothelial carcinoma with radiographic progression or recurrence within 6 months after the last administration of a platinum-containing regimen as an adjuvant, which would be considered failure of a first-line, platinum-containing regimen;
- treatment with a checkpoint inhibitor (i.e. anti-PD-1 or anti-PD-L1), with radiographic progression (optionally, treatment with a combination of platinum-based therapy with PD-1/PD-L1-based therapy); and/or
- HER2 expression of at least 1+ determined by immunohistochemistry.

In certain embodiments, provided herein are methods for treating a subject having metastatic breast cancer (MBC) and one or more (e.g., all) of the following characteristics:
- histologically confirmed MBC;
- no more than 3 prior lines of cytotoxic therapy for metastatic disease;
- previous received treatment with taxane and an anthracycline, unless anthracycline is contraindicated;
- a tumor scoring 1+ or 2+ by IHC, and if scoring is 2+, and the existence of tumor amplification of ERRB2 must be ruled by an FDA approved method; and/or
- radiographic progression after the last line of systemic therapy.

In certain embodiments, provided herein are methods for treating a subject having triple negative breast cancer (TNBC) and one or more (e.g., all) of the following characteristics:
- a tumor having a PD-L1 score (CPS) less than 10 as measured by immunohistochemistry, for example, using Agilent/Dako's PD-L1 immunohistochemistry 22C3 pharmDx assay;
- histologically documented (metastatic or locally advanced) TNBC, including a HER2 status making the subject ineligible for trastuzumab as defined per the American College of Physicians (ACP) guidelines or equivalent, negative ER expression, and negative PR expression:
  - lack of HER2 amplification as determined by in situ hybridization (ratio of HER2 to CEP17 smaller than 2.0 or single probe average HER2 gene copy number smaller than 4 signals/cell), or HER2 expression level 0, 1+, or 2+ as measured by immunohistochemistry, and
  - ER and PR negative (as defined as <1% of cells expressing hormonal receptors via immunohistochemistry analysis);
- has not previously received chemotherapy or targeted systemic therapy for inoperable locally advanced or metastatic TNBC; and/or
- has disease measurable with at least one unidimensional measurable lesion by RECIST 1.1.

In certain embodiments, provided herein are methods for treating a subject having a HER2 3+ tumor and one or more (e.g., all) of the following characteristics:
- any solid tumor except breast cancer or gastric cancer and a history of erbb2 amplification within the tumor and one of the following 1) HER2 3+ scoring by immunohistochemistry documented in the subject's most recent biopsy within 6 months, post radiographic progression on the last line of therapy or 2) HER2 3+ scoring by immunohistochemistry during the screening window; and
- treatment with at least one line of an approved or established therapy.

In certain embodiments, provided herein are methods for treating a subject having gastric cancer and one or more (e.g., all) of the following characteristics:
- advanced (unresectable/recurrent/metastatic) gastric cancer or cancer of the gastro-esophageal junction as per the 7$^{th}$ American Joint Committee on Cancer (AJCC) classification;
- has a HER2 positive tumor per the American College of Physicians (ACP) guidelines, and therefore eligible for trastuzumab treatment;
- previously received treatment with a first line of therapy including a platinum salt and a fluoropyridine in combination with trastuzumab or a biosimilar to trastuzumab;
- has progressed after the first line therapy;
- has received only one line of therapy for the treatment of metastatic disease;
- has disease measurable with at least one unidimensional measurable lesion by RECIST 1.1; and/or
- has a tumor that is not known to be microsatellite instability (MSI) high.

In certain embodiments, provide herein are methods of treating a subject having a HER2 3+ solid tumor and one or more (e.g., all) of the following characteristics:
- has disease measurable with at least one unidimensional measurable lesion by RECIST 1.1;
- has any solid tumor except breast cancer or gastric cancer and a history of erbb2 amplification within the tumor and one of the following 1) HER2 3+ scoring by immunohistochemistry documented in the subject's most recent biopsy within 6 months, post radiographic progression on the last line of therapy, or 2) HER2 3+ scoring by immunohistochemistry during the screening window; and/or
- has received treatment with at least one line of an approved or established therapy.

In certain embodiments, provided herein are methods for treating a subject having a malignancy of epithelial origin and is eligible for treatment with nivolumab in accordance with its label. In certain embodiments, provided herein are methods for treating a subject having a metastatic breast cancer, and has failed to respond to a combination chemotherapy for metastatic disease or relapsed within 6 months of the adjuvant chemotherapy, did not have exposure to taxanes in the last 6 months, and is eligible for treatment with nab-paclitaxel in accordance with its label.

In certain embodiments, provided herein are methods for treating cancer in a subject having treated in accordance with the methods disclosed herein does not meet one or more of the exclusion criteria described in Example 3. In certain embodiments, the subject treated in accordance with the methods disclosed herein does not meet any of the exclusion criteria described in Example 3.

In certain embodiments, provide herein are methods of treating cancer in a subject who:

- is not currently being treated with an immunotherapy, an immunosuppressive drug such as a chemotherapy or systemic corticosteroid (except for a short term treatment of allergic reactions or for the treatment of immunotherapy-related adverse event (irAE) with a systemic steroid, or treatment with a topical or inhalatory steroid with no or minimal systemic effect), or other experimental pharmaceutical product;
- is not currently being treated with a tyrosine kinase inhibitor targeting HER2, or any recombinant molecule targeting HER2 or NKG2D;
- is not currently being treated with a growth factor such as granulocyte colony stimulating factor or granulocyte macrophage colony stimulating factor (except for erythropoietin and erythropoietin analogs);
- is not currently being treated with bisphosphonate or denosumab unless treatment was initiated more than 14 days prior to receiving the first administration of multi-specific binding protein;
- has not previously been treated with drugs that specifically target the HER2 pathway (except subjects treated with a monoclonal antibody and provided a four week washout period, or subjects treated with a tyrosine kinase inhibitor providing a two week washout period);
- is not currently being treated with cytoreductive therapy, radiotherapy (except palliative bone directed radiotherapy), cytokine therapy (except for erythropoietin), major surgery (except diagnostic biopsy), or use of any investigational drug within 28 days prior to treatment with multi-specific binding protein;
- has not previously had a malignant disease within the last three years other than the target malignancy to treated by the multi-specific binding protein (except basal or squamous cell carcinoma of the skin or cervical carcinoma in situ);
- does not have rapidly progressive disease;
- does not have active or a history of central nervous system (CNS) metastases;
- has not previously received an organ transplant (including autologous or allogenic stem cell transplantation);
- does not have significant acute or chronic infections (including a positive test for human immunodeficiency virus (HIV)), or active or latent hepatitis B or active hepatitis C;
- does not have a pre-existing autoimmune disease (except subjects with vitiligo), needing treatment with systemic immunosuppressive agents for more than 28 days within the last three years or clinically relevant immunodeficiencies (e.g., dys-gammaglobulinemia or congenital immunodeficiencies), or fever within seven days;
- does not have known severe hypersensitivity reactions to mAbs (≥Grade 3 NCI-CTCAE v5.0), any history of anaphylaxis, or uncontrolled asthma (e.g., three or more features of partly controlled asthma);
- does not have persisting toxicity related to prior therapy ≥Grade 1 NCI-CTCAE v5.0 (except alopecia and sensory neuropathy ≤Grade 2);
- is not a pregnant or lactating female;
- does not have known alcohol or drug abuse; and/or
- does not have serious cardiac illness or medical conditions including, but not limited to:
  - a history of New York Heart Association class III or IV heart failure or systolic dysfunction (LVEF <55%);
  - high-risk uncontrolled arrhythmias, i.e. tachycardia with a heart rate >100/min at rest;
  - significant ventricular arrhythmia (ventricular tachycardia) or higher-grade AV-block (second degree AV-block Type 2 (Mobitz 2) or third-degree AV-block);
  - angina pectoris requiring anti-anginal medication;
  - clinically significant valvular heart disease;
  - evidence of transmural infarction on electrocardiogram (ECG); or
  - poorly controlled hypertension (defined by: systolic >180 mm Hg or diastolic >100 mm Hg).

It is contemplated that the method disclosed herein of treating a patient having a cancer specified above can be performed with or without combination with a corticosteroid for reducing one or more infusion-related reactions.

Monotherapies and Combinational Use with Other Cancer Therapies

The multi-specific binding protein disclosed herein can be used as a monotherapy or in combination with one or more therapies. In certain embodiments, the multi-specific binding protein is used as a monotherapy in accordance with the dosage regimen disclosed herein. In other embodiments, the multi-specific binding protein is used in combination with one or more therapies administered in accordance with a dosage regimen known to be suitable for treating the particular subject with the particular cancer, and the multi-specific binding protein is administered in accordance with the dosage regimen disclosed herein. In certain embodiments, the method of treatment disclosed herein is used as an adjunct to surgical removal of the primary lesion.

Exemplary therapeutic agents that may be used in combination with the multi-specific binding protein include, for example, radiation, mitomycin, tretinoin, ribomustin, gemcitabine, vincristine, etoposide, cladribine, mitobronitol, methotrexate, doxorubicin, carboquone, pentostatin, nitracrine, zinostatin, cetrorelix, letrozole, raltitrexed, daunorubicin, fadrozole, fotemustine, thymalfasin, sobuzoxane, nedaplatin, cytarabine, bicalutamide, vinorelbine, vesnarinone, aminoglutethimide, amsacrine, proglumide, elliptinium acetate, ketanserin, doxifluridine, etretinate, isotretinoin, streptozocin, nimustine, vindesine, flutamide, drogenil, butocin, carmofur, razoxane, sizofilan, carboplatin, mitolactol, tegafur, ifosfamide, prednimustine, picibanil, levamisole, teniposide, improsulfan, enocitabine, lisuride, oxymetholone, tamoxifen, progesterone, mepitiostane, epitiostanol, formestane, interferon-alpha, interferon-2 alpha, interferon-beta, interferon-gamma (IFN-γ), colony stimulating factor-1, colony stimulating factor-2, denileukin diftitox, interleukin-2, luteinizing hormone releasing factor and variations of the aforementioned agents that may exhibit differential binding to their cognate receptors, or increased or decreased serum half-life.

An additional class of agents that may be used as part of a combination therapy in treating cancer is immune checkpoint inhibitors. Exemplary immune checkpoint inhibitors include agents that inhibit one or more of (i) cytotoxic T lymphocyte-associated antigen 4 (CTLA4), (ii) programmed cell death protein 1 (PD1), (iii) PDL1, (iv) LAG3, (v) B7-H3, (vi) B7-H4, and (vii) TIM3. The CTLA4 inhibitor ipilimumab has been approved by the United States Food and Drug Administration for treating melanoma and may be used as part of a combination therapy described herein.

Yet other agents that may be used as part of a combination therapy in treating cancer are monoclonal antibody agents that target non-checkpoint targets (e.g., herceptin) and non-cytotoxic agents (e.g., tyrosine-kinase inhibitors).

Yet other categories of anti-cancer agents include, for example: (i) an inhibitor selected from an ALK Inhibitor, an ATR Inhibitor, an A2A Antagonist, a Base Excision Repair Inhibitor, a Bcr-Abl Tyrosine Kinase Inhibitor, a Bruton's Tyrosine Kinase Inhibitor, a CDC7 Inhibitor, a CHK1 Inhibitor, a Cyclin-Dependent Kinase Inhibitor, a DNA-PK Inhibitor, an Inhibitor of both DNA-PK and mTOR, a DNMT1 Inhibitor, a DNMT1 Inhibitor plus 2-chloro-deoxy-adenosine, an HDAC Inhibitor, a Hedgehog Signaling Pathway Inhibitor, an IDO Inhibitor, a JAK Inhibitor, a mTOR Inhibitor, a MEK Inhibitor, a MELK Inhibitor, a MTH1 Inhibitor, a PARP Inhibitor, a Phosphoinositide 3-Kinase Inhibitor, an Inhibitor of both PARP1 and DHODH, a Proteasome Inhibitor, a Topoisomerase-II Inhibitor, a Tyrosine Kinase Inhibitor, a VEGFR Inhibitor, and a WEE1 Inhibitor; (ii) an agonist of OX40, CD137, CD40, GITR, CD27, HVEM, TNFRSF25, or ICOS; and (iii) a cytokine selected from IL-12, IL-15, GM-CSF, and G-CSF.

In certain embodiments, the method of the present invention further includes administering to the subject an anti-PD-1 antibody. Many anti-PD-1 antibodies have been developed for therapeutic purposes and are described in, for example, Gong et al., (2018) *J. ImmunoTher Cancer* 6:8.

In certain embodiments, the anti-PD-1 antibody is nivolumab. In certain embodiments, 0.1 to 10 mg/kg, 0.1 to 3 mg/kg, 0.1 to 1 mg/kg, 0.1 to 0.3 mg/kg, 0.3 to 10 mg/kg, 0.3 to 3 mg/kg, 0.3 to 1 mg/kg, 1 to 10 mg/kg, 1 to 3 mg/kg, or 3 to 10 mg/kg of nivolumab is administered to the subject. In certain embodiments, 120 to 600 mg, 120 to 480 mg, 120 to 360 mg, 120 to 240 mg, 240 to 600 mg, 240 to 480 mg, 240 to 360 mg, 360 to 600 mg, 360 to 480 mg, or 480 to 600 mg of nivolumab is administered to the subject. In certain embodiments, 120 mg, 240 mg, 360 mg, 480 mg, or 600 mg of nivolumab is administered to the subject. In certain embodiments, 480 mg of nivolumab is administered on day 1 of the initial treatment cycle. In certain embodiments, if the subject receives one or more subsequent treatment cycles, 480 mg of nivolumab is administered once every four weeks in the subsequent treatment cycles, starting from day 1 of each subsequent treatment cycle. In certain embodiments, nivolumab is administered as a 30 minute, 35 minute, 45 minute, 50 minute, 60 minute, 65 minute, 70 minute, 75 minute, 80 minute, 85 minute, or 90 minute intravenous infusion in four-week treatment cycles.

In certain embodiments, a multi-specific binding protein, pharmaceutical composition, or pharmaceutical formulation disclosed herein is administered as a 30 min., 45 min., 60 min., 75 min., or 90 min. intravenous infusion, and nivolumab is administered as a 30 min., 45 min., 60 min., 75 min., or 90 min. intravenous infusion in four-week treatment cycles. In certain embodiments, the multi-specific binding protein, pharmaceutical composition, or pharmaceutical formulation disclosed herein is administered as a 60 min. intravenous infusion, and nivolumab is administered as a 30 min. intravenous infusion in four-week treatment cycles.

In certain embodiments, a multi-specific binding protein, pharmaceutical composition, or pharmaceutical formulation disclosed herein is administered in a first treatment cycle in combination with nivolumab, where the multi-specific binding protein, pharmaceutical composition, or pharmaceutical formulation and nivolumab are both administered on day 1, and the multi-specific binding protein, pharmaceutical composition, or pharmaceutical formulation is administered alone at day 8. In certain embodiments, the multi-specific binding protein, pharmaceutical composition, or pharmaceutical formulation is administered in combination with nivolumab in subsequent-week treatment cycles after an initial cycle, where the multi-specific binding protein, pharmaceutical composition, or pharmaceutical formulation and nivolumab are both administered on day 1.

In certain embodiments, the anti-PD-1 antibody is pembrolizumab. In certain embodiments, 100 to 300 mg, 110 to 300 mg, 120 to 300 mg, 130 to 300 mg, 140 to 300 mg, 150 to 300 mg, 160 to 300 mg, 170 to 300 mg, 180 to 300 mg. 190 to 300 mg, 200 to 300 mg, 210 to 300 mg, 220 to 300 mg, 230 to 300 mg, 240 to 300 mg, 250 to 300 mg, 260 to 300 mg, 270 to 300 mg, 280 to 300 mg, 290 to 300 mg, 100 to 280 mg, 110 to 280 mg, 120 to 280 mg, 130 to 280 mg, 140 to 280 mg, 150 to 280 mg, 160 to 280 mg, 170 to 280 mg, 180 to 280 mg. 190 to 280 mg, 200 to 280 mg, 210 to 280 mg, 220 to 280 mg, 230 to 280 mg, 240 to 280 mg, 250 to 280 mg, 260 to 280 mg, 270 to 280 mg, 100 to 260 mg, 110 to 260 mg, 120 to 260 mg, 130 to 260 mg, 140 to 260 mg, 150 to 260 mg, 160 to 260 mg, 170 to 260 mg, 180 to 260 mg. 190 to 260 mg, 200 to 260 mg, 210 to 260 mg, 220 to 260 mg, 230 to 260 mg, 240 to 260 mg, 250 to 260 mg, 100 to 240 mg, 110 to 240 mg, 120 to 240 mg, 130 to 240 mg, 140 to 240 mg, 150 to 240 mg, 160 to 240 mg, 170 to 240 mg, 180 to 240 mg. 190 to 240 mg, 200 to 240 mg, 210 to 240 mg, 220 to 240 mg, 230 to 240 mg, 100 to 220 mg, 110 to 220 mg, 120 to 220 mg, 130 to 220 mg, 140 to 220 mg, 150 to 220 mg, 160 to 220 mg, 170 to 220 mg, 180 to 220 mg. 190 to 220 mg, 200 to 220 mg, 210 to 220 mg, 100 to 200 mg, 110 to 200 mg, 120 to 200 mg, 130 to 200 mg, 140 to 200 mg, 150 to 200 mg, 160 to 200 mg, 170 to 200 mg, 180 to 200 mg, or 190 to 200 mg of pembrolizumab is administered to the subject. In certain embodiments, 125 mg, 150 mg, 175 mg, 200 mg, 225 mg, or 250 mg of pembrolizumab is administered to the subject. In certain embodiments, 200 mg of pembrolizumab is administered on Day 1 of the initial treatment cycle. In certain embodiments, if the subject receives one or more subsequent treatment cycles, 200 mg of pembrolizumab is administered once every three weeks in the subsequent treatment cycles, starting from Day 1 of the first subsequent treatment cycle. In certain embodiments, pembrolizumab is administered as a 30 minute, 35 minute, 45 minute, 50 minute, 60 minute, 65 minute, 70 minute, 75 minute, 80 minute, 85 minute, or 90 minute intravenous infusion in three-week treatment cycles.

In certain embodiments, a multi-specific binding protein, pharmaceutical composition, or pharmaceutical formulation disclosed herein is administered as a 30 min., 45 min., 60 min., 75 min., or 90 min. intravenous infusion, and pembrolizumab is administered as a 30 min., 45 min., 60 min., 75 min., or 90 min. intravenous infusion in three-week treatment cycles. In certain embodiments, the multi-specific binding protein, pharmaceutical composition, or pharmaceutical formulation disclosed herein is administered as a 60 min. intravenous infusion, and pembrolizumab is administered as a 30 min. intravenous infusion in three-week treatment cycles.

In certain embodiments, a multi-specific binding protein, pharmaceutical composition, or pharmaceutical formulation disclosed herein is administered in a first treatment cycle in combination with pembrolizumab, where the multi-specific binding protein, pharmaceutical composition, or pharmaceutical formulation and pembrolizumab are both administered on day 1, and the multi-specific binding protein, pharmaceutical composition, or pharmaceutical formulation is administered alone at day 8. In certain embodiments, the multi-specific binding protein, pharmaceutical composition, or pharmaceutical formulation is administered in combination with pembrolizumab in subsequent 3-week treatment cycles after an initial cycle, where the multi-specific binding protein, pharmaceutical composition, or pharmaceutical formulation and pembrolizumab are both administered on day 1.

In certain embodiments, the method of the present invention further includes administering to the subject a cytoskeletal-disrupting chemotherapeutic agent. Many such agents have been developed for therapeutic purposes and are described in, for example, Ong et al., (2020) Cancers 12(1): 238. In certain embodiments, the cytoskeletal-disrupting chemotherapeutic agent is nab-paclitaxel. In certain embodiments, 50 to 300 mg/m$^2$, 50 to 200 mg/m$^2$, 50 to 150 mg/m$^2$, 50 to 100 mg/m$^2$, 100 to 300 mg/m$^2$, 100 to 200 mg/m$^2$, 100 to 150 mg/m$^2$, 150 to 300 mg/m$^2$, 150 to 200 mg/m$^2$, or 200 to 300 mg/m$^2$ of nab-paclitaxel is administered to the subject. In certain embodiments, 80 mg/m$^2$, 100 mg/m$^2$, 125 mg/m$^2$, 200 mg/m$^2$, or 260 mg/m$^2$ of nab-paclitaxel is administered to the subject. In certain embodiments, 100 mg/m$^2$ of nab-paclitaxel is administered on day 1, day 8, and day 15 of the initial treatment cycle. In certain embodiments, if the subject receives one or more subsequent treatment cycles, 100 mg/m$^2$ of nab-paclitaxel is administered three times every four weeks in the subsequent treatment cycles, on day 1, day 8, and day 15 of each subsequent treatment cycle. In certain embodiments, nab-paclitaxel is administered as a 30 minute, 35 minute, 45 minute, 50 minute, 60 minute, 65 minute, 70 minute, 75 minute, 80 minute, 85 minute, or 90 minute intravenous infusion in four-week treatment cycles.

In certain embodiments, a multi-specific binding protein, pharmaceutical composition, or pharmaceutical formulation disclosed herein is administered as a 30 min., 45 min., 60 min., 75 min., or 90 min. intravenous infusion, and nab-paclitaxel is administered as a 30 min., 45 min., 60 min., 75 min., or 90 min. intravenous infusion in four-week treatment cycles. In certain embodiments, the multi-specific binding protein, pharmaceutical composition, or pharmaceutical formulation disclosed herein is administered as a 60 min. intravenous infusion, and nab-paclitaxel is administered as a 30 min. intravenous infusion in four-week treatment cycles.

Therapeutic Outcome

In certain embodiments, the method of treatment disclosed herein results in a disease response or improved survival of the subject or patient. For example, in certain embodiments, the disease response is a complete response, a partial response, or a stable disease. In certain embodiments, the improved survival is improved progression-free survival (PFS) or overall survival. Improvement (e.g., in PFS) can be determined relative to a period prior to initiation of the treatment of the present disclosure. Methods of determining disease response (e.g., complete response, partial response, or stable disease) and patient survival (e.g., PFS, overall survival) for BTC (e.g., advanced BTC, metastatic BTC), or biliary tract tumor therapy, are routine in the art and are contemplated herein. In some embodiments, disease response is evaluated according to RECIST 1.1 after subjecting the treated patient to contrast-enhanced computed tomography (CT) or magnetic resonance imaging (MRI) of the affected area (e.g., chest/abdomen and pelvis covering the area from the superior extent of the thoracic inlet to the symphysis pubis).

EXAMPLES

The disclosure now being generally described, will be more readily understood by reference to the following examples, which are included merely for purposes of illustration of certain aspects and embodiments of the present disclosure, and are not intended to limit the scope of the disclosure in any way.

Example 1: Formulation, Packaging, and Storage of A49-F3'-TriNKET-Trastuzumab

The formulations listed in Table 12 were evaluated, in duplicate and randomized, to assess the effects of the pH and excipients on the stability of A49-F3'-TriNKET-Trastuzumab (Kermit BDS lot 7443-C3, 11.9 mg/mL). A49-F3'-TriNKET-Trastuzumab underwent buffer exchange into the respective buffer and excipient combinations by centrifugal ultrafiltration (Amicon Ultra-4 30k devices MWCO) to a target concentration of 30 mg/mL. Following the final buffer exchange and confirmation of the target concentration, each formulated sample was filter sterilized using a 0.22 μm EMD Millipore Ultrafree—CL centrifugal filter device with Durapore membrane (Fisher Scientific Cat. #UFC40GVOS). Following sterile filtration, each formulation was handled aseptically in a laminar flow hood. The formulated samples were spiked with polysorbate 80 (PS80) to a final concentration of 0.01%. An aliquot of each formulation was removed for time zero testing, and the remaining material was split into two equal sized aliquots into depyrogenated Type 1 borosilicate glass vials, 2 mL×13 mm (West Pharmaceuticals Cat. #68000377), stoppered with 13 mm Fluorotec stoppers (West Pharmaceuticals Cat. #19700302), and sealed. The time zero aliquots were used for the initial time point testing per Table 13. One vial was stored at 2-8° C. and the other vial was placed at 50° C. for a 3-week accelerated stability study. Following the 3-week incubation, the 2-8° C. and 50° C. samples were analyzed according to the test methods indicated in Table 13.

TABLE 12

Formulations evaluated

| Buffer | Excipient | Surfactant | pH | | | | | Conditions | Conc. |
|---|---|---|---|---|---|---|---|---|---|
| 20 mM Histidine | 250 mM Sorbitol 250 mM Sucrose 75 mM NaCl, 125 mM Sorbitol 75 mM NaCl, 125 mM Sucrose | 0.01% PS80 | 5.5 | 5.8 | 6.0 | 6.2 | 6.5 | Time Zero, 3-week incubation at 2-8° C., 3-week incubation at 50° C. | 30 mg/mL |

TABLE 13

Assay panel used in formulation evaluation

| Test Method | Initial | 3-week incubation | |
|---|---|---|---|
| | | 2-8° C. | 50° C. |
| Appearance | X | X | X |
| Concentration, (ϵ = 1.595 mL/cm*mg) | X | X | X |
| pH | X | X | X |
| DLS | X | X | X |
| SEC-HPLC | X | X | X |
| Osmo | X | X | X |
| CE-SDS | | X | X |
| icIEF | | X | X |

An accelerated stability study of A49-F3'-TriNKET-Trastuzumab was executed, in which A49-F3'-TriNKET-Trastuzumab was prepared in 20 formulations as shown in Table 12. Samples were run in duplicate and incubated for 3 weeks at 2-8° C. and 50° C. At time zero and upon conclusion of the 3-week incubation, testing of each formulated sample was performed using the assays as outlined in Table 13. All formulations behaved similarly and were as expected based on appearance, concentration, pH, and osmolality.

Appearance

Samples were viewed in ambient laboratory conditions against a black and white background before the sample vials were opened. Visible particulates were absent in all samples at both time zero and three week conditions.

Ultraviolet Concentration Determination

Protein concentration by ultraviolet (UV) absorption at optical density (OD) 280 nm was determined for each sample and condition. Protein concentrations at time zero, after 3-week incubation at 2-8° C., and after 3-week incubation at 50° C. are summarized in Table 14.

pH Determination

The pH was determined for each sample and condition. The pH values at time zero, after 3-week incubation at 2-8° C., and after 3-week incubation at 50° C. are summarized in Table 15.

Dynamic Light Scattering

Dynamic Light Scattering (DLS) samples were collected at 25° C., following a 300 second equilibration. Five measurements were collected for each sample. Z-average values at time zero, after 3-week incubation at 2-8° C., and after 3-week incubation at 50° C. are summarized in Table 16.

Average polydispersity index (% PDI) was also recorded. The % PDI values at time zero, after 3-week incubation at 2-8° C., and after 3-week incubation at 50° C. are summarized in Table 17.

Further DLS analysis of A49-F3'-TriNKET-Trastuzumab in the samples was performed. The average percentage of monomer polydispersity (% PD) at time zero, after 3-week incubation at 2-8° C., and after 3-week incubation at 50° C. are summarized in Table 18. The average monomer size values at time zero, after 3-week incubation at 2-8° C., and after 3-week incubation at 50° C. are summarized in Table 19.

TABLE 14

Calculated protein concentration from UV absorption

| Buffer | Excipient/ Surfactant | pH | Time Zero | | 3-week incubation | |
|---|---|---|---|---|---|---|
| | | | 1 | 2 | 2-8° C. | 50° C. |
| 20 mM Histidine | 250 mM Sorbitol, 0.01% PS80 | 5.5 | 32.2 | 32.5 | 33.0 | 32.8 | 32.4 | 32.7 |
| | | 5.8 | 30.2 | 32.4 | 31.3 | 32.6 | 31.3 | 32.5 |
| | | 6.0 | 31.0 | 29.9 | 31.0 | 31.1 | 30.9 | 31.7 |
| | | 6.2 | 28.0 | 32.1 | 29.4 | 31.9 | 28.6 | 31.2 |
| | | 6.5 | 31.0 | 27.7 | 33.1 | 28.9 | 33.3 | 28.2 |
| 20 mM Histidine | 250 mM Sucrose, 0.01% PS80 | 5.5 | 31.0 | 30.9 | 31.8 | 33.2 | 31.4 | 31.6 |
| | | 5.8 | 29.1 | 30.2 | 30.6 | 30.5 | 31.0 | 29.8 |
| | | 6.0 | 31.0 | 29.7 | 33.1 | 30.3 | 32.2 | 30.4 |
| | | 6.2 | 30.6 | 31.2 | 31.5 | 32.2 | 31.4 | 32.5 |
| | | 6.5 | 31.4 | 30.6 | 31.6 | 32.4 | 31.0 | 31.6 |
| 20 mM Histidine | 75 mM NaCl, 125 mM Sorbitol, 0.01% PS80 | 5.5 | 28.7 | 31.3 | 30.1 | 31.1 | 29.6 | 30.7 |
| | | 5.8 | 31.9 | 29.5 | 32.1 | 30.7 | 32.5 | 31.4 |
| | | 6.0 | 32.2 | 29.9 | 32.4 | 31.3 | 31.8 | 30.0 |
| | | 6.2 | 30.5 | 29.0 | 30.9 | 29.9 | 30.2 | 29.9 |
| | | 6.5 | 31.6 | 32.0 | 32.4 | 33.6 | 32.4 | 31.5 |
| 20 mM Histidine | 75 mM NaCl, 125 mM Sucrose, 0.01% PS80 | 5.5 | 28.9 | 29.3 | 29.5 | 30.6 | 29.0 | 30.5 |
| | | 5.8 | 30.8 | 31.3 | 31.4 | 31.6 | 31.3 | 31.4 |
| | | 6.0 | 30.9 | 28.6 | 31.1 | 30.9 | 30.4 | 30.3 |
| | | 6.2 | 30.6 | 29.3 | 31.3 | 30.7 | 30.6 | 30.5 |
| | | 6.5 | 31.8 | 30.7 | 30.7 | 29.7 | 30.2 | 29.8 |

TABLE 15 pH values

| Buffer | Excipient/ Surfactant | pH | Time Zero | | 3-week incubation | |
|---|---|---|---|---|---|---|
| | | | 1 | 2 | 2-8° C. | 50° C. |
| 20 mM Histidine | 250 mM Sorbitol, 0.01% PS80 | 5.5 | 5.5 | 5.5 | 5.5 | 5.5 | 5.5 | 5.5 |
| | | 5.8 | 5.7 | 5.8 | 5.8 | 5.8 | 5.8 | 5.7 |
| | | 6.0 | 6.0 | 5.9 | 6.0 | 5.9 | 6.0 | 5.9 |
| | | 6.2 | 6.3 | 6.2 | 6.2 | 6.2 | 6.2 | 6.1 |
| | | 6.5 | 6.4 | 6.4 | 6.5 | 6.4 | 6.5 | 6.4 |
| 20 mM Histidine | 250 mM Sucrose, 0.01% PS80 | 5.5 | 5.5 | 5.5 | 5.5 | 5.5 | 5.5 | 5.5 |
| | | 5.8 | 5.8 | 5.8 | 5.8 | 5.8 | 5.8 | 5.7 |
| | | 6.0 | 6.0 | 5.9 | 6.0 | 6.0 | 6.0 | 6.0 |
| | | 6.2 | 6.2 | 6.2 | 6.1 | 6.1 | 6.1 | 6.1 |
| | | 6.5 | 6.4 | 6.5 | 6.4 | 6.5 | 6.4 | 6.4 |
| 20 mM Histidine | 75 mM NaCl, 125 mM Sorbitol, 0.01% PS80 | 5.5 | 5.5 | 5.5 | 5.4 | 5.5 | 5.5 | 5.5 |
| | | 5.8 | 5.8 | 5.8 | 5.8 | 5.7 | 5.7 | 5.7 |
| | | 6.0 | 5.9 | 6.0 | 5.9 | 6.0 | 5.9 | 5.9 |
| | | 6.2 | 6.2 | 6.2 | 6.2 | 6.1 | 6.1 | 6.1 |
| | | 6.5 | 6.5 | 6.5 | 6.5 | 6.5 | 6.5 | 6.4 |

TABLE 15-continued pH values

| Buffer | Excipient/Surfactant | pH | Time Zero 1 | 2 | 3-week incubation 2-8° C. | | 50° C. | |
|---|---|---|---|---|---|---|---|---|
| 20 mM Histidine | 75 mM NaCl, 125 mM Sucrose, 0.01% PS80 | 5.5 5.8 6.0 6.2 6.5 | 5.5 5.8 6.0 6.2 6.5 | 5.4 5.9 5.9 6.2 6.5 | 5.5 5.8 6.0 6.1 6.4 | 5.5 5.7 5.9 6.2 6.4 | 5.5 5.8 6.0 6.1 6.4 | 5.5 5.7 5.9 6.1 6.4 |

TABLE 16

Z-average values from DLS
Z-Average

| Buffer | Excipient/Surfactant | pH | Time Zero 1 | 2 | 3-week incubation 2-8° C. | | 50° C. | |
|---|---|---|---|---|---|---|---|---|
| 20 mM Histidine | 250 mM Sorbitol, 0.01% PS80 | 5.5 | 8.65 | 9.09 | 8.83 | 8.93 | 10.0 | 10.16 |
| | | 5.8 | 8.86 | 8.54 | 8.80 | 8.62 | 9.52 | 9.46 |
| | | 6.0 | 8.69 | 8.34 | 8.33 | 8.84 | 9.17 | 8.98 |
| | | 6.2 | 8.45 | 8.03 | 8.62 | 7.94 | 8.75 | 9.48 |
| | | 6.5 | 7.47 | 7.78 | 7.30 | 7.91 | 8.75 | 9.48 |
| 20 mM Histidine | 250 mM Sucrose, 0.01% PS80 | 5.5 | 9.86 | 9.58 | 10.58 | 9.53 | 10.41 | 10.61 |
| | | 5.8 | 9.60 | 9.91 | 9.54 | 9.55 | 10.51 | 10.61 |
| | | 6.0 | 9.24 | 9.23 | 9.30 | 9.55 | 10.64 | 10.05 |
| | | 6.2 | 8.90 | 8.80 | 8.96 | 9.12 | 10.11 | 10.26 |
| | | 6.5 | 8.14 | 7.86 | 8.67 | 8.44 | 10.06 | 9.49 |
| 20 mM Histidine | 75 mM NaCl, 125 mM Sorbitol, 0.01% PS80 | 5.5 | 12.33 | 11.89 | 12.12 | 11.88 | 16.36 | 15.60 |
| | | 5.8 | 12.55 | 11.98 | 12.13 | 12.03 | 14.22 | 14.01 |
| | | 6.0 | 12.32 | 13.05 | 12.55 | 12.43 | 14.20 | 13.86 |
| | | 6.2 | 12.42 | 13.10 | 12.81 | 12.79 | 13.61 | 13.81 |
| | | 6.5 | 12.87 | 12.85 | 13.06 | 12.59 | 14.11 | 13.44 |
| 20 mM Histidine | 75 mM NaCl, 125 mM Sucrose, 0.01% PS80 | 5.5 | 12.83 | 12.42 | 13.05 | 12.61 | 16.65 | 16.32 |
| | | 5.8 | 12.89 | 12.68 | 13.19 | 12.65 | 15.61 | 14.68 |
| | | 6.0 | 13.33 | 12.72 | 13.11 | 12.92 | 14.67 | 14.25 |
| | | 6.2 | 13.02 | 13.17 | 13.21 | 13.08 | 14.42 | 14.23 |
| | | 6.5 | 13.22 | 13.47 | 13.44 | 13.39 | 14.48 | 14.16 |

TABLE 17

PDI values from DLS
PDI

| Buffer | Excipient/Surfactant | pH | Time Zero 1 | 2 | 3-week incubation 2-8° C. 1 | 2 | 50° C. 1 | 2 |
|---|---|---|---|---|---|---|---|---|
| 20 mM Histidine | 250 mM Sorbitol, 0.01% PS80 | 5.5 | 0.05 | 0.08 | 0.05 | 0.07 | 0.18 | 0.19 |
| | | 5.8 | 0.05 | 0.01 | 0.06 | 0.08 | 0.15 | 0.14 |
| | | 6.0 | 0.05 | 0.04 | 0.03 | 0.14 | 0.09 | 0.06 |
| | | 6.2 | 0.08 | 0.05 | 0.12 | 0.05 | 0.15 | 0.14 |
| | | 6.5 | 0.11 | 0.05 | 0.09 | 0.12 | 0.17 | 0.19 |
| 20 mM Histidine | 250 mM Sucrose, 0.01% PS80 | 5.5 | 0.05 | 0.07 | 0.16 | 0.07 | 0.12 | 0.09 |
| | | 5.8 | 0.06 | 0.08 | 0.05 | 0.05 | 0.10 | 0.12 |
| | | 6.0 | 0.07 | 0.08 | 0.07 | 0.11 | 0.18 | 0.12 |
| | | 6.2 | 0.05 | 0.05 | 0.08 | 0.10 | 0.09 | 0.15 |
| | | 6.5 | 0.08 | 0.06 | 0.16 | 0.19 | 0.18 | 0.14 |
| 20 mM Histidine | 75 mM NaCl, 125 mM Sorbitol, 0.01% PS80 | 5.5 | 0.06 | 0.02 | 0.03 | 0.01 | 0.22 | 0.19 |
| | | 5.8 | 0.05 | 0.03 | 0.03 | 0.01 | 0.13 | 0.15 |
| | | 6.0 | 0.03 | 0.09 | 0.04 | 0.04 | 0.14 | 0.13 |
| | | 6.2 | 0.02 | 0.12 | 0.06 | 0.07 | 0.12 | 0.11 |
| | | 6.5 | 0.05 | 0.03 | 0.07 | 0.03 | 0.10 | 0.06 |
| 20 mM Histidine | 75 mM NaCl, 125 mM Sucrose, 0.01% PS80 | 5.5 | 0.07 | 0.03 | 0.08 | 0.06 | 0.22 | 0.20 |
| | | 5.8 | 0.04 | 0.03 | 0.08 | 0.03 | 0.18 | 0.15 |
| | | 6.0 | 0.06 | 0.03 | 0.06 | 0.06 | 0.12 | 0.12 |
| | | 6.2 | 0.05 | 0.05 | 0.04 | 0.07 | 0.14 | 0.07 |
| | | 6.5 | 0.03 | 0.06 | 0.05 | 0.05 | 0.09 | 0.10 |

TABLE 18

Monomer % PD values
Monomer % Pd

| Buffer | Excipient/Surfactant | pH | Time Zero 1 | Time Zero 2 | 3-week incubation 2-8° C. 1 | 2-8° C. 2 | 50° C. 1 | 50° C. 2 |
|---|---|---|---|---|---|---|---|---|
| 20 mM Histidine | 250 mM Sorbitol, 0.01% PS80 | 5.5 | 27.0 | 30.9 | 27.7 | 30.8 | 35.0 | 37.0 |
| | | 5.8 | 27.3 | 23.0 | 29.7 | 30.6 | 34.1 | 29.5 |
| | | 6.0 | 27.9 | 26.2 | 25.1 | 29.8 | 30.9 | 26.5 |
| | | 6.2 | 31.0 | 27.5 | 33.8 | 26.3 | 36.4 | 30.6 |
| | | 6.5 | 35.6 | 27.0 | 33.9 | 33.1 | 38.0 | 36.9 |
| 20 mM Histidine | 250 mM Sucrose, 0.01% PS80 | 5.5 | 28.1 | 31.9 | 39.5 | 31.1 | 36.4 | 31.7 |
| | | 5.8 | 29.2 | 30.6 | 28.4 | 28.6 | 33.8 | 35.3 |
| | | 6.0 | 30.4 | 31.3 | 28.8 | 34.8 | 37.2 | 36.3 |
| | | 6.2 | 29.0 | 28.1 | 31.7 | 35.3 | 33.1 | 35.0 |
| | | 6.5 | 31.2 | 29.2 | 36.6 | 36.0 | 38.2 | 39.3 |
| 20 mM Histidine | 75 mM NaCl, 125 mM Sorbitol, 0.01% PS80 | 5.5 | 28.7 | 23.6 | 24.6 | 23.0 | 43.8 | 30.7 |
| | | 5.8 | 26.5 | 24.2 | 24.1 | 23.4 | 29.7 | 34.4 |
| | | 6.0 | 25.1 | 32.1 | 25.9 | 24.1 | 35.1 | 33.0 |
| | | 6.2 | 24.3 | 33.3 | 27.1 | 29.7 | 34.9 | 35.5 |
| | | 6.5 | 26.1 | 24.6 | 29.9 | 24.0 | 33.0 | 26.1 |
| 20 mM Histidine | 75 mM NaCl, 125 mM Sucrose, 0.01% PS80 | 5.5 | 29.3 | 24.7 | 29.6 | 26.5 | 45.7 | 30.8 |
| | | 5.8 | 25.8 | 24.8 | 30.4 | 24.2 | 36.8 | 37.5 |
| | | 6.0 | 29.1 | 24.2 | 28.3 | 27.2 | 36.4 | 35.1 |
| | | 6.2 | 26.6 | 26.8 | 25.7 | 27.5 | 36.2 | 24.5 |
| | | 6.5 | 25.6 | 29.3 | 27.1 | 27.3 | 32.4 | 32.5 |

TABLE 19

Monomer size values
Monomer Size (d.nm)

| Buffer | Excipient/Surfactant | pH | Time Zero 1 | Time Zero 2 | 3-week incubation 2-8° C. 1 | 2-8° C. 2 | 50° C. 1 | 50° C. 2 |
|---|---|---|---|---|---|---|---|---|
| 20 mM Histidine | 250 mM Sorbitol, 0.01% PS80 | 5.5 | 9.22 | 9.96 | 9.46 | 9.73 | 10.80 | 11.07 |
| | | 5.8 | 9.47 | 8.89 | 9.51 | 9.42 | 10.43 | 10.13 |
| | | 6.0 | 9.32 | 8.87 | 8.78 | 9.51 | 10.05 | 9.60 |
| | | 6.2 | 9.27 | 8.60 | 9.54 | 8.45 | 10.68 | 9.84 |
| | | 6.5 | 8.42 | 8.30 | 8.10 | 8.75 | 9.78 | 10.25 |
| 20 mM Histidine | 250 mM Sucrose, 0.01% PS80 | 5.5 | 10.58 | 10.51 | 12.14 | 10.40 | 11.87 | 11.22 |
| | | 5.8 | 10.35 | 10.89 | 10.24 | 10.24 | 11.70 | 11.86 |
| | | 6.0 | 10.11 | 10.17 | 10.10 | 10.82 | 11.70 | 11.47 |
| | | 6.2 | 9.58 | 9.42 | 9.85 | 10.24 | 11.20 | 11.30 |
| | | 6.5 | 8.93 | 8.48 | 9.72 | 9.11 | 11.25 | 10.90 |
| 20 mM Histidine | 75 mM NaCl, 125 mM Sorbitol, 0.01% PS80 | 5.5 | 13.29 | 12.44 | 12.75 | 12.37 | 18.16 | 16.12 |
| | | 5.8 | 13.40 | 12.61 | 12.75 | 12.56 | 15.37 | 15.33 |
| | | 6.0 | 12.99 | 14.35 | 13.34 | 13.10 | 15.73 | 15.23 |
| | | 6.2 | 13.03 | 14.51 | 13.72 | 13.90 | 15.24 | 15.55 |
| | | 6.5 | 13.70 | 13.54 | 14.15 | 13.22 | 15.69 | 14.33 |
| 20 mM Histidine | 75 mM NaCl, 125 mM Sucrose, 0.01% PS80 | 5.5 | 13.94 | 13.09 | 14.25 | 13.46 | 19.09 | 16.75 |
| | | 5.8 | 13.70 | 13.37 | 14.39 | 13.28 | 17.15 | 16.43 |
| | | 6.0 | 14.40 | 13.39 | 14.11 | 13.86 | 16.70 | 15.96 |
| | | 6.2 | 13.87 | 14.11 | 14.00 | 14.06 | 16.29 | 15.17 |
| | | 6.5 | 13.99 | 14.53 | 14.41 | 14.30 | 16.03 | 15.60 |

Figure 18A:
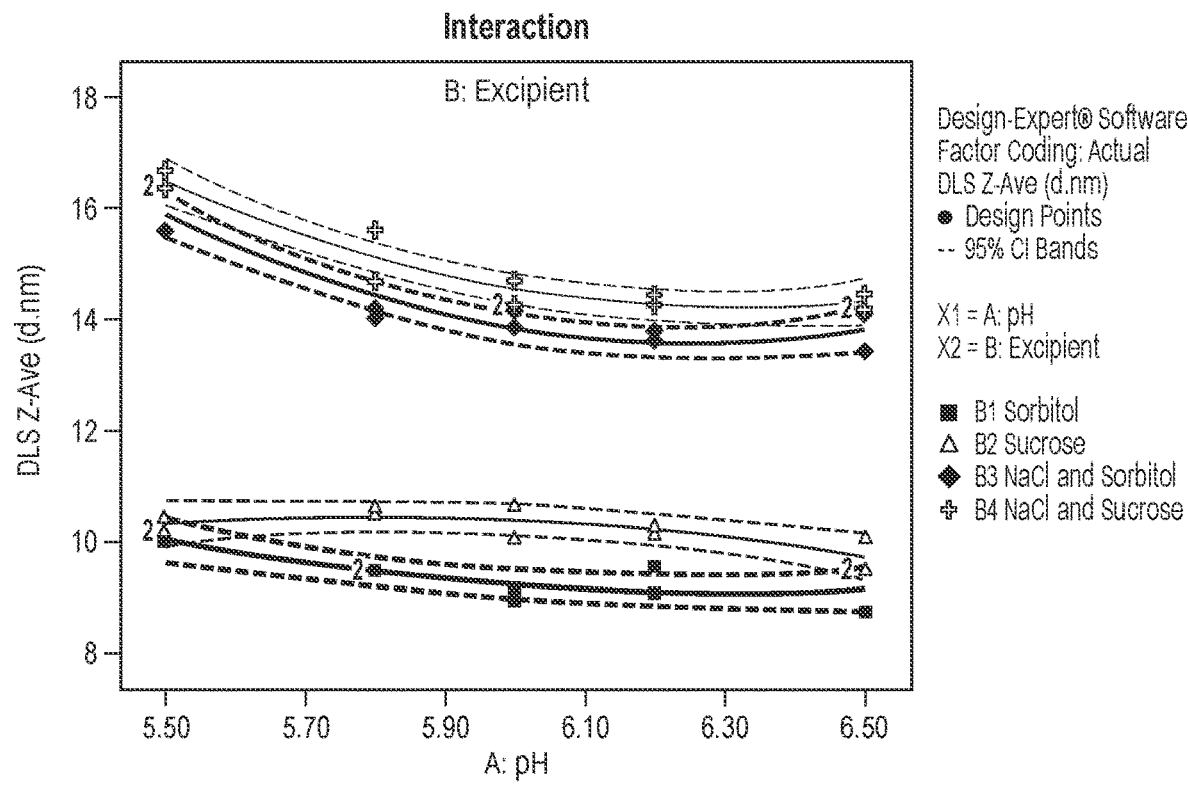
FIG. 18A is an interaction plot for average size as measured by Dynamic Light Scattering (DLS) after a 3-week incubation at 50° C.
Figure 18B:
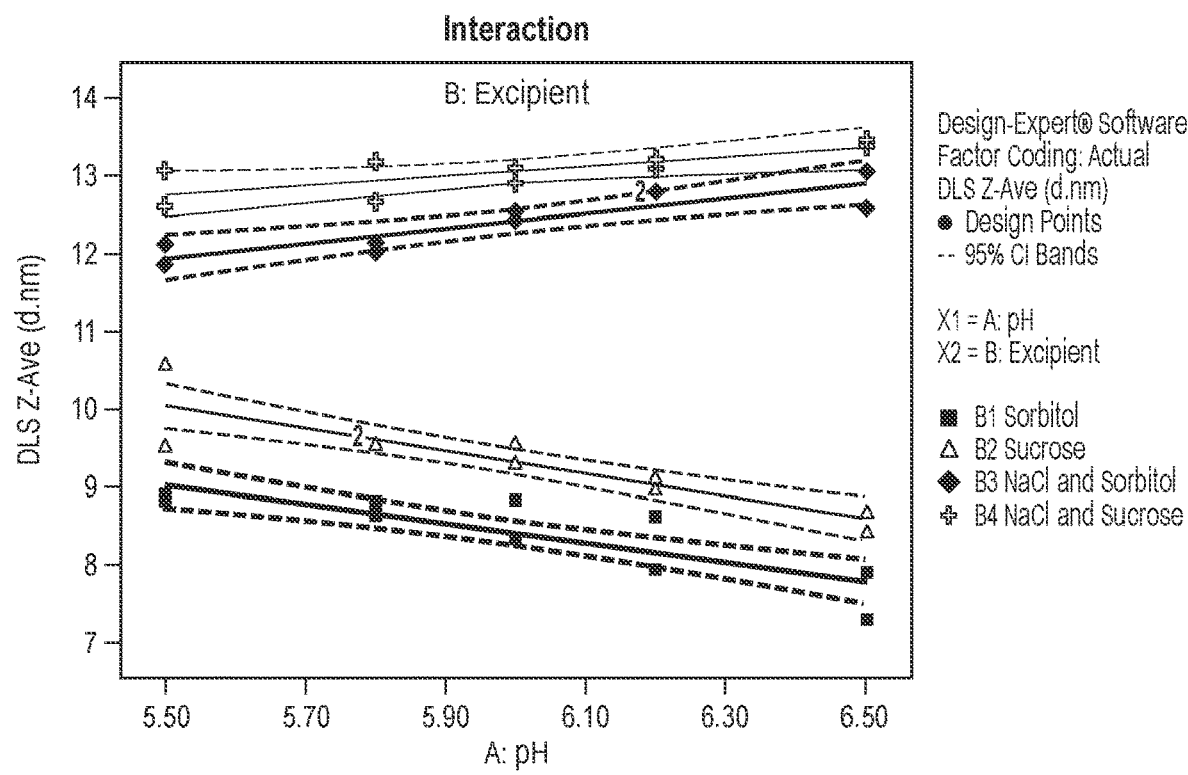
FIG. 18B is an interaction plot for average size as measured by DLS after a 3-week incubation at 2-8° C.
Figure 19A:
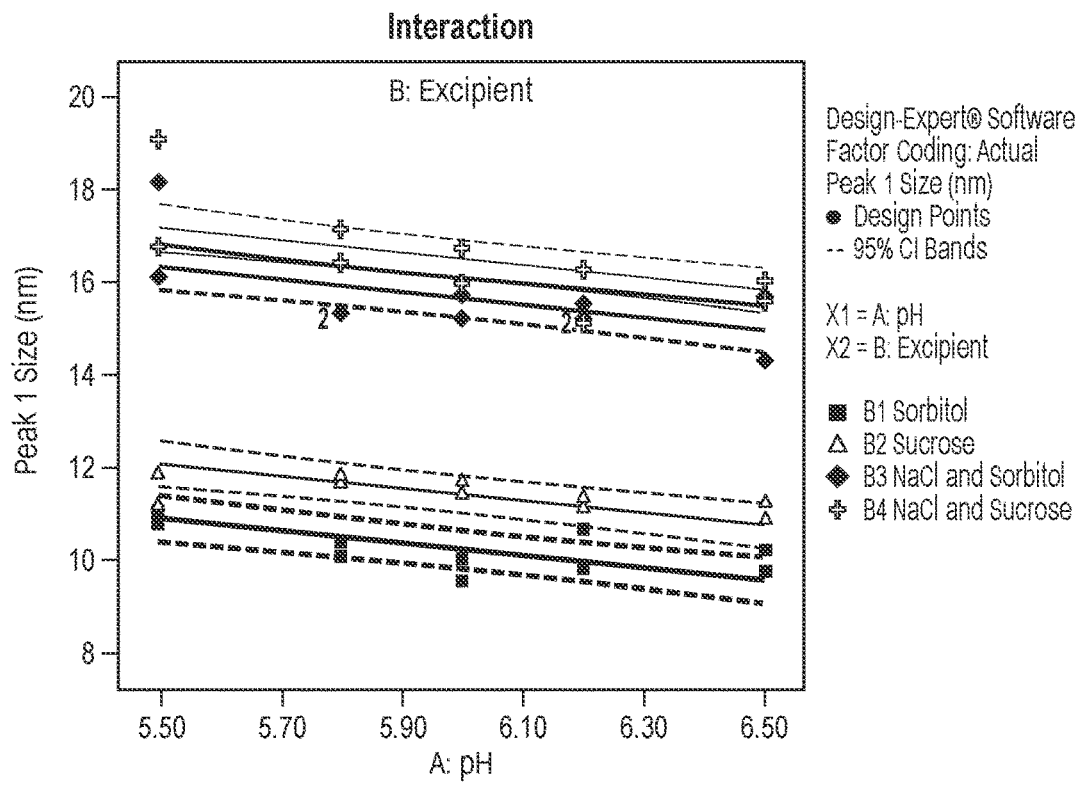
FIG. 19A is an interaction plot for monomer size as measured by DLS after a 3-week incubation at 50° C.
Figure 19B:
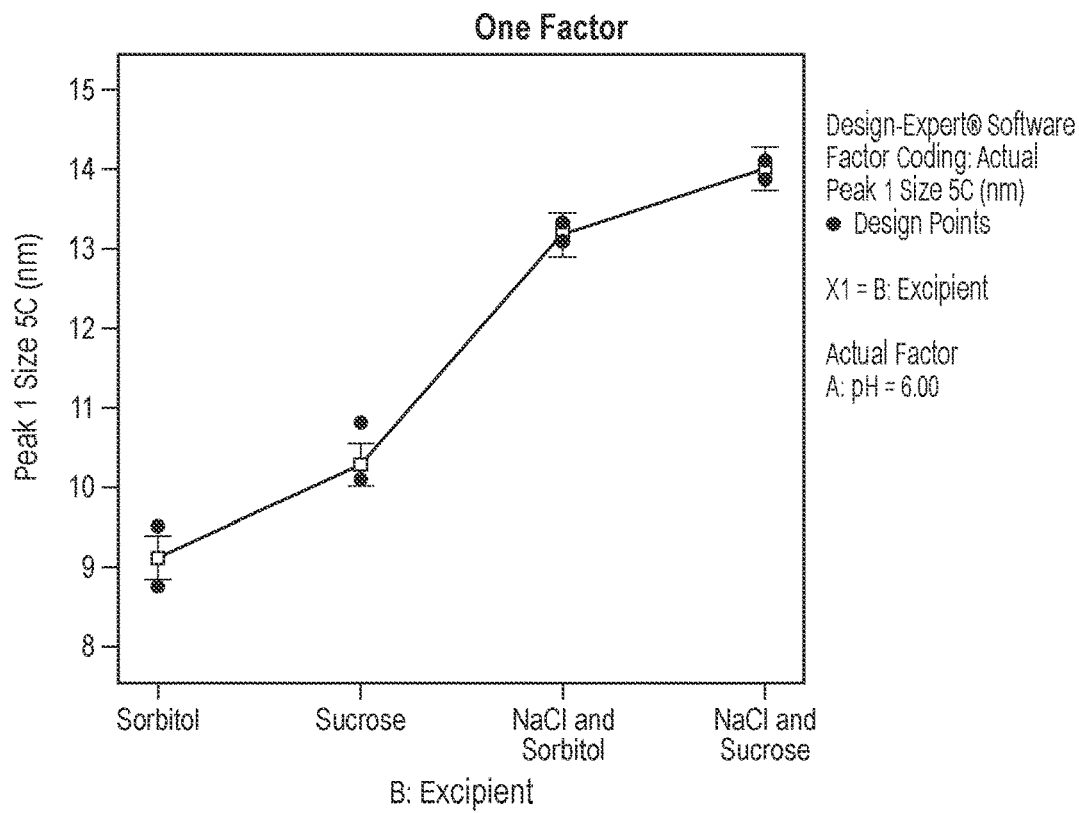
FIG. 19B is an interaction plot for monomer size as measured by DLS after a 3-week incubation at 2-8° C.

As evaluated by DLS, with average sizes and monomer sizes ≤20 nm, and polydispersity (PDI)≤0.300, all A49-F3'-TriNKET-Trastuzumab formulations displayed conformational stability. In evaluating the excipient and pH combinations, sorbitol and sucrose only formulations had lower average sizes relative to the combination formulations NaCl and sorbitol, and NaCl and sucrose, upon incubation for 3 weeks at 2-8° C. and 50° C. (comparative modeling shown in FIG. 18A and FIG. 18B). Average monomer size was also lower in sorbitol and sucrose only formulations compared to the combination formulations with NaCl after incubation for 3 weeks at 2-8° C. and 50° C. (FIG. 19A and FIG. 19B).

Size Exclusion Chromatography (SEC)

Size exclusion chromatography was performed in order to determine the percentage of high molecular weight species (% HMW), percentage of main species (% Main), and percentage of low molecular weight species (% LMW). Samples were diluted to 2.0 mg/mL in mobile phase buffer (containing 100 mM phosphate, 150 mM sodium chloride pH 7.3) and injected at a 100 μg load. Separation was performed with a Tosoh G3000SWxl (7.8×300 mm, cat. #08541) column with detection at 280 nm with 8 nm bandwidth. Samples were analyzed in real time, at time zero, and following a 3-week incubation at either 2-8° C. or 50°

C. The % HMW values are summarized in Table 20, the % main values are summarized in Table 21, and the % LMW values are summarized in Table 22.

TABLE 20

% HMW SEC
% HMW

| Buffer | Excipient/ Surfactant | pH | Time Zero 1 | Time Zero 2 | 3-week incubation 2-8° C. 1 | 3-week incubation 2-8° C. 2 | 3-week incubation 50° C. 1 | 3-week incubation 50° C. 2 |
|---|---|---|---|---|---|---|---|---|
| 20 mM Histidine | 250 mM Sorbitol, 0.01% PS80 | 5.5 | 0.6 | 0.5 | 0.6 | 0.6 | 3.1 | 3.2 |
| | | 5.8 | 0.6 | 0.6 | 0.6 | 0.6 | 2.9 | 2.9 |
| | | 6.0 | 0.6 | 0.6 | 0.6 | 0.6 | 3.0 | 2.9 |
| | | 6.2 | 0.6 | 0.6 | 0.7 | 0.7 | 3.1 | 3.0 |
| | | 6.5 | 0.6 | 0.6 | 0.8 | 0.7 | 3.5 | 3.2 |
| | 250 mM Sucrose, 0.01% PS80 | 5.5 | 0.5 | 0.5 | 0.6 | 0.6 | 3.2 | 2.8 |
| | | 5.8 | 0.5 | 0.6 | 0.6 | 0.6 | 3.1 | 3.0 |
| | | 6.0 | 0.5 | 0.6 | 0.6 | 0.6 | 3.2 | 2.9 |
| | | 6.2 | 0.6 | 0.6 | 0.7 | 0.7 | 3.3 | 3.2 |
| | | 6.5 | 0.6 | 0.6 | 0.7 | 0.7 | 3.4 | 3.5 |
| | 75 mM NaCl, 125 mM Sorbitol, 0.01% PS80 | 5.5 | 0.6 | 0.6 | 0.6 | 0.6 | 6.1 | 5.6 |
| | | 5.8 | 0.6 | 0.6 | 0.7 | 0.7 | 4.7 | 4.8 |
| | | 6.0 | 0.6 | 0.6 | 0.7 | 0.7 | 4.5 | 4.3 |
| | | 6.2 | 0.6 | 0.6 | 0.7 | 0.7 | 4.2 | 4.1 |
| | | 6.5 | 0.6 | 0.7 | 0.8 | 0.8 | 4.3 | 4.3 |
| | 75 mM NaCl, 125 mM Sucrose, 0.01% PS80 | 5.5 | 0.6 | 0.5 | 0.6 | 0.6 | 5.9 | 5.7 |
| | | 5.8 | 0.6 | 0.6 | 0.6 | 0.6 | 5.0 | 4.9 |
| | | 6.0 | 0.6 | 0.6 | 0.7 | 0.7 | 4.5 | 4.5 |
| | | 6.2 | 0.6 | 0.6 | 0.7 | 0.7 | 4.3 | 4.1 |
| | | 6.5 | 0.6 | 0.6 | 0.8 | 0.7 | 4.0 | 4.1 |

TABLE 21

% Main Peak SEC
% Main Peak

| Buffer | Excipient/ Surfactant | pH | Time Zero 1 | Time Zero 2 | 3-week incubation 2-8° C. 1 | 3-week incubation 2-8° C. 2 | 3-week incubation 50° C. 1 | 3-week incubation 50° C. 2 |
|---|---|---|---|---|---|---|---|---|
| 20 mM Histidine | 250 mM Sorbitol, 0.01% PS80 | 5.5 | 99.2 | 99.2 | 98.9 | 99.0 | 94.6 | 94.7 |
| | | 5.8 | 99.1 | 99.1 | 98.9 | 98.8 | 95.2 | 95.1 |
| | | 6.0 | 99.1 | 99.1 | 98.9 | 98.8 | 95.1 | 95.2 |
| | | 6.2 | 99.1 | 99.0 | 98.8 | 98.8 | 95.1 | 95.2 |
| | | 6.5 | 99.1 | 99.1 | 98.8 | 98.8 | 94.6 | 94.9 |
| 20 mM Histidine | 250 mM Sucrose, 0.01% PS80 | 5.5 | 99.2 | 99.1 | 98.9 | 98.8 | 94.5 | 95.0 |
| | | 5.8 | 99.1 | 99.1 | 98.8 | 98.7 | 94.7 | 94.9 |
| | | 6.0 | 99.2 | 99.1 | 98.9 | 98.8 | 94.9 | 95.1 |
| | | 6.2 | 99.1 | 99.0 | 98.7 | 98.7 | 94.6 | 94.9 |
| | | 6.5 | 99.1 | 99.0 | 98.7 | 98.6 | 94.6 | 94.4 |
| 20 mM Histidine | 75 mM NaCl, 125 mM Sorbitol, 0.01% PS80 | 5.5 | 99.1 | 99.2 | 98.9 | 99.0 | 91.3 | 92.0 |
| | | 5.8 | 99.1 | 99.1 | 98.9 | 98.9 | 93.2 | 93.2 |
| | | 6.0 | 99.2 | 99.0 | 98.9 | 98.9 | 93.5 | 93.7 |
| | | 6.2 | 99.1 | 99.1 | 98.9 | 98.9 | 94.0 | 93.9 |
| | | 6.5 | 99.1 | 99.1 | 98.8 | 98.8 | 93.7 | 93.8 |
| 20 mM Histidine | 75 mM NaCl, 125 mM Sucrose, 0.01% PS80 | 5.5 | 99.1 | 99.2 | 98.9 | 99.0 | 91.3 | 91.9 |
| | | 5.8 | 99.2 | 99.1 | 98.9 | 98.8 | 92.7 | 93.0 |
| | | 6.0 | 99.1 | 99.1 | 98.9 | 98.9 | 93.5 | 93.4 |
| | | 6.2 | 99.0 | 99.1 | 98.9 | 98.9 | 93.6 | 93.8 |
| | | 6.5 | 99.1 | 99.1 | 98.8 | 98.8 | 93.9 | 94.0 |

TABLE 22

% LMW SEC
% LMW

| Buffer | Excipient/ Surfactant | pH | Time Zero 1 | Time Zero 2 | 3-week incubation 2-8° C. 1 | 3-week incubation 2-8° C. 2 | 3-week incubation 50° C. 1 | 3-week incubation 50° C. 2 |
|---|---|---|---|---|---|---|---|---|
| 20 mM Histidine | 250 mM Sorbitol, 0.01% PS80 | 5.5 | 0.3 | 0.3 | 0.5 | 0.5 | 2.3 | 2.2 |
| | | 5.8 | 0.4 | 0.3 | 0.5 | 0.5 | 2.0 | 2.0 |
| | | 6.0 | 0.3 | 0.3 | 0.5 | 0.6 | 1.9 | 1.8 |
| | | 6.2 | 0.3 | 0.4 | 0.5 | 0.5 | 1.8 | 1.8 |
| | | 6.5 | 0.2 | 0.3 | 0.4 | 0.5 | 1.9 | 1.9 |
| 20 mM Histidine | 250 mM Sucrose, 0.01% PS80 | 5.5 | 0.3 | 0.3 | 0.6 | 0.6 | 2.3 | 2.2 |
| | | 5.8 | 0.4 | 0.4 | 0.6 | 0.7 | 2.2 | 2.1 |
| | | 6.0 | 0.3 | 0.4 | 0.5 | 0.6 | 1.9 | 2.0 |
| | | 6.2 | 0.3 | 0.4 | 0.7 | 0.6 | 2.1 | 1.9 |
| | | 6.5 | 0.3 | 0.4 | 0.6 | 0.7 | 2.1 | 2.1 |
| 20 mM Histidine | 75 mM NaCl, 125 mM Sorbitol, 0.01% PS80 | 5.5 | 0.4 | 0.3 | 0.5 | 0.4 | 2.6 | 2.4 |
| | | 5.8 | 0.3 | 0.3 | 0.4 | 0.5 | 2.1 | 2.0 |
| | | 6.0 | 0.2 | 0.4 | 0.4 | 0.4 | 2.0 | 2.0 |
| | | 6.2 | 0.3 | 0.3 | 0.4 | 0.4 | 1.9 | 2.0 |
| | | 6.5 | 0.3 | 0.3 | 0.4 | 0.4 | 1.9 | 1.9 |
| 20 mM Histidine | 75 mM NaCl, 125 mM Sucrose, 0.01% PS80 | 5.5 | 0.3 | 0.3 | 0.5 | 0.5 | 2.8 | 2.4 |
| | | 5.8 | 0.3 | 0.3 | 0.5 | 0.5 | 2.2 | 2.1 |
| | | 6.0 | 0.3 | 0.3 | 0.4 | 0.4 | 2.1 | 2.0 |
| | | 6.2 | 0.4 | 0.3 | 0.4 | 0.4 | 2.0 | 2.1 |
| | | 6.5 | 0.3 | 0.3 | 0.5 | 0.5 | 2.1 | 1.9 |

Figure 20A:
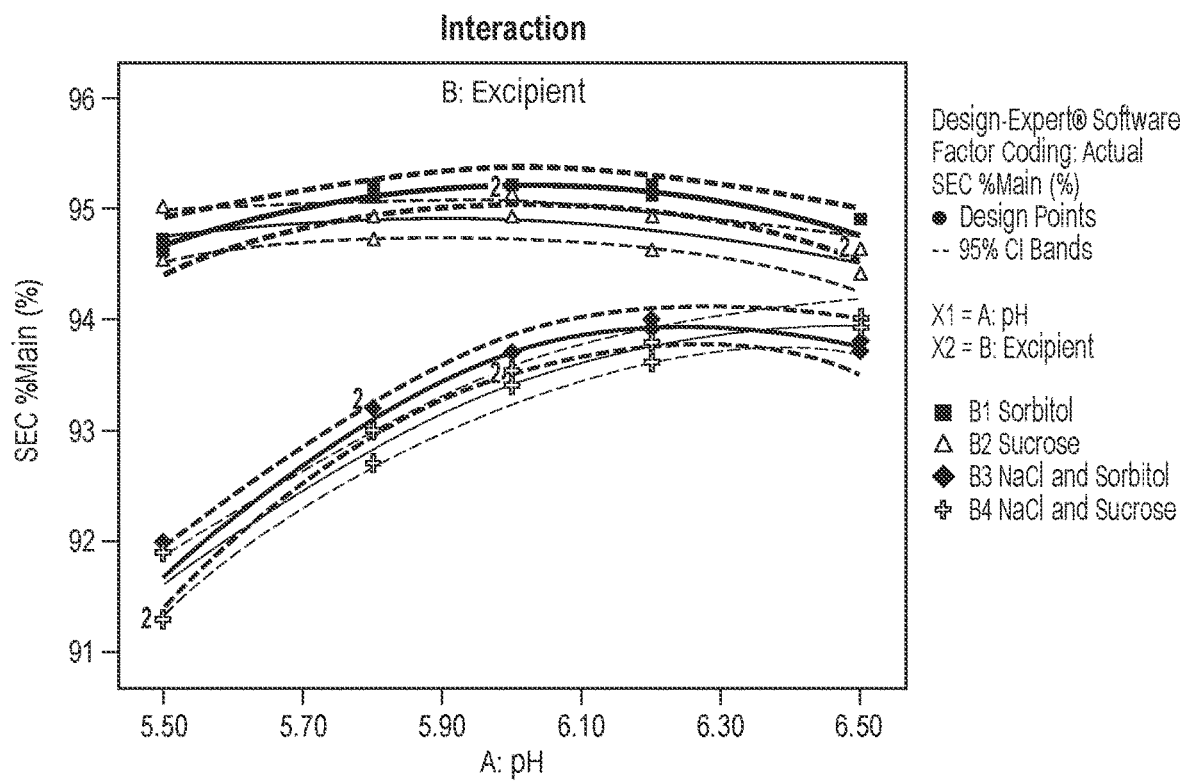
FIG. 20A is an interaction plot for % main species determined by Size Exclusion Chromatography (SEC) for a 3-week incubation at 50° C.
Figure 22A:
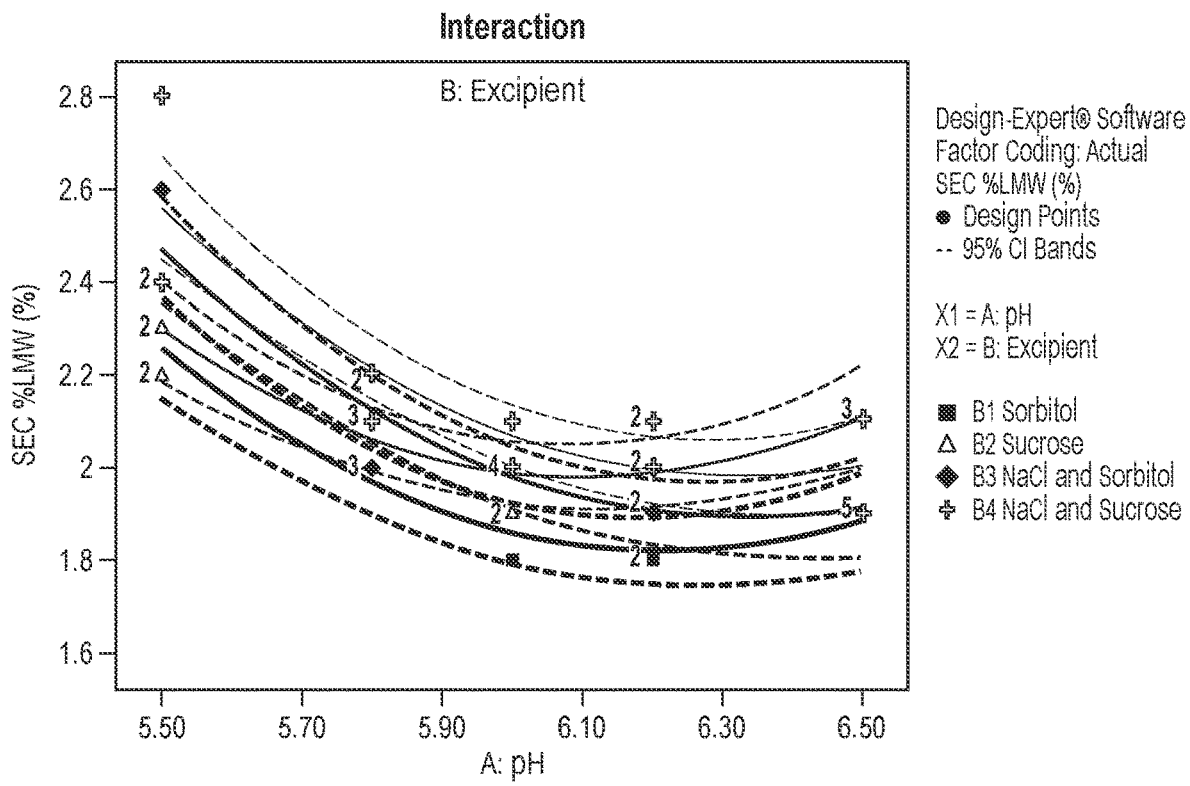
FIG. 22A is an interaction plot for percent Low Molecular Weight (% LMW) species determined by SEC for a 3-week incubation at 50° C.

After 3-week incubation at 50° C., the formulated samples possessed % main peak values ranging from 91.3%-95.2%, with those formulations possessing only sorbitol and sucrose maintaining greater % main peak and lower % HMW species (shown respectively in FIG. 20A and FIG. 20A) relative to the combination excipients NaCl and sorbitol, and NaCl and sucrose. Importantly, both single excipients sucrose and sorbitol maintained % main peak species across the pH range 5.5-6.5, and both displayed only slightly elevated % HMW species as the pH increased from 5.5 to 6.5. The % LMW species trended lower as the pH increased from 5.5 to about 6.2 for all excipients (FIG. 22A).

Figure 20B:
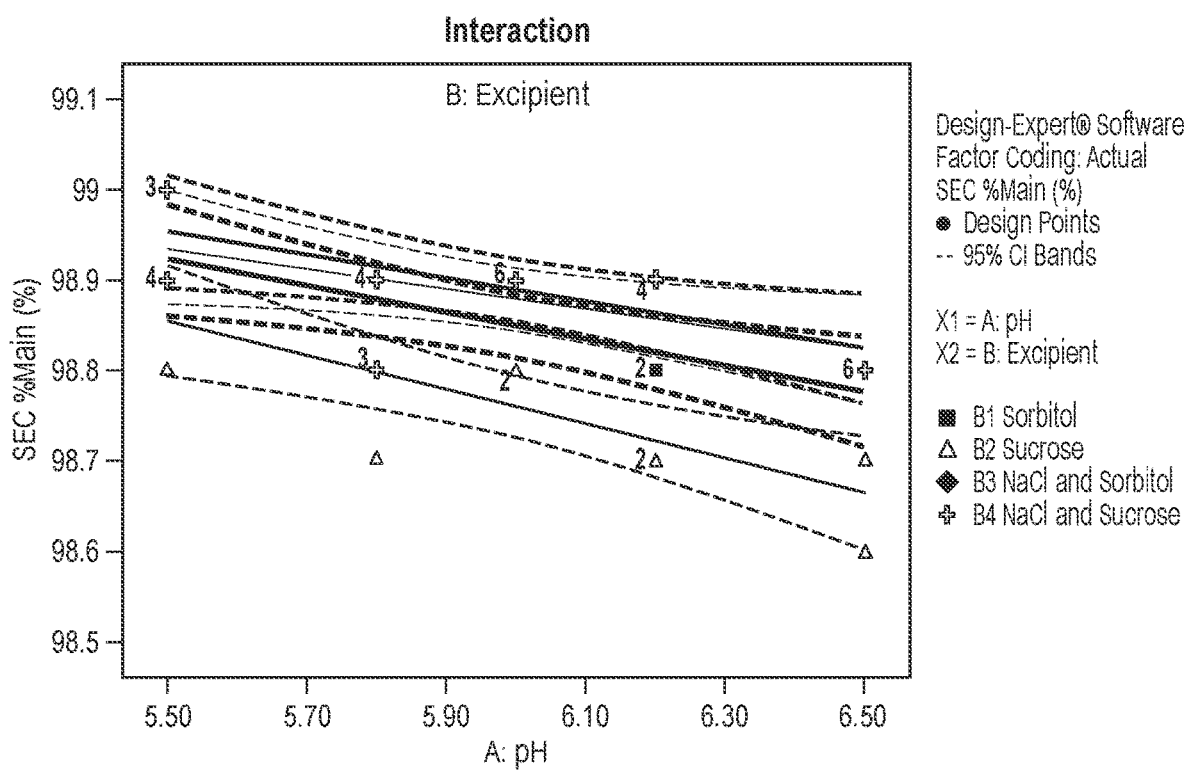
FIG. 20B is an interaction plot for % main species determined by SEC for a 3-week incubation at 2-8° C.
Figure 21A:
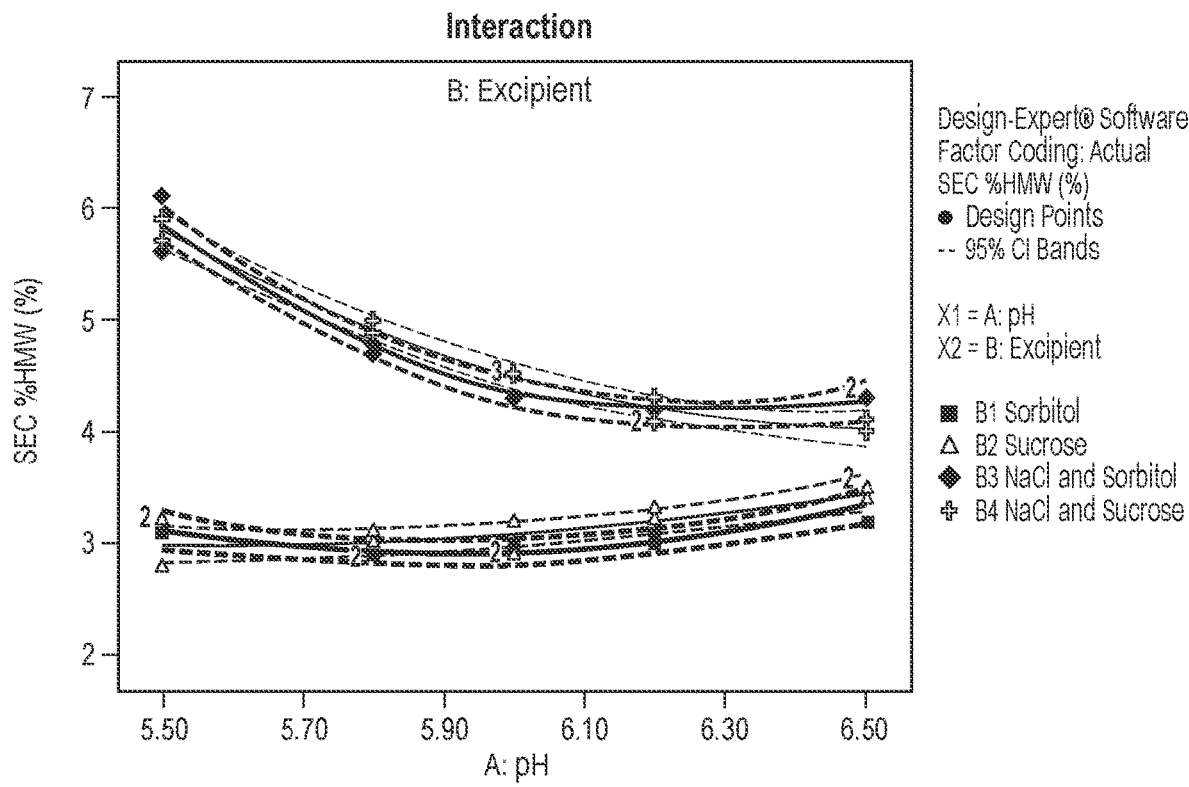
FIG. 21A is an interaction plot for percent High Molecular Weight (% HMW) species determined by SEC for a 3-week incubation at 50° C.
Figure 21B:
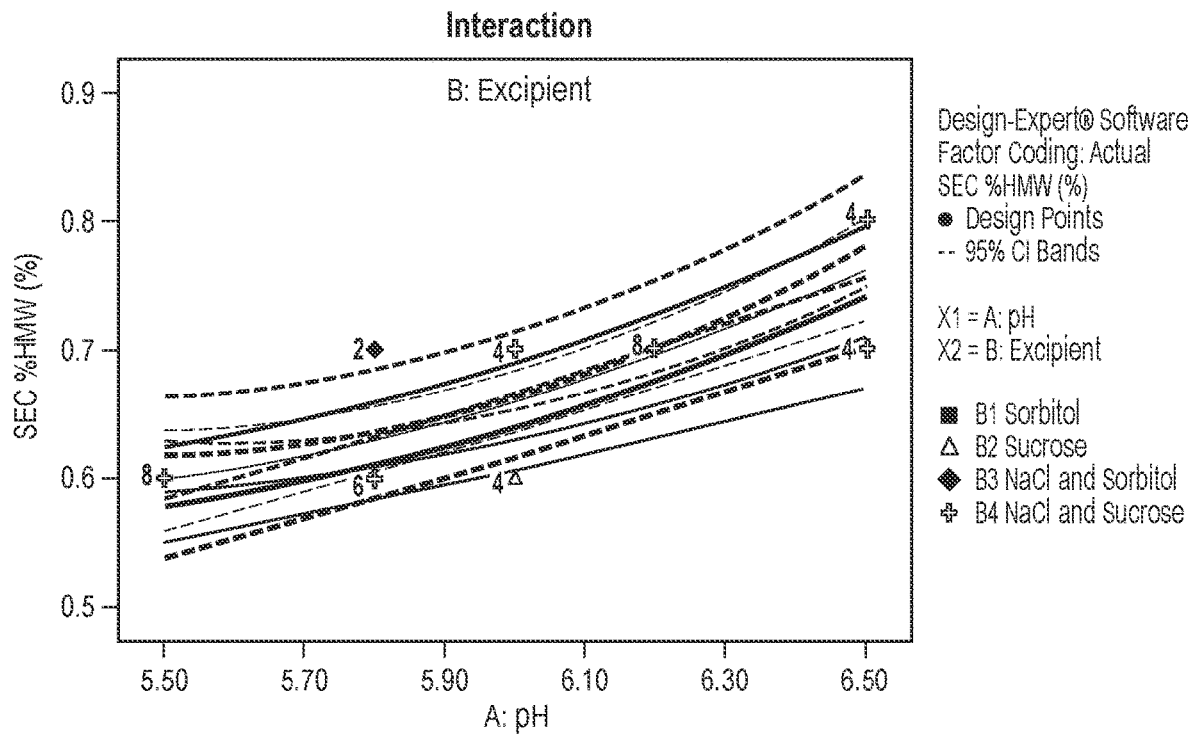
FIG. 21B is an interaction plot for % HMW species determined by SEC for a 3-week incubation at 2-8° C.
Figure 22B:
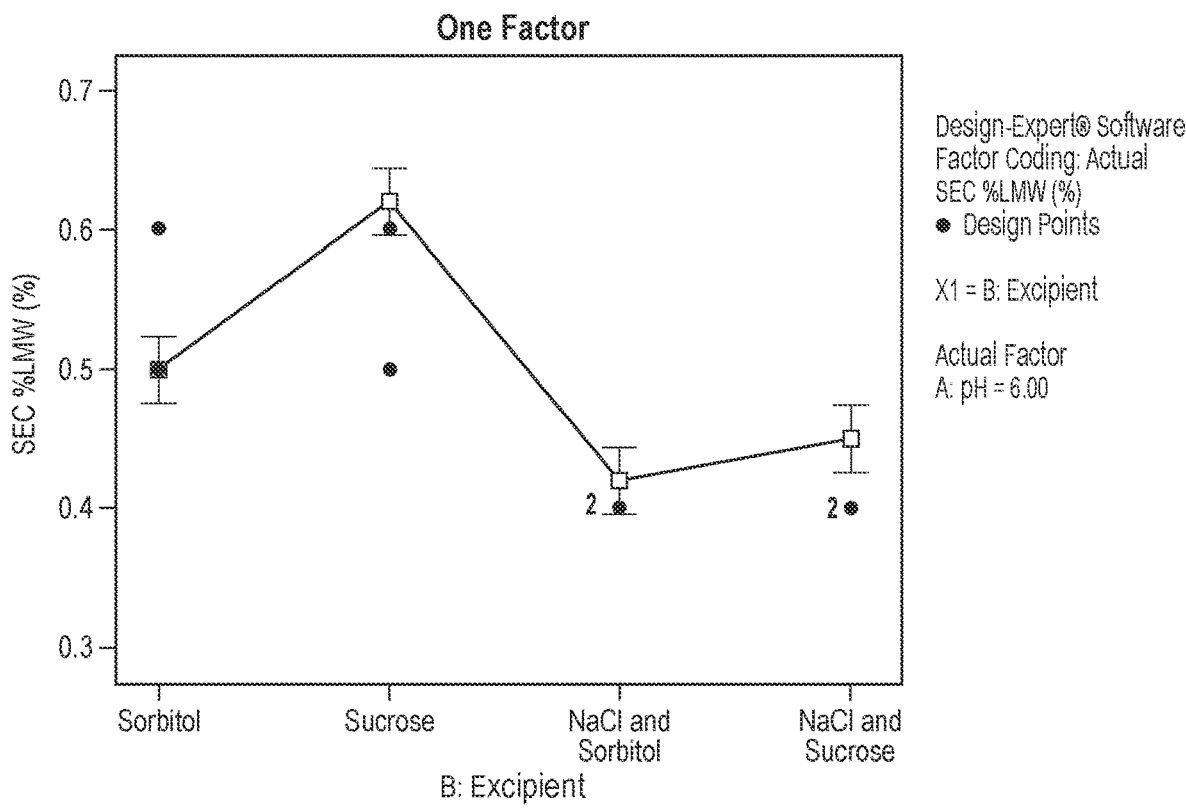
FIG. 22B is an interaction plot for % LMW species determined by SEC for a 3-week incubation at 2-8° C. at pH 6.0.

After 3-week incubation at 2-8° C., all the formulated samples maintained a percentage of main species peak greater than 98%. The % main peak was greater for lower pH values (5.5) versus higher pH values (pH 6.5) as shown in FIG. 20B. The single excipients sorbitol and sucrose trended towards lower % HMW relative to the combination excipients NaCl and sorbitol, and NaCl and sucrose. For all excipients, increased pH trended towards increased % HMW species (FIG. 20B). The % LMW species trended lower for the combination excipients but was pH independent (FIG. 22B).

Osmolality

The osmolality of all samples was measured by freezing point depression. The osmolality was maintained for all samples across all conditions. The osmolality data at time zero, after 3-week incubation at 2-8° C., and after 3-week incubation at 50° C. are summarized in in Table 23.

TABLE 23

Osmolality values

| Buffer | Excipient/ Surfactant | pH | Time Zero | | 3-week incubation | | | |
|---|---|---|---|---|---|---|---|---|
| | | | | | 2-8° C. | | 50° C. | |
| | | | 1 | 2 | 1 | 2 | 1 | 2 |
| 20 mM Histidine | 250 mM Sorbitol, 0.01% PS80 | 5.5 | 314 | 319 | 309 | 315 | 309 | 317 |
| | | 5.8 | 310 | 314 | 317 | 320 | 307 | 320 |
| | | 6.0 | 309 | 299 | 311 | 303 | 313 | 301 |
| | | 6.2 | 304 | 351 | 304 | 354 | 308 | 354 |
| | | 6.5 | 304 | 302 | 297 | 298 | 301 | 300 |
| 20 mM Histidine | 250 mM Sucrose, 0.01% PS80 | 5.5 | 343 | 347 | 342 | 348 | 354 | 360 |
| | | 5.8 | 349 | 352 | 350 | 351 | 362 | 364 |
| | | 6.0 | 344 | 340 | 345 | 337 | 348 | 346 |
| | | 6.2 | 343 | 339 | 346 | 344 | 349 | 348 |
| | | 6.5 | 335 | 337 | 332 | 340 | 334 | 344 |
| 20 mM Histidine | 75 mM NaCl, 125 mM Sorbitol, 0.01% PS80 | 5.5 | 322 | 326 | 321 | 330 | 322 | 330 |
| | | 5.8 | 327 | 317 | 326 | 320 | 330 | 320 |
| | | 6.0 | 323 | 372 | 317 | 376 | 320 | 375 |
| | | 6.2 | 313 | 310 | 309 | 308 | 311 | 315 |
| | | 6.5 | 313 | 312 | 312 | 316 | 313 | 313 |
| 20 mM Histidine | 75 mM NaCl, 125 mM Sucrose, 0.01% PS80 | 5.5 | 348 | 331 | 345 | 338 | 354 | 343 |
| | | 5.8 | 343 | 345 | 340 | 350 | 349 | 354 |
| | | 6.0 | 347 | 339 | 344 | 338 | 346 | 343 |
| | | 6.2 | 341 | 335 | 337 | 338 | 343 | 337 |
| | | 6.5 | 342 | 339 | 332 | 343 | 339 | 342 |

Imaged Capillary Isoelectric Focusing (icIEF)

For determining charge-variant analysis, Imaged Capillary Isoelectric Focusing (icIEF) was used. Charge heterogeneity was evaluated by diluting starting material and samples to 5 mg/mL in water then combined with master mix, at a ratio of 10 μL of sample to 90 μL of master mix. The master mix was a combination of 1% Methylcellulose, Pharmalyte 3-10, Pharmalyte 8-10.5, pI marker 5.12, pI marker 9.50, and DI water. A system suitability standard was prepared and run prior to running the samples, which were run in 96-well plate format. Method parameters utilized were as follows: focusing period #1=1 min, 1500 V, focusing period #2=8 min, 3000 V, detection=5 exposures, sample load=55 s, lower pI marker=5.12, 300 pixels, upper pI marker=9.50, 1800 pixels. Starting material was run every 18 injections to ensure consistent reads.

The "main peak" was identified as the main peak in the formulated samples at time zero. After incubation, the peak with the same elution time may have decreased and no longer represented the peak with the greatest area under curve, but was still identified as the "main peak." The percentage of protein present in an acidic fraction (% acidic) values after 3-week incubation at 2-8° C. and after 3-week incubation at 50° C. are summarized in Table 24. The percentage of protein present in the main peak fraction (% main peak) values are summarized in Table 25. The percentage of protein present in a basic fraction (% basic) values are summarized in Table 26.

TABLE 24

% Acidic icIEF

| Buffer | Excipient/ Surfactant | pH | 3-week incubation | | | |
|---|---|---|---|---|---|---|
| | | | 2-8° C. | | 50° C. | |
| | | | 1 | 2 | 1 | 2 |
| 20 mM Histidine | 250 mM Sorbitol, | 5.5 | 35.8 | 36.0 | 73.1 | 73.3 |
| | | 5.8 | 34.3 | 36.2 | 74.5 | 75.0 |

TABLE 24-continued

% Acidic icIEF

| Buffer | Excipient/ Surfactant | pH | 3-week incubation | | | |
|---|---|---|---|---|---|---|
| | | | 2-8° C. | | 50° C. | |
| | | | 1 | 2 | 1 | 2 |
| | 0.01% PS80 | 6.0 | 36.0 | 36.2 | 76.1 | 75.5 |
| | | 6.2 | 36.2 | 36.9 | 77.0 | 75.8 |
| | | 6.5 | 36.7 | 35.7 | 81.1 | 80.4 |
| 20 mM Histidine | 250 mM Sucrose, 0.01% PS80 | 5.5 | 34.5 | 36.5 | 81.6 | 80.5 |
| | | 5.8 | 35.0 | 36.5 | 81.4 | 80.8 |
| | | 6.0 | 34.7 | 34.5 | 79.0 | 78.4 |
| | | 6.2 | 36.1 | 36.4 | 79.8 | 80.1 |
| | | 6.5 | 36.5 | 37.2 | 81.0 | 81.5 |

TABLE 24-continued

% Acidic icIEF

| Buffer | Excipient/Surfactant | pH | 3-week incubation |  |  |  |
|---|---|---|---|---|---|---|
| | | | 2-8° C. | | 50° C. | |
| | | | 1 | 2 | 1 | 2 |
| 20 mM Histidine | 75 mM NaCl, 125 mM Sorbitol, 0.01% PS80 | 5.5 | 36.1 | 36.3 | 70.6 | 70.8 |
| | | 5.8 | 35.1 | 36.4 | 73.7 | 73.1 |
| | | 6.0 | 36.3 | 35.6 | 75.0 | 74.2 |
| | | 6.2 | 35.3 | 35.2 | 76.4 | 76.3 |
| | | 6.5 | 36.4 | 35.5 | 78.9 | 78.6 |
| 20 mM Histidine | 75 mM NaCl, 125 mM Sucrose, 0.01% PS80 | 5.5 | 35.0 | 36.1 | 75.7 | 74.5 |
| | | 5.8 | 35.3 | 36.4 | 77.0 | 75.9 |
| | | 6.0 | 36.4 | 36.6 | 78.0 | 77.4 |
| | | 6.2 | 35.0 | 36.9 | 78.1 | 76.5 |
| | | 6.5 | 38.4 | 36.8 | 79.6 | 78.5 |

TABLE 25

% Main Peak icIEF

| Buffer | Excipient/Surfactant | pH | 3-week incubation |  |  |  |
|---|---|---|---|---|---|---|
| | | | 2-8° C. | | 50° C. | |
| | | | 1 | 2 | 1 | 2 |
| 20 mM Histidine | 250 mM Sorbitol, 0.01% PS80 | 5.5 | 60.8 | 60.4 | 21.5 | 21.8 |
| | | 5.8 | 62.2 | 60.2 | 21.4 | 21.0 |
| | | 6.0 | 60.3 | 60.3 | 20.4 | 20.9 |
| | | 6.2 | 60.4 | 59.5 | 19.8 | 20.8 |
| | | 6.5 | 59.9 | 60.9 | 16.1 | 17.2 |
| 20 mM Histidine | 250 mM Sucrose, 0.01% PS80 | 5.5 | 62.0 | 59.9 | 14.9 | 16.0 |
| | | 5.8 | 61.6 | 59.8 | 15.6 | 16.0 |
| | | 6.0 | 61.9 | 62.0 | 17.7 | 18.3 |
| | | 6.2 | 60.5 | 60.1 | 17.5 | 17.0 |
| | | 6.5 | 60.2 | 59.3 | 16.3 | 15.7 |
| 20 mM Histidine | 75 mM NaCl, 125 mM Sorbitol, 0.01% PS80 | 5.5 | 60.4 | 60.2 | 20.5 | 22.7 |
| | | 5.8 | 61.4 | 60.1 | 21.8 | 22.1 |
| | | 6.0 | 60.3 | 60.9 | 20.8 | 22.0 |
| | | 6.2 | 61.4 | 61.4 | 19.9 | 20.4 |
| | | 6.5 | 60.2 | 61.2 | 18.2 | 18.4 |
| 20 mM Histidine | 75 mM NaCl, 125 mM Sucrose, 0.01% PS80 | 5.5 | 61.5 | 60.4 | 18.9 | 20.4 |
| | | 5.8 | 61.2 | 60.1 | 19.0 | 20.1 |
| | | 6.0 | 60.2 | 59.9 | 18.7 | 18.9 |
| | | 6.2 | 61.6 | 59.6 | 18.7 | 20.3 |
| | | 6.5 | 58.3 | 59.7 | 17.6 | 18.4 |

TABLE 26

% Basic Peak icIEF

| Buffer | Excipient/Surfactant | pH | 3-week incubation |  |  |  |
|---|---|---|---|---|---|---|
| | | | 2-8° C. | | 50° C. | |
| | | | 1 | 2 | 1 | 2 |
| 20 mM Histidine | 250 mM Sorbitol, 0.01% PS80 | 5.5 | 3.4 | 3.6 | 5.4 | 4.9 |
| | | 5.8 | 3.5 | 3.5 | 4.1 | 3.9 |
| | | 6.0 | 3.6 | 3.5 | 3.5 | 3.7 |
| | | 6.2 | 3.4 | 3.6 | 3.2 | 3.4 |
| | | 6.5 | 3.3 | 3.3 | 2.8 | 2.4 |
| 20 mM Histidine | 250 mM Sucrose, 0.01% PS80 | 5.5 | 3.5 | 3.6 | 3.6 | 3.5 |
| | | 5.8 | 3.4 | 3.7 | 3.0 | 3.2 |
| | | 6.0 | 3.4 | 3.5 | 3.3 | 3.3 |
| | | 6.2 | 3.4 | 3.5 | 2.7 | 2.9 |
| | | 6.5 | 3.4 | 3.5 | 2.7 | 2.8 |
| 20 mM Histidine | 75 mM NaCl, 125 mM Sorbitol, 0.01% PS80 | 5.5 | 3.6 | 3.5 | 8.8 | 6.5 |
| | | 5.8 | 3.5 | 3.5 | 4.5 | 4.8 |
| | | 6.0 | 3.4 | 3.5 | 4.3 | 3.8 |
| | | 6.2 | 3.4 | 3.4 | 3.7 | 3.3 |
| | | 6.5 | 3.4 | 3.3 | 2.9 | 3.0 |

TABLE 26-continued

% Basic Peak icIEF

| Buffer | Excipient/Surfactant | pH | 3-week incubation |  |  |  |
|---|---|---|---|---|---|---|
| | | | 2-8° C. | | 50° C. | |
| | | | 1 | 2 | 1 | 2 |
| 20 mM Histidine | 75 mM NaCl, 125 mM Sucrose, 0.01% PS80 | 5.5 | 3.5 | 3.5 | 5.4 | 5.1 |
| | | 5.8 | 3.5 | 3.5 | 4.0 | 4.0 |
| | | 6.0 | 3.4 | 3.4 | 3.3 | 3.7 |
| | | 6.2 | 3.4 | 3.5 | 3.2 | 3.2 |
| | | 6.5 | 3.3 | 3.5 | 2.8 | 3.0 |

Figure 23A:
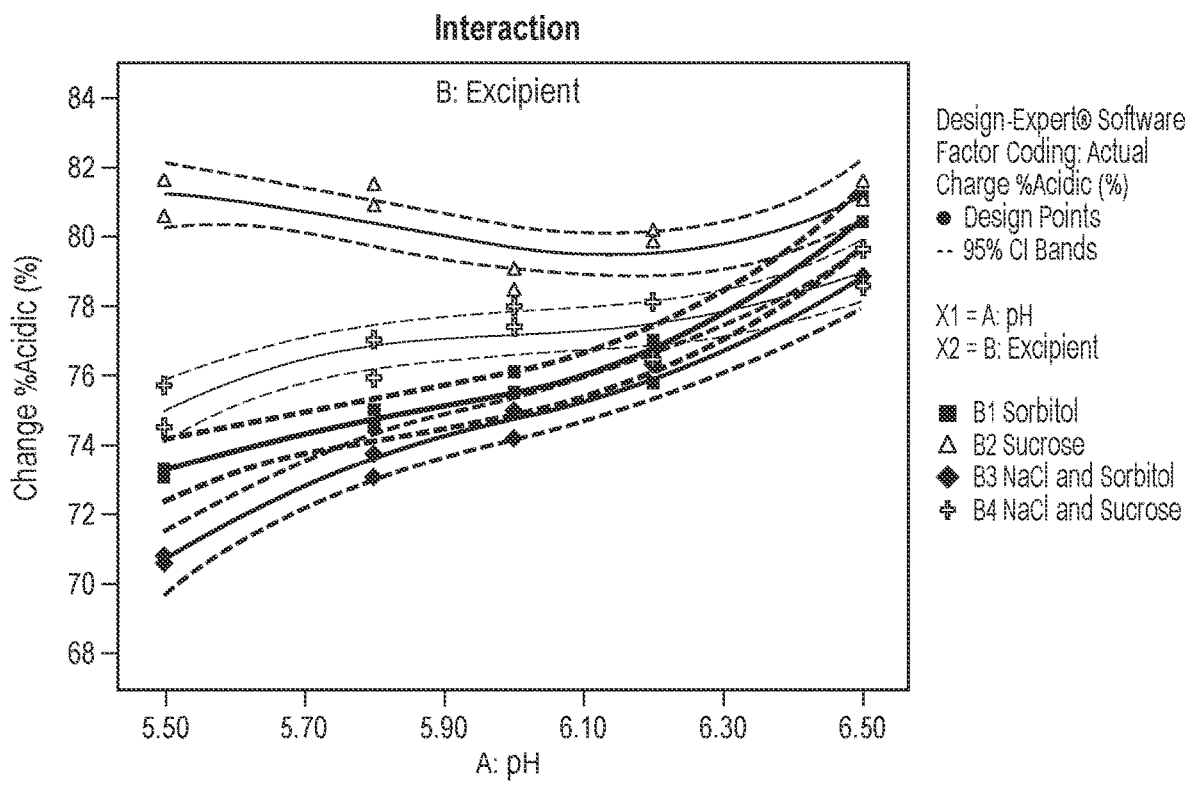
FIG. 23A is an interaction plot for % acidic species determined by Imaged Capillary Isoelectric Focusing (icIEF) for a 3-week incubation at 50° C.
Figure 23B:
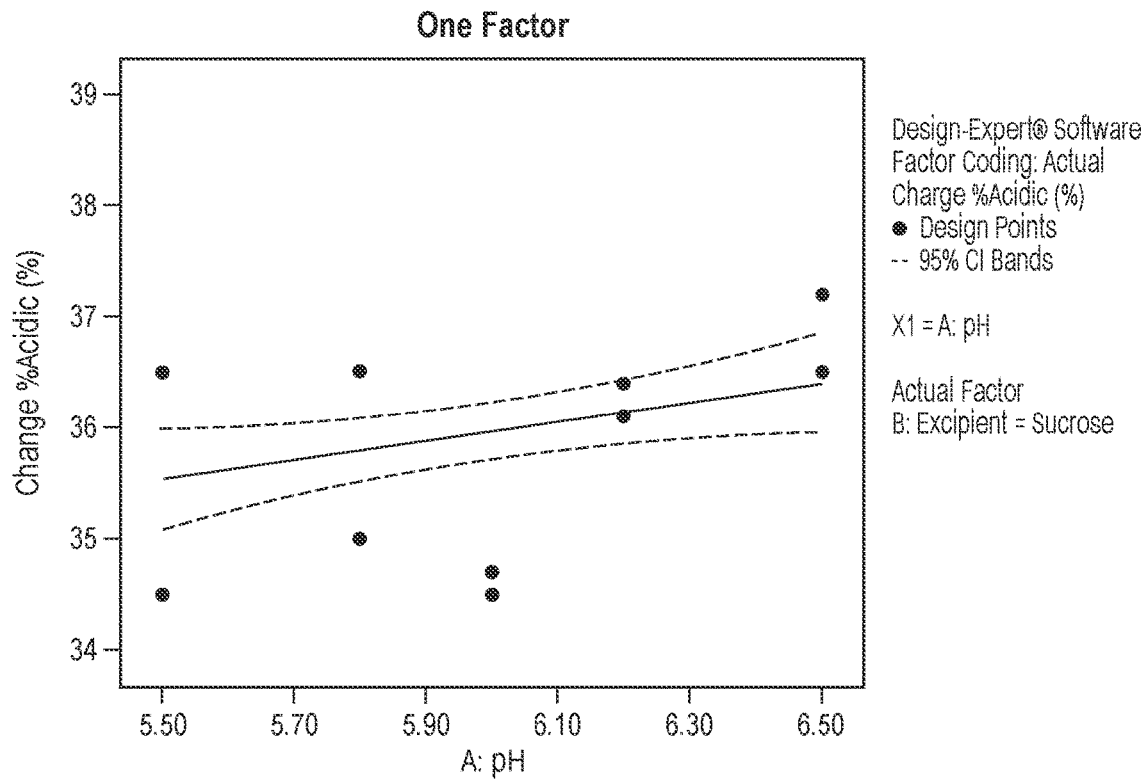
FIG. 23B is an interaction plot for % basic species for sucrose only as determined by icIEF for a 3-week incubation 4-8° C.
Figure 24A:
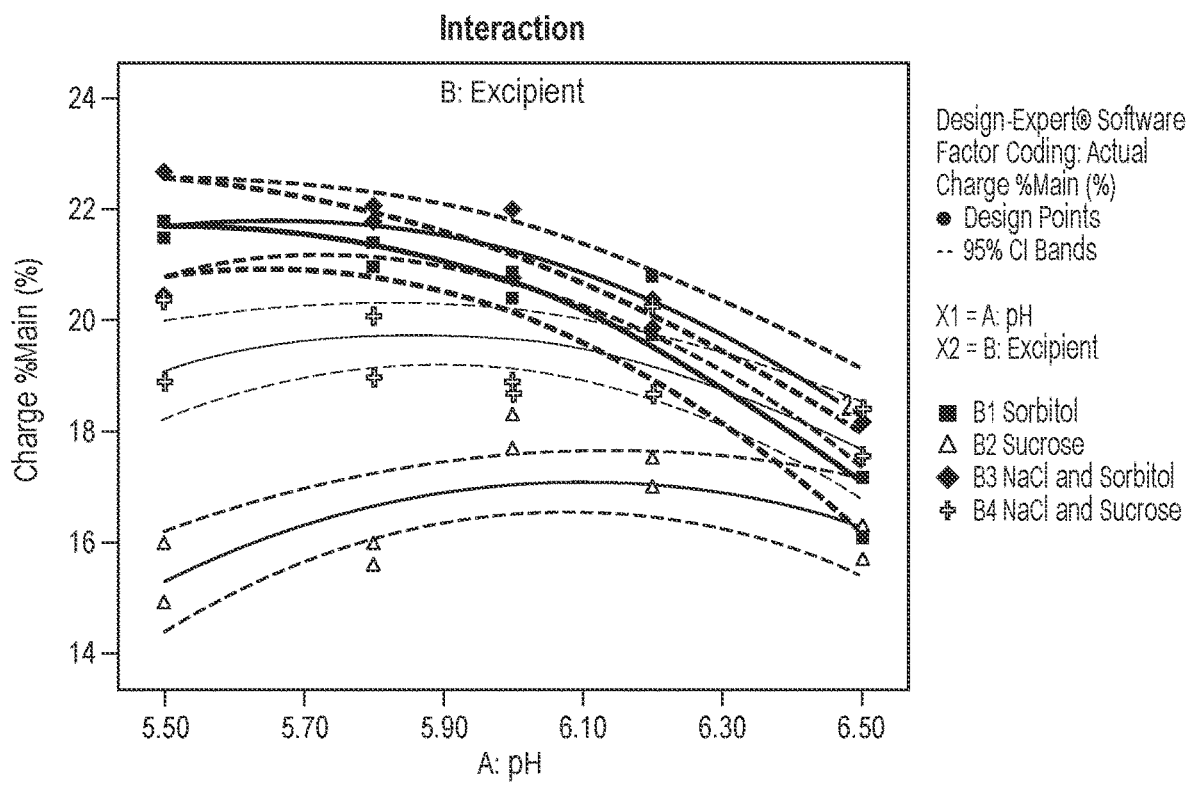
FIG. 24A is an interaction plot for % main species determined by icIEF for a 3-week incubation at 50° C.
Figure 24B:
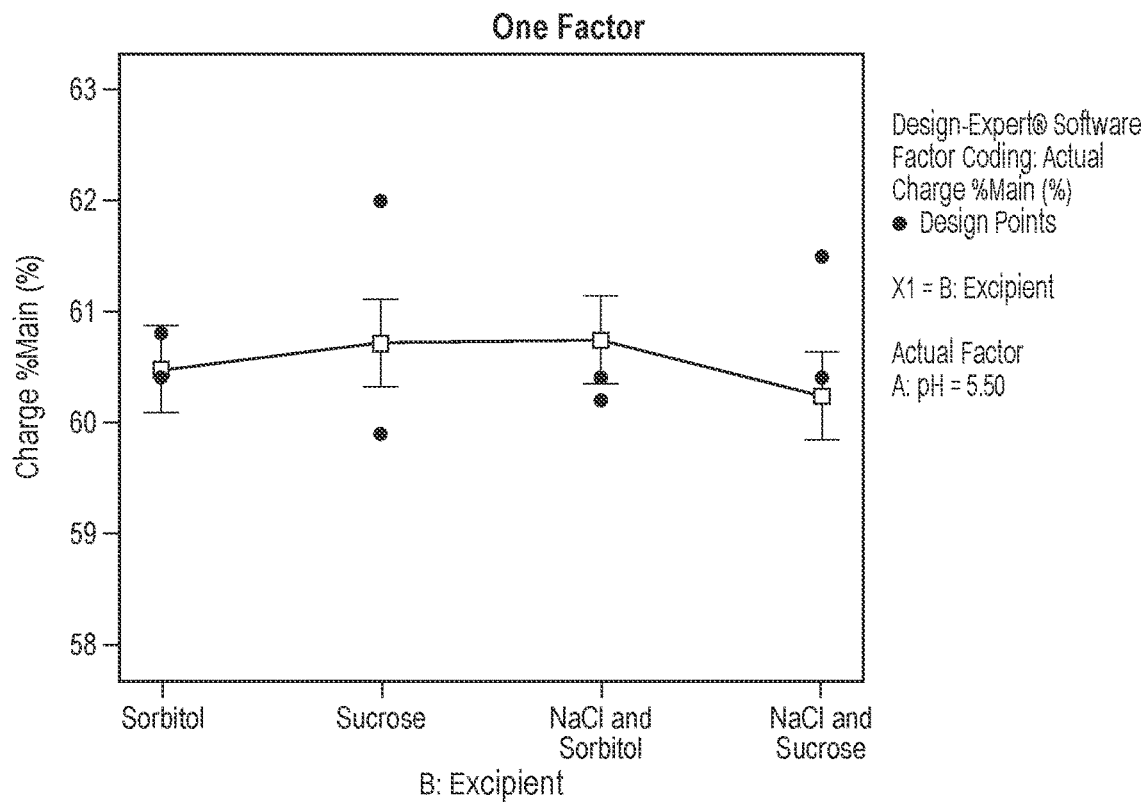
FIGS. 24B-24D are interaction plots for % main species in the sucrose only formulation, determined by icIEF, for a 3-week incubation at 4° C. at pH 5.5 (FIG. 24B), pH 6.0 (FIG. 24C), and pH 6.5 (FIG. 24D).
Figure 24C:
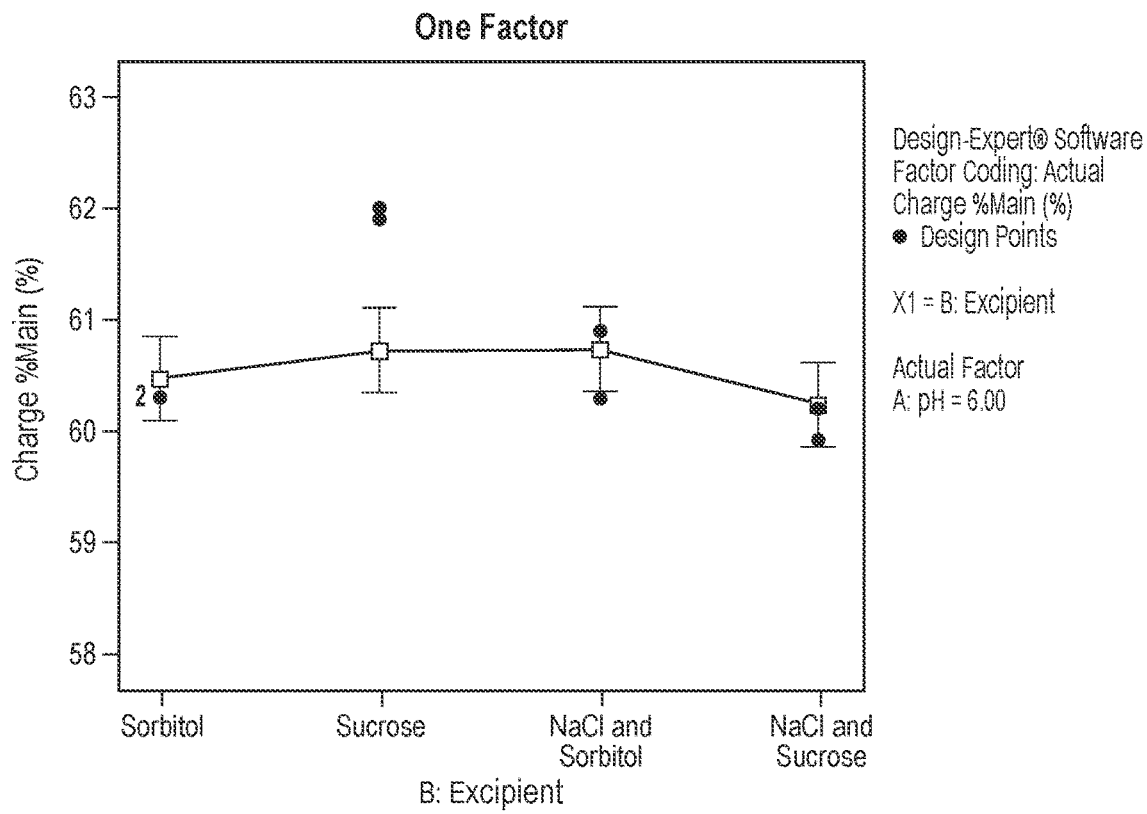
Figure 24D:
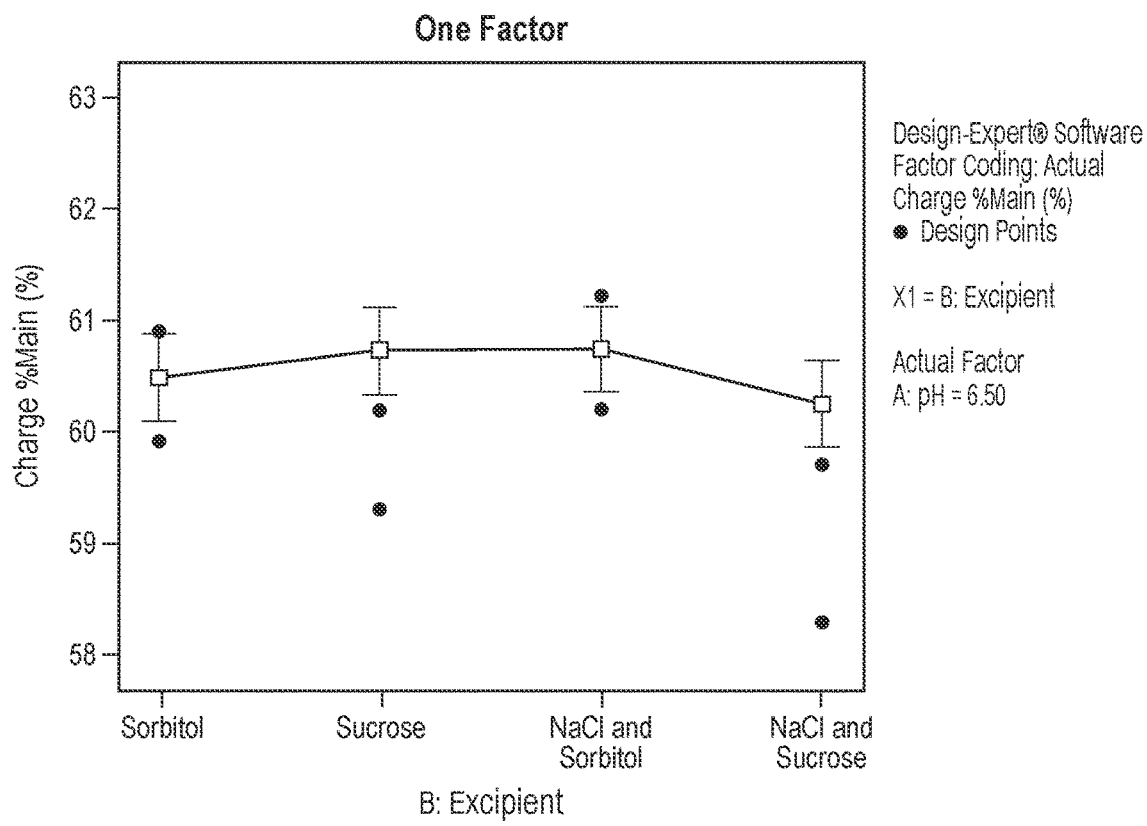
Figure 25A:
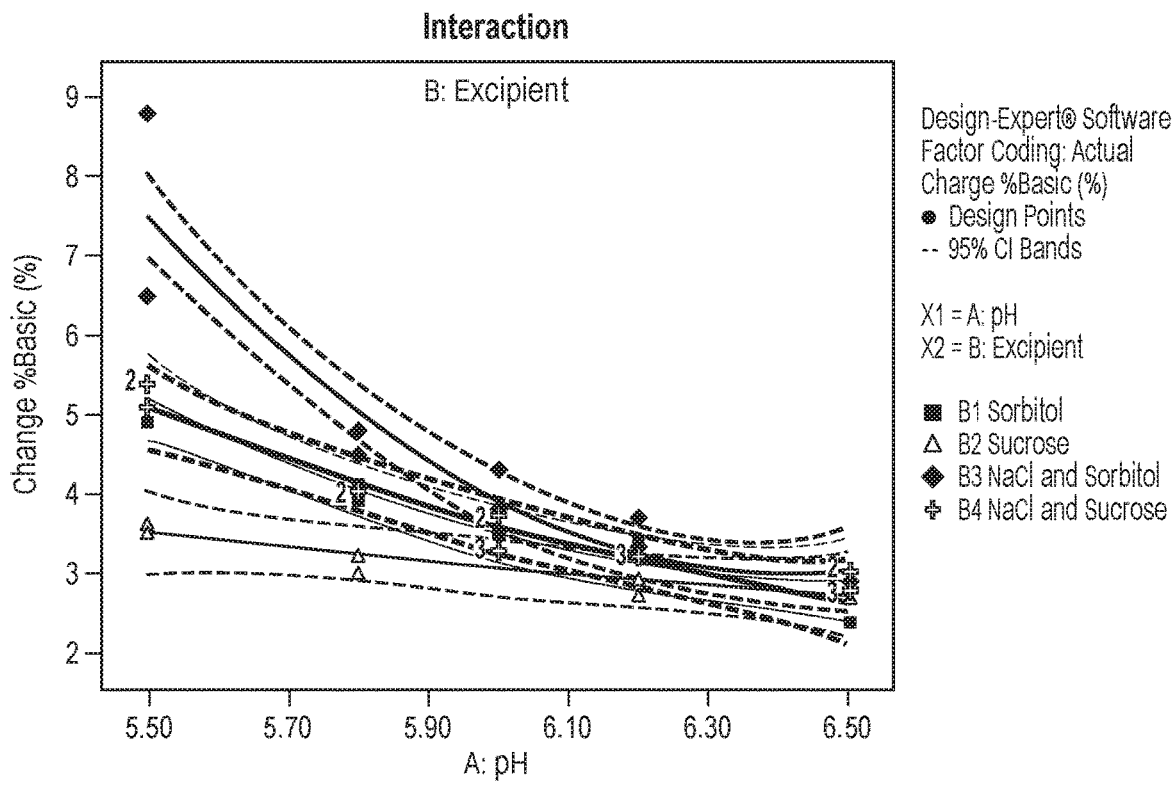
FIG. 25A is an interaction plot for % basic species determined by icIEF for a 3-week incubation at 50° C.
Figure 25B:
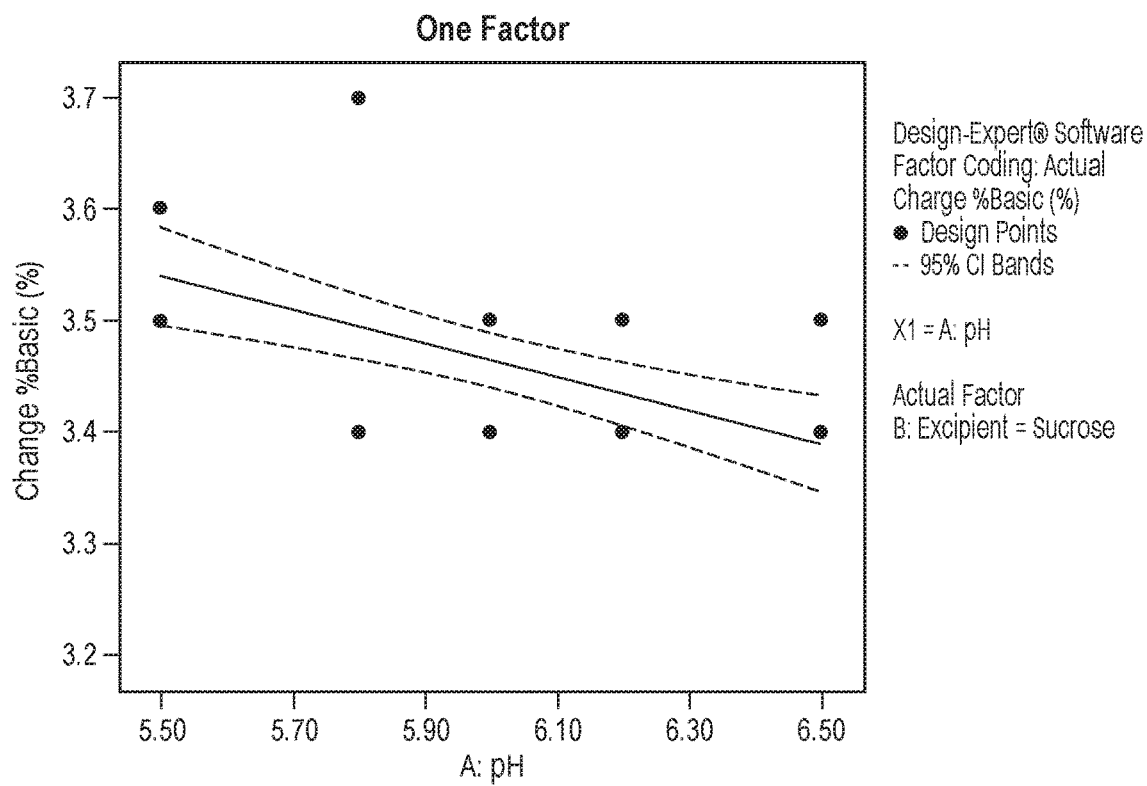
FIG. 25B is an interaction plot for % basic species for sucrose only as determined by icIEF for a 3-week incubation 2-8° C.

For the formulated samples after 3-week incubation at 2-8° C., the % main peak values ranged from 58.3%-62.2%, the % acidic values ranged from 34.3%-38.4%, and the % basic values ranged from 3.3%-3.7%. There was not a significant model to fit the % main peak data, indicating that neither pH nor excipient had a significant effect on the icIEF values (FIGS. 24B-24D). The excipient was also not significant in modeling the % acidic and % basic species, and the % acidic species tended to increase with pH while the % basic species decreased (FIG. 23B and FIG. 25B). The changes were marginal, however, as observed by the narrow ranges for all values.

For the formulated samples after 3-week incubation at 50° C., the % main peak values ranged from 14.9%-22.7%, the % acidic values ranged from 70.6%-81.6%, and the % basic values ranged from 2.4%-8.8%. The data indicates a shift from the % main peak species to % acidic species, with % basic remaining relatively consistent with the 3-week 2-8° C. incubation results. In evaluating the 3-week 50° C. formulated samples, the samples possessing sucrose as the only excipient possessed the highest % acidic species (FIG. 23A) and lowest % main peak and % basic species (FIG. 24A and FIG. 25A). This was consistent across all pH values (5.5-6.5) while the formulations possessing the other 3 excipients trended towards lower % acidic species at lower pH values that increased with increasing pH.

Capillary Electrophoresis (CE)

Reduced capillary gel electrophoresis was performed to assess purity. SDS-CGE was evaluated using a Sciex PA800+ with UV detection at 220 nm. Samples were prepared by diluting 100 μg sample in Beckman SDS sample buffer and adding 5 μL β-Mercaptoethanol. Samples were heated at 70° C. for 10 minutes. Separation occurred over 20 minutes using normal polarity, 1 minute ramp, 15 kV voltage and 20 psi pressure. The capillary length was 30.2 cm, with the length to the detector as 10.2 cm. Starting material was used as a reference. A summary of sample percentage purity is shown in Table 27. A summary of percentage of sample impurities is shown in Table 28.

TABLE 27

% Purity

| Buffer | Excipient/Surfactant | pH | 3-week incubation |  |  |  |
|---|---|---|---|---|---|---|
| | | | 2-8° C. | | 50° C. | |
| | | | 1 | 2 | 1 | 2 |
| 20 mM Histidine | 250 mM Sorbitol, 0.01% PS80 | 5.5 | 98.8 | 98.7 | 91.3 | 92.8 |
| | | 5.8 | 98.9 | 98.7 | 92.9 | 92.7 |
| | | 6.0 | 98.8 | 98.2 | 94.1 | 93.3 |
| | | 6.2 | 98.7 | 98.6 | 93.5 | 93.4 |
| | | 6.5 | 98.9 | 98.8 | 92.2 | 92.5 |

TABLE 27-continued

% Purity

| Buffer | Excipient/Surfactant | pH | 3-week incubation 2-8° C. 1 | 2 | 50° C. 1 | 2 |
|---|---|---|---|---|---|---|
| 20 mM Histidine | 250 mM Sucrose, 0.01% PS80 | 5.5 | 99.0 | 98.8 | 91.5 | 93.1 |
| | | 5.8 | 98.8 | 98.5 | 93.5 | 93.9 |
| | | 6.0 | 98.9 | 98.7 | 94.0 | 93.8 |
| | | 6.2 | 98.9 | 98.7 | 92.6 | 93.0 |
| | | 6.5 | 98.7 | 98.7 | 93.0 | 92.2 |
| 20 mM Histidine | 75 mM NaCl, 125 mM Sorbitol, 0.01% PS80 | 5.5 | 99.1 | 98.7 | 89.9 | 89.8 |
| | | 5.8 | 98.7 | 98.7 | 90.6 | 92.2 |
| | | 6.0 | 98.0 | 98.5 | 92.9 | 93.2 |
| | | 6.2 | 98.7 | 99.1 | 94.7 | 93.5 |
| | | 6.5 | 98.9 | 99.0 | 92.9 | 93.2 |
| 20 mM Histidine | 75 mM NaCl, 125 mM Sucrose, 0.01% PS80 | 5.5 | 98.7 | 98.5 | 91.1 | 89.8 |
| | | 5.8 | 98.8 | 99.1 | 93.9 | 92.8 |
| | | 6.0 | 99.0 | 99.2 | 93.1 | 92.7 |
| | | 6.2 | 99.0 | 98.7 | 93.3 | 92.9 |
| | | 6.5 | 97.2 | 98.9 | 93.9 | 94.3 |

TABLE 28

% Impurities

| Buffer | Excipient/Surfactant | pH | 3-week incubation 2-8° C. 1 | 2 | 50° C. 1 | 2 |
|---|---|---|---|---|---|---|
| 20 mM Histidine | 250 mM Sorbitol, 0.01% PS80 | 5.5 | 1.2 | 1.3 | 8.7 | 7.2 |
| | | 5.8 | 1.1 | 1.3 | 7.1 | 7.3 |
| | | 6.0 | 1.2 | 1.8 | 5.9 | 6.7 |
| | | 6.2 | 1.3 | 1.4 | 6.5 | 6.6 |
| | | 6.5 | 1.1 | 1.2 | 7.8 | 7.5 |
| 20 mM Histidine | 250 mM Sucrose, 0.01% PS80 | 5.5 | 1.0 | 1.2 | 8.5 | 6.9 |
| | | 5.8 | 1.2 | 1.5 | 6.5 | 6.1 |
| | | 6.0 | 1.1 | 1.3 | 6.0 | 6.2 |
| | | 6.2 | 1.1 | 1.3 | 7.4 | 7.0 |
| | | 6.5 | 1.3 | 1.3 | 7.0 | 7.8 |
| 20 mM Histidine | 75 mM NaCl, 125 mM Sorbitol, 0.01% PS80 | 5.5 | 0.9 | 1.3 | 10.1 | 10.2 |
| | | 5.8 | 1.3 | 1.3 | 9.4 | 7.8 |
| | | 6.0 | 2.0 | 1.5 | 7.1 | 6.8 |
| | | 6.2 | 1.3 | 0.9 | 5.3 | 6.5 |
| | | 6.5 | 1.1 | 1.0 | 7.1 | 6.8 |
| 20 mM Histidine | 75 mM NaCl, 125 mM Sucrose, 0.01% PS80 | 5.5 | 1.3 | 1.5 | 8.9 | 10.2 |
| | | 5.8 | 1.2 | 0.9 | 6.1 | 7.2 |
| | | 6.0 | 1.0 | 0.8 | 6.9 | 7.3 |
| | | 6.2 | 1.0 | 1.3 | 6.7 | 7.1 |
| | | 6.5 | 2.8 | 1.1 | 6.1 | 5.7 |

Non-reduced capillary gel electrophoresis was also performed to assess purity. SDS-CGE was evaluated using a Sciex PA800+ with UV detection at 220 nm. Samples were prepared by diluting 100 µg sample in Beckman SDS sample buffer and adding 5 µL of 250 mM iodoacetamide. Samples were heated at 70° C. for 10 minutes. Separation occurred over 20 minutes using normal polarity, 1 minute ramp, 15 kV voltage and 20 psi pressure. The capillary length was 30.2 cm, with the length to the detector as 10.2 cm. Starting material was used as a reference. A summary of the % HMW CE (NR) data is shown in Table 29. A summary of the % main peak CE (NR) data is shown in Table 30. A summary of the % LMW CE (NR) data is shown in Table 31.

TABLE 29

% HMW CE (NR)

| Buffer | Excipient/Surfactant | pH | 3-week incubation 2-8° C. 1 | 2 | 50° C. 1 | 2 |
|---|---|---|---|---|---|---|
| 20 mM Histidine | 250 mM Sorbitol, 0.01% PS80 | 5.5 | 1.2 | 1.3 | 1.4 | 2.0 |
| | | 5.8 | 1.3 | 1.1 | 2.0 | 1.1 |
| | | 6.0 | 1.1 | 0.8 | 2.1 | 1.8 |
| | | 6.2 | 1.0 | 1.1 | 2.3 | 1.8 |
| | | 6.5 | 0.9 | 1.0 | 2.6 | 2.3 |
| 20 mM Histidine | 250 mM Sucrose, 0.01% PS80 | 5.5 | 1.3 | 1.1 | 1.4 | 1.1 |
| | | 5.8 | 1.0 | 1.2 | 2.0 | 1.8 |
| | | 6.0 | 1.1 | 0.9 | 2.3 | 2.2 |
| | | 6.2 | 1.0 | 0.9 | 2.5 | 2.1 |
| | | 6.5 | 0.8 | 0.6 | 2.3 | 2.0 |
| 20 mM Histidine | 75 mM NaCl, 125 mM Sorbitol, 0.01% PS80 | 5.5 | 1.3 | 1.5 | 2.1 | 1.5 |
| | | 5.8 | 0.6 | 1.5 | 2.4 | 1.8 |
| | | 6.0 | 1.2 | 1.3 | 2.1 | 2.1 |
| | | 6.2 | 0.9 | 1.2 | 3.0 | 2.6 |
| | | 6.5 | 1.2 | 1.2 | 3.0 | 3.2 |
| 20 mM Histidine | 75 mM NaCl, 125 mM Sucrose, 0.01% PS80 | 5.5 | 1.4 | 1.3 | 2.3 | 1.6 |
| | | 5.8 | 1.0 | 1.2 | 2.5 | 2.4 |
| | | 6.0 | 1.1 | 1.0 | 2.7 | 2.2 |
| | | 6.2 | 1.0 | 1.4 | 2.7 | 2.3 |
| | | 6.5 | 1.1 | 1.1 | 2.7 | 2.8 |

TABLE 30

% Main Peak CE (NR)

| Buffer | Excipient/Surfactant | pH | 3-week incubation 2-8° C. 1 | 2 | 50° C. 1 | 2 |
|---|---|---|---|---|---|---|
| 20 mM Histidine | 250 mM Sorbitol, 0.01% PS80 | 5.5 | 96.1 | 95.9 | 87.7 | 87.6 |
| | | 5.8 | 95.8 | 95.9 | 90.0 | 90.6 |
| | | 6.0 | 95.9 | 96.1 | 88.3 | 90.4 |
| | | 6.2 | 95.9 | 96.0 | 88.3 | 90.8 |
| | | 6.5 | 95.7 | 95.6 | 89.4 | 88.1 |
| 20 mM Histidine | 250 mM Sucrose, 0.01% PS80 | 5.5 | 95.7 | 95.9 | 90.0 | 90.7 |
| | | 5.8 | 95.7 | 95.9 | 88.4 | 89.3 |
| | | 6.0 | 95.9 | 96.2 | 89.6 | 88.9 |
| | | 6.2 | 95.9 | 96.0 | 89.6 | 90.3 |
| | | 6.5 | 95.8 | 95.9 | 88.5 | 90.4 |
| 20 mM Histidine | 75 mM NaCl, 125 mM Sorbitol, 0.01% PS80 | 5.5 | 95.7 | 95.8 | 88.1 | 88.8 |
| | | 5.8 | 95.7 | 95.5 | 87.5 | 89.7 |
| | | 6.0 | 95.5 | 95.7 | 88.1 | 89.7 |
| | | 6.2 | 95.9 | 95.7 | 88.0 | 87.8 |
| | | 6.5 | 95.6 | 95.9 | 87.6 | 87.4 |
| 20 mM Histidine | 75 mM NaCl, 125 mM Sucrose, 0.01% PS80 | 5.5 | 95.3 | 95.7 | 87.9 | 88.6 |
| | | 5.8 | 95.8 | 95.8 | 88.9 | 87.5 |
| | | 6.0 | 95.8 | 95.7 | 87.7 | 89.6 |
| | | 6.2 | 95.7 | 95.3 | 89.0 | 89.9 |
| | | 6.5 | 95.4 | 95.5 | 87.9 | 88.3 |

TABLE 31

% LMW CE (NR)

| Buffer | Excipient/Surfactant | pH | 3-week incubation 2-8° C. 1 | 2 | 50° C. 1 | 2 |
|---|---|---|---|---|---|---|
| 20 mM Histidine | 250 mM Sorbitol, 0.01% PS80 | 5.5 | 2.7 | 2.8 | 10.9 | 10.5 |
| | | 5.8 | 2.9 | 3.1 | 7.9 | 8.2 |
| | | 6.0 | 3.1 | 3.1 | 9.6 | 7.8 |
| | | 6.2 | 3.1 | 3.3 | 9.4 | 7.3 |
| | | 6.5 | 3.4 | 3.4 | 7.9 | 9.5 |

TABLE 31-continued

% LMW CE (NR)

| Buffer | Excipient/ Surfactant | pH | 2-8° C. 1 | 2-8° C. 2 | 50° C. 1 | 50° C. 2 |
|---|---|---|---|---|---|---|
| 20 mM Histidine | 250 mM Sucrose, 0.01% PS80 | 5.5 | 2.9 | 2.9 | 8.6 | 8.2 |
| | | 5.8 | 3.3 | 2.9 | 9.5 | 8.9 |
| | | 6.0 | 2.9 | 3.0 | 8.1 | 8.9 |
| | | 6.2 | 3.1 | 3.1 | 7.9 | 7.6 |
| | | 6.5 | 3.5 | 3.5 | 9.3 | 7.6 |
| 20 mM Histidine | 75 mM NaCl, 125 mM Sorbitol, 0.01% PS80 | 5.5 | 3.0 | 2.8 | 9.8 | 9.7 |
| | | 5.8 | 3.7 | 3.0 | 10.1 | 8.5 |
| | | 6.0 | 3.3 | 3.0 | 9.8 | 8.2 |
| | | 6.2 | 3.3 | 3.1 | 9.0 | 9.6 |
| | | 6.5 | 3.3 | 2.8 | 9.3 | 9.4 |
| 20 mM Histidine | 75 mM NaCl, 125 mM Sucrose, 0.01% PS80 | 5.5 | 3.3 | 3.1 | 9.8 | 9.8 |
| | | 5.8 | 3.1 | 3.0 | 8.6 | 10.1 |
| | | 6.0 | 3.1 | 3.2 | 9.6 | 8.2 |
| | | 6.2 | 3.3 | 3.3 | 8.3 | 7.8 |
| | | 6.5 | 3.5 | 3.4 | 9.3 | 8.9 |

Figure 26A:
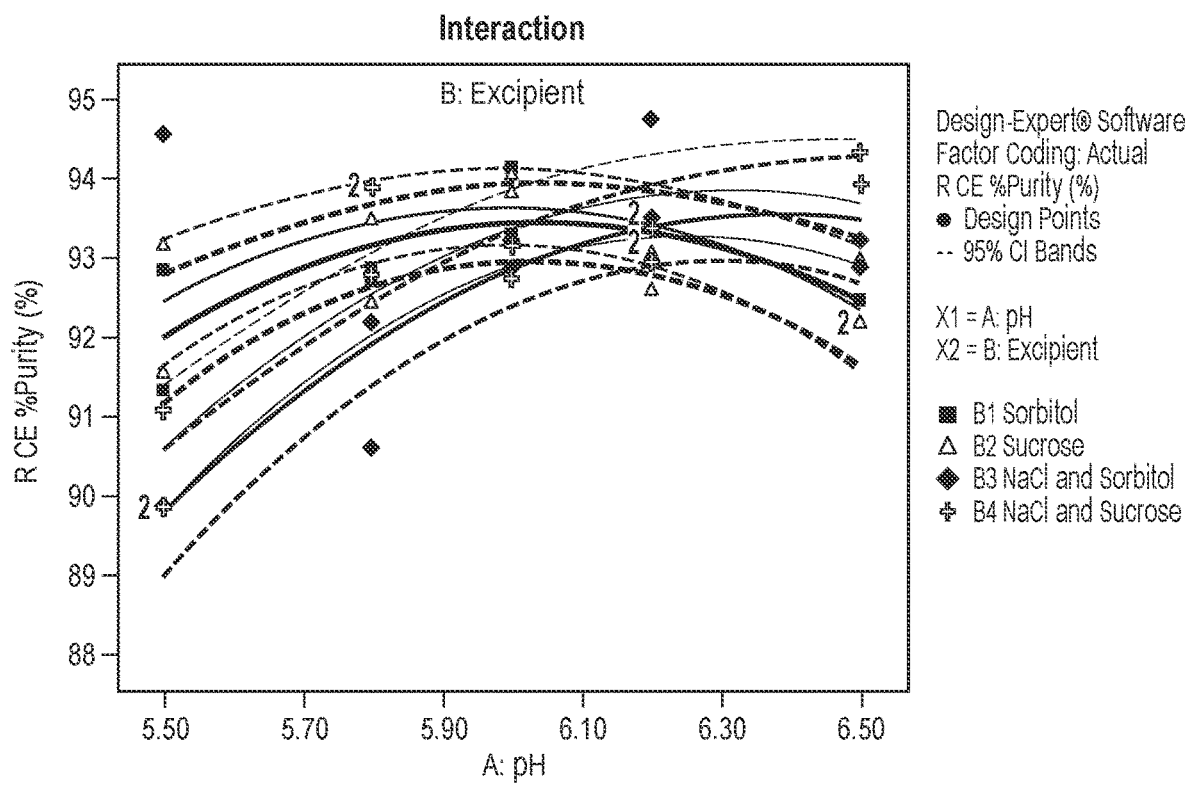
FIG. 26A is an interaction plot for % purity determined by Capillary Electrophoresis (CE) for a 3-week incubation at 50° C.
Figure 26B:
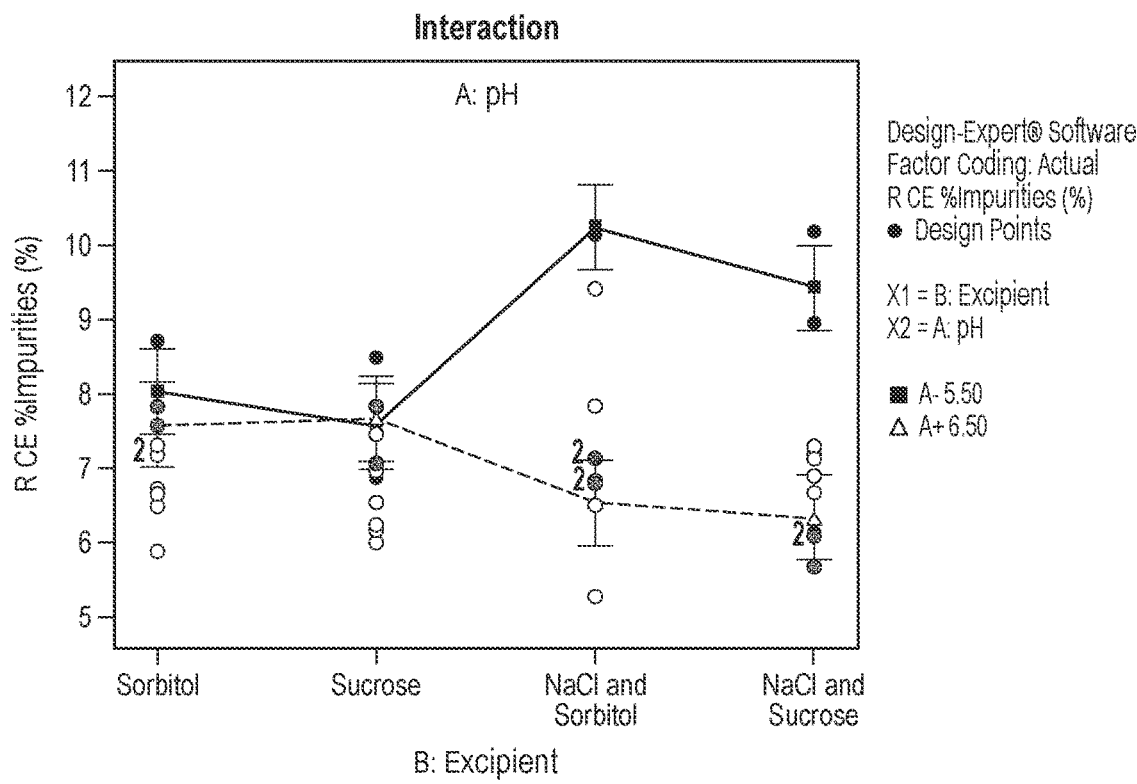
FIG. 26B is an interaction plot for % impurities determined by CE for a 3-week incubation at 50° C.

As evaluated by reduced CE, among the 3-week 50° C. samples, the % purity values for the sorbitol only and sucrose only formulations were maintained across the pH range (pH 5.5-6.5) (FIG. 26A), while the combination excipients displayed more variability regarding pH in that the % purity was reduced at lower pH values (5.5 versus 6.5) (FIG. 26B).

Figure 27A:
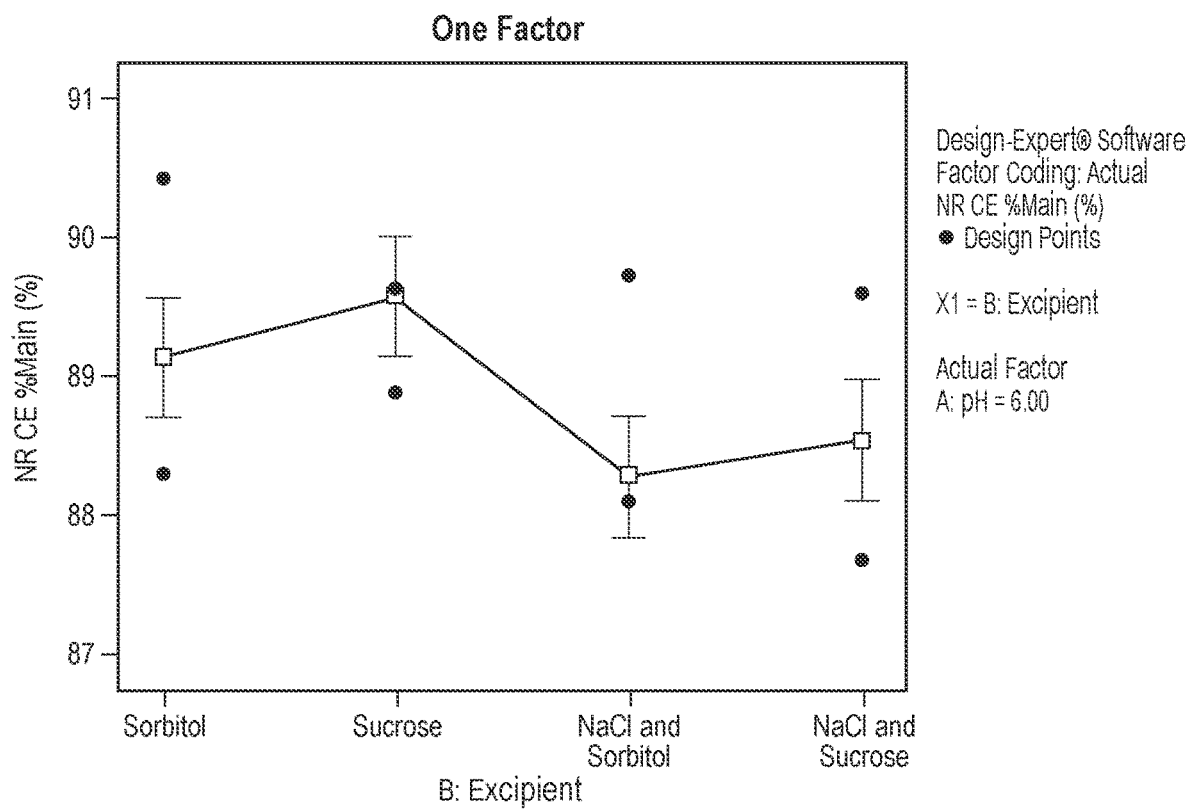
FIG. 27A is an interaction plot for % main species determined by Capillary Electrophoresis (Non-Reduced) (CE (NR)) for a 3-week incubation at 50° C. at pH 6.0.
Figure 28A:
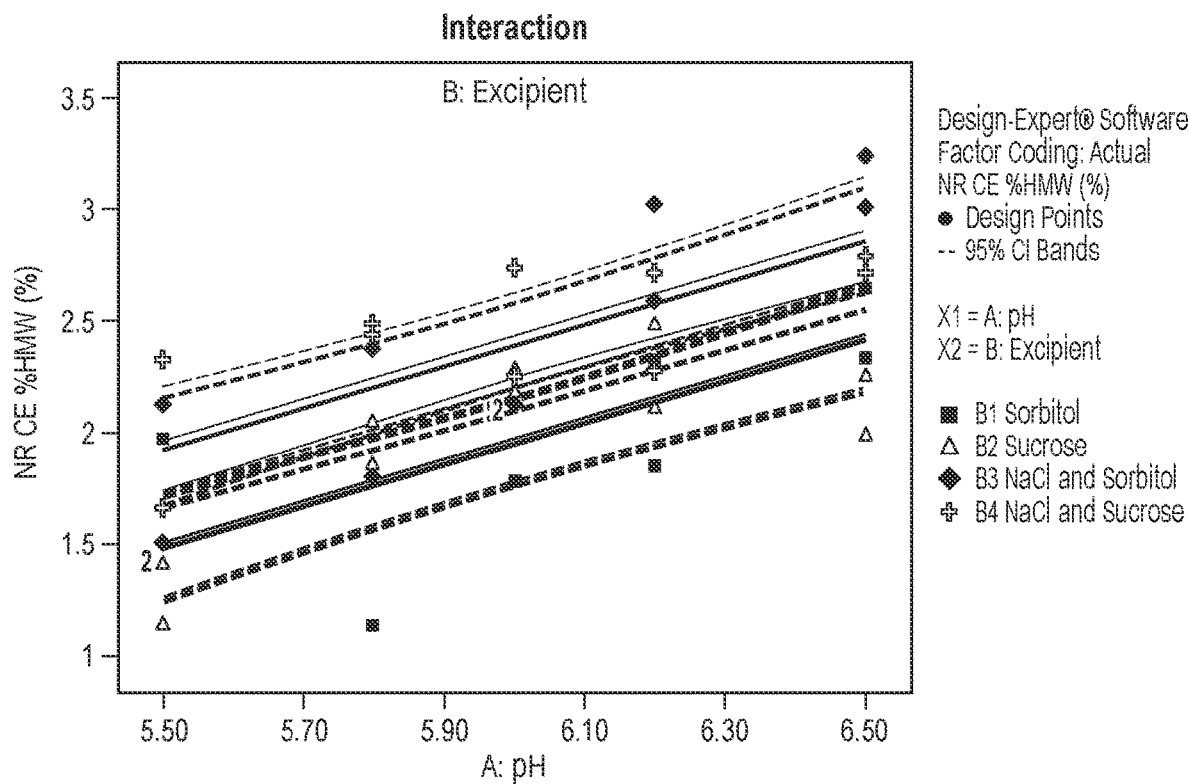
FIG. 28A is an interaction plot for % HMW species determined by CE (NR) for a 3-week incubation at 50° C.
Figure 28B:
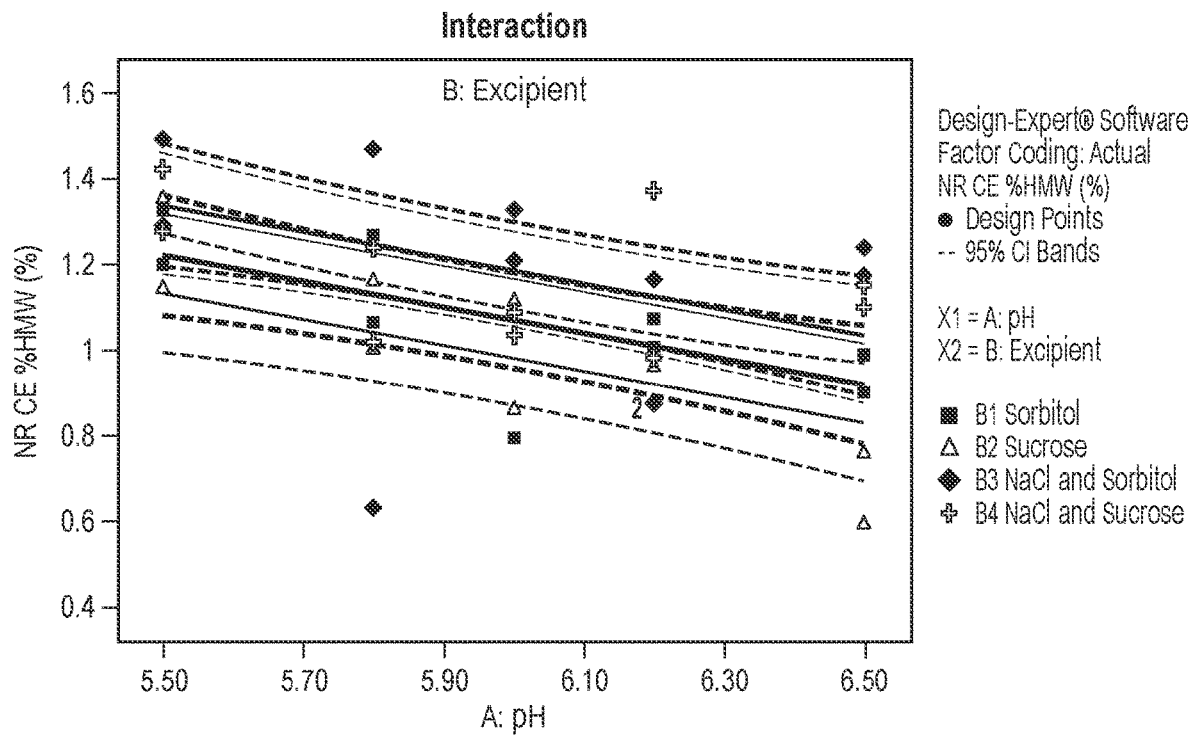
FIG. 28B shows the interaction plot for % HMW species determined by CE (NR) for a 3-week incubation at 2-8° C.
Figure 29A:
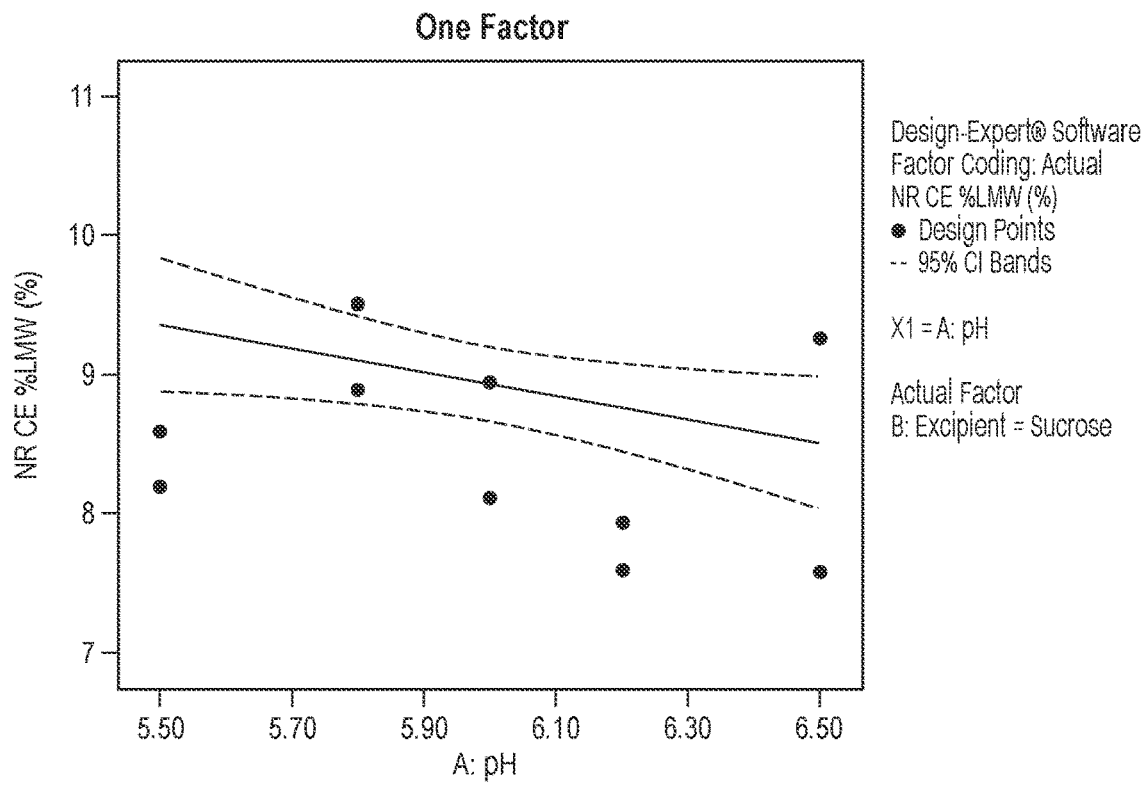
FIG. 29A is an interaction plot for % LMW species for sucrose only as determined by CE (NR) for a 3-week incubation at 50° C.
Figure 29B:
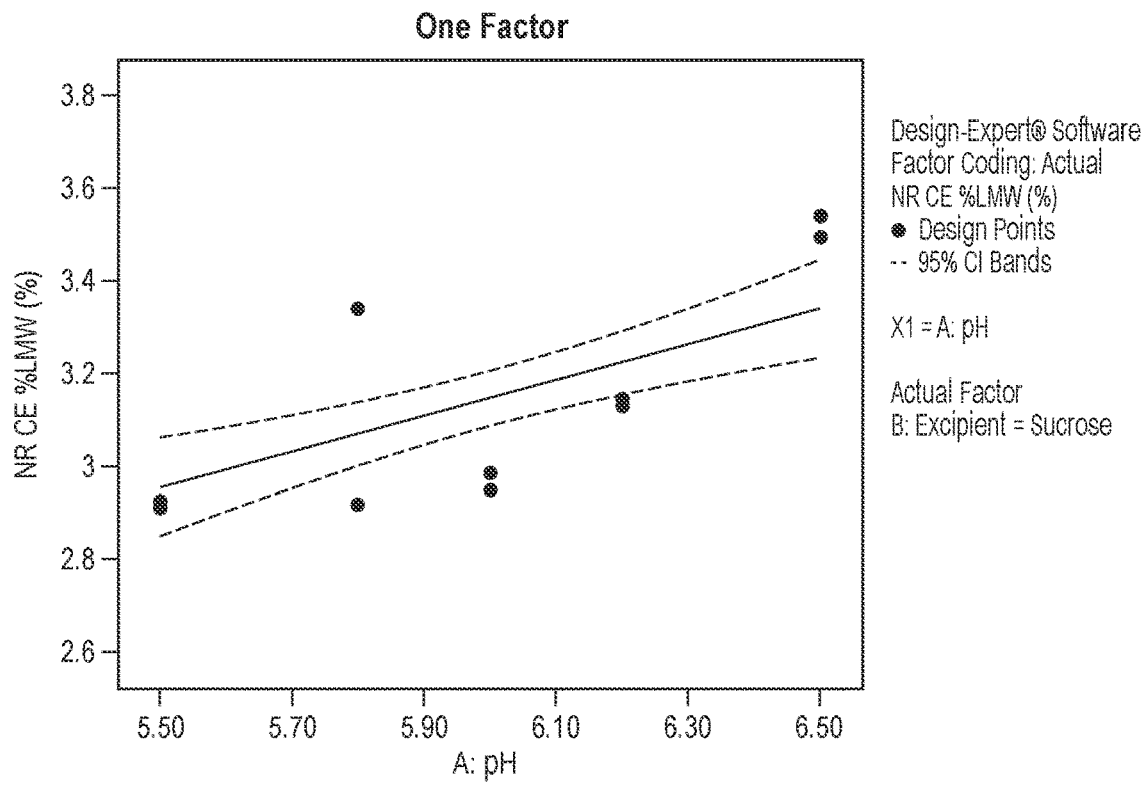
FIG. 29B is an interaction plot for % LMW species for sucrose only as determined by CE (NR) for a 3-week incubation at 2-8° C.

As evaluated by non-reduced CE, among the 3-week 50° C. samples, the formulations including sorbitol only or sucrose only had lower % HMW species relative to the combination excipients NaCl and sorbitol and NaCl and sucrose (FIG. 27A and FIG. 28A). The pH level did not have a significant effect on the % main peak values.

Figure 27B:
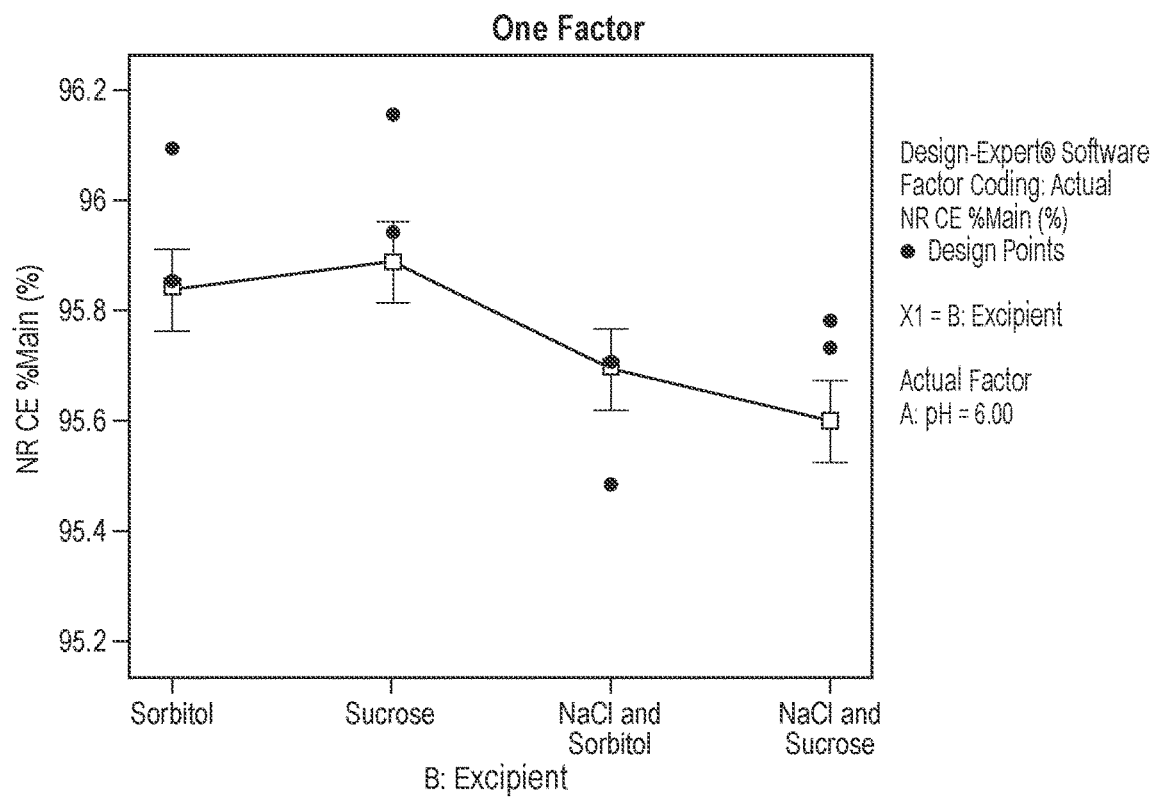
FIG. 27B is an interaction plot for % main species determined by CE (NR) for a 3-week incubation at 2-8° C. at pH 6.0.

As evaluated by reduced and non-reduced CE, there was not a significant model to fit the reduced CE data for the 3-week 2-8° C. samples, and for the non-reduced CE data the sorbitol and sucrose only formulations possessed greater % main peak species (FIG. 27B).

Statistical Analysis

Trends were analyzed using Design Expert v9 software. A summary of the analyses is shown in Table 32. Bolded models were not included in the final optimization assessment.

TABLE 32

Summary of Analysis Models

| Condition | Assay | Response | Model | Comments |
|---|---|---|---|---|
| 3 Weeks 50° C. | DLS | Z-Average | RCubic | |
| | | PDI | RLinear | excipient not significant |
| | | Monomer Size | Linear | |
| | | % Pd | No model chosen | |
| | SEC | % HMW | RCubic | |
| | | % Main | RCubic | |
| | | % LMW | Quadratic | |
| | icIEF | % Acidic | Cubic | |
| | | % Main | Quadratic | |
| | | % Basic | RCubic | |
| | CE (R & NR) | % Purity | Quadratic | |
| | | % Impurities | Quadratic | |
| | | % Main | RLinear | pH not significant |
| | | % HMW | Linear | |
| | | % LMW | RLinear | excipient not significant |
| 3 Weeks 2-8° C. | DLS | Z-Average | 2FI | |
| | | PDI | Linear | |
| | | Monomer Size | RLinear | pH not significant |
| | | % Pd | Linear | |
| | SEC | % HMW | RQuadratic | |
| | | % Main | Linear | |
| | | % LMW | RLinear | pH not significant |
| | icIEF | % Acidic | RLinear | excipient not significant |
| | | % Main | No model chosen | no significant model |
| | | % Basic | RLinear | excipient not significant |
| | CE (R & NR) | % Purity | No model chosen | no significant model |
| | | % Impurities | No model chosen | no significant model |
| | | % Main | RLinear | pH not significant |
| | | % HMW | Linear | |
| | | % LMW | RLinear | excipient not significant |

Excipient Selection

Performance of the formulations containing 250 mM sorbitol or 250 mM sucrose as the excipient was more desirable than the formulations containing a combination of sorbitol and NaCl or of sucrose and NaCl. Therefore, the optimal formulations for A49-F3'-TriNKET-Trastuzumab were determined to be 20 mM histidine, 250 mM sucrose or sorbitol, and 0.01% PS 80, at pH 6.0.

Example 2: High-Concentration Formulations of A49-F3'-TriNKET-Trastuzumab

The feasibility of a high-concentration A49-F3'-TriNKET-Trastuzumab formulation was assessed in two phases: an assessment of the solubility limit and short-term stability of the formulation.

To assess solubility, A49-F3'-TriNKET-Trastuzumab drug substance from the ultrafiltration/diafiltration (UF/DF) load was exchanged into a pH 6 buffer of 20 mM histidine and 250 mM sucrose, identical to a pharmaceutical formulation selected in Example 1 and used in the clinical study described in Example 3, but without polysorbate-80. The A49-F3'-TriNKET-Trastuzumab was then concentrated to approximately 233 mg/mL and held at both 5° C. and 25° C. with intermittent checks on the A49-F3'-TriNKET-Trastuzumab protein concentration. Table 33 shows the average concentrations of A49-F3'-TriNKET-Trastuzumab in each storage condition at all timepoints.

TABLE 33

Concentrations of A49-F3'-TriNKET-Trastuzumab in high-concentration formulations

| Sample name | Storage | Average concentration (mg/mL) |
| --- | --- | --- |
| GMP UF/DF load material | NA | 4.4 |
| Buffer exchanged material | NA | 5.4 |
| Concentrated material (measured neat) | T0 | 234 |
| | T = 24 h, 2-8° C. | 233 |
| | T = 48 h, 2-8° C. | 223 |
| | T = 5 days, 2-8° C. | 223 |
| | T = 24 h, 25° C. | 232 |
| | T = 48 h, 25° C. | 223 |
| | T = 5 days, 25° C. | 223 |

Figure 30:
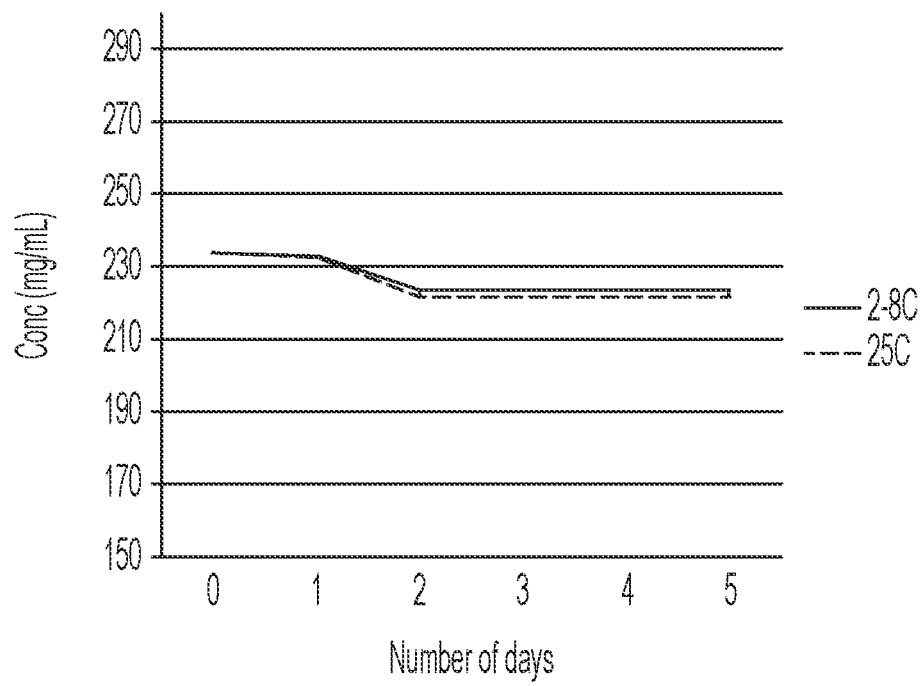
FIG. 30 is a graph of concentration curves of A49-F3'-TriNKET-Trastuzumab over time in formulations stored at 2-8° C. or 25° C.

The A49-F3'-TriNKET-Trastuzumab concentration settled to approximately 222-223 mg/mL after 48 hours at each condition and remained at 222-223 mg/mL after 120 hours (FIG. 30). This suggests that the solubility limit of A49-F3'-TriNKET-Trastuzumab in this formulation is approximately 222 mg/mL.

Figure 31A:
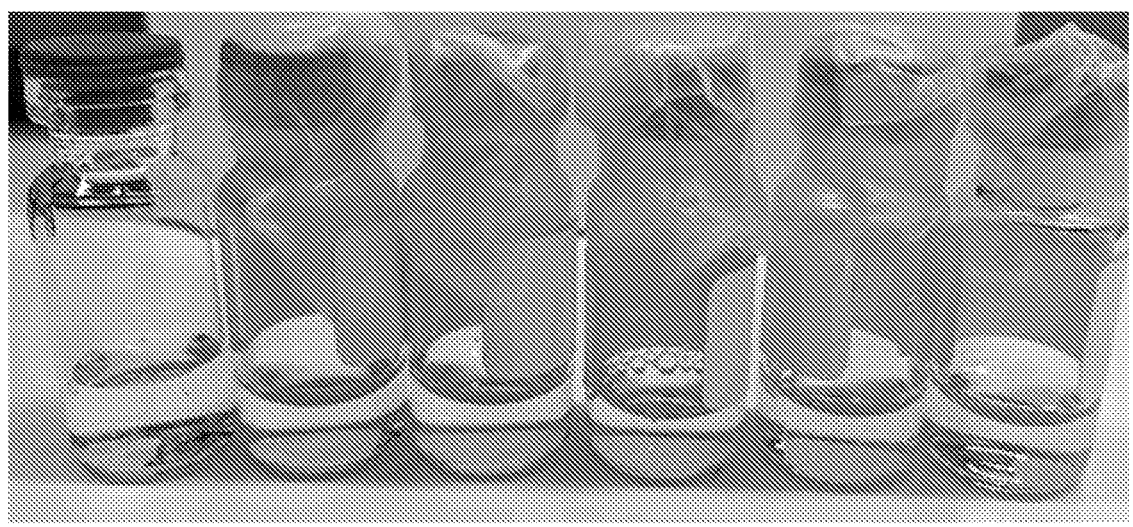
FIG. 31A is an image of vials containing formulations of A49-F3'-TriNKET-Trastuzumab in varying concentrations of polysorbate-80.
Figure 31B:
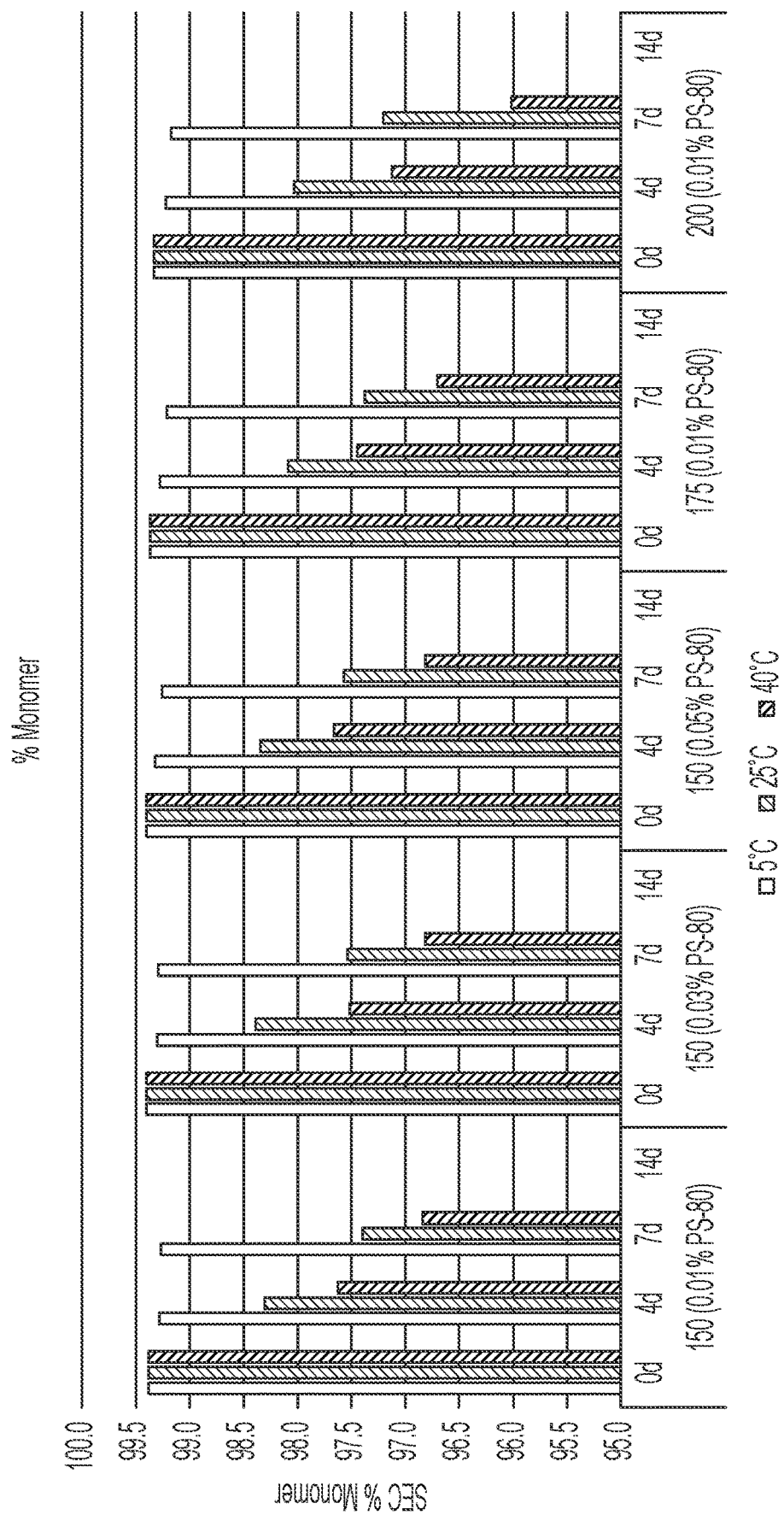
FIG. 31B is a graph of % Monomer species of A49-F3'-TriNKET-Trastuzumab in formulations stored at varying temperatures at specific time points as measured by size-exclusion high-performance liquid chromatography (SE-HPLC).

The short-term stability was assessed by preparing samples as described above to protein concentrations of 150 mg/mL, 175 mg/mL, and 200 mg/mL. The solution at each concentration was spiked with 0.01% (w/v) polysorbate-80, identical to a pharmaceutical formulation selected in Example 1 and used in the clinical study described in Example 3. Two additional solutions at the 150 mg/mL concentration were prepared with 0.3% (w/v) polysorbate-80 and 0.05% (w/v) polysorbate-80, respectively, to assess the impact of polysorbate-80 concentration on the stability of high concentration A49-F3'-TriNKET-Trastuzumab. Each condition was stored at 5° C., 25° C., and 40° C. and sampled weekly for limited product quality testing, consisting of appearance (FIG. 31A), A49-F3'-TriNKET-Trastuzumab concentration, and purity by size-exclusion high-performance liquid chromatography (SE-HPLC) (FIG. 31B). The results demonstrate that A49-F3'-TriNKET-Trastuzumab remains stable in these formulations at both 5° C. and 25° C. for two weeks.

Example 3: Treatment of Locally Advanced or Metastatic Solid Tumor with A49-F3'-TriNKET-Trastuzumab Objectives This clinical study is designed with two phases: a dose escalation phase and efficacy followed by an efficacy expansion cohorts phase. The primary objective of the dose escalation phase of the study is to assess the safety and tolerability of A49-F3'-TriNKET-Trastuzumab, and to determine the maximum tolerated dose of A49-F3'-TriNKET-Trastuzumab in patients with advanced (unresectable, recurrent or metastatic) solid tumors for whom no effective standard therapy exists or have recurrent or are intolerant of standard therapy(ies). The primary objective of the efficacy expansion cohorts phase of the study is to assess the overall response rate (ORR) according to the modified Response Evaluation Criteria in Solid Tumors version 1.1 (mRECIST 1.1).

The secondary objectives of this clinical study are:
- to characterize the pharmacokinetics of A49-F3'-TriNKET-Trastuzumab;
- to evaluate immunogenicity of A49-F3'-TriNKET-Trastuzumab and to correlate its immunogenicity to its exposure and clinical activity;
- to assess duration of response (DOR) of A49-F3'-TriNKET-Trastuzumab;
- to assess best overall response (BOR);
- to assess progression free survival (PFS) for A49-F3'-TriNKET-Trastuzumab;
- to assess overall survival (OS) time; and
- to assess the safety of A49-F3'-TriNKET-Trastuzumab in combination therapy with pembrolizumab.

Study Design

This study is a Phase I/II, open-label, dose escalation study with a consecutive parallel-group efficacy expansion study, designed to determine the safety, tolerability, pharmacokinetic(s) (PK), pharmacodynamic(s) (PD), and preliminary anti-tumor activity of A49-F3'-TriNKET-Trastuzumab alone and in combination with pembrolizumab. This study consists of two parts:

(1) Dose Escalation Part (Phase I) is divided into the following three phases:
 (A) accelerated titration;
 (B) "3+3" dose escalation; and
 (C) safety/pharmacokinetic(s) (PK)/pharmacodynamic(s) (PD) expansion cohorts (2) Efficacy Expansion Cohort Part (Phase II) is divided into the following four cohorts:
 (A) Urothelial bladder cancer (UBC)
 (B) Metastatic breast cancer (MBC)
 (C) Basket solid tumors with high HER2 expression (HER2 3+)
 (D) Combination therapy with pembrolizumab.

In one exemplary embodiment, patients enrolled in the dose escalation part and in the efficacy expansion part (the UBC, MBC, or Basket [HER2 3+] cohorts) receive A49-F3'-TriNKET-Trastuzumab as monotherapy intravenously as a 1-hour infusion in 4-week treatment cycles. For treatment cycle 1, patients receive A49-F3'-TriNKET-Trastuzumab at day 1, day 8, and day 15. For treatment cycle 2 and subsequent cycles, patients receive A49-F3'-TriNKET-Trastuzumab once every 2 weeks (e.g., day 1 and day 15)

until confirmed progression, unacceptable toxicity (as described in this example under section 'Dose-Limiting Toxicity (DLT)'), or any reason for withdrawal from the trial or investigational medicinal product (IMP) occurrence. Patients enrolled in the combination therapy with pembrolizumab cohort of the efficacy expansion cohorts part receive A49-F3'-TriNKET-Trastuzumab as a 1-hour IV infusion and pembrolizumab as a 30-minute IV infusion in 3-week treatment cycles. In one exemplary embodiment, 200 mg of pembrolizumab is administered per its label with A49-F3'-TriNKET-Trastuzumab.

For treatment cycle 1, patients receive A49-F3'-TriNKET-Trastuzumab and pembrolizumab at day 1, and A49-F3'-TriNKET-Trastuzumab alone at day 8. For treatment cycle 2 and subsequent cycles, patients receive A49-F3'-TriNKET-Trastuzumab and pembrolizumab once every 3 weeks on day 1 of every cycle until confirmed progression, unacceptable toxicity (as described in this example under section 'Dose-Limiting Toxicity (DLT')), or any reason for withdrawal from the trial or IMP occurrence.

Patients who experience a confirmed complete response (CR) receive treatment for a maximum of 12 months after confirmation, at the discretion of the investigator. Treatment beyond 12 months is permissible if the patient will benefit from continued treatment.

Figure 32A:
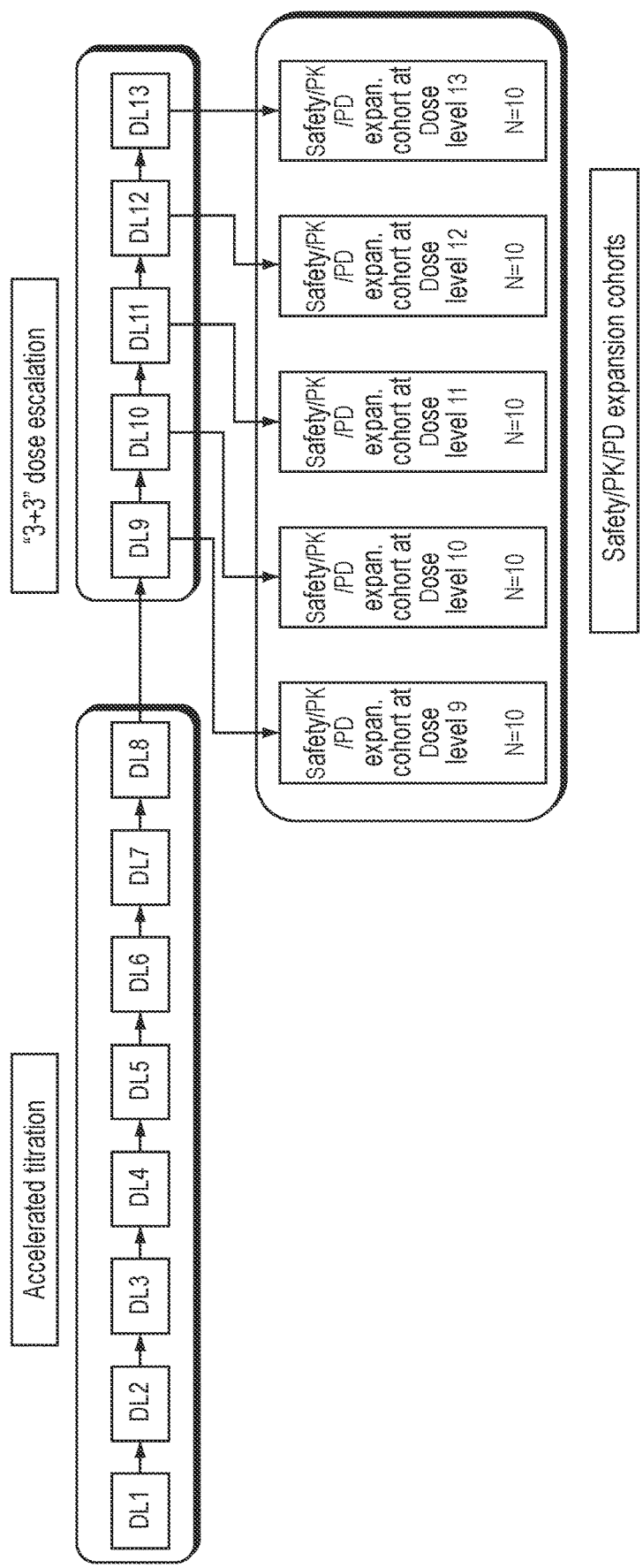
FIGS. 32A-32B is a schematic diagram of a clinical trial design.
Figure 32B:
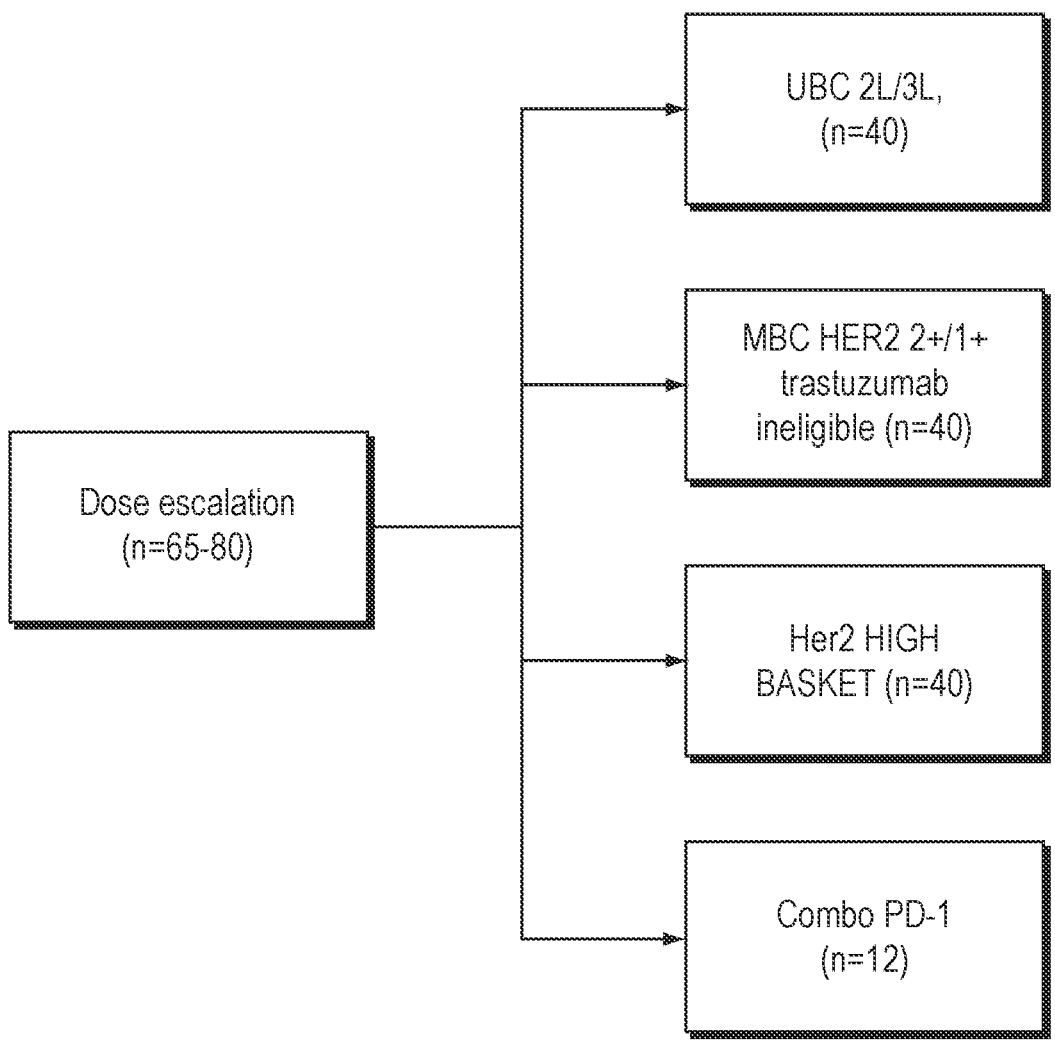

FIG. 32A and FIG. 32B are schematic diagrams of the clinical trial design. FIG. 32A describes the trial design for dose escalation phase. FIG. 32B describes the trial design for efficacy expansion cohorts phase.

Inclusion Criteria

The general inclusion criteria for patients enrolled in any of the cohorts in the clinical study of this example include:
  signed written informed consent;
  ≥18 years in age (including male and female patients);
  histologically or cytologically proven locally advanced or metastatic solid tumors, for which no standard therapy exists, or standard therapy has failed;
  primary tumor must have documented HER2 expression by immunohistochemistry;
  ECOG performance status of 0 or 1 at study entry and an estimated life expectancy of at least 3 months;
  baseline left ventricular ejection fraction (LVEF)≥55% as measured by echocardiography (preferred) or multigated acquisition (MUGA) scan;
  adequate hematological function defined by white blood cell (WBC) count ≥3×10$^9$/L with absolute neutrophil count (ANC)≥1.5×10$^9$/L, lymphocyte count ≥0.5×10$^9$/L, platelet count ≥75×10$^9$/L, and hemoglobin ≥9 g/dL (may have been transfused);
  adequate hepatic function defined by a total bilirubin level ≤1.5×the upper limit of normal (ULN), an aspartate aminotransferase (AST) level ≤2.5×ULN, and an alanine aminotransferase (ALT) level ≤2.5× ULN or, for patients with documented metastatic disease to the liver, AST and ALT levels ≤5×ULN;
  adequate renal function defined by an estimated creatinine clearance ≥50 mL/min according to the Cockcroft-Gault formula; and
  effective contraception for women of child bearing potential (WOCBP) patients as defined by WHO guidelines for 1 "highly effective" method or 2 "effective" methods.

The additional inclusion criteria for patients enrolled in the accelerated titration or "3+3" dose escalation phase of the dose escalation part described in this example include:
  evidence of objective disease, but a measurable lesion is not required; and
  availability of an archived tumor biopsy (≤6 months old, at least 8 slides) or fresh biopsy obtained within the screening window (at least 10 slides and 3 cores).

The additional inclusion criteria for patients enrolled in the safety/PK/PD expansion cohorts phase of the dose escalation part described in this example include:
  a fresh tumor biopsy obtained during the screening window to have Formalin Fixed Paraffin Embedded (FFPE) paraffin block or enough unstained slides to perform IHC (at least 3 slides unstained) with at least 12 slides overall and with at least 3 fresh cores; and
  HER2 by IHC of at least 1+ at screening.

The additional inclusion criteria for patients enrolled in the UBC expansion cohort described in this example include:
  histologically or cytologically documented locally advanced or metastatic transitional cell carcinoma of the urothelium (including renal pelvis, ureters, urinary urothelial, urethra);
  radiographic disease progression after the subject's last line of therapy;
  treatment with one (and no more than one) platinum-containing regimen (e.g., platinum plus another agent such as gemcitabine, methotrexate, vinblastine, doxorubicin, etc.) for inoperable locally advanced or metastatic urothelial carcinoma with radiographic progression or recurrence within 6 months after the last administration of a platinum-containing regimen as an adjuvant, which would be considered failure of a first-line, platinum-containing regimen;
  treatment with a checkpoint inhibitor (i.e., anti-PD-1 or anti-PD-L1), with radiographic progression (optionally treatment with a combination of platinum-based therapy with PD-1/PD-L1-based therapy);
  HER2 expression of at least 1+ by IHC; and
  availability of a fresh tumor biopsy obtained during the screening window to have Formalin Fixed Paraffin Embedded (FFPE) paraffin block or enough unstained slides to perform IHC (at least 3 slides unstained) with at least 12 slides overall and with at least 3 fresh cores.

The additional inclusion criteria for patients enrolled in the MBC expansion cohort described in this example include:
  histologically confirmed MBC;
  no more than 3 prior lines of cytotoxic therapy for metastatic disease;
  previous treatment with taxane and an anthracycline unless anthracycline is contraindicated;
  tumor scoring 1+ or 2+ by IHC, and if scoring is 2+, the existence of tumor amplification of ERRB2 must be ruled by an FDA approved method;
  radiographic progression after the last line of systemic therapy; and
  availability of a fresh tumor biopsy obtained during the screening window to have Formalin Fixed Paraffin Embedded (FFPE) paraffin block or enough unstained slides to perform IHC (at least 3 slides unstained) with at least 12 slides overall and with at least 3 fresh cores.

The additional inclusion criteria for patients enrolled in the basket (HER2 3+) cohort described in this example include:
  any solid tumor except breast cancer or gastric cancer and a history of ERBB2 amplification within the tumor and one of the following 1) HER2 3+ scoring by IHC documented in the most recent biopsy within 6 months, post radiographic progression on the last line of therapy or 2) HER 3+ scoring by IHC during the screening window;

treatment with at least one line of an approved or established therapy; and availability of a fresh tumor biopsy obtained during the screening window to have Formalin Fixed Paraffin Embedded (FFPE) paraffin block or enough unstained slides to perform IHC (at least 3 slides unstained) with at least 12 slides overall and with at least 3 fresh cores.

The additional inclusion criteria for patients enrolled in the combination therapy with pembrolizumab cohort phase of the efficacy expansion part described in this example include:

eligibility to receive pembrolizumab per its label for a malignancy of epithelial origin; and availability of a fresh tumor biopsy obtained during the screening window to have Formalin Fixed Paraffin Embedded (FFPE) paraffin block or enough unstained slides to perform IHC (at least 3 slides unstained) with at least 12 slides overall and with at least 3 fresh cores.

Exclusion Criteria

The exclusion criteria for patients enrolled in the clinical study of this example include:

Concurrent treatment with a non-permitted drug including:

immunotherapy, immunosuppressive drugs (including chemotherapy or systemic corticosteroids except for short term treatment of allergic reactions or for the treatment of irAEs), or other experimental pharmaceutical products;

Exceptions:
short term administration of systemic steroid (e.g., for allergic reactions or the management of irAEs);
steroids with no or minimal systemic effect (topical, inhalation);

TKIs targeting HER2, or any recombinant molecule targeting HER2 or NKG2D;

Growth factors (granulocyte colony stimulating factor or granulocyte macrophage colony stimulating factor);

Exception:
erythropoietin and erythropoietin analogs may be prescribed; or

Bisphosphonate or denosumab treatment;
Exception: bisphosphonate or denosumab unless it has been initiated more than 14 days prior to receiving the first administration of A49-F3'-TriNKET-Trastuzumab.

Previous treatment with drugs that specifically target the HER2 pathway.
Exception: mAb or tyrosine kinase inhibitor (TKI) providing a washout period (4 weeks for mAbs or protein therapeutics and 2 weeks for a TKI).

Concurrent anticancer treatment (e.g., cytoreductive therapy, radiotherapy (with the exception of palliative bone directed radiotherapy), immune therapy, or cytokine therapy except for erythropoietin), major surgery (excluding prior diagnostic biopsy), concurrent systemic therapy with steroids or other immunosuppressive agents, or use of any investigational drug within 28 days before the start of study treatment.
Exceptions:
short-term administration of systemic steroids (e.g., for allergic reactions or the management of irAEs); or bisphosphonates provided that treatment was initiated at least 14 days before the first dose of A49-F3'-TriNKET-Trastuzumab.

Previous malignant disease other than the target malignancy to be investigated in this study within the last 3 years, with the exception of basal or squamous cell carcinoma of the skin or cervical carcinoma in situ.

Rapidly progressive disease.

Active or history of central nervous system (CNS) metastases.

Receipt of any organ transplantation including autologous or allogeneic stem-cell transplantation.

Significant acute or chronic infections (including historic positive test for human immunodeficiency virus (HIV), or active or latent hepatitis B or active hepatitis C tested during the screening window).

Preexisting autoimmune disease (except for patients with vitiligo) needing treatment with systemic immunosuppressive agents for more than 28 days within the last 3 years or clinically relevant immunodeficiencies (e.g., dys-gammaglobulinemia or congenital immunodeficiencies), or fever within 7 days of day 1.

Known severe hypersensitivity reactions to mAbs (≥Grade 3 NCI-CTCAE v5.0), any history of anaphylaxis, or uncontrolled asthma (e.g., 3 or more features of partly controlled asthma).

Persisting toxicity related to prior therapy >Grade 1 NCI-CTCAE v5.0, however alopecia and sensory neuropathy ≤Grade 2 is acceptable.

Pregnancy or lactation in females during the study.

Known alcohol or drug abuse.

Serious cardiac illness or medical conditions including but not limited to:
History of New York Heart Association class III or IV heart failure or systolic dysfunction (LVEF <55%);
High-risk uncontrolled arrhythmias i.e., tachycardia with a heart rate >100/min at rest;
Significant ventricular arrhythmia (ventricular tachycardia) or higher-grade AV-block (second degree AV-block Type 2 (Mobitz 2) or third-degree AV-block);
Angina pectoris requiring anti-anginal medication;
Clinically significant valvular heart disease;
Evidence of transmural infarction on ECG;
Poorly controlled hypertension (defined by: systolic >180 mm Hg or diastolic >100 mm Hg); and
Clinically relevant uncontrolled cardiac risk factors, clinically relevant pulmonary disease or any clinically relevant medical condition in the opinion of the Investigator that may limit participation in this study.

All other significant diseases (e.g., inflammatory bowel disease), which, in the opinion of the Investigator, might impair the patient's ability to participate.

Any psychiatric condition that would prohibit the understanding or rendering of informed consent.

Legal incapacity or limited legal capacity.

Incapability of giving signed informed consent, which includes compliance with the requirements and restrictions listed in the informed consent form (ICF) and in this protocol.

Dose-Limiting Toxicity (DLT)

At each cohort, safety and tolerability is assessed. Dose-limiting toxicity (DLT) is evaluated in the first 21 days for the patients enrolled in the dose escalation part and in the pembrolizumab combination cohort. A DLT is a ≥grade 3 adverse drug reaction according to the National Cancer Institute-Common Terminology Criteria for Adverse Events (NCI-CTCAE) v5.0, occurring in the DLT evaluation period of the dose escalation cohorts. Adverse drug reactions may be adverse events suspected to be related to A49-F3'-TriNKET-Trastuzumab by the investigator and/or sponsor. DLT is defined as any of the following occurring within the first 21 days of treatment for the patients enrolled in the dose escalation part and in the pembrolizumab combination cohort:

Any grade 3 to 4 non-hematological toxicity except:
   i. grade 3 nausea, vomiting, and diarrhea lasting <72 hours in the absence of maximal medical therapy;
   ii. grade 4 vomiting and diarrhea lasting <72 hours in the absence of maximal medical therapy;
   iii. grade 3 fatigue <5 days;
   iv. grade 3 hypertension in the absence of maximal medical therapy.

Any of the following hematological toxicities:
   i. grade 4 neutropenia >5 days;
   ii. grade 3 thrombocytopenia with hemorrhage;
   iii. grade 4 thrombocytopenia.
Exception for single laboratory values out of normal range that are unlikely related to study treatment according to the Investigator, do not have any clinical correlate, and resolve to ≤Grade 1 within 7 days with adequate medical management.

The observation period for DLTs may include the first 3 weeks of investigational medicinal product treatment in the dose escalation part for all dose cohorts for all patients with data used for implementing the dose-escalation algorithm for determination of the maximum tolerated dose (MTD). Additional patients may be enrolled in the dose escalation phase and may have adverse events collected; optionally, these patients may not have a specific DLT observation period. Safety monitoring committee may adopt a conservative approach in ascribing the relevance of the treatment related-toxicity to drug. A treatment-related serious adverse event is ascribed as related to drug except where a clear relationship to the underlying disease or recognized co-morbidities is evident.

Safety is assessed through the recording, reporting, and analysis of baseline medical conditions, adverse events (AEs), physical examination findings, including vital signs and determination of left ventricular ejection fraction, electrocardiogram, and laboratory tests.

Dosage and Administration
A49-F3'-TriNKET-Trastuzumab Dose Escalation
A dose level is assigned to each patient at trial entry. The dose levels are adapted for weight changes as needed. The decision to escalate to the next dose level is based on safety assessments after all patients of a cohort have reached day 21 (DLT evaluation period). In certain embodiments, patients receive IV infusion of A49-F3'-TriNKET-Trastuzumab over 1 hour (e.g., 50 to 70 minutes) once every two weeks. Dosage of A49-F3'-TriNKET-Trastuzumab is calculated based on the weight of the patient as determined on the day prior to or the day of each drug administration. In an exemplary embodiment, the starting dose of A49-F3'-TriNKET-Trastuzumab is $5.2 \times 10^{-5}$ mg/kg and the first 8 dose levels (DLs) follow an accelerated design of dose escalation and consist of single patient cohorts with escalation steps of no greater than 3.3-fold. In the event a DLT is observed, the dose escalation is switched to a "3+3" design with accrual of 5 additional patients at the dose level where the DLT is observed.

Similar to the accelerated titration phase, dose escalation will proceed with no greater than a 3.3-fold increase between dose levels in the "3+3" escalation phase. Table 34 outlines the starting dose according to body weight (mg/kg) and dose levels (DL) of the escalation scheme.

TABLE 34

Exemplary DLs (in mg/kg body weight) in "accelerated titration" and "3 + 3" dose escalation phase.

| "accelerated titration" | | | | | | | |
|---|---|---|---|---|---|---|---|
| DL1 | DL2 | DL3 | DL4 | DL5 | DL6 | DL7 | DL8 |
| $5.2 \times 10^{-5}$ | $1.6 \times 10^{-4}$ | $5.2 \times 10^{-4}$ | $1.6 \times 10^{-3}$ | $5.2 \times 10^{-3}$ | $1.6 \times 10^{-2}$ | $5.2 \times 10^{-2}$ | $1.6 \times 10^{-1}$ |

| "3 + 3" dose escalation | | | | |
|---|---|---|---|---|
| DL9 | DL10 | DL11 | DL12 | DL13 |
| 0.52 | 1.6 | 5.2 | 10 | 20 |

In an exemplary embodiment, three patients are initially enrolled into a given dose cohort during the "3+3" phase. After the first patient is enrolled, the second is enrolled no sooner than 2 days after the second injection of A49-F3'-TriNKET-Trastuzumab to the first patient. The first administration of A49-F3'-TriNKET-Trastuzumab is given to the third patient after at least 48 hours of follow-up after the administration of A49-F3'-TriNKET-Trastuzumab to the second patient. More than 3 patients may be enrolled at a particular dose cohort (e.g., in the event of a DLT observed in the first 3 patients of a particular cohort, or after 3 patients have been enrolled at DL 7) without any pre-defined interval between treatment start, unless an infusion reaction or a cytokine release syndrome, or any Grade 3 or higher treatment related toxicity is observed during the treatment of the first 3 patients. In such an instance, the same pre-defined intervals for the first 3 patients are repeated. In the event, no DLT is observed in any of these patients, the study proceeds to enroll 3 additional patients into the next higher dose cohort. If 1 patient develops a DLT at a specific dose, an additional 3 patients are enrolled into that same dose cohort. Development of DLTs in more than 1 of 6 patients in a specific dose cohort suggests that the MTD has been exceeded, and further dose escalation is not pursued (see Dose-Limiting Toxicity (DLT) section in this example).

In an exemplary embodiment, once the safety of the DL 10 (1.6 mg/kg) is established by the safety monitoring committee, up to 10 additional patients (for a total of up to 16 patients per DL) are treated at DL9 in order to increase the safety, PK, and PD database at that DL, while accrual will carry on at DL 11 following the "3+3" rules. A similar process is applied for DLs 10 to 13. Accrual in the Safety/

PK/PD Expansion Cohorts phase continue to proceed without a pre-defined observation period. Mandatory tumor biopsies are performed at screening (within 30 days before 1st investigational medicinal product) and within 1 to 7 days prior to 6th investigational medicinal product dose. The safety information is generated during the treatment of these patients and is communicated to the safety monitoring committee. The same process is implemented for the subsequent DLs of the Safety/PK/PD expansion cohorts.

Efficacy Expansion Cohorts Dosage

As mentioned previously in this example, there are 4 efficacy expansion cohorts: UBC; MBC; basket (HER2 3+) cohort with patients with HER2 high expressing solid tumors who have received at least 1 first-line treatment consisting of an established or an approved therapy; and combination therapy with pembrolizumab. The accrual in these cohorts is initiated as follows:

3 monotherapy cohorts are initiated after dose determination and schedule of A49-F3'-TriNKET-Trastuzumab in the first three cohorts (UBC, MBC, and basket (HER2 3+).

Once the safety of DL11 is established, the accrual of the safety run-in for the combination of A49-F3'-TriNKET-Trastuzumab with pembrolizumab is initiated. The doses of A49-F3'-TriNKET-Trastuzumab to be combined with pembrolizumab are declared safe during the "3+3" dose escalation with A49-F3'-TriNKET-Trastuzumab as a monotherapy, before testing in combination with pembrolizumab.

In the first three efficacy expansion cohorts, patients receive A49-F3'-TriNKET-Trastuzumab as monotherapy. Up to 40 patients may be enrolled in each of these three expansion cohorts, with a futility analysis occurring after the first 20 patients in each cohort have been observed for at least 3 months. Mandatory tumor biopsies are performed at screening (within 30 days before $1^{st}$ investigational medicinal product) and within 1 to 7 days prior to the $6^{th}$ investigational medicinal product dose.

In the combination therapy with pembrolizumab efficacy expansion cohort, patients receive A49-F3'-TriNKET-Trastuzumab at DL 10 (as a 1-hour IV infusion) and pembrolizumab at the approved dose of 200 mg (as a 30-minute IV infusion), in 3-week treatment cycles. This safety run-in exercise follows with the same "3+3" design described before. The patients in this study meet the inclusion criteria of patients described in the 'Inclusion Criteria' section.

Safety During Efficacy Expansion Cohorts (A49-F3'-TriNKET-Trastuzumab Monotherapy Cohorts)

All safety information from participating patients is monitored on an ongoing basis by the safety monitoring committee. In an exemplary embodiment, a group of 20 patients are enrolled and followed up for 4 weeks. Subsequently, such safety review occurs within 4 weeks after 40 patients are treated and followed up for at least 4 weeks. Then, a similar process is implemented each time 40 patients are enrolled and followed up for at least 4 weeks.

Safety During Efficacy Expansion Cohort (A49-F3'-TriNKET-Trastuzumab Combination Therapy with Pembrolizumab Cohort)

All safety information from participating patients is monitored on an ongoing basis similar to as described for the "3+3" Dose Escalation part. For each patient, safety and tolerability data is reviewed for the 21-day DLT evaluation period, and progression to further dose administrations determined. A group of 20 patients are enrolled and followed up for 3 weeks if combination treatment is safe to proceed.

Endpoints

The study is designed to evaluate primary and secondary endpoints to assess clinical benefits of A49-F3'-TriNKET-Trastuzumab, optionally in combination with pembrolizumab as treatment for patients with locally advanced or metastatic solid tumors.

Primary Endpoints and Analysis of Primary Endpoints

Occurrence of DLTs during the first three weeks of treatment is measured as a primary endpoint in the dose escalation part. Maximum tolerated dose (MTD) is determined during the dose escalation part and is defined as the highest dose level (DL) at which no more than 1 patient out of 6 patients treated experiences a DLT event. Maximum tolerated dose is determined through the individual patient data from the dose escalation part. Additionally, for the final statistical analysis, the following may be analyzed:

at each dose level, the number and proportion of patients in the DLT population who experience a DLT during the first DLT evaluation period;

at each dose level, the number and proportion of treatment-emergent adverse events experienced by patients in the DLT population during the first DLT evaluation period.

A confirmed overall response rate per mRECIST 1.1, as adjudicated by an independent endpoint review committee (IERC) is measured as a primary endpoint for the efficacy expansion cohorts. Overall response rate is defined as the best response obtained among all tumor assessment visits after start of trial treatment until documented disease progression, taking into account the following requirements for confirmation. For complete response and partial response, confirmation of the response according to mRECIST 1.1 is required. Confirmation may be evaluated at the regularly scheduled 6-week assessment interval, but no sooner than 4 weeks after the initial documentation of complete response or partial response. Confirmation of partial response may be confirmed at an assessment later than the next assessment after the initial documentation of partial response.

A best overall response of stable disease may require that an overall response of stable disease is determined at a timepoint at least 37 days after start of study treatment. The response at each scheduled tumor assessment and the best overall response is listed for each patient.

Secondary Endpoints and Analysis of Secondary Endpoints

Secondary endpoints for the study may include the following:

number, severity, and duration of treatment-emergent adverse events for all dose groups/indications according to the NCI-CTCAE v5.0;

number, severity, and duration of treatment related adverse events according to NCI-CTCAE v5.0;

duration of response according to mRECIST 1.1;

pharmacokinetics profile;

best overall response according to mRECIST 1.1;

progression free survival according to mRECIST 1.1;

overall survival time;

progressive disease profile;

serum titers of anti-A49-F3'-TriNKET-Trastuzumab antibodies;

expression of HER2 on tumor tissue;

ERBB2 status (amplified/non-amplified, mutated/non-mutated);

unconfirmed response at Week 13 according to mRECIST 1.1 (for Safety/PK/PD expansion cohorts); and progression free survival time, according to mRECIST 1.1, per IERC; duration of response according to mRECIST 1.1, per IERC (for the efficacy expansion cohorts).

Efficacy Parameters

The primary efficacy parameter in the expansion part is the best overall response according to mRECIST 1.1. The ORR will be determined according to mRECIST 1. The overall response rate is evaluated over the whole trial period. For a best overall response of partial response or complete response, confirmation of the response according to mRECIST 1.1 is required. The response at each scheduled tumor assessment and the best overall response is listed for each patient. The number and proportion of overall response rate (defined as complete response+ partial response) is tabulated by cohort. For the HER2 high basket cohort, the number and proportion of overall response rate is tabulated for each tumor type for which there are more than 5 patients enrolled and treated for 4 weeks. Tumor types represented by fewer than 5 patients (from 1 patient to 4 patient) is represented as one sub-group. Duration of response, according to mRECIST 1.1, is calculated for each patient with a confirmed response in the expansion cohorts and is analyzed using the Kaplan-Meier method in all cohorts. Progression free survival time and overall survival time is presented in patient listings and analyzed using the Kaplan-Meier method in the full analysis set of the expansion cohorts that enrolled the full planned number of patients.

Pharmacokinetic Profile

Serum concentrations of A49-F3'-TriNKET-Trastuzumab is determined by a validated method. The following PK parameters are estimated and reported:

AUC0→t: Area under the concentration-time curve from the time of dosing to the time of the last observation (calculated by linear trapezoidal summation);

AUC0→∞: Area under the curve from the time of dosing extrapolated to infinity (calculated by the linear trapezoidal summation and extrapolated to infinity using Clast/λz);

λz: Terminal elimination rate constant. The value of λz is determined from the slope of the regression line of log (concentration) vs. time with the following constraints: (i) there must be at least 3 consecutive measurable concentrations, (ii) all concentrations must be declining with time, and (iii) the correlation coefficient (r) of regression must be ≥0.95;

Cmax: Maximum serum concentration observed post-dose;

tmax: Time at which the Cmax occurs; and t½: Elimination half-life, determined as 0.693/λz.

The PK parameters are summarized using descriptive statistics. Individual as well as mean concentration-time plots are depicted. Unresolved missing data may be imputed when the analysis integrity is affected. The conservative principle is used for data imputation.

Serum titers of anti-drug antibodies: The safety immunogenicity testing strategy is implemented and conducted in line with:

Immunogenicity Assessment of Biotechnology-Derived Therapeutic Proteins (see Guideline on Immunogenicity Assessment of Therapeutic Proteins. 18 May 2017 EMEA/CHMP/BMWP/14327/2006 Rev 1 Committee for Medicinal Products for Human Use (CHMP); European Medicines Agency);

Immunogenicity assessment of mAbs intended for in vivo clinical use (see Guideline on Immunogenicity Assessment of Monoclonal Antibodies Intended for In Vivo Clinical Use. 24 May 2012 EMA/CHMP/BMWP/86289/2010 Committee for Medicinal Products for Human Use (CHMP); European Medicines Agency);

FDA (2009, draft) Guidance for Industry: Assay Development for Immunogenicity Testing of Therapeutic Proteins.

A qualified method that uses an acid dissociation step to detect anti-drug (i.e., anti-A49-F3'-TriNKET-Trastuzumab) antibodies in the presence of excess drug in human serum is applied. Removal of drug after acid treatment is not required. ADA titers of positive samples is determined.

Biomarkers

Summary statistics for biomarkers are provided for all preplanned timepoints, separately for each DL or cohort. Changes to baseline levels are presented as applicable. Profiles over time are displayed on a per patient basis.

Safety Analyses

The extent of exposure to A49-F3'-TriNKET-Trastuzumab is characterized by duration (weeks), number of administrations, cumulative dose (mg/kg), dose intensity (mg/kg/week), relative dose intensity (actual dose given/planned dose), number of dose reductions, and number of dose delays. Safety analyses are performed on the safety population. The safety endpoints are tabulated by DL and cohort, using descriptive statistics. Safety assessments are based on review of the incidence of adverse events including adverse events of special interest, adverse drug reactions, and changes in vital signs, electrocardiograms, body weight, and laboratory values (hematology and serum chemistry). The on-treatment period is defined as the time from the first dose of study treatment to the last dose of study treatment+30 days, or the earliest date of new anticancer therapy−1 day, whichever occurs first.

Adverse Events (AEs)

Adverse events are coded according to Medical Dictionary for Regulatory Activities (MedDRA). Severity of AEs is graded using the NCI-CTCAE v5.0 toxicity grading scale. Treatment-emergent adverse events (TEAEs) are those AEs with onset dates during the on-treatment period, or if the worsening of an event is during the on-treatment period. The incidence of TEAEs regardless of attribution and AEs defined as possibly related to A49-F3'-TriNKET-Trastuzumab are summarized by preferred term and system organ class and described in terms of intensity and relationship to A49-F3'-TriNKET-Trastuzumab. All premature/permanent discontinuations are summarized by primary reason for study withdrawal. Duration TEAEs is defined as the time between onset and resolution to baseline. Duration of Grade 3 and 4 is defined by the time period during which a particular TEAE reaches a Grade 3 or 4 severity during its course. Descriptive statistics are examined for indications of dose-related ADRs.

Laboratory Variables

Laboratory results are classified by Grade according to NCI-CTCAE. The worst on-trial Grades after the first trial treatment are summarized. Shifts in toxicity grading from first treatment to highest grade are displayed. Results for variables that are not part of NCI-CTCAE are presented as below, within, or above normal limits. Only patients with post-baseline laboratory values are included in these analyses.

PE (Including Vital Signs, 12-Lead Electrocardiograms, and Transthoracic Echocardiography (TT-ECHO)/MUGA)

PE data, including vital signs (body temperature, respiratory rate, heart rate, and blood pressure) and 12-lead ECG are recorded.

Example 4: Treatment of Locally Advanced or Metastatic Solid Tumor with A49-F3'-TriNKET-Trastuzumab Objectives Similarly to the study described in Example 3, this clinical study is designed with two phases: a dose escalation phase and efficacy followed by an efficacy expansion cohorts phase. The primary objective of the dose escalation phase of the study is to assess the safety and tolerability of A49-F3'-TriNKET-Trastuzumab, and to determine the maximum tolerated dose of A49-F3'-TriNKET-Trastuzumab in patients with advanced (unresectable, recurrent or metastatic) solid tumors for whom no effective standard therapy exists or have recurrent or are intolerant of standard therapy(ies). The primary objective of the efficacy expansion cohorts phase of the study is to assess the overall response rate (ORR) according to the Response Evaluation Criteria in Solid Tumors version 1.1 (RECIST 1.1).

The secondary objectives of this clinical study are:
- to characterize the pharmacokinetics of A49-F3'-TriNKET-Trastuzumab;
- to evaluate immunogenicity of A49-F3'-TriNKET-Trastuzumab and to correlate its immunogenicity to its exposure and clinical activity;
- to assess duration of response (DOR) of A49-F3'-TriNKET-Trastuzumab;
- to assess best overall response (BOR);
- to assess progression free survival (PFS) for A49-F3'-TriNKET-Trastuzumab;
- to assess overall survival (OS) time; and
- to assess the safety of A49-F3'-TriNKET-Trastuzumab in combination therapy with pembrolizumab, nivolumab, or nab-paclitaxel.

Study Design

This study is a Phase I/II, open-label, dose escalation study with a consecutive parallel-group efficacy expansion study, designed to determine the safety, tolerability, pharmacokinetic(s) (PK), pharmacodynamic(s) (PD), and preliminary anti-tumor activity of A49-F3'-TriNKET-Trastuzumab alone and in combination with pembrolizumab, nivolumab, or nab-paclitaxel. This study consists of two parts:

(1) Dose Escalation Part (Phase I) is divided into the following three phases:
  (A) accelerated titration;
  (B) "3+3" dose escalation with A49-F3'-TriNKET-Trastuzumab administered as a monotherapy, or as a combination therapy (e.g., with nivolumab, or nab-paclitaxel); and
  (C) safety/pharmacokinetic(s) (PK)/pharmacodynamic(s) (PD) expansion cohorts with A49-F3'-TriNKET-Trastuzumab administered as a monotherapy, or as a combination therapy (e.g., with nivolumab, or nab-paclitaxel), and (2) Efficacy Expansion Cohort Part (Phase II) is divided into the following five cohorts:
  (A) HER2 high gastric cancer (in combination with nivolumab);
  (B) HER2 high esophageal cancer (in combination with nivolumab);
  (C) Urothelial bladder cancer (UBC) expressing HER2;
  (D) Metastatic triple negative breast cancer (TNBC) in combination with nab-paclitaxel; and
  (E) Basket solid tumors with high HER2 expression (HER2 3+).

Combination with Nivolumab

For DL1 through DL11, A49-F3'-TriNKET-Trastuzumab is administered as an intravenous infusion up to 2 hours but no less than 1 hour for all infusions. Starting at DL12 and higher, patients receiving nivolumab combination treatment are administered A49-F3'-TriNKET-Trastuzumab (as an intravenous infusion over a period of at least 3 hours and up to 4 hours on days 1, 8, and 15 of C1 and up to 2 hours but no less than 1 hour for all subsequent infusions) and nivolumab at 480 mg (as a 30-minute intravenous infusion), in 4-week treatment cycles.

Combination with Nab-Paclitaxel

For DL1 through DL11, F3'-TriNKET-Trastuzumab is administered as an intravenous infusion of up to 2 hours but no less than 1 hour for all infusions. Starting at DL12 and higher, patients in the combination with nab-paclitaxel cohort are administered F3'-TriNKET-Trastuzumab (as an intravenous infusion over a period of at least 3 hours and up to 4 hours on days 1, 8, and 15 of C1 and up to 2 hours but no less than 1 hour for all subsequent infusions) and nab-paclitaxel at a dose of 100 mg/m$^2$ (as a 30-minute intravenous infusion), in 4-week treatment cycles.

Inclusion Criteria

Patients in the dose escalation phase ("accelerated titration" and "3+3" dose escalation parts) have the following inclusion criteria.

Histologically or cytologically proven locally advanced or metastatic solid tumors, for which no standard therapy exists, or standard therapy has failed. HER2 expression by immunohistochemistry and/or erbb2 amplification and/or erbb2 activating mutations must be documented on either archival tissue or fresh tumor biopsy.

Patients in the nivolumab "3+3" cohort have the following inclusion criteria.

Patients are eligible to receive nivolumab per its label for a malignancy of epithelial origin or have a tumor that does not have a standard therapy or standard therapy has failed.

Patients have received an anti PD-1 or an anti PD-L1 as a previous line of therapy; or has not received anti PD-1 or anti-PD-L1 as a previous line of therapy and has experienced a Grade 3 or 4 drug related toxicity, or a Grade 2 drug related toxicity related to prior checkpoint therapy impacting the lungs or the neurological system related to the prior anti-PD-1 or anti PD-L1 therapy.

Patients in the nab-paclitaxel "3+3" cohort have the following inclusion criteria.

Patients are eligible for treatment with nab-paclitaxel per its label, which includes metastatic breast cancer, after failure of combination chemotherapy for metastatic disease or relapse within 6 months of adjuvant chemotherapy. In this case, additional inclusion criteria also includes no exposure to taxanes in the last 6 months.

OR

Patients have a tumor that does not have a standard therapy or standard therapy has failed. In this case, patients should also not have been treated with a taxane over the last 6 months.

OR

Patients have a first line advanced (unresectable/recurrent/metastatic) TNBC.

Patients in the safety/PK/PD expansion part (dose escalation phase) have the following inclusion criteria.

Histologically or cytologically proven locally advanced or metastatic solid tumors, for which no standard therapy exists, or standard therapy has failed. A patient tumor must have documented HER2 expression by immunohistochemistry using a CLIA accredited (or equivalent) method.

Disease must be measurable with at least 1 unidimensional measurable lesion by RECIST 1.1.

Availability of a screening biopsy obtained from relapsed metastatic or locally advanced disease (if applicable), obtained within the screening window. Tumor tissue from bone metastases is not evaluable for PD-L1 expression and is not acceptable.

HER2 levels measured by immunohistochemistry of at least 1+ at screening (archival tissue is acceptable to determine HER2 status).

Patients in the nivolumab expansion cohort additionally have the following inclusion criteria.

Patients are eligible to receive nivolumab per its label for a malignancy of epithelial origin.

OR

There is no standard therapy for the patient, or standard therapy has failed.

A grade 3 or 4 drug related toxicity during the treatment with the anti PE-1 or anti PD-L1.

A grade 2 drug related toxicity related to prior checkpoint therapy that impacted either the lungs or the neurological system.

Patients in the nab-paclitaxel expansion cohort have the following inclusion criteria.

Patients are eligible for treatment with nab-paclitaxel per its label, which includes metastatic breast cancer, after failure of combination chemotherapy for metastatic disease or relapse within 6 months of adjuvant chemotherapy. In this case, additional inclusion criteria also includes no exposure to taxanes in the last 6 months.

OR

Patients have a tumor that does not have a standard therapy or standard therapy has failed. In this case, patients should also not have been treated with a taxane over the last 6 months.

OR

Patients have a first line advanced (unresectable/recurrent/metastatic) TNBC.

Patients in the UBC efficacy expansion cohort have the following inclusion criteria.

Histologically or cytologically documented locally advanced or metastatic transitional cell carcinoma of the urothelium (including renal pelvis, ureters, urinary bladder, urethra).

Patients have radiographic disease progression after their last line of therapy.

Patients have received one (and no more than one) platinum-containing regimen (e.g., platinum plus another agent such as gemcitabine, methotrexate, vinblastine, doxorubicin) for inoperable locally advanced or metastatic urothelial carcinoma with radiographic progression or with recurrence within 6 months after the last administration of a platinum-containing regimen as an adjuvant, which would be considered failure of a first-line, platinum-containing regimen. Combination of a platinum-based therapy with PD-1/PD-L1-based therapy may be acceptable.

Patients have at least 1+ expression of HER2 by IHC (a CLIA-accredited [or equivalent] test), using the assessment guidelines set forth for gastric cancer.

Availability of a screening biopsy obtained from relapsed metastatic or locally advanced disease (if applicable), obtained within the screening window. Tumor tissue from bone metastases is not evaluable for PD-L1 expression and is not acceptable.

Patients in the TNBC efficacy expansion cohort have the following inclusion criteria.

A tumor with a PD-L1 score (CPS) less than 10 as measured by immunohistochemistry, for example, using Agilent/Dako's PD-L1 IHC 22C3 pharmDx assay.

Histologically documented (metastatic or locally advanced) TNBC, including a HER2 status making the subject ineligible for trastuzumab as defined per the American College of Physicians (ACP) guidelines or equivalent, negative ER expression, and negative PR expression.

Lack of HER2 amplification as determined by in situ hybridization (ratio of HER2 to CEP17<2.0 or single probe average HER2 gene copy number <4 signals/cell), or HER2 expression level 0, 1+, or 2+ as measured by immunohistochemistry.

ER and PR negativity are defined as <1% of cells expressing hormonal receptors via immunohistochemistry analysis.

Availability of a screening biopsy obtained from relapsed metastatic or locally advanced disease (if applicable), obtained within the screening window. Tumor tissue from bone metastases is not evaluable for PD-L1 expression and is not acceptable.

No prior chemotherapy or targeted systemic therapy for inoperable locally advanced or metastatic TNBC.

Radiation therapy or endocrine therapy for metastatic disease is permitted. There is no required minimum washout period for these therapies. Patients should be recovered from the effects of radiation.

Prior chemotherapy (including taxanes) in the neoadjuvant or adjuvant setting is allowable if treatment was completed ≥12 months prior to enrollment.

Disease must be measurable with at least 1 unidimensional measurable lesion by RECIST 1.1

Patients in the gastric cancer cohort have the following inclusion criteria.

Advanced (unresectable/recurrent/metastatic) gastric cancer or cancer of the gastro-esophageal junction per the 7th AJCC classification.

Patients have a tumor has been declared HER2 positive (meaning, eligible for treatment with trastuzumab) per the ACP guidelines.

Patients have received a first line of therapy that included a platinum salt and a fluoropyridine in combination with trastuzumab or a biosimilar to trastuzumab.

Patients have progressed after the first line therapy.

Patients have received only one line of therapy for the treatment of metastatic disease.

Disease is measurable with at least 1 unidimensional measurable lesion by RECIST 1.1.

Availability of a screening biopsy obtained from relapsed metastatic or locally advanced disease (if applicable), obtained within the screening window. Tumor tissue from bone metastases is not evaluable for PD-L1 expression and is not acceptable.

Patient has a tumor not known to be microsatellite instability (MSI) high at the moment of the inclusion (patients whose tumor is discovered to be MSI high during the study will stay on study and that information will be captured in the statistical analysis plan).

Patients in the adenocarcinoma of the esophagus cohort have the following inclusion criteria.

Patients have advanced (unresectable/recurrent/metastatic) esophageal cancer per the 7th AJCC classification.

Patient have a tumor have been declared HER2 positive (meaning, eligible for treatment with trastuzumab) per the ACP guidelines.

Patients have received a first line of therapy that included a platinum salt and a fluoropyridine in combination with trastuzumab or a biosimilar to trastuzumab; the first line treatment should not have included an anti PD-1.

Patients have progressed after the first line therapy.

Patients have received only one line of therapy for the treatment of metastatic disease.

Disease is measurable with at least 1 unidimensional measurable lesion by RECIST 1.1.

Availability of a screening biopsy obtained from relapsed metastatic or locally advanced disease (if applicable), obtained within the screening window. Tumor tissue from bone metastases is not evaluable for PD-L1 expression and is not acceptable.

Patients have a tumor not known to be microsatellite instability (MSI) high at the moment of the inclusion (patients whose tumor is discovered to be MSI high during the study will stay on study and that information will be captured in the statistical analysis plan).

Patients in the HER2 3+ solid tumors efficacy expansion cohort have the following inclusion criteria.

Disease is measurable with at least 1 unidimensional measurable lesion by RECIST 1.1.

Patients have any solid tumor (except breast cancer or gastric cancer) and history of erbb2 amplification on tumor and one of the following: 1) HER2 3+ by IHC documented in the most recent biopsy within 6 months, post radiographic progression on the last line; or 2) HER 3+ by IHC during the screening window.

Patients have received at least one approved or established line of therapy.

Availability of a screening biopsy obtained from relapsed metastatic or locally advanced disease (if applicable), obtained within the screening window. Tumor tissue from bone metastases is not evaluable for PD-L1 expression and is not acceptable.

Patients have a tumor not known to be microsatellite instability (MSI) high at the moment of the inclusion (patients whose tumor is discovered to be MSI high during the study will stay on study and that information will be captured in the statistical analysis plan).

Exclusion Criteria

The exclusion criteria for patients enrolled in the clinical study of this example include:

Concurrent treatment with a non-permitted drug as in Non-Permitted Medicines and Therapies section. Previous treatment with drugs that specifically target the HER2 pathway (mAb or Tyrosine Kinase Inhibitor [TKI]) is acceptable providing washout period (4 weeks for mAbs or protein therapeutics and 2 weeks for a TKI).

Concurrent anticancer treatment (e.g., cytoreductive therapy, radiotherapy [with the exception of palliative bone directed radiotherapy], immune therapy, or cytokine therapy except for erythropoietin), major surgery (excluding prior diagnostic biopsy), concurrent systemic therapy with steroids or other immunosuppressive agents, or use of any investigational drug within 28 days before the start of study treatment. Short-term administration of systemic steroids (for allergic reactions or the management of irAEs) is allowed. Note: Patients receiving bisphosphonates or denosumab are eligible provided treatment was initiated at least 14 days before the first dose of F3'-TriNKET-Trastuzumab.

Previous malignant disease other than the target malignancy to be investigated in this study within the last 3 years, with the exception of basal or squamous cell carcinoma of the skin, low-grade prostate cancer (Gleason score 6 or less), or cervical carcinoma in situ.

Life expectancy of less than 3 months.

Patients with brain metastases are excluded unless all of the following criteria are met:
  a. CNS lesions are asymptomatic and previously treated
  b. Patient does not require ongoing steroid treatment daily for replacement for adrenal insufficiency (except oral steroids at a dose less than ≤10 mg prednisone [or equivalent])
  c. Imaging demonstrates stability of disease 28 days from last treatment for CNS metastases Receipt of any organ transplantation including autologous or allogeneic stem-cell transplantation.

Significant acute or chronic infections (including historic positive test for human immunodeficiency virus [HIV], or active or latent hepatitis B or active hepatitis C tested during the screening window).

Preexisting autoimmune disease (except for patients with vitiligo) needing treatment with systemic immunosuppressive agents for more than 28 days within the last 3 years or clinically relevant immunodeficiencies (e.g., dys-gammaglobulinemia or congenital immunodeficiencies), or fever Grade 2 or higher within 7 days of day 1. Patients with a history of autoimmune-related hypothyroidism on a stable dose of thyroid replacement hormone may be eligible for this study. Patients with controlled Type 1 diabetes mellitus on a stable insulin regimen may be eligible for this study.

Known severe hypersensitivity reactions to mAbs (≥Grade 3 NCI-CTCAE v5.0), any history of anaphylaxis, or uncontrolled asthma (i.e., 3 or more features of partly controlled asthma).

Persisting toxicity related to prior therapy ≥Grade 1 NCI-CTCAE v5.0, however alopecia, endocrinopathies ≤Grade 2, and sensory neuropathy ≤Grade 2 is acceptable.

Pregnancy or lactation in females during the study.

Known alcohol or drug abuse.

Serious cardiac illness or medical conditions including but not limited to:
  a. History of New York Heart Association class III or IV heart failure or systolic dysfunction (LVEF <55%).
  b. High-risk uncontrolled arrhythmias i.e., tachycardia with a heart rate >100/min at rest.
  c. Significant ventricular arrhythmia (ventricular tachycardia) or higher-grade AV-block (second degree AV-block Type 2 [Mobitz 2] or third-degree AV-block).
  d. Angina pectoris requiring anti-anginal medication.
  e. Clinically significant valvular heart disease.
  f. Evidence of transmural infarction on ECG.
  g. Poorly controlled hypertension (defined by: systolic >180 mm Hg or diastolic >100 mm Hg).

h. Clinically relevant uncontrolled cardiac risk factors, clinically relevant pulmonary disease or any clinically relevant medical condition that may limit participation in this study.

Severe dyspnea at rest due to complications of advanced malignancy or requiring supplementary oxygen therapy.

All other significant diseases (e.g., inflammatory bowel disease), which might impair the patient's ability to participate.

Any psychiatric condition that would prohibit the understanding or rendering of informed consent.

Legal incapacity or limited legal capacity.

Incapability of giving signed informed consent, which includes compliance with the requirements and restrictions listed in the informed consent form (ICF) and in this protocol.

Dose Limiting Toxicities

Dose-limiting toxicities are as previously described in Example 3.

Dosage and Administration

Phase II—Efficacy Expansion Cohorts

Two cohorts are administered F3'-TriNKET-Trastuzumab as a monotherapy:
UBC expressing HER2; and
Basket (HER2 3+) patients with HER2 high expressing solid tumors who have received at least 1 first-line treatment consisting of an established or an approved therapy.

Two cohorts are administered F3'-TriNKET-Trastuzumab as a combination therapy with nivolumab:
gastric cancer HER2 high; and
esophageal cancer HER2 high.

One cohort is administered F3'-TriNKET-Trastuzumab as a combination therapy with nab-paclitaxel:
patients with advanced (locally recurrent/unresectable/metastatic) TNBC.

In one exemplary embodiment, patients are administered with an initial eight doses of A49-F3'-TriNKET-Trastuzumab following an accelerated dose escalation with escalation steps no greater than 3.3-fold. Table 35 outlines the starting dose according to body weight (mg/kg) and dose levels (DL) of the escalation scheme.

diphenhydramine, and a corticosteroid (e.g., methylprednisolone). On C1D8 onwards, prophylactic premedication will include acetaminophen and diphenhydramine only.

Nivolumab

Nivolumab is used at the approved dose of 480 mg (as per its label) in the Combination Therapy with Nivolumab Cohort of the Dose Escalation Part (Phase I) of the study.

Nivolumab is administered on day 1 of each 28 day cycle, as described in its label.

In the combination therapy with nivolumab cohort, dose escalation will proceed beginning with A49-F3'-TriNKET-Trastuzumab at DL10 and nivolumab at 480 mg (as a 30-minute intravenous infusion), in 4-week treatment cycles. Nivolumab will be administered before the administration of A49-F3'-TriNKET-Trastuzumab.

Nab-Paclitaxel.

Administration in the nab-paclitaxel cohort will proceed beginning with A49-F3'-TriNKET-Trastuzumab at DL10 and nab-paclitaxel at a dose of 100 mg/m$^2$ (as a 30-minute intravenous infusion), each at day 1, day 8, and day 15 (per its label) of Cycle 1.

In subsequent cycles, A49-F3'-TriNKET-Trastuzumab will be administered on days 1 and day 15 and nab-paclitaxel on days 1, day 8 and day 15.

Nab-paclitaxel will be administered prior to the administration of A49-F3'-TriNKET-Trastuzumab.

Endpoints

The study is designed to evaluate primary and secondary endpoints to assess clinical benefits of A49-F3'-TriNKET-Trastuzumab, optionally in combination with nivolumab or nab-paclitaxel b as treatment for patients with locally advanced or metastatic solid tumors.

Primary Endpoints and Analysis of Primary Endpoints

Occurrence of DLTs during the first three weeks of treatment is measured as a primary endpoint in the dose escalation part.

A confirmed overall response rate per RECIST 1.1, as adjudicated by an independent endpoint review committee (IERC) is measured as a primary endpoint for the efficacy expansion cohorts.

Secondary Endpoints and Analysis of Secondary Endpoints

Secondary endpoints for the study may include the following:

TABLE 35

Exemplary DLs (in mg/kg body weight) in "accelerated titration" escalation phase.
"accelerated titration"

| DL1 | DL2 | DL3 | DL4 | DL5 | DL6 | DL7 | DL8 |
|---|---|---|---|---|---|---|---|
| $5.2 \times 10^{-5}$ | $1.6 \times 10^{-4}$ | $5.2 \times 10^{-4}$ | $1.6 \times 10^{-3}$ | $5.2 \times 10^{-3}$ | $1.6 \times 10^{-2}$ | $5.2 \times 10^{-2}$ | $1.6 \times 10^{-1}$ |

In an exemplary "3+3" dose escalation part, the next six dose levels are described in Table 36.

TABLE 36

Exemplary DLs (in mg/kg body weight) in
"3 + 3" dose escalation phase.

"3 + 3" dose escalation

| DL9 | DL10 | DL11 | DL12 | DL13 | DL14 |
|---|---|---|---|---|---|
| 0.52 | 1.6 | 5.2 | 10 | 15 | 20 |

On cycle 1, day 1 (C1D1), a subject is administered prophylactic premedication including acetaminophen, number, severity, and duration of treatment-emergent adverse events for all dose groups/indications according to the NCI-CTCAE v5.0;
number, severity, and duration of treatment related adverse events according to NCI-CTCAE v5.0;
duration of response according to RECIST 1.1;
pharmacokinetics profile;
best overall response according to RECIST 1.1;
progression free survival according to RECIST 1.1; overall survival time;
progressive disease profile;
serum titers of anti-A49-F3'-TriNKET-Trastuzumab antibodies;
expression of HER2 on tumor tissue;

ERBB2 status (amplified/non-amplified, mutated/non-mutated);
unconfirmed response at Week 13 according to RECIST 1.1 (for Safety/PK/PD expansion cohorts); and
progression free survival time, according to RECIST 1.1; duration of response according to RECIST 1.1 (for the efficacy expansion cohorts).

Efficacy Parameters

Clinical efficacy parameters will be analyzed descriptively in the full analysis set. Response rates will in addition be calculated in the efficacy population according to further specifications in the statistical analysis plan. Pooling of data from secondary and efficacy expansion cohorts may be considered to enhance precision of estimates. Further details will be specified in the statistical analysis plan.

The primary efficacy parameter in the expansion part is the best overall response according to RECIST 1.1.

The overall response rate assessment will be determined according to RECIST 1.1. The overall response rate will be evaluated over the whole trial period. For a best overall response of partial response or complete response, confirmation of the response according to RECIST 1.1 will be required. The response at each scheduled tumor assessment and the best overall response will be listed for each patient. The number and proportion of overall response rate (defined as complete response+ partial response) will be tabulated by cohort. For the HER2 high basket cohort, the number and proportion of overall response rate will be tabulated for each tumor types for which there are more than 5 patients enrolled and treated for 4 weeks. Tumor types represented by less than 5 patients (from 1 patient to 4 patient) will be represented as one sub-group.

Duration of response, according to RECIST 1.1, will be calculated for each patient with a confirmed response in the expansion cohorts and will be analyzed using the Kaplan-Meier method in all cohorts.

Progression free survival time and overall survival time will be presented in patient listings and analyzed using the Kaplan-Meier method in the full analysis set analysis set of the expansion cohorts that enrolled the full planned number of patients.

Pharmacokinetic profile, serum titers of anti-drug antibodies, biomarkers, safety analyses, adverse events, laboratory variables, and physical examination are all assessed as previously described in Example 3.

Example 5: Reduction of Infusion-Related Reactions to A49-F3'-TriNKET-Trastuzumab This example describes combination therapies designed to mitigate infusion-related reactions to A49-F3'-TriNKET-Trastuzumab in the clinical study described in Example 4. The A49-F3'-TriNKET-Trastuzumab infusion is administered over a period of up to two hours and no less than one hour.

It was observed, during the execution of the clinical study of Example 4, that administration of antipyretic and antihistamine was not sufficient to adequately prevent the occurrence of such infusion-related reactions. Specifically, two patients were treated with 0.52 mg/kg of A49-F3'-TriNKET-Trastuzumab. One patient had a Grade 1 cytokine release syndrome (CRS) event and the other patient had a Grade 2 CRS event. In view of these infusion-related reactions, an improved regimen was developed to increase the probability of completing the first administration of A49-F3'-TriNKET-Trastuzumab, when the risk of Grade 2 infusion-related reaction is the greatest.

In order to mitigate infusion-related reactions, in both the monotherapy and the nivolumab and nab-paclitaxel combination cohorts, a premedication regimen of 125 mg of methylprednisolone (or equivalent) was administered intravenously within 60 minutes of each patient's first infusion of A49-F3'-TriNKET-Trastuzumab for patients who received an initial dose of at least 0.52 mg/kg (DL9) of A49-F3'-TriNKET-Trastuzumab. In addition, 40-50 mg of diphenhydramine (or equivalent) and 800-1000 mg of acetaminophen was administered intravenously (or oral equivalent) approximately 30 to 60 minutes prior to each dose of A49-F3'-TriNKET-Trastuzumab for patients who received an initial dose of at least 0.052 mg/kg (DL7) of A49-F3'-TriNKET-Trastuzumab. Methylprednisolone (or equivalent) was provided only with the first A49-F3'-TriNKET-Trastuzumab administration, i.e., on day 1 of the first four-week treatment cycle.

It was observed that methylprednisolone dramatically reduced the incidence of infusion-related reactions. Four patients were treated with 0.52 mg/kg of A49-F3'-TriNKET-Trastuzumab by intravenous infusion and received 125 mg of methylprednisolone prior to the infusion. Only one of the patients had a Grade 2 infusion-related reaction. The infusion was interrupted while the patient was treated. The event resolved and the infusion was restarted. The patient tolerated the rest of the infusion without any further event. The other three patients did not experience any infusion-related reaction.

Further infusion-related reactions were observed in the clinical study, as summarized in Table 37 below. Methylprednisolone (or equivalent) was provided only to the patients who received an initial dose of 0.52 mg/kg or greater (i.e., DL9 or above) of A49-F3'-TriNKET-Trastuzumab.

TABLE 37

Infusion-related reactions in Patients Receiving A49-F3'-TriNKET-Trastuzumab

| Patient group | Number of infusion-related reactions per dose level | Total number of infusion-related reactions |
|---|---|---|
| 3 + 3 dose escalation phase (monotherapy) (n = 17)* | DL9: 3 events (n = 6)<br>DL10: 1 event (n = 3)<br>DL11: 2 events (n = 4)<br>DL12: 2 events (n = 4) | 8 events |
| 3 + 3 dose escalation phase. Combination Therapy with Nab-Paclitaxel (n = 4) | DL10: 1 event (n = 4) | 1 event |
| 3 + 3 dose escalation phase. Combination Therapy with Nivolumab (n = 4) | DL10: 0 event (n = 3)<br>DL11: 0 event (n = 1) | 0 event |
| Accelerated-titration phase (n = 10) | DL1: 0 event (n = 1)<br>DL2: 0 event (n = 1)<br>DL3: 0 event (n = 1)<br>DL4: 0 event (n = 1)<br>DL5: 1 event (n = 1)<br>DL6: 0 event (n = 1)<br>DL7: 3 events (n = 2)<br>DL8: 3 events (n = 2) | 7 events |
| Safety/PK/PD expansion cohort (n = 29) | DL9: 8 events (n = 10)<br>DL10: 0 event (n = 10)<br>DL11: 1 event (n = 9) | 9 events |

*Throughout this table, "n" refers to the number of patients in the patient group or at the dose level.

As shown in Table 37, a total of 18 infusion-related reactions were observed with the 54 patients who received 0.52 mg/kg or greater (i.e., DL9 or above) of A49-F3'-TriNKET-Trastuzumab, on average, 0.33 infusion-related reactions per patient. By contrast, a total of 6 infusion-related reactions were observed with the 4 patients who received lower than 0.16 mg/kg (i.e., DL7) or 0.52 mg/kg (i.e., DL8) of A49-F3'-TriNKET-Trastuzumab, on average, 1.5 infusion-related reactions per patient. It has been understood that in general, greater doses of protein-based oncotherapies can be associated with more severe infusion-related reactions. As such, in the absence of methylprednisolone (or equivalent) administration, the number of reactions per patient in the high dose groups (DL9 to DL12) would have been expected to be at least 1.5, if not more. The smaller number actually observed (0.33) indicates that the methylprednisolone (or equivalent) administration in these patient groups substantially improved infusion-related reactions to A49-F3'-TriNKET-Trastuzumab.

Example 6: Cytotoxicity of A49-F3'-TriNKET-Trastuzumab

Human cancer cell lines expressing HER2 were used to assess tumor antigen binding of a TriNKET (A49-F3'-TriNKET-Trastuzumab and monoclonal antibodies in the presence of NK cells. The cell lines used are listed in Table 38.

TABLE 38

Cell Lines used in Cytolysis Assays

| Cell Line Name | Description | ATCC Cat# |
| --- | --- | --- |
| SKBR-3 | HER2+ Breast adenocarcinoma | HTB-30 |
| H661 | Large cell lung cancer | HTB-183 |
| 786-0 | Renal cell adenocarcinoma | CRL-1932 |
| ZR-75-1 | Luminal A invasive ductal carcinoma | CRL-1500 |
| MCF-7 | Luminal A invasive ductal carcinoma | HTB-22 |
| BT20 | TNBC Basal A | HTB-19 |
| Hs578T | TNBC Basal B | HTB-126 |
| DU4475 | TNBC Basal A | HTB-123 |

The absolute numbers of HER2 proteins expressed on the surface of each cell of these cell lines were measured by flow cytometry. A49-F3'-TriNKET-Trastuzumab was labeled using an Alexa Fluor 647 Antibody Labeling Kit (Thermo Fisher, A20186). Saturating concentrations of the labeled TriNKET were determined by dissociating target cells with TrypLE in prewarmed culture media. Cells were resuspended in 1×PBS, adjusted to 1×10$^6$/ml and 50 µl (5×10$^4$) cells were plated in each well in duplicate. Live/Dead staining mix was prepared by diluting stock Zombie NIR (423105) or Zombie Aqua Fixable Viability dye (423102) 1:1000 in 1×PBS. Cells were pelleted, and resuspended in 50 µl Live/Dead staining mix, and incubated for 15 min at RT. Cells were washed 2× with FACS buffer, and resuspended in 50 µl serially diluted (3-fold; starting at 500 nM) labeled TriNKETs in FACS buffer. Cells were incubated for 1 hour in the dark on ice. Cells were washed 2× with FACS buffer, and resuspended in 50 µl fixation buffer (BioLegend) Cells were fixed for 10 min at RT. Cells were washed 2× with FACS buffer and analyzed on a BD FACSCelesta2 HTS machine.

For surface receptor quantitation, target-expressing cells were dissociated, plated in duplicate, and stained with Live/Dead dye as described above. Cells were then washed 2× with FACS buffer, and incubated with saturating concentrations of labeled TriNKET for 1 hour in the dark on ice. Cells were then washed, fixed and prepared for analysis on a BD FACSCelesta2 HTS machine as described above. Quantum Alexa Fluor 647 MESF beads (Bangs Laboratories, 647) were run on the same analysis setting to establish a calibration curve. Data was analyzed in FlowJo v10.7.1 (BD). Cells were gated for singlets (FSC-H vs FSC-A), and live cells (FSC-H vs Live/Dead). Manufacturer pre-defined MESF values and geometric mean fluorescence intensity (gMFI) values of Alexa Fluor 647 beads were log-transformed in Prism 9.0 using a non-linear fit to establish a calibration curve. Log-transformed gMFI values from TriNKET-stained cells were interpolated from calibration curve in Prism 9.0. Interpolated values were converted to non-log values, background was subtracted (as determined by the unstained cell population), and normalized for the degree of labeling. Rounded average receptor number of duplicate wells are reported in Table 39.

TABLE 39

HER2 expression on Cell Lines used in Cytolysis Assays

| Cell Line | Average Receptor Number | HER2 Expression |
| --- | --- | --- |
| SKBR-3 | 678,876 | High |
| H661 | 44,066 | Medium |
| 786-0 | 10,881 | Low |
| ZR-75-1 | 57,692 | Medium |
| MCF-7 | 9,078 | Low |
| BT20 | 9,197 | Low |
| Hs578T | 4,146 | Low |
| DU4475 | 647 | Low |

To prepare NK cells, PBMCs were isolated from human peripheral blood buffy coats using density gradient centrifugation and were washed. NK cells were isolated from the PBMCs using a MACS negative selection technique with magnetic beads. NK cell (CD3$^-$CD56$^+$) purity was routinely confirmed to be greater than 90% of the harvested cells. The isolated NK cells were rested overnight and used the following day in cytotoxicity assays.

To conduct the DELFIA cytotoxicity assay, the HER2-expressing human cancer cell lines described above were harvested from culture. The cells were washed with HBS, and resuspended in growth media at 10$^6$ cells/mL for labeling with BATDA reagent (Perkin Elmer AD0116). Manufacturer instructions were followed for labeling of the target cells. After labeling, the cells were washed three times with HBS, and were resuspended at 0.5×10$^5$/mL in primary NK cell culture media.

Rested human NK cells or KHYG-1-CD16V-expressing cells were removed from culture and pelleted, the cells were resuspended in NK cell culture media at 0.1-2×10$^6$ cells/mL depending upon the desired effector to target ratio (E:T). Assays using NK cells were performed using a 5:1 E:T ratio and a 10:1 E:T ratio with KHYG-1-CD16V cells. 4× A49-F3'-TriNKET-Trastuzumab and trastuzumab were prepared in primary NK cell culture media. In a round bottom TC 96-well plate, 100 µl of labeled target cells, 50 µl of 4× TriNKET/mAb, and 50 µl of effector cells were added. Control wells for background were prepared by pelleting labeled target cells, and 100 µl of the supernatant was added to background wells, containing 100 µl of primary NK cell culture media. Spontaneous release wells were prepared by adding 100 µl of labeled target cells to wells containing 100 µl of primary NK cell culture media. Maximum release wells were prepared by adding 100 µl of labeled target cells to wells containing 80 µl of primary NK cell culture media and 20 µl of 10% TritonX-100 solution. The assay plate was incubated at 37° C. with 5% CO$_2$ for 2-3 hours.

After culturing for 2-3 hours, the plate was removed from the incubator and the cells were pelleted by centrifugation at 300 g for 3 minutes. 20 µl of culture supernatant were transferred to a clean microplate provided from the manufacturer, and 200 µl of room temperature europium solution were added to each well. The plate was protected from light and incubated on a plate shaker at 250 rpm for 15 minutes. Fluorescence levels were read using either Victor 3 or SpectraMax i3x instruments.

The percentage of specific lysis was calculated as: % Specific lysis=(Experimental release−Spontaneous release)/(Maximum release−Spontaneous release)*100%

Figure 33A:
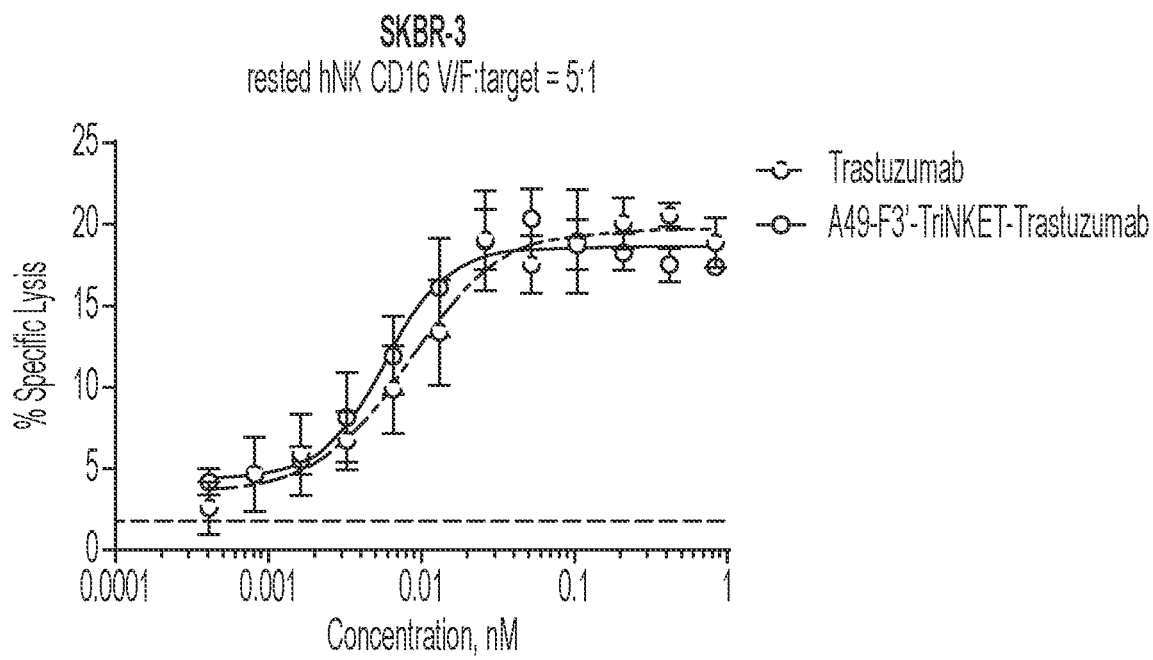
FIGS. 33A-33C are line graphs showing the cytotoxicity of A49-F3'-TriNKET-Trastuzumab and trastuzumab on SKBR-3 (FIG. 33A), H661 (FIG. 33B), and 786-0 (FIG. 33C) cancer cells in the presence of NK cells.
Figure 33B:
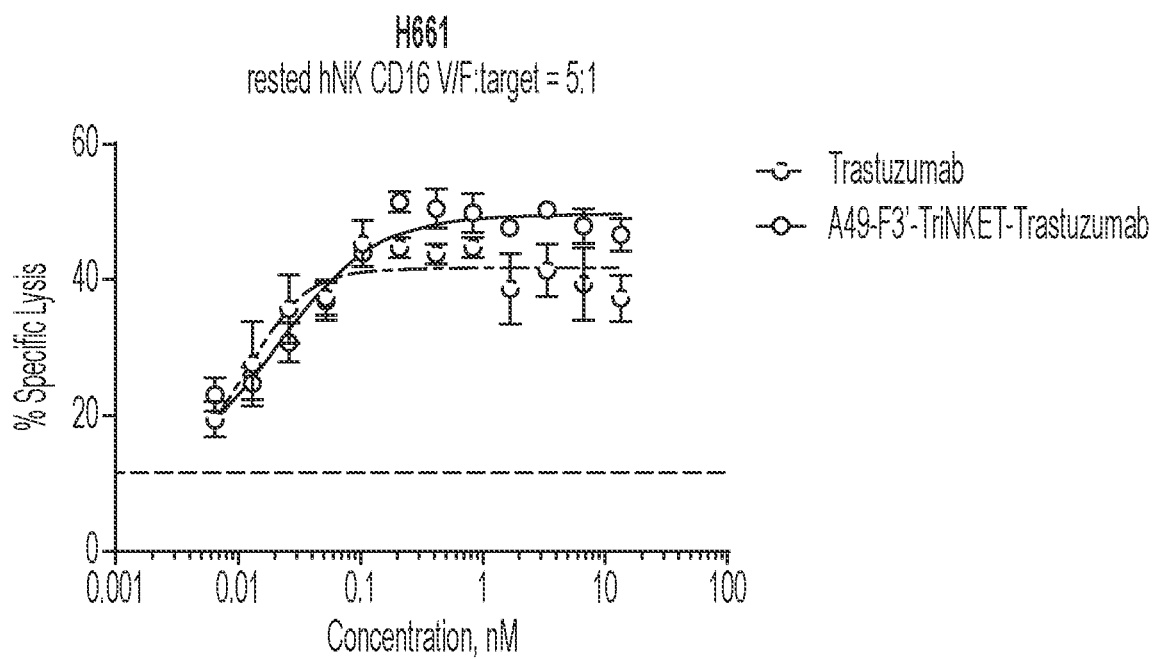
Figure 33C:
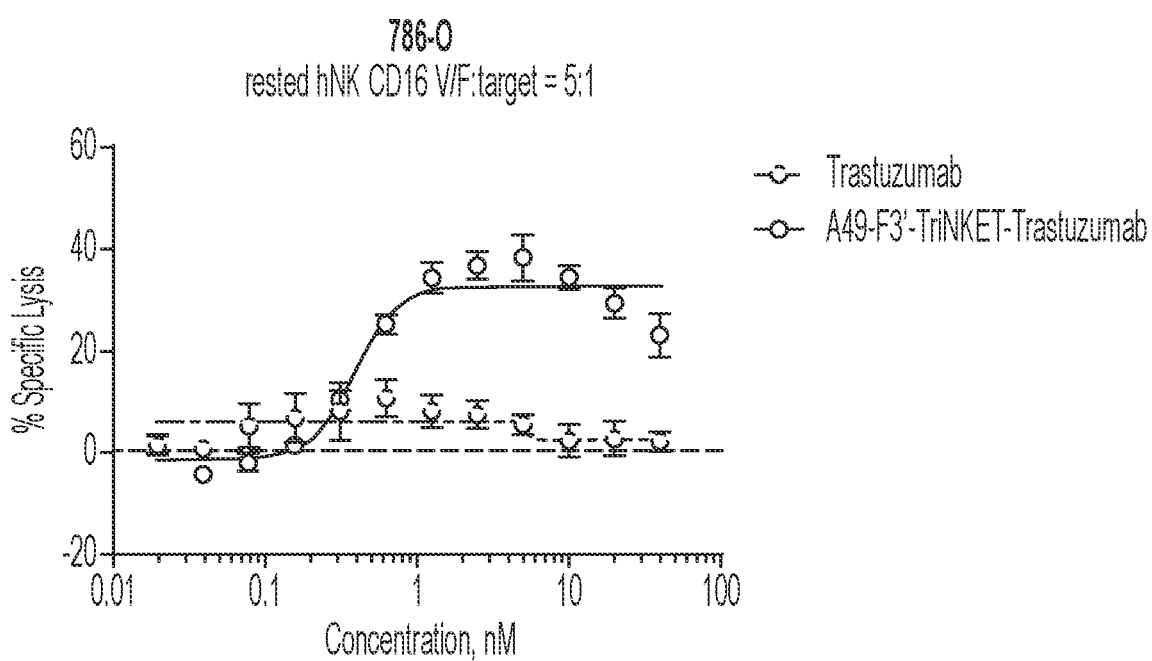

As shown in FIG. 33A-FIG. 33C, A49-F3'-TriNKET-Trastuzumab was more potent at promoting NK cell-mediated cytolysis of SKBR-3 (FIG. 33A) and 786-0 (FIG. 33C) cells than trastuzumab alone and comparable cytolysis against H661 cells (FIG. 33B). Against SKBR-3 cells (HER2 high), A49-F3'-TriNKET-Trastuzumab demonstrated an EC50 of 0.008±0.003 nM across 3 healthy donors in enhancing NK cell-mediated cytolysis, and exhibited a 2.5-fold higher potency than trastuzumab in triggering NK cell-mediated killing. Maximum lysis for A49-F3'-TriNKET-Trastuzumab and trastuzumab varied among experiments and individual donors. Against H661 cells (HER2 medium), A49-F3'-TriNKET-Trastuzumab and trastuzumab exhibited similar potency (EC50 of 0.054±0.032 nM) in triggering NK cell-mediated killing, with maximum lysis in the presence of A49-F3'-TriNKET-Trastuzumab being higher. Against the 786-0 renal cell carcinoma cells (HER2 low), only A49-F3'-TriNKET-Trastuzumab, but not trastuzumab, was effective in inducing target cell lysis (EC50 0.638±0.461 nM).

Figure 34A:
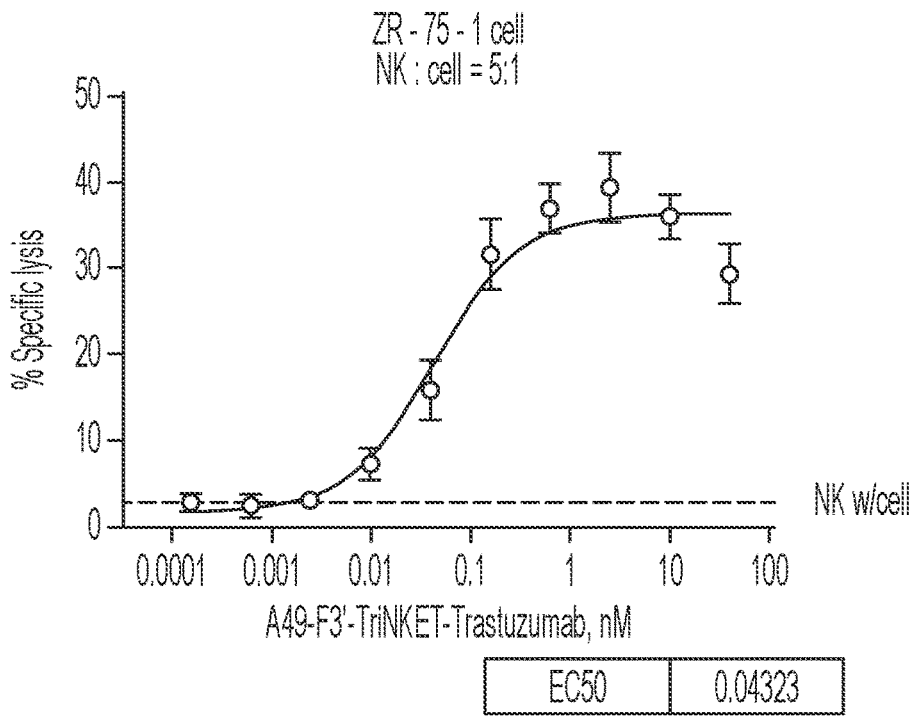
FIGS. 34A-34B are line graphs showing the cytotoxicity of A49-F3'-TriNKET-Trastuzumab and trastuzumab on ZR-75-1 (FIG. 34A) and MCF-7 (FIG. 34B) cancer cells in the presence of NK cells.
Figure 34B:
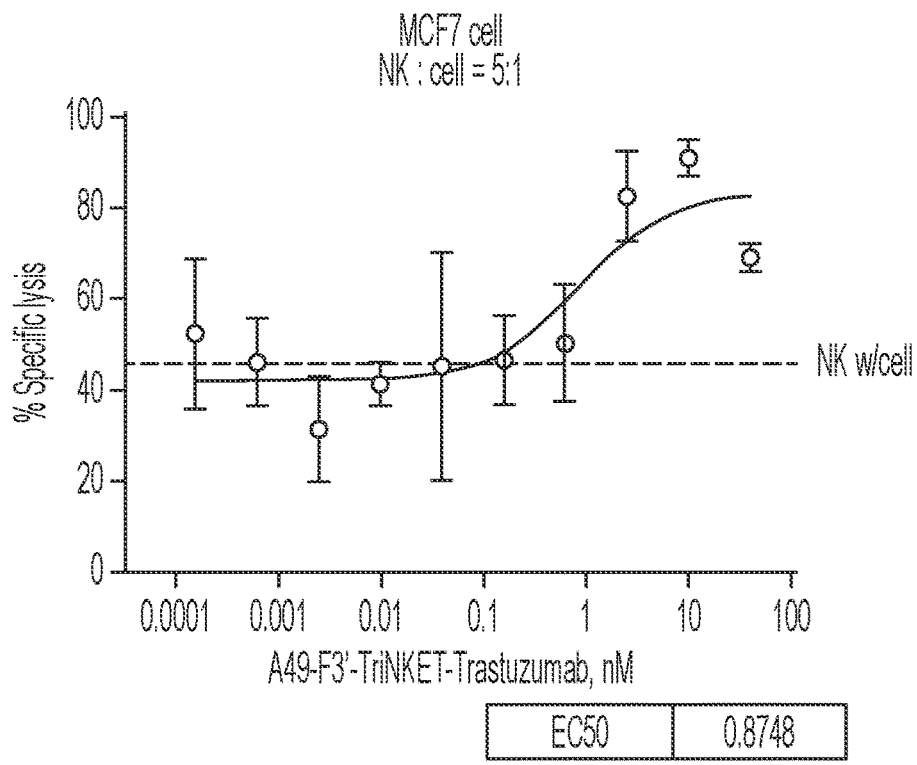

The ability of A49-F3'-TriNKET-Trastuzumab to enhance NK cell-mediated killing was assessed using two hormone receptor (HR)+ HER2− luminal A breast cancer cell lines. The ZR75-1 cells are estrogen receptor (ER) positive, progesterone receptor (PR)+/− and HER2 medium. MCF-7 cells are ER+, PR+ and HER2 low. As shown in FIG. 34A, A49-F3'-TriNKET-Trastuzumab demonstrated high potency in lysis of ZR75-1 cells with an EC50 of 0.043 nM. A49-F3'-TriNKET-Trastuzumab also enhanced NK cell-mediated killing against MCF-7 cells compared to NK cells alone with an EC50 of 0.878 nM (FIG. 34B).

Figure 35A:
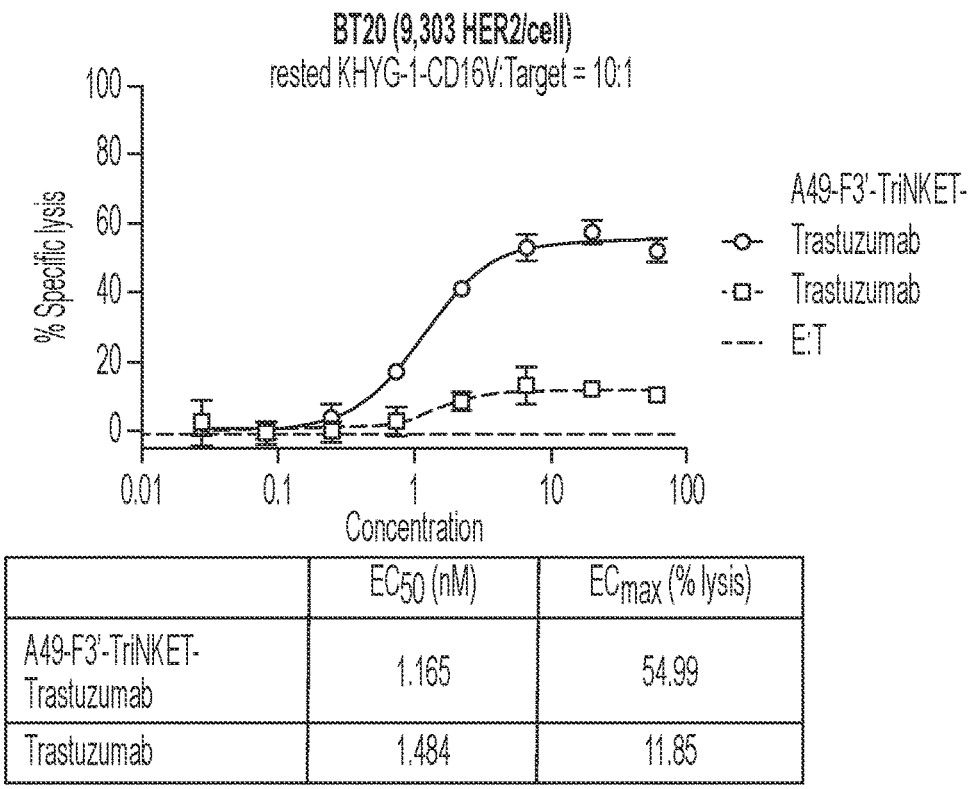
FIGS. 35A-35C are line graphs showing the cytotoxicity of A49-F3'-TriNKET-Trastuzumab and trastuzumab on BT-20 (FIG. 35A), Hs578T (FIG. 35B) and DU4475 (FIG. 35C) cancer cells in the presence of KHYG-1-CD16V cells.
Figure 35B:
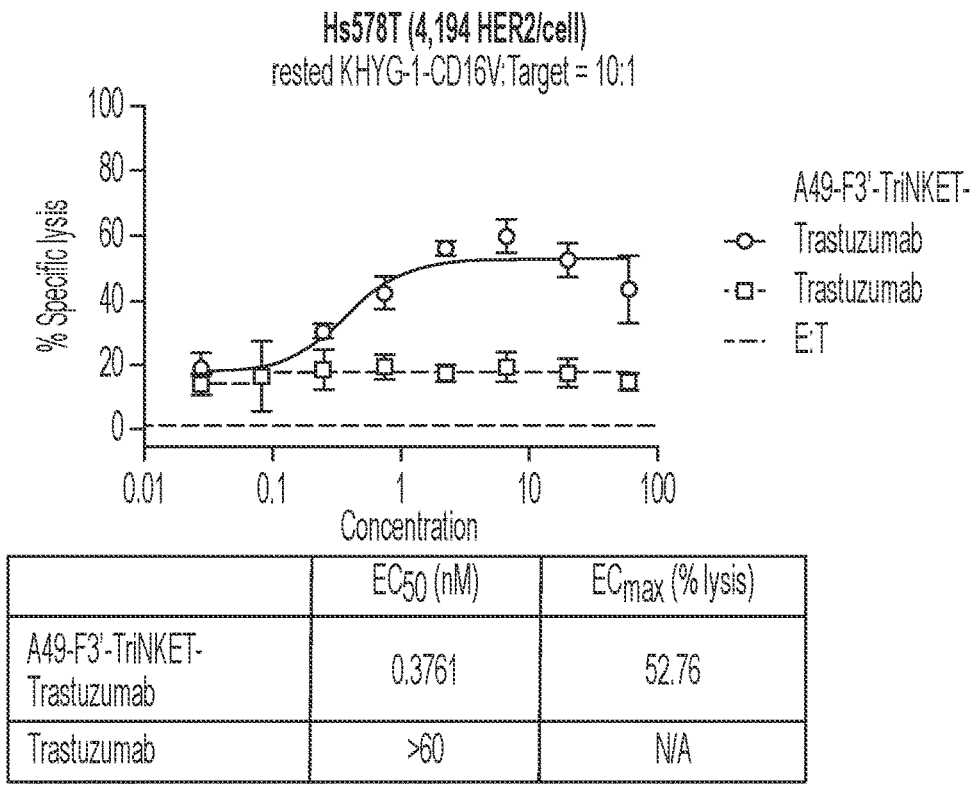
Figure 35C:
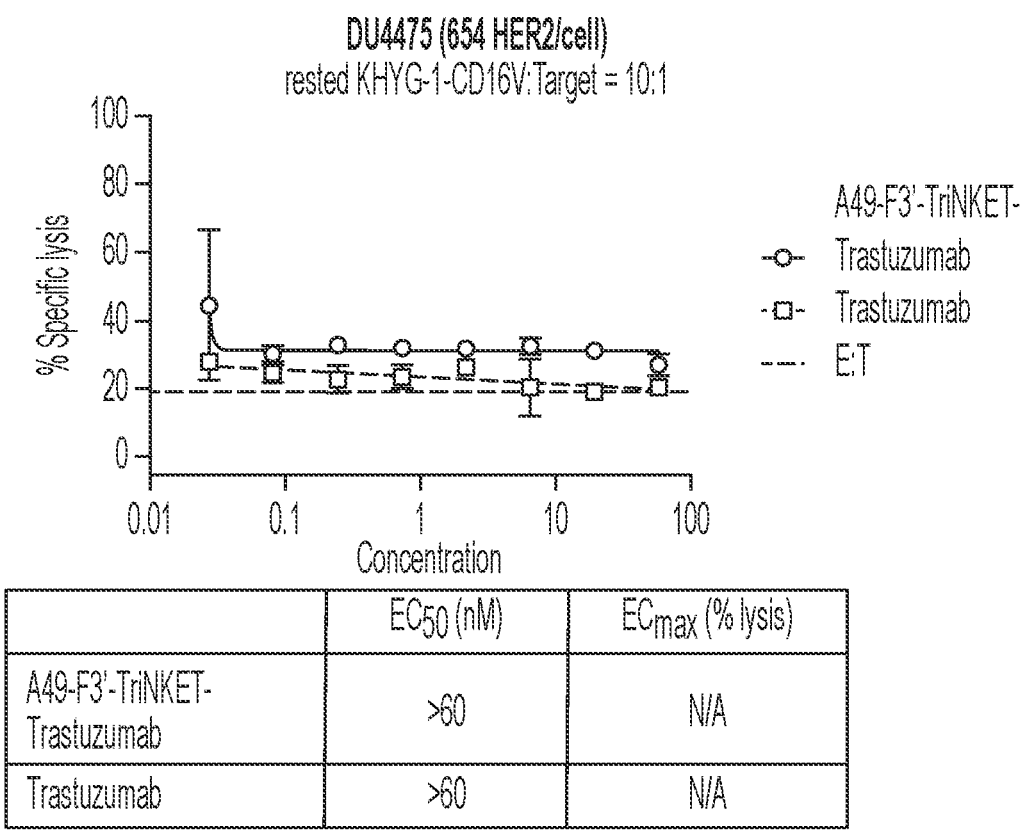

As shown in FIG. 35A-35B, A49-F3'-TriNKET-Trastuzumab was more potent at promoting cell-mediated cytolysis by KHYG-1-CD16V cells of BT-20 and Hs578T TNBC cells than trastuzumab alone. A49-F3'-TriNKET-Trastuzumab demonstrated an EC50 of 1.16 nM and a max lysis of 54.99% compared to trastuzumab (1.48 nM and 11.85% max lysis) against the BT-20 cell line (FIG. 35A). While trastuzumab had no impact on KHYG-1-CD16V cell-mediated killing against Hs578T cells, A49-F3'-TriNKET-Trastuzumab enhanced KHYG-1-CD16V cell killing with an EC50 of 0.376 nM and 52.76% max lysis (FIG. 35B). Neither A49-F3'-TriNKET-Trastuzumab nor trastuzumab enhanced KHYG-1-CD16V cell-mediated killing of DU4475 cells (FIG. 35C). All three cell lines assessed had low levels of HER2 expression.

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Various structural elements of the different embodiments and various disclosed method steps may be utilized in various combinations and permutations, and all such variants are to be considered forms of the disclosure. Scope of the disclosure is thus indicated by the appended claims rather than by the foregoing description, and all changes that come within the meaning and range of equivalency of the claims are intended to be embraced therein.

---

What is claimed is:

1. A method of treating a breast cancer, the method comprising administering a therapeutically effective amount of a multi-specific binding protein to a subject in need thereof,
  wherein the breast cancer is positive for a hormone receptor and:
    (i) has a HER2 expression level scored as 2+ as determined by immunohistochemistry (IHC), but not ERBB2 gene amplification as determined by an in situ hybridization (ISH) assay, or
    (ii) has a HER2 expression level scored as 1+ as determined by IHC;
  wherein the multi-specific binding protein comprises:
    (a) a first antigen-binding site that binds NKG2D;
    (b) a second antigen-binding site that binds HER2; and
    (c) an antibody Fc domain or a portion thereof sufficient to bind CD16, or a third antigen-binding site that binds CD16.

2. The method of claim 1, wherein the hormone receptor is estrogen receptor, progesterone receptor, or both.

3. The method of claim 1, wherein the multi-specific binding protein is administered to the subject in an initial four-week treatment cycle on Day 1, Day 8, and Day 15, but not Day 22.

4. The method of claim 3, further comprising administering to the subject, after the initial treatment cycle, the multi-specific binding protein in one or more subsequent four-week treatment cycles, wherein the multi-specific binding protein is administered on Day 1 and Day 15 in each subsequent treatment cycle.

5. The method of claim 4, wherein each of the doses comprises the multi-specific binding protein at an amount selected from the group consisting of 5 mg/kg, 10 mg/kg, 15 mg/kg, and 20 mg/kg, administered by intravenous infusion.

6. The method of claim 3, further comprising administering to the subject, on Day 1 of the initial four-week treatment cycle, a therapeutically effective amount of a corticosteroid to reduce one or more infusion-related reactions to the multi-specific binding protein.

7. The method of claim 6, wherein the corticosteroid is a glucocorticoid selected from the group consisting of methylprednisolone, dexamethasone, hydrocortisone, prednisone, prednisolone, fluticasone, flumethasone, fluocinolone, budesonide, beclomethasone, ciclesonide, cortisone, triamcinolone, betamethasone, deflazacort, difluprednate, loteprednol, paramethasone, tixocortol, and pharmaceutically acceptable salts thereof.

8. The method of claim 6, wherein the infusion-related reactions comprise cytokine release syndrome, anaphylaxis, chills, fever, hypotension, hypertension, rigors, headache, dizziness, itching, sore throat, laryngeal edema, angioedema, flushing, rash, bronchospasm, tachycardia, bradycardia, auricular fibrillation, hypoxia, dyspnea, respiratory distress, chest tightness, nausea, vomiting, shivering, tremors, pain, tiredness, insomnia, asthenia, hypersensitivity, and/or diarrhea.

9. The method of claim 1, further comprising administering to the subject a chemotherapy.

10. The method of claim 1, wherein the first antigen-binding site that binds NKG2D comprises:
  (a) a heavy chain variable domain (VH) comprising complementarity-determining region 1 (CDR1), complementarity-determining region 2 (CDR2), and complementarity-determining region 3 (CDR3) sequences represented by the amino acid sequences of SEQ ID NOs: 168, 96, and 188, respectively; and
  (b) a light chain variable domain (VL) comprising CDR1, CDR2, and CDR3 sequences represented by the amino acid sequences of SEQ ID NOs: 99, 100, and 101, respectively.

11. The method of claim 10, wherein
  (a) the VH comprises CDR1, CDR2, and CDR3 sequences represented by the amino acid sequences of SEQ ID NOs: 168, 96, and 169, respectively; and (b) the VL comprises CDR1, CDR2, and CDR3 sequences represented by the amino acid sequences of SEQ ID NOs: 99, 100, and 101, respectively.

12. The method of claim 11, wherein the VH comprises an amino acid sequence at least 90% identical to SEQ ID NO:94, and the VL comprises an amino acid sequence at least 90% identical to SEQ ID NO:98.

13. The method of claim 1, wherein the second antigen-binding site that binds HER2 comprises:
    (a) a VH comprising CDR1, CDR2, and CDR3 sequences represented by the amino acid sequences of SEQ ID NOs: 115, 116, and 117, respectively; and
    (b) a VL comprising CDR1, CDR2, and CDR3 sequences represented by the amino acid sequences of SEQ ID NOs: 119, 120, and 121, respectively.

14. The method of claim 13, wherein the VH comprises an amino acid sequence at least 90% identical to SEQ ID NO:195, and the VL comprises an amino acid sequence at least 90% identical to SEQ ID NO:196.

15. The method of claim 1, wherein the first antigen-binding site that binds NKG2D is a Fab, and the second antigen-binding site that binds HER2 is an scFv.

16. The method of claim 15, wherein element (c) of the multi-specific binding protein is an antibody Fc domain, wherein the antibody Fc domain comprises a first antibody Fc sequence linked to a C-terminus of a heavy chain portion of the first antigen-binding site and a second antibody Fc sequence linked to a C-terminus of the second antigen-binding site via a hinge comprising Ala-Ser, and wherein the first and second antibody Fc sequences comprise different mutations that promote heterodimerization.

17. The method of claim 16, wherein the first antibody Fc sequence is a human IgG1 Fc sequence comprising K360E and K409W substitutions, and the second antibody Fc sequence is a human IgG1 Fc sequence comprising Q347R, D399V, and F405T substitutions, according to the EU numbering system.

18. The method of claim 1, wherein the multi-specific binding protein comprises:
    (a) a first polypeptide comprising the amino acid sequence of SEQ ID NO:141;
    (b) a second polypeptide comprising the amino acid sequence of SEQ ID NO: 140; and
    (c) a third polypeptide comprising the amino acid sequence of SEQ ID NO:142.

19. The method of claim 5, wherein each of the doses in the one or more subsequent treatment cycles comprises 10 mg/kg of the multi-specific binding protein administered by intravenous infusion.

20. The method of claim 19, wherein the multi-specific binding protein comprises:
    (a) a first polypeptide comprising the amino acid sequence of SEQ ID NO:141;
    (b) a second polypeptide comprising the amino acid sequence of SEQ ID NO:140; and
    (c) a third polypeptide comprising the amino acid sequence of SEQ ID NO:142.

* * * * *